(12) United States Patent
Ple et al.

(10) Patent No.: US 8,153,643 B2
(45) Date of Patent: Apr. 10, 2012

(54) QUINAZOLINE DERIVATIVES

(75) Inventors: Patrick Ple, Reims (FR); Frederic Henri Jung, Reims (FR)

(73) Assignee: AstraZeneca AB, Sodertalje (SE)

( * ) Notice: Subject to any disclaimer, the term of this patent is extended or adjusted under 35 U.S.C. 154(b) by 1323 days.

(21) Appl. No.: 11/665,125

(22) PCT Filed: Oct. 7, 2005

(86) PCT No.: PCT/GB2005/003846
§ 371 (c)(1),
(2), (4) Date: Apr. 11, 2007

(87) PCT Pub. No.: WO2006/040520
PCT Pub. Date: Apr. 20, 2006

(65) Prior Publication Data
US 2009/0233924 A1      Sep. 17, 2009

(30) Foreign Application Priority Data
Oct. 12, 2004   (EP) ..................................... 04292417

(51) Int. Cl.
A61K 31/517 (2006.01)
C07D 403/02 (2006.01)
C07D 403/10 (2006.01)

(52) U.S. Cl. .................................. 514/266.23; 544/284

(58) Field of Classification Search .................. None
See application file for complete search history.

(56) References Cited

U.S. PATENT DOCUMENTS

| | | | |
|---|---|---|---|
| 6,017,919 A | 1/2000 | Inaba et al. | |
| 6,531,291 B1 | 3/2003 | Kabbash et al. | |
| 6,881,553 B2 | 4/2005 | Kabbash et al. | |
| 7,056,942 B2 * | 6/2006 | Hildesheim et al. | 514/411 |
| 7,973,164 B2 | 7/2011 | Jung et al. | |
| 2003/0187002 A1 | 10/2003 | Mortlock et al. | |
| 2006/0160803 A1 | 7/2006 | Adams et al. | |
| 2009/0036474 A1 | 2/2009 | Ple et al. | |
| 2009/0036485 A1 | 2/2009 | Jung et al. | |
| 2009/0042910 A1 | 2/2009 | Jung et al. | |
| 2009/0076074 A1 | 3/2009 | Jung et al. | |
| 2009/0076075 A1 | 3/2009 | Jung et al. | |
| 2009/0233950 A1 | 9/2009 | Jung et al. | |

FOREIGN PATENT DOCUMENTS

| | | |
|---|---|---|
| EP | 0566226 | 10/1993 |
| EP | 0837063 | 4/1998 |
| EP | 1541563 | 6/2005 |
| EP | 1541564 | 6/2005 |
| EP | 1661889 | 5/2006 |
| WO | WO 92/20642 | 11/1992 |
| WO | WO 96/09294 A | 3/1996 |
| WO | WO 96/15118 A | 5/1996 |
| WO | WO 96/39145 | 12/1996 |
| WO | WO 97/03069 A | 1/1997 |
| WO | WO 97/30034 | 8/1997 |
| WO | WO 99/47529 | 9/1999 |
| WO | WO 00/20402 | 4/2000 |
| WO | WO 00/21955 A | 4/2000 |
| WO | WO 00/47212 | 8/2000 |
| WO | WO 01/19788 | 3/2001 |
| WO | WO 01/21594 | 3/2001 |
| WO | WO 01/21594 A | 3/2001 |
| WO | WO 01/21595 | 3/2001 |
| WO | WO 01/21596 | 3/2001 |
| WO | WO 01/21597 | 3/2001 |
| WO | WO 03/055491 | 7/2001 |
| WO | WO 01/55116 | 8/2001 |
| WO | WO 02/00649 | 1/2002 |
| WO | WO 02/17712 | 3/2002 |
| WO | WO 02/051831 | 7/2002 |
| WO | WO 02/092571 | 11/2002 |
| WO | WO 03/037274 | 5/2003 |
| WO | WO 03/040108 | 5/2003 |
| WO | WO 03/040109 | 5/2003 |
| WO | WO 03/064413 | 8/2003 |
| WO | WO 03/099771 | 12/2003 |
| WO | WO 2004/058752 | 7/2004 |
| WO | WO 2004/058781 A | 7/2004 |
| WO | WO 2004/058782 | 7/2004 |
| WO | WO 2004/094410 | 11/2004 |
| WO | WO 2004/098528 | 11/2004 |

(Continued)

OTHER PUBLICATIONS

Jantzen and Robinson. Modern Pharmaceutics, 1996, p. 596.*
Clarke et al. Oncogene, 2003, 22, pp. 722-733.*
Hofer et al. Neoplasia, 2004, X(Y), pp. 1-10.*
Witmer et al. Journal of Histochemistry & Cytochemistry, 2004, 52(1), 39-52.*
Heldin. Upsala Journal of Medical Sciences, 2004, 109, 165-178.*
U.S. Appl. No. 11/665,115, filed Apr. 11, 2007, Ple et al., WO 2006/040526, Apr. 20, 2006.
U.S. Appl. No. 11/665,124, filed Apr. 11, 2007, Ple et al., WO 2006/040522, Apr. 20, 2006.

*Primary Examiner* — Noble Jarrell
(74) *Attorney, Agent, or Firm* — AstraZeneca AB

(57) ABSTRACT

The invention concerns quinazoline derivatives of Formula (I) or a pharmaceutically-acceptable salt, solvate or pro-drug thereof, wherein each of $X^1$, p, $R^1$, q, $R^2$, $R^3$, $R^4$, $R^5$, Ring A, r and $R^6$ has any of the meanings defined hereinbefore in the description; processes for their preparation, pharmaceutical compositions containing them and their use in the manufacture of a medicament for use in the treatment of cell proliferative disorders or in the treatment of disease states associated with angiogenesis and/or vascular permeability.

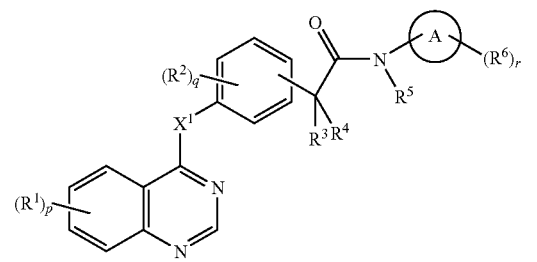

(I)

10 Claims, No Drawings

FOREIGN PATENT DOCUMENTS

| WO | WO 2004/105764 | 12/2004 |
| WO | WO 2004/113324 | 12/2004 |
| WO | WO 2004-113324 A | 12/2004 |
| WO | WO 2005/014582 | 2/2005 |
| WO | WO 2005/021554 | 3/2005 |
| WO | WO 2005/030140 | 4/2005 |
| WO | WO 2006/040522 | 4/2006 |
| WO | WO 2006/040526 | 4/2006 |
| WO | WO 2006/076706 | 7/2006 |
| WO | WO 2006/117552 | 11/2006 |
| WO | WO 2006/117570 | 11/2006 |
| WO | WO 2007/099317 | 9/2007 |
| WO | WO 2007/099323 | 9/2007 |
| WO | WO 2007/099326 | 9/2007 |
| WO | WO 2007/099335 | 9/2007 |
| WO | WO 2007/113548 | 10/2007 |
| WO | WO 2007/113565 | 10/2007 |

* cited by examiner

QUINAZOLINE DERIVATIVES

The invention concerns certain novel quinazoline derivatives, or pharmaceutically-acceptable salts thereof, which possess anti-cancer activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of cancers in a warm-blooded animal such as man, including use in the prevention or treatment of solid tumour disease.

Many of the current treatment regimes for the abnormal cell growth found in cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-cancer agents which act by mechanisms other than the inhibition of DNA synthesis have the potential to display enhanced selectivity of action.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine, autocrine and endocrine factors. By binding to specific transmembrane receptors, growth factor ligands communicate extracellular signals to the intracellular signalling pathways, thereby causing the individual cell to respond to extracellular signals. Many of these signal transduction processes utilise the reversible process of the phosphorylation of proteins involving specific kinases and phosphatases.

As phosphorylation is such an important regulatory mechanism in the signal transduction process, it is not surprising that aberrations in the process result in abnormal cell differentiation, transformation and growth. For example, it has been discovered that a cell may become cancerous by virtue of the transformation of a portion of its DNA into an oncogene. Several such oncogenes encode proteins which are receptors for growth factors, for example tyrosine kinase enzymes. Tyrosine kinases may also be mutated to constitutively active forms that result in the transformation of a variety of human cells. Alternatively, the over-expression of normal tyrosine kinase enzymes may also result in abnormal cell proliferation.

Tyrosine kinase enzymes may be divided into two groups: the receptor tyrosine kinases and the non-receptor tyrosine kinases. About 90 tyrosine kinase have been identified in the human genome, of which about 60 are of the receptor type and about 30 are of the non-receptor type. These can be categorised into 20 receptor tyrosine kinase sub-families according to the families of growth factors that they bind and into 10 non-receptor tyrosine kinase sub-families (Robinson et al, *Oncogene*, 2000, 19, 5548-5557). The classification includes the EGF family of receptor tyrosine kinases such as the EGF, TGFα, Neu and erbB receptors, the insulin family of receptor tyrosine kinases such as the insulin and IGF1 receptors and insulin-related receptor (IRR) and the Class III family of receptor tyrosine kinases such as the platelet-derived growth factor (PDGF) receptor tyrosine kinases, for example the PDGFα and PDGFβ receptors, the stem cell factor receptor tyrosine kinase (SCF RTK (commonly known as c-Kit), the fms-related tyrosine kinase 3 (Flt3) receptor tyrosine kinase and the colony-stimulating factor 1 receptor (CSF-1R) tyrosine kinase.

It has been discovered that such mutated and over-expressed forms of tyrosine kinases are present in a large proportion of common human cancers such as the leukaemias, breast cancer, prostate cancer, non-small cell lung cancer (NSCLC) including adenocarcinomas and squamous cell cancer of the lung, gastrointestinal cancer including colon, rectal and stomach cancer, bladder cancer, oesophageal cancer, ovarian cancer and pancreatic cancer. As further human tumour tissues are tested, it is expected that the widespread prevalence and relevance of tyrosine kinases will be further established. For example, it has been shown that EGFR tyrosine kinase is mutated and/or over-expressed in several human cancers including in tumours of the lung, head and neck, gastrointestinal tract, breast, oesophagus, ovary, uterus, bladder and thyroid.

Platelet-derived growth factor (PDGF) is a major mitogen for connective tissue cells and other cell types. The PDGF receptors comprising PDGFα and PDGFβ receptor isozymes display enhanced activity in blood vessel disease (for example atherosclerosis and restenosis, for example in the process of restenosis subsequent to balloon angioplasty and heart arterial by-pass surgery). Such enhanced PDGF receptor kinase activity is also observed in other cell proliferative disorders such as fibrotic diseases (for example kidney fibrosis, hepatic cirrhosis, lung fibrosis and multicystic renal dysplasia), glomerulonephiritis, inflammatory diseases (for example rheumatoid arthritis and inflammatory bowel disease), multiple sclerosis, psoriasis, hypersensitivity reactions of the skin, allergic asthma, insulin-dependent diabetes, diabetic retinopathy and diabetic nephropathy.

The PDGF receptors can also contribute to cell transformation in cancers and leukaemias by autocrine stimulation of cell growth. It has been shown that PDGF receptor kinases are mutated and/or over-expressed in several human cancers including in tumours of the lung (non-small cell lung cancer and small cell lung cancer), gastrointestine (such as colon, rectal and stomach tumours), prostate, breast, kidney, liver, brain (such as glioblastoma), oesophagus, ovary, pancreas and skin (such as dermatofibrosarcoma protruberans) and in leukaemias and lymphomas such as chronic myelogenous leukaemia (CML), chronic myelomonocytic leukaemia (CMML), acute lymphocyte leukaemia (ALL) and multiple myeloma. Enhanced cell signalling by way of the PDGF receptor tyrosine kinases can contribute to a variety of cellular effects including cell proliferation, cellular mobility and invasiveness, cell permeability and cellular apoptosis.

Accordingly, antagonism of the activity of PDGF receptor kinases is expected to be beneficial in the treatment of a number of cell proliferative disorders such as cancer, especially in inhibiting tumour growth and metastasis and in inhibiting the progression of leukaemia.

In addition, PDGF is involved in angiogenesis, the process of forming new blood vessels, that is critical for continuing tumour growth. Normally, angiogenesis plays an important role in processes such as embryonic development, wound healing and several components of female reproductive function. However, undesirable or pathological angiogenesis has been associated with a number of disease states including diabetic retinopathy, psoriasis, cancer, rheumatoid arthritis, atheroma, Kaposi's sarcoma and haemangioma. Angiogenesis is stimulated via the promotion of the growth of endothelial cells. Several polypeptides with in vitro endothelial cell growth promoting activity have been identified including acidic and basic fibroblast growth factors (aFGF and bFGF)

and vascular endothelial growth factor (VEGF). By virtue of the restricted expression of its receptors, the growth factor activity of VEGF, in contrast to that of aFGF and bFGF, is relatively specific towards endothelial cells. Recent evidence indicates that VEGF is an important stimulator of both normal and pathological angiogenesis and vascular permeability. This cytokine induces a vascular sprouting phenotype by inducing endothelial cell proliferation, protease expression and migration which subsequently leads to the formation of capillary tubes that promote the formation of the hyperpermeable, immature vascular network which is characteristic of pathological angiogenesis. The receptor tyrosine kinase (RTK) sub-family that binds VEGF comprises the kinase insert domain-containing receptor KDR (also referred to as Flk-1), the fms-like tyrosine kinase receptor Flt-1 and the fms-like tyrosine kinase receptor Flt-4. Two of these related RTKs, namely Flt-1 and KDR, have been shown to bind VEGF with high affinity.

Accordingly, antagonism of the activity of VEGF is expected to be beneficial in the treatment of a number of disease states that are associated with angiogenesis and/or increased vascular permeability such as cancer, especially in inhibiting the development of tumours.

It is known that several compounds with PDGF receptor kinase inhibitory activity are progressing toward clinical development. The 2-anilinopyrimidine derivative known as imatinib (STI571; *Nature Reviews,* 2002, 1, 493-502; *Cancer Research,* 1996, 56, 100-104) has been shown to inhibit PDGF receptor kinase activity although its current clinical use is for the treatment of CML based on its additional activity as an inhibitor of BCR-ABL kinase. STI571 inhibits the growth of glioblastoma tumours arising from injection into the brains of nude mice of the human glioblastoma lines U343 and U87 (*Cancer Research,* 2000, 60, 5143-5150). The compound also inhibits the in vivo growth of dermatofibrosarcoma protruberans cell cultures (*Cancer Research,* 2001, 61, 5778-5783). Based on the PDGF receptor kinase inhibitory activity of the compound, clinical trials are being carried out in glioblastoma and in prostate cancer. Several other PDGF receptor kinase inhibitors are being investigated including quinoline, quinazoline and quinoxaline derivatives (*Cytokine & Growth Factor Reviews,* 2004, 15, 229-235).

It is known from International Patent Application WO 92/20642 that certain aryl and heteroaryl compounds inhibit EGF and/or PDGF receptor tyrosine kinase. There is the disclosure of certain quinazoline derivatives therein but no specific mention is made therein of 2-phenylacetamide derivatives; in particular, there is no specific mention made therein of quinazoline-substituted 2-phenylacetamide derivatives.

It is disclosed in many published patent applications that 4-anilinoquinazolines and 4-aryloxyquinazolines possess tyrosine kinase enzyme inhibitory activity. For example, International Patent Applications WO 96/09294, WO 96/15118 and WO 97/03069 are concerned with such compounds that are stated to possess receptor tyrosine kinase inhibitory activity such as EGF (erbB1) and/or erbB2 receptor tyrosine kinase inhibitory activity. For example, International Patent Applications WO 00/21955 and WO 00/47212 are concerned with such compounds that possess antiangiogenic and/or vascular permeability reducing activity based on antagonism of the activity of VEGF. However, there is no specific mention therein of 2-phenylacetamide derivatives; in particular, there is no specific mention made therein of quinazoline-substituted 2-phenylacetamide derivatives.

As stated above, although STI571 is the only compound with PDGF receptor kinase inhibitory activity that appears to have yet reached the market, that compound possesses approximately equipotent activity against various other kinase enzymes. There is still a need for further compounds with PDGF receptor kinase inhibitory activity that may be useful for the treatment of cell proliferation disorders such as cancer.

We have now found that surprisingly certain novel quinazoline-substituted 2-phenylacetamide derivatives possess potent activity against cell proliferative disorders. It is believed that the compounds provide a useful treatment of cell proliferative disorders, for example to provide an antitumour effect, by way of a contribution from inhibition of PDGF receptor tyrosine kinases.

A further characteristic of hyperproliferative diseases such as cancer is damage to the cellular pathways that control progress through the cell cycle which, in normal eukaryotic cells, involves an ordered cascade of protein phosphorylation. As for signal transduction mechanisms, several families of protein kinases appear to play critical roles in the cell cycle cascade. The most widely studied of these cell cycle regulators is the cyclin dependent kinase family (the CDKs). Activity of specific CDKs at specific times is essential both to initiate and coordinate progress through the cell cycle. For example, the CDK4 protein appears to control entry into the cell cycle (the G0-G1-S transition) by phosphorylating the retinoblastoma gene product pRb which stimulates the release of the transcription factor E2F from pRb which, in turn, acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and Cyclin D protein levels increased in many human tumours.

More recently, protein kinases that are structurally distinct from the CDK family have been identified which play critical roles in regulating the cell cycle and which also appear to be important in oncogenesis. They include the human homologues of the *Drosophila* aurora and *S. cerevisiae* Ipl1 proteins. The three human homologues of these genes Aurora-A, Aurora-B and Aurora-C encode cell cycle regulated serine-threonine protein kinases that show a peak of expression and kinase activity through G2 and mitosis. Several observations implicate the involvement of human aurora proteins in cancer, especially Aurora-A and Aurora-B. Abrogation of Aurora-A expression and function by antisense oligonucleotide treatment of human tumour cell lines leads to cell cycle arrest and exerts an anti-proliferative effect. Additionally, small molecule inhibitors of Aurora-A and Aurora-B have been demonstrated to have an anti-proliferative effect in human tumour cells.

It is disclosed in International Patent Applications WO 01/21594 and WO 01/21596 that certain quinazoline derivatives that carry an anilino or phenoxy group linked to the 4-position of the quinazoline ring possess Aurora kinase inhibitory activity. There is no mention therein of 2-phenylacetamide derivatives; in particular, there is no specific mention made therein of quinazoline-substituted 2-phenylacetamide derivatives.

It is disclosed in International Patent Applications WO 01/55116, WO 02/00649, WO 03/055491 and WO 04/058781 that certain quinazoline derivatives that carry a heteroaryl group linked to the 4-position of the quinazoline ring by, for example, a NH or O group possess Aurora kinase inhibitory activity. There is no mention therein of 2-phenylacetamide derivatives; in particular, there is no specific mention made therein of quinazoline-substituted 2-phenylacetamide derivatives.

As stated above, we have now found that surprisingly certain novel quinazoline-substituted 2-phenylacetamide derivatives possess potent activity against cell proliferative disorders. Without wishing to imply that the compounds disclosed in the present invention possess pharmacological activity only by virtue of an effect on one or two biological processes, it is believed that the compounds provide a useful treatment of cell proliferative disorders, for example to provide an anti-tumour effect, by way of a contribution from inhibition of PDGF receptor tyrosine kinases. In particular, it is believed that the compounds of the present invention provide a useful treatment of cell proliferative disorders by way of a contribution from inhibition of the PDGFα and/or PDGFβ receptor tyrosine kinases.

Generally the compounds of the present invention possess potent inhibitory activity against the PDGF receptor family of tyrosine kinases, for example the PDGFα and/or PDGFβ receptor tyrosine kinases, and against VEGF receptor tyrosine kinases, for example KDR and Flt-1, whilst possessing less potent inhibitory activity against other tyrosine kinase enzymes such as the EGF receptor tyrosine kinase. Furthermore, certain compounds of the present invention possess substantially better potency against the PDGF receptor family of tyrosine kinases, particularly against the PDGFβ receptor tyrosine kinase, and against VEGF receptor tyrosine kinases, particularly against KDR, than against EGF receptor tyrosine kinase. Such compounds possess sufficient potency that they may be used in an amount sufficient to inhibit the PDGF receptor family of tyrosine kinases, particularly PDGFβ receptor tyrosine kinase, and to inhibit VEGF receptor tyrosine kinases, particularly KDR, whilst demonstrating little activity against EGF receptor tyrosine kinase.

According to one aspect of the invention there is provided a quinazoline derivative of the Formula I

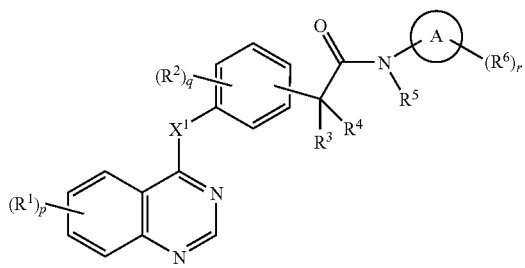

I wherein $X^1$ is O or $N(R^7)$ where $R^7$ is hydrogen or (1-8C)alkyl;

p is 0, 1, 2 or 3;

each $R^1$ group, which may be the same or different, is selected from halogeno, trifluoromethyl, cyano, hydroxy, mercapto, amino, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino and di-[(1-6C)alkyl]amino, or from a group of the formula:

$Q^1$-$X^2$— wherein $X^2$ is a direct bond or is selected from O, S, SO, $SO_2$, $N(R^8)$, Co, $CON(R^8)$, $N(R^8)CO$, $OC(R^8)_2$ and $N(R^8)C(R)_2$, wherein each $R^8$ is hydrogen or (1-8C)alkyl, and $Q^1$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any aryl, (3-8C)cycloalkyl, (3-8C)cycloalkenyl, heteroaryl or heterocyclyl group within a $R^1$ substituent optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^3$—$R^9$ wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl, or from a group of the formula:

—$X^4$-$Q^2$ wherein $X^4$ is a direct bond or is selected from O, CO and $N(R^{11})$, wherein $R^{11}$ is hydrogen or (1-8C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within a substituent on $R^1$ optionally bears a (1-3C)alkylenedioxy group, and wherein any heterocyclyl group within a $R^1$ substituent optionally bears 1 or 2 oxo or thioxo substituents, and wherein any CH, $CH_2$ or $CH_3$ group within a $R^1$ substituent optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, S, SO, $SO_2$, $N(R^{12})$, CO, $CH(OR^{12})$, $CON(R^{12})$, $N(R^{12})CO$, $N(R^{12})CON(R^{12})$, $SO_2N(R^{12})$, $N(R^{12})SO_2$, $CH=CH$ and $C\equiv C$ wherein $R^{12}$ is hydrogen or (1-8C)alkyl, or, when the inserted group is $N(R^{12})$, $R^{12}$ may also be (2-6C)alkanoyl;

q is 0, 1 or 2;

each $R^2$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino;

$R^3$ is hydrogen, (1-8C)alkyl, (2-8C)alkenyl or (2-8C)alkynyl;

$R^4$ is hydrogen, hydroxy, (1-8C)alkyl, (2-8C)alkenyl or (2-8C)alkynyl or a group of the formula:

—$X^5$—$R^{13}$ wherein $X^5$ is a direct bond or is selected from O and $N(R^{14})$, wherein $R^{14}$ is hydrogen or (1-8C)alkyl, and $R^{13}$ is hydrogen, (1-8C)alkyl, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxycarbonyl-(1-6C)alkyl, (2-6C)alkanoylamino-(1-6C)alkyl or N-(1-6C)alkyl-(2-6C)alkanoylamino-(1-6C)alkyl;

or $R^3$ and $R^4$ together with the carbon atom to which they are attached form a (3-8C)cycloalkyl group;

$R^5$ is hydrogen, (1-8C)alkyl, (2-8C)alkenyl or (2-8C)alkynyl or a group of the formula:

—$X^6$—$R^{15}$ wherein $X^6$ is a direct bond or is selected from O and $N(R^{16})$, wherein $R^{16}$ is hydrogen or (1-8C)alkyl, and $R^{15}$ is halogeno-(1-6C)alkyl, hydroxy-(1-6C)alkyl, (1-6C)alkoxy-(1-6C)alkyl or cyano-(1-6C)alkyl;

Ring A is a 6-membered monocyclic or a 10-membered bicyclic aryl ring or a 5- or 6-membered monocyclic or a 9- or 10-membered bicyclic heteroaryl ring with up to three ring heteroatoms selected from oxygen, nitrogen and sulphur;

r is 0, 1, 2 or 3; and each $R^6$ group, which may be the same or different, is selected from halogeno, trifluoromethyl, cyano, hydroxy, mercapto, amino, carboxy, carbamoyl, sulphamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^7$—$R^{17}$ wherein $X^7$ is a direct bond or is selected from O and $N(R^{18})$, wherein $R^{18}$ is hydrogen or (1-8C)alkyl, and $R^{17}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, sulphamoyl-(1-6C)alkyl, N-(1-6C)alkylsulphamoyl-(1-6C)alkyl, N,N-di-[(1-6C)alkyl]sulphamoyl-(1-6C)alkyl, ureido-(1-6C)allyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or from a group of the formula:

—$X^8$-$Q^3$ wherein $X^8$ is a direct bond or is selected from O, S, SO, $SO_2$, $N(R^{19})$, CO, $CH(OR^{19})$, $CON(R^{19})$, $N(R^{19})CO$, $N(R^{19})CON(R^{19})$, $SO_2N(R^{19})$, $N(R^{19})SO_2$, $C(R^{19})_2O$, $C(R^{19})_2S$ and $C(R^{19})_2N(R^{19})$, wherein each $R^{19}$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or two $R^6$ groups together form a bivalent group that spans adjacent ring positions on Ring A selected from $OC(R^{20})_2O$, $OC(R^{20})_2C(R^{20})_2O$, $OC(R^{20})_2C(R^{20})_2$, $C(R^{20})_2OC(R^{20})_2$, $C(R^{20})_2C(R^{20})_2C(R^{20})_2$, $C(R^{20})_2C(R^{20})_2C(R^{20})_2C(R^{20})_2$, $OC(R^{20})_2N(R^{21})$, $N(R^{21})C(R^{20})_2N(R^{21})$, $N(R^{21})C(R^{20})_2C(R^{20})_2$, $N(R^{21})C(R^{20})_2C(R^{20})_2C(R^{20})_2$, $OC(R^{20})_2C(R^{20})_2N(R^{21})$, $C(R^{20})_2N(R^{21})C(R^{20})_2$, $CO.N(R^{20})C(R^{20})_2$, $N(R^{20})CO.C(R^{20})_2$, $N(R^{21})C(R^{20})_2CO$, $CO.N(R^{20})CO$, $N(R^{21})N(R^{20})CO$, $N(R^{20})CO.N(R^{20})$, $O.CO.N(R^{20})$, $O.CO.C(R^{20})_2$ and $CO.OC(R^{20})_2$ wherein each $R^{20}$ is hydrogen, (1-8C)alkyl, (2-8C)alkenyl or (2-8C)alkynyl, and wherein $R^{21}$ is hydrogen, (1-8C)alkyl, (2-8C)alkenyl, (2-8C)alkynyl or (2-6C)alkanoyl, and wherein any aryl, (3-8C)cycloalkyl, (3-8C)cycloalkenyl, heteroaryl or heterocyclyl group within an $R^6$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^9$—$R^{22}$ wherein $X^9$ is a direct bond or is selected from O and $N(R^{23})$, wherein $R^{23}$ is hydrogen or (1-8C)alkyl, and $R^{22}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

—$X^{10}$-$Q^4$ wherein $X^{10}$ is a direct bond or is selected from O, CO and $N(R^{24})$, wherein $R^{24}$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within an $R^6$ group optionally bears a (1-3C)alkylenedioxy group, and wherein any heterocyclyl group within an $R^6$ group optionally bears 1 or 2 oxo or thioxo substituents, and wherein any CH, $CH_2$ or $CH_3$ group within an $R^6$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within an $R^6$ group are optionally separated by the insertion into the chain of a group selected from O, S, SO, $SO_2$, $N(R^{25})$, $N(R^{25})CO$, $CON(R^{25})$, $N(R^{25})CON(R^{25})$, CO, $CH(OR^{25})$, $N(R^{25})SO_2$, $SO_2N(R^{25})$, CH=CH and C≡C wherein $R^{25}$ is hydrogen or (1-8C)alkyl, or, when the inserted group is $N(R^{25})$, $R^{25}$ may also be (2-6C)alkanoyl;

or a pharmaceutically-acceptable salt, solvate or pro-drug thereof.

In this specification the generic term "(1-8C)alkyl" includes both straight-chain and branched-chain alkyl groups such as propyl, isopropyl and tert-butyl, and also (3-8C)cycloalkyl groups such as cyclopropyl, cyclobutyl, cyclopentyl, cyclohexyl and cycloheptyl, and also (3-6C)cycloalkyl-(1-2C)alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and (3-5C)cycloalkyl-(1-2C)alkoxy groups, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and (3-5C)cycloalkyl-(1-2C)alkylamino groups, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6Calkyl]amino includes di-[(3-6C)cycloalkyl]amino groups and di-[(3-5C)cycloalkyl-(1-2C)alkyl]amino groups, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula I defined above may exhibit the phenomenon of tautomerism. In particular, tautomerism may affect heteroaryl rings within the definition of Ring A or heterocyclic groups within the $R^1$ and $R^6$ groups that bear 1 or 2 oxo or thioxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples.

In structural Formula I, it is to be understood that there is a hydrogen atom at the 2-position on the quinazoline ring. It is to be understood thereby that the $R^1$ substituents may only be located at the 5-, 6-, 7- or 8-positions on the quinazoline ring i.e. that the 2-position remains unsubstituted. Conveniently, the $R^1$ substituents may only be located at the 5-, 6- or 7-positions on the quinazoline ring.

In structural Formula I, it is further to be understood that any $R^2$ group that may be present on the central phenyl group may be located at any available position. Conveniently, there is a single $R^2$ group. More conveniently, no $R^2$ group is present (q=0).

In structural Formula I, it is to be understood that the —C($R^3$)($R^4$)—CON($R^5$) group may be located at any available position on the central phenyl group. Conveniently, the —C($R^3$)($R^4$)—CON($R^5$) group is located at the 3- or 4-position (relative to the $X^1$ group). More conveniently, the —C($R^3$)($R^4$)—CON($R^5$) group is located at the 4-position (relative to the $X^1$ group).

In structural Formula I, it is to be understood that any $R^6$ group may be located at any available position on Ring A. For example, an $R^6$ group may be located at the 3- or 4-position (relative to the CON($R^5$) group) when Ring A is a 6-membered ring or, for example, it may be located at the 3-position (relative to the CON($R^5$) group) when Ring A is a 5-membered ring.

Suitable values for the generic radicals referred to above include those set out below.

A suitable value for any one of the 'Q' groups ($Q^1$ to $Q^4$) within the $R^1$ or $R^6$ groups when the 'Q' group is aryl or for the aryl group within any 'Q' group is, for example, phenyl or naphthyl, preferably phenyl.

A suitable value for any one of the 'Q' groups ($Q^1$ or $Q^3$) within the $R^1$ or $R^6$ groups when the 'Q' group is (3-8C)cycloalkyl or for the (3-8C)cycloalkyl group within any 'Q' group is, for example, cyclopropyl, cyclobutyl, cyclopentyl, cyclohexyl, cycloheptyl, bicyclo[2.2.1]heptyl or cyclooctyl.

A suitable value for the (3-8C)cycloalkyl group formed when $R^3$ and $R^4$ together with the carbon atom to which they are attached form a (3-8C)cycloalkyl group is, for example, cyclopropyl, cyclobutyl, cyclopentyl, cyclohexyl or cycloheptyl.

A suitable value for any one of the 'Q' groups ($Q^1$ or $Q^3$) within the $R^1$ or $R^6$ groups when the 'Q' group is (3-8C)cycloalkenyl or for the (3-8C)cycloalkenyl group within any 'Q' group is, for example, cyclobutenyl, cyclopentenyl, cyclohexenyl, cycloheptenyl or cyclooctenyl.

A suitable value for any one of the 'Q' groups ($Q^1$ to $Q^4$) within the $R^1$ or $R^6$ groups when the 'Q' group is heteroaryl or for the heteroaryl group within any 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^4$) within the $R^1$ or $R^6$ groups when the 'Q' group is heterocyclyl or for the heterocyclyl group within any 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl or tetrahydropyrimidinyl, preferably tetrahydrofuranyl, tetrahydropyranyl, tetrahydrothiopyranyl, pyrrolinyl, pyrrolidinyl, morpholinyl, piperidinyl, piperazinyl, indolinyl or isoindolinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 4-oxo-1,4-dihydropyridinyl, 2,5-dioxopyrrolidinyl, 2,5-dioxoimidazolidinyl or 2,6-dioxopiperidinyl.

A suitable value for any 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-8C)cycloalkyl-(1-6C)alkyl, (3-8C)cycloalkenyl-(1-6C)alkyl or heterocyclyl-(1-6C)alkyl group is present.

A suitable value for Ring A when it is a 6-membered monocyclic or a 10-membered bicyclic aryl ring or a 5- or 6-membered monocyclic or a 9- or 10-membered bicyclic heteroaryl ring with up to three ring heteroatoms selected from oxygen, nitrogen and sulphur is, for example, phenyl, naphthyl, furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, benzotriazolyl, quinolyl, isoquinolyl, quinazolinyl, quinoxalinyl, cinnolinyl or naphthyridinyl. Conveniently, Ring A is a phenyl, furyl, pyrrolyl, thienyl, oxazolyl, isoxazolyl, imidazolyl, pyrazolyl, thiazolyl, pyridyl, pyrimidinyl, pyrazinyl or pyridazinyl ring. More conveniently, Ring A is a phenyl, pyridyl, pyrimidinyl, pyrazinyl or pyridazinyl ring.

Suitable values for any of the 'R' groups ($R^1$ to $R^{25}$), or for various groups within an $R^1$, $R^2$ or $R^6$ substituent include:—
for halogeno fluoro, chloro, bromo and iodo;
for (1-8C)alkyl: methyl, ethyl, propyl, isopropyl, tert-butyl, cyclobutyl, cyclohexyl, cyclohexylmethyl and 2-cyclopropylethyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulphinyl: methylsulphinyl and ethylsulphinyl;
for (1-6C)alkylsulphonyl: methylsulphonyl and ethylsulphonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl, propionyl and isobutyryl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N'-(1-6C)alkylureido: N'-methylureido and N'-ethylureido;
for N',N'-di-[(1-6C)alkyl]ureido: N',N'-dimethylureido and N'-methyl-N'-ethylureido;
for N-(1-6C)alkylureido: N-methylureido and N-ethylureido;
for N,N'-di-[(1-6C)alkyl]ureido: N,N'-dimethylureido, N-methyl-N'-ethylureido and N-ethyl-N'-methylureido;
for N,N',N'-di-[(1-6C)alkyl]ureido: N,N',N'-trimethylureido, N-ethyl-N',N'-dimethylureido and N-methyl-N',N'-diethylureido;
for N-(1-6C)alkylsulphamoyl: N-methylsulphamoyl and N-ethylsulphamoyl;
for N,N-di-[(1-6C)alkyl]sulphamoyl: N,N-dimethylsulphamoyl;
for (1-6C)alkanesulphonylamino: methanesulphonylamino and ethanesulphonylamino;
for N-(1-6C)alkyl-(1-6C)alkanesulphonylamino: N-methylmethanesulphonylamino and N-methylethanesulphonylamino;
for halogeno-(1-6C)alkyl: chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl;
for hydroxy-(1-6C)alkyl: hydroxymethyl, 2-hydroxyethyl, 1-hydroxyethyl and 3-hydroxypropyl;
for mercapto-(1-6C)alkyl: mercaptomethyl, 2-mercaptoethyl, 1-mercaptoethyl and 3-mercaptopropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for (1-6C)alkylthio-(1-6C)alkyl: methylthiomethyl, ethylthiomethyl, 2-methylthioethyl, 1-methylthioethyl and 3-methylthiopropyl;

for (1-6C)alkylsulphinyl-(1-6C)alkyl: methylsulphinylmethyl, ethylsulphinylmethyl, 2-methylsulphinylethyl, 1-methylsulphinylethyl and 3-methylsulphinylpropyl;

for (1-6C)alkylsulphonyl-(1-6C)alkyl: methylsulphonylmethyl, ethylsulphonylmethyl, 2-methylsulphonylethyl, 1-methylsulphonylethyl and 3-methylsulphonylpropyl;

for cyano-(1-6C)alkyl: cyanomethyl, 2-cyanoethyl, 1-cyanoethyl and 3-cyanopropyl;

for amino-(1-6C)alkyl: aminomethyl, 2-aminoethyl, 1-aminoethyl, 3-aminopropyl, 1-aminopropyl and 5-aminopropyl;

for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;

for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;

for (2-6C)alkanoylamino-(1-6C)alkyl: acetamidomethyl, propionamidomethyl, 2-acetamidoethyl and 1-acetamidoethyl;

for N-(1-6C)alkyl-(2-6C)alkanoylamino-(1-6C)alkyl: N-methylacetamidomethyl, N-methylpropionamidomethyl, 2-(N-methylacetamido)ethyl and 1-(N-methylacetamido)ethyl;

for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl.

for ureido-(1-6C)alkyl: ureidomethyl, 2-ureidoethyl and 1-ureidoethyl;

for N'-(1-6C)alkylureido-(1-6C)alkyl: N'-methylureidomethyl, 2-(N'-methylureido)ethyl and 1-(N'-methylureido)ethyl;

for N',N'-di-[(1-6C)alkyl]ureido-(1-6C)alkyl: N',N'-dimethylureidomethyl, 2-(N',N'-dimethylureido)ethyl and 1-(N',N'-dimethylureido)ethyl;

for N-(1-6C)alkylureido-(1-6C)alkyl: N-methylureidomethyl, 2-(N-methylureido)ethyl and 1-(N-methylureido)ethyl;

for N,N'-di-[(1-6C)alkyl]ureido-(1-6C)alkyl: N,N'-dimethylureidomethyl, 2-(N,N'-dimethylureido)ethyl and 1-(N,N'-dimethylureido)ethyl;

for N,N',N'-di-[(1-6C)alkyl]ureido-(1-6C)alkyl: N,N',N'-trimethylureidomethyl, 2-(N,N',N'-trimethylureido)ethyl and 1-(N,N',N'-trimethylureido)ethyl;

for carboxy-(1-6C)alkyl: carboxymethyl, 1-carboxyethyl, 2-carboxyethyl, 3-carboxypropyl and 4-carboxybutyl;

for (1-6C)alkoxycarbonyl-(1-6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1-6C)alkyl: carbamoylmethyl, 1-carbamoylethyl, 2-carbamoylethyl and 3-carbamoylpropyl;

for N-(1-6C)alkylcarbamoyl-(1-6C)alkyl: N-methylcarbainoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1-6C)alkyl]carbamoyl-(1-6C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl;

for sulphamoyl-(1-6C)alkyl: sulphamoylmethyl, 1-sulphamoylethyl, 2-sulphamoylethyl and 3-sulphamoylpropyl;

for N-(1-6C)alkylsulphamoyl-(1-6C)alkyl: N-methylsulphamoylmethyl, 1-(N-methylsulphamoyl)ethyl, 2-(N-methylsulphamoyl)ethyl, and 3-(N-methylsulphamoyl)propyl;

for N,N-di-[(1-6C)alkyl]sulphamoyl-(1-6C)alkyl: N,N-dimethylsulphamoylmethyl, 1-(N,N-dimethylsulphamoyl)ethyl, 2-(N,N-dimethylsulphamoyl)ethyl and 3-(N,N-dimethylsulphamoyl)propyl;

for (1-6C)alkanesulphonylamino-(1-6C)alkyl: methanesulphonylaminomethyl, 2-(methanesulphonylamino)ethyl and 1-(methanesulphonylamino)ethyl; and for N-(1-6C)alkyl-(1-6C)alkanesulphonylamino-(1-6C)alkyl: N-methylmethanesulphonylaminomethyl, 2-(N-methylmethanesulphonylamino)ethyl and 1-(N-methylmethanesulphonylamino)ethyl.

A suitable value for a (1-3C)alkylenedioxy group that may be present within a $R^1$ or $R^6$ group is, for example, methylenedioxy, ethylidenedioxy, isopropylidenedioxy or ethylenedioxy and the oxygen atoms thereof occupy adjacent ring positions.

When, as defined hereinbefore, an $R^1$ group forms a group of the formula $Q^1$-$X^2$— and, for example, $X^2$ is a $OC(R^8)_2$ linking group, it is the carbon atom, not the oxygen atom, of the $OC(R^8)_2$ linking group which is attached to the quinazoline ring and the oxygen atom is attached to the $Q^1$ group. Similarly, when, as defined hereinbefore, an $R^6$ group forms a group of the formula —$X^8$-$Q^3$ and, for example, $X^8$ is a $C(R^{19})_2O$ linking group, it is the oxygen atom of the $C(R^{19})_2O$ linking group which is attached to the $Q^3$ group.

A suitable (2-6C)alkylene chain within a $R^1$ or $R^6$ group is, for example, an ethylene, trimethylene, tetramethylene or pentamethylene chain.

As defined hereinbefore, adjacent carbon atoms in any (2-6C)alkylene chain within a $R^1$ or $R^6$ group may be optionally separated by the insertion into the chain of a group such as O, $CON(R^{12})$ or CON(R) respectively, and C≡C. For example, insertion of an O atom into the alkylene chain within a 4-methoxybutoxy group gives rise to, for example, a 2-(2-methoxyethoxy)ethoxy group, for example, insertion of a C≡C group into the ethylene chain within a 2-hydroxyethoxy group gives rise to a 4-hydroxybut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $R^1$ or $R^6$ group optionally bears on each said CH, $CH_2$ or $CH_3$ group one or more halogeno or (1-8C)alkyl substituents, there is suitably 1 halogeno or (1-8C)alkyl substituent present on each said CH group, there are suitably 1 or 2 such substituents present on each said $CH_2$ group and there are suitably 1, 2 or 3 such substituents present on each said $CH_3$ group.

When, as defined hereinbefore, any CH, $CH_2$ or $CH_3$ group within a $R^1$ or $R^6$ group optionally bears on each said CH, $CH_2$ or $CH_3$ group a substituent as defined hereinbefore, suitable $R^1$ or $R^6$ groups so formed include, for example, hydroxy-substituted (1-8C)alkyl groups such as hydroxymethyl, 1-hydroxyethyl and 2-hydroxyethyl, hydroxy-substituted (1-6C)alkoxy groups such as 2-hydroxypropoxy and 3-hydroxypropoxy, (1-6C)alkoxy-substituted (1-6C)alkoxy groups such as 2-methoxyethoxy and 3-ethoxypropoxy, hydroxy-substituted amino-(2-6C)alkoxy groups such as 3-amino-2-hydroxypropoxy, hydroxy-substituted (1-6C)alkylamino-(2-6C)alkoxy groups such as 2-hydroxy-3-methylaminopropoxy, hydroxy-substituted di-[(1-6C)alkyl]amino-(2-6C)alkoxy groups such as 3-dimethylamino-2- hydroxypropoxy, hydroxy-substituted amino-(2-6C)alkylamino groups such as 3-amino-2-hydroxypropylamino, hydroxy-substituted (1-6C)alkylamino-(2-6C)alkylamino groups such as 2-hydroxy-3-methylaminopropylamino and hydroxy-substituted di-[(1-6C)alkyl]amino-(2-6C)alkylamino groups such as 3-dimethylamino-2-hydroxypropylamino.

When, as defined hereinbefore, any CH, $CH_2$ or $CH_3$ group within a $R^1$ or $R^6$ group optionally bears on each said CH, $CH_2$ or $CH_3$ group a substituent as defined hereinbefore, suitable $R^1$ or $R^6$ groups so formed also include, for example, hydroxy-substituted (1-6C)alkylamino-(1-6C)alkyl groups such as 2-hydroxy-3-methylaminopropyl and 2-hydroxyethylaminomethyl and hydroxy-substituted di-[(1-6C)alkyl]amino-(1-6C)alkyl groups such as 3-dimethylamino-2-hydroxypropyl and di-(2-hydroxyethyl)aminomethyl.

It is further to be understood that when, as defined hereinbefore, any CH, $CH_2$ or $CH_3$ group within a $R^1$ or $R^6$ group optionally bears on each said CH, $CH_2$ or $CH_3$ group a substituent as defined hereinbefore, such an optional substituent may be present on a CH, $CH_2$ or $CH_3$ group within the hereinbefore defined substituents that may be present on an aryl, heteroaryl or heterocyclyl group within a $R^1$ or $R^6$ group. For example, if the $R^1$ or $R^6$ group includes an aryl or heteroaryl group that is substituted by a (1-8C)alkyl group, the (1-8C) alkyl group may be optionally substituted on a CH, $CH_2$ or $CH_3$ group therein by one of the hereinbefore defined substituents therefor. For example, if the $R^1$ or $R^6$ group includes a heteroaryl group that is substituted by, for example, a (1-6C) alkylamino-(1-6C)alkyl group, the terminal $CH_3$ group of the (1-6C)alkylamino group may be further substituted by, for example, a (1-6C)alkylsulphonyl group or a (2-6C)alkanoyl group. For example, the $R^1$ or $R^6$ group may be a heteroaryl group such as a thienyl group that is substituted by a N-(2-methylsulphonylethyl)aminomethyl group such that $R^1$ or $R^6$ is, for example, a 5-[N-(2-methylsulphonylethyl)aminomethyl]thien-2-yl group. Further, for example, if the $R^1$ or $R^6$ group includes a heterocyclyl group such as a piperidinyl or piperazinyl group that is substituted on a nitrogen atom thereof by, for example, a (2-6C)alkanoyl group, the terminal $CH_3$ group of the (2-6C)alkanoyl group may be further substituted by, for example, a di-[(1-6C)alkyl]amino group. For example, the $R^1$ or $R^6$ group may be a N-(2-dimethylaminoacetyl)piperidin-4-yl group or a 4-(2-dimethylaminoacetyl)piperazin-1-yl group. Further, for example, if the $R^1$ or $R^6$ group includes a heterocyclyl group such as a azetidinyl, piperidinyl or piperazinyl group that is substituted on a nitrogen atom thereof by, for example, a (2-6C)alkanoyl group, a $CH_2$ group of the (2-6C)alkanoyl group may be further substituted by, for example, a hydroxy group. For example, the $R^1$ or $R^6$ group may be a N-(2-hydroxypropionyl)piperidin-4-yl group.

As defined hereinbefore, two $R^6$ groups together may form a bivalent group, for example $OC(R^{20})_2O$, that spans adjacent ring positions on Ring A. When Ring A is, for example, a phenyl group, a suitable group so formed is a 2,3-methylenedioxyphenyl or a 3,4-methylenedioxyphenyl group. When a further optional $R^6$ group is present, for example a halogeno group, a suitable group so formed is, for example, a 6-fluoro-2,3-methylenedioxyphenyl group. Further, when Ring A is, for example, a phenyl group and two $R^6$ groups together form, for example, a $OC(R^{20})_2C(R^{20})_2$ group, a suitable group so formed is, for example, a 2,3-dihydrobenzofuran-5-yl group or a 2,3-dihydrobenzofuran-6-yl group. Further, when Ring A is, for example, a phenyl group and two $R^6$ groups together form, for example, a $N(R^{21})C(R^{20})_2C(R^{20})_2$ group, a suitable group so formed is, for example, an indolin-5-yl group or a indolin-6-yl group. Further, when Ring A is, for example, a phenyl group and two $R^6$ groups together form, for example, a $N(R^{21})CO.C(R^{20})_2$ group, a suitable group so formed is, for example, a 2-oxoindolin-5-yl group or a 2-oxoindolin-6-yl group.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

A suitable pharmaceutically-acceptable solvate of a compound of the Formula I is, for example, a hydrate such as a hemi-hydrate, a mono-hydrate, a di-hydrate or a tri-hydrate or an alternative quantity thereof.

The compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced-compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);

g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C) alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses a carboxy group is, for example, an in vivo cleavable amide thereof, for example an amide formed with an amine such as ammonia, a (1-4C) alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C) alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

According to an aspect of the invention there is provided a quinazoline derivative of the Formula I
wherein $X^1$ is O or $N(R^7)$ where $R^7$ is hydrogen or (1-8C) alkyl;
p is 0, 1, 2 or 3;
each $R^1$ group, which may be the same or different, is selected from halogeno, trifluoromethyl, cyano, hydroxy, mercapto, amino, (1-8C)alkyl, (2-8C)alkenyl, (2-8C)alkynyl, (1-6C)alkoxy, (2-6C)alkenyloxy, (2-6C)alkynyloxy, (1-6C) alkylthio, (1-6C)alkylsulphinyl, (1-6C)alkylsulphonyl, (1-6C)alkylamino and di-[(1-6C)alkyl]amino, from a group of the formula:

$$Q^1-X^2-$$

wherein $X^2$ is a direct bond or is selected from O, S, SO, $SO_2$, $N(R^8)$, CO, $CON(R^8)$, $N(R^8)CO$, $OC(R^8)_2$ and $N(R^8)C(R^8)_2$, wherein each $R^8$ is hydrogen or (1-8C)alkyl, and $Q^1$ is aryl, aryl-(1-6C)alkyl, (3-8C)cycloalkyl, (3-8C)cycloalkyl-(1-6C) alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any aryl, (3-8C)cycloalkyl, (3-8C)cycloalkenyl, heteroaryl or heterocyclyl group within a $R^1$ substituent optionally bears 1, 2 or 3 substituents, which may be the same or different, selected from halogeno, trifluoromethyl, cyano, nitro, hydroxy, amino, carboxy, carbamoyl, ureido, (1-8C) alkyl, (2-8C)alkenyl, (2-8C)alkynyl, (1-6C)alkoxy, (2-6C) alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl] ureido, N,N',N'-tri-[(1-6C)alkyl]ureido, N-(1-6C) alkylsulphamoyl, N,N-di-[(1-6C)alkyl]sulphamoyl, (1-6C) alkanesulphonylamino and N-(1-6C)alkyl-(1-6C) alkanesulphonylamino, or from a group of the formula:

$$-X^3-R^9$$

wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C) alkylamino-(1-6C)alkyl, di-[(1-6C)alkyl]amino-(1-6C) alkyl, (2-6C)alkanoylamino-(1-6C)alkyl, N-(1-6C)alkyl-(2-6C)alkanoylamino-(1-6C)alkyl, (1-6C) alkoxycarbonylamino-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl, or from a group of the formula:

$$-X^4-Q^2$$

wherein $X^4$ is a direct bond or is selected from O, CO and $N(R^{11})$, wherein $R^{11}$ is hydrogen or (1-8C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C) alkoxy, and wherein any aryl, heteroaryl or heterocyclyl group within a substituent on $R^1$ optionally bears a (1-3C)alkylenedioxy group, and wherein any heterocyclyl group within a $R^1$ substituent optionally bears 1 or 2 oxo or thioxo substituents, and wherein any CH, CH$_2$ or CH$_3$ group within a $R^1$ substituent optionally bears on each said CH, CH$_2$ or CH$_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, S, SO, SO$_2$, N($R^{12}$), Co, CH(O$R^{12}$), CON($R^{12}$), N($R^{12}$)CO, N($R^{12}$)CON($R^{12}$), SO$_2$N($R^{12}$), N($R^{12}$)SO$_2$, CH=CH and C≡C wherein $R^{12}$ is hydrogen or (1-8C)alkyl, or, when the inserted group is N($R^{12}$), $R^{12}$ may also be (2-6C)alkanoyl;

q is 0, 1 or 2;

each $R^2$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino;

$R^3$ is hydrogen, (1-8C)alkyl, (2-8C)alkenyl or (2-8C)alkynyl;

$R^4$ is hydrogen, hydroxy, (1-8C)alkyl, (2-8C)alkenyl or (2-8C)alkynyl or a group of the formula:

—$X^5$—$R^{13}$ wherein $X^5$ is a direct bond or is selected from O and N($R^{14}$), wherein $R^{14}$ is hydrogen or (1-8C)alkyl, and $R^{13}$ is halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxycarbonyl-(1-6C)alkyl, (2-6C)alkanoylamino-(1-6C)alkyl or N-(1-6C)alkyl-(2-6C)alkanoylamino-(1-6C)alkyl;

or $R^3$ and $R^4$ together with the carbon atom to which they are attached form a (3-8C)cycloalkyl group;

$R^5$ is hydrogen, (1-8C)alkyl, (2-8C)alkenyl or (2-8C)alkynyl or a group of the formula:

—$X^6$—$R^{15}$ wherein $X^6$ is a direct bond or is selected from O and N($R^{16}$), wherein $R^{16}$ is hydrogen or (1-8C)alkyl, and $R^{15}$ is halogeno-(1-6C)alkyl, hydroxy-(1-6C)alkyl, (1-6C)alkoxy-(1-6C)alkyl or cyano-(1-6C)alkyl;

Ring A is a 6-membered monocyclic or a 10-membered bicyclic aryl ring or a 5- or 6-membered monocyclic or a 9- or 10-membered bicyclic heteroaryl ring with up to three ring heteroatoms selected from oxygen, nitrogen and sulphur;

r is 0, 1, 2 or 3; and each $R^6$ group, which may be the same or different, is selected from halogeno, trifluoromethyl, cyano, hydroxy, mercapto, amino, carboxy, carbamoyl, sulphamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^7$—$R^{17}$ wherein $X^7$ is a direct bond or is selected from O and N($R^{18}$), wherein $R^{18}$ is hydrogen or (1-8C)alkyl, and $R^{17}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, sulphamoyl-(1-6C)alkyl, N-(1-6C)alkylsulphamoyl-(1-6C)alkyl, N,N-di-[(1-6C)alkyl]sulphamoyl-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or from a group of the formula:

—$X^8$-$Q^3$ wherein $X^8$ is a direct bond or is selected from O, S, SO, SO$_2$, N($R^{19}$), CO, CH(O$R^{19}$), CON($R^{19}$), N($R^{19}$)CO, N($R^{19}$)CON($R^{19}$), SO$_2$N($R^{19}$), N($R^{19}$)SO$_2$, C($R^{19}$)$_2$O, C($R^{19}$)$_2$S and C($R^{19}$)$_2$N($R^{19}$), wherein each $R^{19}$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or two $R^6$ groups together form a bivalent group that spans adjacent ring positions on Ring A selected from OC($R^{20}$)$_2$O, OC($R^{20}$)$_2$C($R^{20}$)$_2$O, OC($R^{20}$)$_2$C($R^{20}$)$_2$, C($R^{20}$)$_2$OC($R^{20}$)$_2$, OC($R^{20}$)$_2$N($R^{21}$), N($R^{21}$)C($R^{20}$)$_2$N($R^{21}$), N($R^{21}$)C($R^{20}$)$_2$C($R^{20}$)$_2$, C($R^{20}$)$_2$N($R^{21}$)C($R^{20}$)$_2$, CO.N($R^{20}$)C($R^{20}$)$_2$, N($R^{20}$)CO.C($R^{20}$)$_2$, N($R^{21}$)C($R^{20}$)$_2$CO, CO.N($R^{20}$)CO, N($R^{21}$)N($R^{20}$)CO, N($R^{20}$)CO.N($R^{20}$), O.CO.N($R^{20}$), O.CO.C($R^{20}$)$_2$ and CO.OC($R^{20}$)$_2$ wherein each $R^{20}$ is hydrogen, (1-8C)alkyl, (2-8C)alkenyl or (2-8C)alkynyl, and wherein $R^{21}$ is hydrogen, (1-8C)alkyl, (2-8C)alkenyl, (2-8C)alkynyl or (2-6C)alkanoyl, and wherein any aryl, (3-8C)cycloalkyl, (3-8C)cycloalkenyl, heteroaryl or heterocyclyl group within an $R^6$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)

alkanesulphonylamino and N-(1-6C)alkyl-(1-6C)alkanesulphonylamino, or from a group of the formula:

—$X^9$—$R^{22}$ wherein $X^9$ is a direct bond or is selected from O and N($R^{23}$), wherein $R^{23}$ is hydrogen or (1-8C)alkyl, and $R^{22}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

—$X^{10}$-$Q^4$ wherein $X^{10}$ is a direct bond or is selected from O, CO and N($R^{24}$), wherein $R^{24}$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within an $R^6$ group optionally bears a (1-3C)alkylenedioxy group, and wherein any heterocyclyl group within an $R^6$ group optionally bears 1 or 2 oxo or thioxo substituents, and wherein any CH, $CH_2$ or $CH_3$ group within an $R^6$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within an $R^6$ group are optionally separated by the insertion into the chain of a group selected from O, S, SO, $SO_2$, N($R^{25}$), N($R^{25}$)CO, CON($R^{25}$), N($R^{25}$)CON($R^{25}$), CO, CH(O$R^{25}$), N($R^{25}$)$SO_2$, $SO_2$N($R^{25}$), CH=CH and C≡C wherein $R^{25}$ is hydrogen or (1-8C)alkyl, or, when the inserted group is N($R^{25}$), $R^{25}$ may also be (2-6C)alkanoyl;

or a pharmaceutically-acceptable salt, solvate or pro-drug thereof.

Particular novel compounds of the invention include, for example, quinazoline derivatives of the Formula I, or pharmaceutically-acceptable salts, solvates or pro-drugs thereof, wherein, unless otherwise stated, each of $X^1$, p, $R^1$, q, $R^2$, $R^3$, $R^4$, $R^5$, Ring A, r and $R^6$ has any of the meanings defined hereinbefore or in paragraphs (a) to (ccc) hereinafter:—

(a) $X^1$ is O or NH;
(b) $X^1$ is O;
(c) $X^1$ is NH;
(d) p is 1, 2 or 3, and each $R^1$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (2-6C)alkenyloxy, (2-6C)alkynyloxy, (1-6C)alkylamino and di-[(1-6C)alkyl]amino, or from a group of the formula:

$Q^1$-$X^2$— wherein $X^2$ is a direct bond or is selected from O, N($R^8$), CON($R^8$), N($R^8$)CO and OC($R^5$)$_2$ wherein $R^8$ is hydrogen or (1-8C)alkyl, and $Q^1$ is aryl, aryl-(1-6C)alkyl, (3-8C)cycloalkyl-(1-6C)alkyl, heteroaryl, heteroaryl-(1-6C)alkyl, heterocyclyl or heterocyclyl-(1-6C)alkyl, and wherein any aryl, (3-8C)cycloalkyl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-8C)alkyl, (2-8C)alkenyl, (2-8C)alkynyl, (1-6C)alkoxy, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (2-6C)alkanoylamino and N-(1-6C)alkyl-(2-6C)alkanoylamino, or from a group of the formula:

—$X^3$—$R^9$ wherein $X^3$ is a direct bond or is selected from O and N($R^{10}$), wherein $R^{10}$ is hydrogen or (1-8C)alkyl, and $R^9$ is halogeno-(1-6C)alkyl, hydroxy-(1-6C)alkyl, (1-6C)alkoxy-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

—$X^4$-$Q^2$ wherein $X^4$ is a direct bond or is selected from O, CO and N($R^{11}$), wherein $R^{11}$ is hydrogen or (1-8C)alkyl, and $Q^2$ is heterocyclyl or heterocyclyl-(1-6C)alkyl which optionally bears 1 or 2 substituents, which may be the same or different, selected from halogeno, (1-8C)alkyl and (1-6C)alkoxy, and wherein any heterocyclyl group within a substituent on $R^1$ optionally bears a (1-3C)alkylenedioxy group, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more halogeno or (1-8C)alkyl groups and/or a substituent selected from hydroxy, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent-carbon atoms in any (2-6C)alkylene chain within a $R^1$ substituent are optionally separated by the insertion into the chain of a group selected from O, N($R^{12}$), CON($R^{12}$), N($R^{12}$)CO, CH=CH and C≡C wherein $R^{12}$ is hydrogen or (1-8C)alkyl, or, when the inserted group is N($R^{12}$), $R^{12}$ may also be (2-6C)alkanoyl;

(e) p is 1 and the $R^1$ group is located at the 5-, 6- or 7-position or p is 2 and the $R^1$ groups, which may be the same or different, are located at the 5- and 7-positions or at the 6- and 7-positions and each $R^1$ group is selected from fluoro, chloro, trifluoromethyl, hydroxy, amino, methyl, ethyl, propyl, butyl, vinyl, allyl, but-3-enyl, ethynyl, 2-propynyl, but-3-ynyl, methoxy, ethoxy, propoxy, isopropoxy, butoxy, allyloxy, but-3-enyloxy, ethynyloxy, 2-propynyloxy, but-3-ynyloxy, methylamino, ethylamino, propylamino, dimethylamino, diethylamino and dipropylamino, or from a group of the formula:

$$Q^1-X^2-$$

wherein $X^2$ is a direct bond or is selected from O, NH, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-(1,2,3,6-tetrahydropyridin-1-yl)ethyl, 3-(1,2,3,6-tetrahydropyridin-1-yl)propyl, 4-(1,2,3,6-tetrahydropyridin-1-yl)butyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any aryl, (3-8C)cycloalkyl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, methylamino, dimethylamino, acetyl, propionyl, isobutyryl, N-methylcarbamoyl, N,N-dimethylcarbamoyl, methylenedioxy, ethylidendioxy and isopropylidenedioxy, or optionally bears 1 substituent selected from a group of the formula:

$$-X^3-R^9$$

wherein $X^3$ is a direct bond or is selected from O and NH and $R^9$ is 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl or N-methylacetamidomethyl, and from a group of the formula:

$$-X^4-Q^2$$

wherein $X^4$ is a direct bond or is selected from O, CO and NH and $Q^2$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents, and wherein any CH, CH$_2$ or CH$_3$ group within a $R^1$ substituent optionally bears on each said CH, CH$_2$ or CH$_3$ group one or more fluoro, chloro or methyl groups or a substituent selected from hydroxy, amino, cyano, methoxy, methylsulphonyl, methylamino, dimethylamino, diisopropylamino, N-ethyl-N-methylamino, N-isopropyl-N-methylamino, acetyl, acetamido and N-methylacetamido, and wherein adjacent carbon atoms in any (2-6C)alkylene chain within a $R^1$ substituent are optionally separated by the insertion into the chain of a group selected from O, NH, N(Me), N(COMe), CONH, NHCO, CH=CH and C≡C;

(f) each of p and $R^1$ has any of the meanings defined in paragraphs (d) and (e) hereinbefore except that when $R^1$ is a group of the formula:

$$Q^1-X^2-$$

$X^2$ may not be a direct bond;

(g) p is 1 and the $R^1$ group is located at the 5-, 6- or 7-position or p is 2 and the $R^1$ groups, which may be the same or different, are located at the 5- and 7-positions or at the 6- and 7-positions and each $R^1$ is selected from hydroxy, amino, methyl, ethyl, propyl, butyl, vinyl, ethynyl, methoxy, ethoxy, propoxy, isopropoxy, butoxy, but-3-enyloxy, methylamino, ethylamino, dimethylamino, diethylamino, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-(1,2,3,6-tetrahydropyridin-1-yl)ethoxy 3-(1,2,3,6-tetrahydropyridin-1-yl)propoxy, 4-(1,2,3,6-tetrahydropyridin-1-yl)butoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, ethoxy, N-methylcarbamoyl, N,N-dimethylcarbamoyl, methylenedioxy, ethylidendioxy and isopropylidenedioxy, and a pyrrolidin-2-yl, piperidin-3-yl, piperidin-4-yl, piperazin-1-yl or homopiperazin-1-yl group within a $R^1$ substituent is optionally N-substituted with allyl, 2-propynyl, methylsulphonyl, ethylsulphonyl, acetyl, propionyl, isobutyryl, 2-fluoroethyl, 2,2-difluoroethyl, 2,2,2-trifluoroethyl, 3-fluoropropyl, 3,3-difluoropropyl, 3,3,3-trifluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more fluoro, chloro or methyl groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetamido and N-methylacetamido, and wherein adjacent carbon atoms in any (2-6C)alkylene chain within a $R^1$ substituent are optionally separated by the insertion into the chain of a group selected from O, NH, N(Me), CH=CH and C≡C;

(h) p is 1 and the $R^1$ group is located at the 7-position or p is 2 and the $R^1$ groups, which may be the same or different, are located at the 6- and 7-positions and each $R^1$ is selected from hydroxy, amino, methyl, ethyl, methoxy, ethoxy, propoxy, isopropoxy, butoxy, methylamino, ethylamino, dimethylamino, diethylamino, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino, and wherein adjacent carbon atoms in any (2-6C)alkylene chain within a $R^1$ substituent are optionally separated by the insertion into the chain of a group selected from O, NH, CH=CH and C≡C;

(i) p is 1 and the $R^1$ group is located at the 5-position or p is 2 and the $R^1$ groups, which may be the same or different, are located at the 5- and 7-positions and each $R^1$ is selected from hydroxy, amino, methyl, ethyl, methoxy, ethoxy, propoxy, isopropoxy, butoxy, methylamino, ethylamino, dimethylamino, diethylamino, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 3-piperidinyloxy, 4-piperidinyloxy, piperidin-3-ylmethoxy, piperidin-4-ylmethoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy, 3-homopiperazin-1-ylpropoxy, cyclobutyloxy, cyclopentyloxy and cyclohexyloxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino, and wherein adjacent carbon atoms in any (2-6C)alkylene chain within a $R^1$ substituent are optionally separated by the insertion into the chain of a group selected from O, NH, CH=CH and C≡C;

(j) p is 2 and the $R^1$ groups, which may be the same or different, are located at the 6- and 7-positions and the $R^1$ group at the 6-position is selected from hydroxy, methoxy, ethoxy and propoxy, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, CH$_2$ or CH$_3$ group within a $R^1$ substituent optionally bears on each said CH, CH$_2$ or CH$_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

(k) p is 2 and the $R^1$ groups, which may be the same or different, are located at the 5- and 7-positions and the $R^1$ group at the 5-position is selected from methoxy, ethoxy, propoxy, isopropoxy, butoxy, tetrahydrofuran-3-yloxy, tetrahydropyran-4-yloxy, pyrrolidin-3-yloxy, pyrrolidin-2-ylmethoxy, 3-piperidinyloxy, 4-piperidinyloxy, piperidin-3-ylmethoxy, piperidin-4-ylmethoxy, cyclobutyloxy, cyclopentyloxy and cyclohexyloxy, and the $R^1$ group at the 7-position is selected from hydroxy, methoxy, ethoxy, propoxy, isopropoxy, butoxy, 2-pyrrolidin-1-ylethoxy, 3-pyrrolidin-1-ylpropoxy, 4-pyrrolidin-1-ylbutoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, CH$_2$ or CH$_3$ group within a $R^1$ substituent optionally bears on each said CH, CH$_2$ or CH$_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

(l) q is 0;

(m) q is 1 or 2 and each $R^2$ group, which may be the same or different, is selected from halogeno, trifluoromethyl, cyano, hydroxy, amino, (1-8C)alkyl, (2-8C)alkenyl, (2-8C)alynyl, (1-6C)alkoxy, (1-6C)alkylamino and di-[(1-6C)alkyl]amino;

(n) q is 1 or 2 and each $R^2$ group, which may be the same or different, is selected from fluoro, chloro, trifluoromethyl, cyano, hydroxy, amino, methyl, methoxy, methylamino and dimethylamino;

(o) q is 1 and the $R^2$ group is selected from fluoro, chloro, trifluoromethyl, hydroxy, amino, methyl, methoxy, methylamino and dimethylamino;

(p) $R^3$ is hydrogen, methyl or ethyl;

(q) $R^3$ is hydrogen;

(r) $R^4$ is hydrogen, hydroxy, methyl or ethyl or a group of the formula:

$$-X^5-R^{13}$$

wherein $X^5$ is a direct bond or is selected from O and NH and $R^{13}$ is 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, 2-cyanoethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl or N-methylacetamidomethyl;

(s) $R^4$ is hydrogen, hydroxy, methyl, ethyl, propyl, 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, 2-cyanoethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl or N-methylacetamidomethyl;

(t) $R^4$ is hydrogen, methyl or ethyl;

(u) $R^4$ is hydrogen;

(v) $R^3$ and $R^4$ together with the carbon atom to which they are attached form a cyclopropyl, cyclobutyl, cyclopentyl or cyclohexyl group;

(w) $R^5$ is hydrogen, methyl, ethyl, propyl, allyl, 2-propynyl, 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, 2-cyanoethyl or 3-cyanopropyl;

(x) $R^5$ is hydrogen, methyl or ethyl;

(y) $R^5$ is hydrogen;

(z) the —C($R^3$)($R^4$)—CON($R^5$) group is located at the 3- or 4-position (relative to the $X^1$ group);

(aa) the —C($R^3$)($R^4$)—CON($R^5$) group is located at the 3-position (relative to the $X^1$ group);

(bb) the —C($R^3$)($R^4$)—CON($R^5$) group is located at the 4-position (relative to the $X^1$ group);

(cc) Ring A is a 6-membered monocyclic aryl ring or a 5- or 6-membered monocyclic heteroaryl ring with up to three ring heteroatoms selected from oxygen, nitrogen and sulphur;

(dd) Ring A is a phenyl ring;

(ee) Ring A is a 6-membered monocyclic heteroaryl ring with up to three nitrogen heteroatoms;

(ff) Ring A is a 5-membered monocyclic heteroaryl ring with up to three ring heteroatoms selected from oxygen, nitrogen and sulphur;

(gg) Ring A is a phenyl, furyl, pyrrolyl, thienyl, oxazolyl, isoxazolyl, imidazolyl, pyrazolyl, thiazolyl, pyridyl, pyrimidinyl, pyrazinyl or pyridazinyl ring;

(hh) Ring A is a phenyl, pyridyl, pyrimidinyl, pyrazinyl or pyridazinyl ring;

(ii) when Ring A is a 6-membered ring, and one or two $R^6$ groups are present, one $R^6$ group is located at the 3- or 4-position (relative to the $CON(R^5)$ group);
(jj) when Ring A is a 5-membered ring, and one or two $R^6$ groups are present, one $R^6$ group is located at the 3-position (relative to the $CON(R^5)$ group);
(kk) Ring A is a phenyl, pyridyl, pyrimidinyl, pyrazinyl or pyridazinyl ring that bears one or two $R^6$ groups and one $R^6$ group is located at the 3- or 4-position (relative to the $CON(R^5)$ group);
(ll) Ring A is a 9- or 10-membered bicyclic heteroaryl ring with up to three ring heteroatoms selected from oxygen, nitrogen and sulphur;
(mm) Ring A is a benzofuranyl, indolyl, benzothienyl, benzoxazolyl, benzimidazolyl, benzothiazolyl, indazolyl, benzotriazolyl, 1H-pyrrolo[3,2-b]pyridinyl, quinolyl, isoquinolyl, quinazolinyl, quinoxalinyl or naphthyridinyl ring;
(nn) Ring A is a indolyl, benzoxazolyl, benzimidazolyl, benzothiazolyl, indazolyl, benzotriazolyl, quinolyl, isoquinolyl, quinoxalinyl or naphthyridinyl ring;
(oo) r is 1, 2 or 3 and each $R^6$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino;
(pp) r is 1 or 2 and each $R^6$ group, which may be the same or different, is selected from fluoro, chloro, trifluoromethyl, cyano, hydroxy, amino, methyl, methoxy, methylamino and dimethylamino;
(qq) r is 1 and the $R^6$ group is selected from fluoro, chloro, trifluoromethyl, hydroxy, amino, methyl, methoxy, methylamino and dimethylamino;
(rr) r is 1, 2 or 3 and one $R^6$ group is a group of the formula:

—$X^7$—$R^{17}$ wherein $X^7$ is a direct bond or is selected from O and $N(R^{18})$, wherein $R^{18}$ is hydrogen or (1-8C)alkyl, and $R^{17}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl provided that, when $X^7$ is O or $N(R^{18})$, there are at least two carbon atoms between $X^7$ and any heteroatom in the $R^{17}$ group, or one $R^6$ is a group of the formula:

—$X^8$-$Q^3$ wherein $X^8$ is a direct bond or is selected from O, $N(R^{19})$, $CON(R^{19})$, $N(R^{19})CO$ and $C(R^{19})_2O$, wherein each $R^{19}$ is hydrogen or (1-8C)alkyl, and $Q^3$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl provided that, when $X^8$ is selected from O, $N(R^{19})$, $CON(R^{19})$ or $C(R^{19})_2O$, there are at least two carbon atoms between $X^8$ and any heteroatom in $Q^3$ that is not in a heteroaryl ring, and any other $R^6$ group that is present is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any aryl, (3-8C)cycloalkyl, heteroaryl or heterocyclyl group within an $R^6$ group optionally bears 1, 2 or 3 substituents, which may be the same or different, selected from halogeno, trifluoromethyl, cyano, hydroxy, amino, carboxy, carbamoyl, ureido, (1-8C)alkyl, (2-8C)alkenyl, (2-8C)alkynyl, (1-6C)alkoxy, (1-6C)alkylamino and di-[(1-6C)alkyl]amino, or from a group of the formula:

—$X^9$—$R^{22}$ wherein $X^9$ is a direct bond or is selected from O and $N(R^{23})$, wherein $R^{23}$ is hydrogen or (1-8C)alkyl, and $R^{22}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within an $R^6$ group optionally bears 1 or 2 oxo or thioxo substituents, and wherein any $CH$, $CH_2$ or $CH_3$ group within an $R^6$ group optionally bears on each said $CH$, $CH_2$ or $CH_3$ group one or more halogeno or (1-8C)alkyl substituents and/or a substituent selected from hydroxy, amino, cyano, carboxy, carbamoyl, ureido, (3-8C)alkenyl, (3-8C)alkynyl, 1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino;
(ss) r is 1, 2 or 3 and one $R^6$ group is a group of the formula:

—$X^7$—$R^{17}$ wherein $X^7$ is a direct bond or is selected from O and $N(R^{18})$, wherein $R^{18}$ is hydrogen or (1-8C)alkyl, and $R^{17}$ is hydroxy-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, provided that, when $X^7$ is O or $N(R^{18})$, there are at least two carbon atoms between $X^7$ and any heteroatom in the $R^{17}$ group, and any other $R^6$ group that is present is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any aryl, (3-8C)cycloalkyl, heteroaryl or heterocyclyl group within the $R^6$ group optionally bears 1 or 2 substituents, which may be the same or different, selected from halogeno, trifluoromethyl, cyano, hydroxy, amino, (1-8C)alkyl, (1-6C)alkoxy, (1-6C)alkylamino and di-[(1-6C)alkyl]amino, or from a group of the formula:

—$X^9$—$R^{22}$ wherein $X^9$ is a direct bond and $R^{22}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any $CH$, $CH_2$ or $CH_3$ group within the $R^6$ group optionally bears on each said $CH$, $CH_2$ or $CH_3$ group 1, 2 or 3 halogeno or (1-8C)alkyl substituents and/or a substituent selected from hydroxy, amino, cyano, (3-8C)alkenyl, (3-8C)alkynyl, (1-6C)alkoxy, (1-6C)alkylsulphonyl, (1-6C)alkylamino, di-[(1-6C)alkyl]amino, (2-6C)alkanoylamino and N-(1-6C)alkyl-(2-6C)alkanoylamino;

(tt) r is 1, 2 or 3 and one $R^6$ group is a group of the formula:

wherein $X^7$ is a direct bond or is selected from O and $N(R^{18})$, wherein $R^{18}$ is hydrogen or (1-8C)alkyl, and $R^{17}$ is hydroxy-(1-6C)alkyl, (1-6C)alkoxy-(1-6C)alkyl, amino-(1-6C)alkyl, (1-6C)alkylamino-(1-6C)alkyl, di-[(1-6C)alkyl]amino-(1-6C)alkyl, aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, provided that, when $X^7$ is O or $N(R^{18})$, there are at least two carbon atoms between $X^7$ and any heteroatom in the $R^{17}$ group, and any other $R^6$ group that is present is selected from halogeno, trifluoromethyl, cyano, hydroxy, amino, (1-8C)alkyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any aryl, (3-8C)cycloalkyl, heteroaryl or heterocyclyl group within the $R^6$ group optionally bears 1 or 2 substituents, which may be the same or different, selected from halogeno, trifluoromethyl, hydroxy, amino, (1-8C)alkyl, (1-6C)alkoxy, (1-6C)alkylamino, di-[(1-6C)alkyl]amino, hydroxy-(1-6C)alkyl, amino-(1-6C)alkyl, (1-6C)alkylamino-(1-6C)alkyl and di-[(1-6C)alkyl]amino-(1-6C)alkyl;

(uu) r is 1 or 2 and one $R^6$ group is a group of the formula:

wherein $X^7$ is a direct bond or is selected from O, NH and N(Me), and $R^{17}$ is hydroxymethyl, 1-hydroxyethyl, 2-hydroxyethyl, 1-hydroxy-1-methylethyl, 3-hydroxypropyl, cyanomethyl, 1-cyanoethyl, 2-cyanoethyl, 1-cyano-1-methylethyl, 3-cyanopropyl, aminomethyl, 1-aminoethyl, 2-aminoethyl, 1-amino-1-methylethyl, 3-aminopropyl, methylaminomethyl, 1-methylaminoethyl, 2-methylaminoethyl, 1-methylamino-1-methylethyl, 3-methylaminopropyl, ethylaminomethyl, 1-ethylaminoethyl, 2-ethylaminoethyl, 1-ethylamino-1-methylethyl, 3-ethylaminopropyl, dimethylaminomethyl, 1-dimethylaminoethyl, 2-dimethylaminoethyl, 1-dimethylamino-1-methylethyl, 3-dimethylaminopropyl, phenyl, benzyl, cyclopropyl, cyclobutyl, cyclopentyl, cyclohexyl, furyl, thienyl, oxazolyl, imidazolyl, thiazolyl, pyridyl, pyrimidinyl, tetrahydrofuranyl, tetrahydropyranyl, tetrahydrothiopyranyl, pyrrolinyl, pyrrolidinyl, imidazolidinyl, pyrazolidinyl, morpholinyl, tetrahydro-1,4-thiazinyl, piperidinyl, homopiperidinyl, piperazinyl, homopiperazinyl, indolinyl, isoindolinyl, pyrrolinylmethyl, pyrrolidinylmethyl, 2-pyrrolidinylethyl, 3-pyrrolidinylpropyl, imidazolidinylmethyl, pyrazolidinylmethyl, morpholinylmethyl, 2-(morpholinyl)ethyl, 3-(morpholinyl)propyl, tetrahydro-1,4-thiazinylmethyl, 2-(tetrahydro-1,4-thiazinyl)ethyl, 3-(tetrahydro-1,4-thiazinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^7$ is O, NH or N(Me), there are at least two carbon atoms between $X^7$ and any heteroatom in the $R^{17}$ group, and wherein any aryl, (3-8C)cycloalkyl, heteroaryl or heterocyclyl group within the $R^6$ group optionally bears 1 or 2 substituents, which may be the same or different, selected from fluoro, chloro, trifluoromethyl, hydroxy, amino, methyl, ethyl, methoxy, ethoxy, methylamino, dimethylamine, hydroxymethyl, 2-hydroxyethyl, 3-hydroxypropyl, aminomethyl, 2-aminoethyl, 3-aminopropyl, methylaminomethyl, 2-methylaminoethyl, 3-methylaminopropyl, dimethylaminomethyl, 2-dimethylaminoethyl and 3-dimethylaminopropyl, and any other $R^6$ group that is present is selected from fluoro, chloro, trifluoromethyl, cyano, hydroxy, amino, methyl, methoxy, methylamino and dimethylamino;

(vv) r is 1 or 2 and the first $R^6$ group is a group of the formula:

wherein $X^7$ is a direct bond or O and $R^{17}$ is hydroxymethyl, 1-hydroxyethyl, 2-hydroxyethyl, 3-hydroxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^7$ is O, there are at least two carbon atoms between $X^7$ and any heteroatom in the $R^{17}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(ww) r is 1 or 2 and the first $R^6$ group is selected from hydroxymethyl, 1-hydroxyethyl, 2-hydroxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, dimethylaminomethyl, 1-dimethylaminoethyl, 2-dimethylaminoethyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl and homopiperazinylmethyl, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(xx) r is 1 or 2 and the first $R^6$ group is selected from fluoro, chloro, cyano, hydroxy, amino, methyl, ethyl, propyl, isopropyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, 1-hydroxyethyl, aminomethyl, methylaminomethyl, ethylaminomethyl, propylaminomethyl, isopropylaminomethyl, cyclopropylaminomethyl, 2-hydroxyethylaminomethyl, dimethylaminomethyl, diethylaminomethyl, N-ethyl-N-methylaminomethyl, cyclopropylaminomethyl, N-cyclopropyl-N-methylaminomethyl, furylmethylaminomethyl, pyrrolylmethylaminomethyl, pyridylmethylaminomethyl, phenyl, furyl, thienyl, imidazolyl, oxazolyl, thiazolyl, pyrrolidinyl, morpholinyl, piperidinyl, homopiperidinyl, piperazinyl, homopiperazinyl, azetidinylmethyl, pyrrolidinylmethyl, morpholinylmethyl, piperidinylmethyl, homopiperidinylmethyl, piperazinylmethyl and homopiperazinylmethyl, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino, dimethylamino, hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(yy) two $R^6$ groups together form a bivalent group that spans adjacent ring positions on Ring A selected from $OC(R^{20})_2O$, $OC(R^{20})_2C(R^{20})_2$, $C(R^{20})_2OC(R^{20})_2$, $C(R^{20})_2C(R^{20})_2C(R^{20})_2$, $C(R^{20})_2C(R^{20})_2C(R^{20})_2C(R^{20})_2$, $OC(R^{20})_2N(R^{21})$, $N(R^{21})C(R^{20})_2N(R^{21})$, $N(R^{21})C(R^{20})_2C(R^{20})_2$, $N(R^{21})C(R^{20})_2C(R^{20})_2C(R^{20})_2$ and $C(R^{20})_2N(R^{21})C(R^{20})_2$, wherein each of $R^{20}$ and $R^{21}$ is hydrogen, (1-8C)alkyl, (2-8C)alkenyl or (2-8C)alkynyl;

(zz) two $R^6$ groups together form a bivalent group that spans adjacent ring positions on Ring A selected from $OC(R^{20})_2O$, $OC(R^{20})_2C(R^{20})_2$, $C(R^{20})_2OC(R^{20})_2$, $OC(R^{20})_2N(R^{21})$, $N(R^{21})C(R^{20})_2N(R^{21})$, $N(R^{21})C(R^{20})_2C(R^{20})_2$ and $C(R^{20})_2N(R^{21})C(R^{20})_2$ wherein each of $R^{20}$ and $R^{21}$ is hydrogen, (1-8C)alkyl, (2-8C)alkenyl or (2-8C)alkynyl;

(aaa) two $R^6$ groups together form a bivalent group that spans adjacent ring positions on Ring A selected from $OC(R^{20})_2O$, $OC(R^{20})_2C(R^{20})_2O$, $C(R^{20})_2OC(R^{20})_2$, $OC(R^{20})_2N(R^{21})$, $N(R^{21})C(R^{20})_2N(R^{21})$ and $C(R^{20})_2N(R^{21})C(R^{20})_2$, wherein each of $R^{20}$ and $R^{21}$ is hydrogen, methyl, ethyl or propyl;

(bbb) two $R^6$ groups together form a bivalent group that spans adjacent ring positions on Ring A selected from $OCH_2O$, $OCH_2CH_2O$, $CH_2OCH_2$, $OCH_2NH$, $NHCH_2NH$ and $CH_2NHCH_2$; and (ccc) two $R^6$ groups together form a bivalent group that spans adjacent ring positions on Ring A selected from $OCH_2O$ and $OCH_2CH_2O$.

A particular compound of the invention is a quinazoline derivative of the Formula I wherein:—

$X^1$ is O or NH;

p is 2 and the $R^1$ groups, which may be the same or different, are located at the 6- and 7-positions and the $R^1$ group at the 6-position is selected from hydroxy, methoxy, ethoxy and propoxy, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any $CH$, $CH_2$ or $CH_3$ group within a $R^1$ substituent optionally bears on each said $CH$, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, hydroxy, amino, methyl, methoxy, methylamino and dimethylamino;

the $-C(R^3)(R^4)-CON(R^5)$ group is located at the 4-position (relative to the $X^1$ group);

each of $R^3$, $R^4$ and $R^5$ is hydrogen;

Ring A is a phenyl, pyridyl, pyrimidinyl, pyrazinyl or pyridazinyl ring; and r is 1 or 2 and one $R^6$ group is located at the 3- or 4-position (relative to the $CON(R^5)$ group), and each $R^6$ group, which may be the same or different, is selected from fluoro, chloro, trifluoromethyl, cyano, hydroxy, amino, methyl, methoxy, methylamino and dimethylamino, or the first $R^6$ group is located at the 3- or 4-position (relative to the $CON(R^5)$ group) and is a group of the formula:

$$-X^7-R^{17}$$

wherein $X^7$ is a direct bond or O and $R^{17}$ is hydroxymethyl, 1-hydroxyethyl, 2-hydroxyethyl, 3-hydroxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^7$ is O, there are at least two carbon atoms between $X^7$ and any heteroatom in the $R^{17}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O or NH;

p is 2 and the $R^1$ groups, which may be the same or different, are located at the 6- and 7-positions and the $R^1$ group at the 6-position is selected from hydroxy, methoxy, ethoxy and propoxy, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, hydroxy, amino, methyl, methoxy, methylamino and dimethylamino;

the $—C(R^3)(R^4)—CON(R^5)$ group is located at the 4-position (relative to the $X^1$ group);

each of $R^3$, $R^4$ and $R^5$ is hydrogen;

Ring A is a phenyl, pyridyl, pyrimidinyl, pyrazinyl or pyridazinyl ring; and r is 1 or 2 and one $R^6$ group is located at the 3- or 4-position (relative to the $CON(R^5)$ group), and each $R^6$ group, which may be the same or different, is selected from fluoro, chloro, trifluoromethyl, cyano, hydroxy, amino, methyl, methoxy, methylamino and dimethylamino, or the first $R^6$ group is located at the 3- or 4-position (relative to the $CON(R^5)$ group) and is selected from hydroxymethyl, 1-hydroxyethyl, 2-hydroxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, dimethylaminomethyl, 1-dimethylaminoethyl, 2-dimethylaminoethyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl and homopiperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino and any such heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 6-methoxy group and the second $R^1$ group is located at the 7-position and is selected from methoxy, ethoxy, 2-methoxyethoxy, 3-methoxypropoxy, 2-methylsulphonylethoxy, 3-methylsulphonylpropoxy, 2-(2-methoxyethoxy)ethoxy, 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4-isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-(4-pyridyloxy)ethoxy, 3-pyridylmethoxy and 2-cyanopyrid-4-ylmethoxy;

q is 0;

the $—C(R^3)(R^4)—CON(R^5)$ group is located at the 4-position (relative to the $X^1$ group);

each of $R^3$, $R^4$ and $R^5$ is hydrogen;

Ring A is a phenyl or pyridyl ring; and r is 1 or 2 and one $R^6$ group is located at the 3- or 4-position (relative to the $CON(R^5)$ group), and each $R^6$ group, which may be the same or different, is selected from fluoro, chloro, trifluoromethyl, hydroxy, amino, methyl, methoxy, methylamino and dimethylamino, or the first $R^6$ group is located at the 3- or 4-position (relative to the CON($R^5$) group) and is selected from hydroxymethyl, 1-hydroxyethyl, 2-hydroxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, dimethylaminomethyl, 1-dimethylaminoethyl, 2-dimethylaminoethyl, pyrrolidinylmethyl, morpholinylmethyl, piperidinylmethyl and piperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino, and any second $R^6$ group that is present is selected from fluoro, chloro, trifluoromethyl, cyano, hydroxy, amino, methyl, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 6-methoxy group and the second $R^1$ group is located at the 7-position and is selected from methoxy, ethoxy and 2-methoxyethoxy;

q is 0;

the —C($R^3$)($R^4$)—CON($R^5$) group is located at the 4-position (relative to the $X^1$ group);

each of $R^3$, $R^4$ and $R^5$ is hydrogen;

Ring A is phenyl; and r is 1 or 2 and one $R^6$ group is located at the 3-position (relative to the CON($R^5$) group), and each $R^6$ group, which may be the same or different, is selected from fluoro, chloro, methoxy, methylamino and dimethylamino, or the first $R^6$ group is located at the 3-position (relative to the CON($R^5$) group) and is selected from hydroxymethyl, 1-hydroxyethyl, aminomethyl, 1-aminoethyl, methylaminomethyl, 1-methylaminoethyl, dimethylaminomethyl and 1-dimethylaminoethyl, and any second $R^6$ group that is present is selected from fluoro, chloro, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O or NH;

p is 2 and the $R^1$ groups, which may be the same or different, are located at the 5- and 7-positions and the $R^1$ group at the 5-position is selected from methoxy, ethoxy, propoxy, isopropoxy, butoxy, tetrahydrofuran-3-yloxy, tetrahydropyran-4-yloxy, pyrrolidin-3-yloxy, pyrrolidin-2-ylmethoxy, 3-piperidinyloxy, 4-piperidinyloxy, piperidin-3-ylmethoxy, piperidin-4-ylmethoxy, cyclobutyloxy, cyclopentyloxy and cyclohexyloxy, and the $R^1$ group at the 7-position is selected from hydroxy, methoxy, ethoxy, propoxy, isopropoxy, butoxy, 2-pyrrolidin-1-ylethoxy, 3-pyrrolidin-1-ylpropoxy, 4-pyrrolidin-1-ylbutoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-ylethoxy, 3-(1,1-dioxotetrahydro-4H-1,4-thiazin-4-yl)propoxy, 2-piperidinoethoxy, 3-piperidinopropoxy, 4-piperidinobutoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, hydroxy, amino, methyl, methoxy, methylamino and dimethylamino;

the —C($R^3$)($R^4$)—CON($R^5$) group is located at the 4-position (relative to the $X^1$ group);

each of $R^3$, $R^4$ and $R^5$ is hydrogen;

Ring A is a phenyl, pyridyl, pyrimidinyl, pyrazinyl or pyridazinyl ring; and r is 1 or 2 and one $R^6$ group is located at the 3- or 4-position (relative to the CON($R^5$) group), and each $R^6$ group, which may be the same or different, is selected from fluoro, chloro, trifluoromethyl, cyano, hydroxy, amino, methyl, methoxy, methylamino and dimethylamino, or the first $R^6$ group is located at the 3- or 4-position (relative to the CON($R^5$) group) and is a group of the formula:

$$-X^7-R^{17}$$

wherein $X^7$ is a direct bond or O and $R^{17}$ is hydroxymethyl, 1-hydroxyethyl, 2-hydroxyethyl, 3-hydroxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^7$ is O, there are at least two carbon atoms between $X^7$ and any heteroatom in the $R^{17}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O or NH;

p is 2 and the $R^1$ groups, which may be the same or different, are located at the 5- and 7-positions and the $R^1$ group at the 5-position is selected from methoxy, ethoxy, propoxy, isopropoxy, butoxy, tetrahydrofuran-3-yloxy, tetrahydropyran-4-yloxy, pyrrolidin-3-yloxy, pyrrolidin-2-ylmethoxy, 3-piperidinyloxy, 4-piperidinyloxy, piperidin-3-ylmethoxy, piperidin-4-ylmethoxy, cyclobutyloxy, cyclopentyloxy and cyclohexyloxy, and the $R^1$ group at the 7-position is selected from hydroxy, methoxy, ethoxy, propoxy, isopropoxy, butoxy, 2-pyrrolidin-1-ylethoxy, 3-pyrrolidin-1-ylpropoxy, 4-pyrrolidin-1-ylbutoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, hydroxy, amino, methyl, methoxy, methylamino and dimethylamino;

the $—C(R^3)(R^4)—CON(R^5)$ group is located at the 4-position (relative to the $X^1$ group);

each of $R^3$, $R^4$ and $R^5$ is hydrogen;

Ring A is a phenyl, pyridyl, pyrimidinyl, pyrazinyl or pyridazinyl ring; and r is 1 or 2 and one $R^6$ group is located at the 3- or 4-position (relative to the $CON(R^5)$ group), and each $R^6$ group, which may be the same or different, is selected from fluoro, chloro, trifluoromethyl, cyano, hydroxy, amino, methyl, methoxy, methylamino and dimethylamino, or the first $R^6$ group is located at the 3- or 4-position (relative to the $CON(R^5)$ group) and is selected from hydroxymethyl, 1-hydroxyethyl, 2-hydroxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, dimethylaminomethyl, 1-dimethylaminoethyl, 2-dimethylaminoethyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, morpholinylmethyl, 2-(morpholinyl) ethyl, piperidinylmethyl, 2-(piperidinyl)ethyl, homopiperidinylmethyl, piperazinylmethyl, 2-(piperazinyl)ethyl and homopiperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino and any such heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt, solvate or pro-drug thereof.

A further particular compound of the invention is a quinazoline derivative of the Formula I wherein:—

$X^1$ is O;

p is 1 and the $R^1$ group is located at the 5-position and is selected from methoxy, ethoxy, propoxy, isopropoxy, tetrahydropyran-4-yloxy, 4-piperidinyloxy and N-methylpiperidin-4-yloxy, or p is 2 and the first $R^1$ group is located at the 5-position and is selected from the group of substituents listed immediately above, and the second $R^1$ group is located at the 7-position and is selected from methoxy, ethoxy, 2-methoxyethoxy, 3-methoxypropoxy, 2-methylsulphonylethoxy, 3-methylsulphonylpropoxy, 2-(2-methoxyethoxy)ethoxy, 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 3-(4-acetylpiperazin-1-yl)propoxy, 2-(4-isobutyrylpiperazin-1-yl)ethoxy, 3-(4-isobutyrylpiperazin-1-yl)propoxy, 2-[4-(2,2,2-trifluoroethyl)piperazin-1-yl]ethoxy and 3-[4-(2,2,2-trifluoroethyl)piperazin-1-yl]propoxy;

q is 0;

the $—C(R^3)(R^4)—CON(R^5)$ group is located at the 4-position (relative to the $X^1$ group);

each of $R^3$, $R^4$ and $R^5$ is hydrogen;

Ring A is a phenyl or pyridyl ring; and r is 1 or 2 and one $R^6$ group is located at the 3- or 4-position (relative to the $CON(R^5)$ group), and each $R^6$ group, which may be the same or different, is selected from fluoro, chloro, trifluoromethyl, hydroxy, amino, methyl, methoxy, methylamino and dimethylamino, or the first $R^6$ group is located at the 3- or 4-position (relative to the $CON(R^5)$ group) and is selected from hydroxymethyl, 1-hydroxyethyl, 2-hydroxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, dimethylaminomethyl, 1-dimethylaminoethyl, 2-dimethylaminoethyl, pyrrolidinylmethyl, morpholinylmethyl, piperidinylmethyl and piperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino, and any second $R^6$ group that is present is selected from fluoro, chloro, trifluoromethyl, cyano, hydroxy, amino, methyl, methoxy, methylamino and dimethylamino;
or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 5-methoxy group and the second $R^1$ group is located at the 7-position and is selected from methoxy, ethoxy and 2-methoxyethoxy;

q is 0;

the —C($R^3$)($R^4$)—CON($R^5$) group is located at the 4-position (relative to the $X^1$ group);

each of $R^3$, $R^4$ and $R^5$ is hydrogen;

Ring A is phenyl; and r is 1 or 2 and one $R^6$ group is located at the 3-position (relative to the CON($R^5$) group), and each $R^6$ group, which may be the same or different, is selected from fluoro, chloro, methoxy, methylamino and dimethylamino, or the first $R^1$ group is located at the 3-position (relative to the CON($R^5$) group) and is selected from hydroxymethyl, 1-hydroxyethyl, aminomethyl, 1-aminoethyl, methylaminomethyl, 1-methylaminoethyl, dimethylaminomethyl and 1-dimethylaminoethyl, and any second $R^6$ group that is present is selected from fluoro, chloro, methoxy, methylamino and dimethylamino;
or a pharmaceutically-acceptable salt, solvate or pro-drug thereof.

Further particular compounds of the invention are quinazoline derivatives of the Formula I wherein each of p, $R^1$, $X^1$, q, $R^2$, $R^3$, $R^4$, $R^5$ and Ring A has any of the meanings defined hereinbefore in the various definitions of particular compounds of the invention provided that two $R^6$ groups together form a bivalent group that spans adjacent ring positions on Ring A selected from OCH$_2$O, OCH$_2$CH$_2$O, CH$_2$OCH$_2$, OCH$_2$NH, NHCH$_2$NH and CH$_2$NHCH$_2$;
or pharmaceutically-acceptable salts, solvates or pro-drugs thereof.

Further particular compounds of the invention are quinazoline derivatives of the Formula I wherein each of p, $R^1$, $X^1$, q, $R^2$, $R^3$, $R^4$ and $R^5$ has any of the meanings defined hereinbefore in the various definitions of particular compounds of the invention provided that Ring A is phenyl and two $R^6$ groups together form a OCH$_2$O bivalent group that spans the 2,3- or 3,4-positions on said phenyl ring;
or pharmaceutically-acceptable salts, solvates or pro-drugs thereof A further particular compound of the invention is a quinazoline derivative of the Formula I wherein:—

$X^1$ is O;

p is 2 and the $R^1$ groups, which may be the same or different, are located at the 6- and 7-positions and are selected from methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

q is 0 or q is 1 and the $R^2$ group is fluoro, chloro, methyl or methoxy;

the —C($R^3$)($R^4$)—CON($R^5$) group is located at the 4-position (relative to the $X^1$ group);

each of $R^3$, $R^4$ and $R^5$ is hydrogen;

Ring A is phenyl; and r is 1 or 2 and the first $R^6$ group is located at the 3-position (relative to the CON($R^5$) group) and is selected from hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, 2-furylmethylaminomethyl, pyrrolylmethylaminomethyl, pyridylmethylaminomethyl, azetidinylmethyl, pyrrolidinylmethyl, morpholinylmethyl, piperidinylmethyl, homopiperidinylmethyl, piperazinylmethyl and homopiperazinylmethyl, and any second $R^6$ group that is present is selected from fluoro, chloro, methyl, ethyl, methoxy and ethoxy, and wherein any heterocyclyl group within the $R^6$ group optionally bears a methyl, ethyl or hydroxymethyl substituent;

or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 6-methoxy group and the second $R^1$ group is located at the 7-position and is selected from methoxy, ethoxy, 2-hydroxyethoxy and 2-methoxyethoxy;

q is 0 or q is 1 and the $R^2$ group is fluoro;

the —C($R^3$)($R^4$)—CON($R^5$) group is located at the 4-position (relative to the $X^1$ group);

each of $R^3$, $R^4$ and $R^5$ is hydrogen;

Ring A is phenyl; and r is 1 or 2 and the first $R^6$ group is located at the 3-position (relative to the CON($R^5$) group) and is selected from hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, azetidin-1-ylmethyl, pyrrolidin-1-ylmethyl, morpholinomethyl, piperidinomethyl and piperazin-1-ylmethyl, and any second $R^6$ group that is present is selected from fluoro, chloro, methyl, ethyl, methoxy and ethoxy, and wherein any heterocyclyl group within the $R^6$ group optionally bears a methyl, ethyl or hydroxymethyl substituent;

or a pharmaceutically-acceptable salt, solvate or pro-drug thereof.

A further particular compound of the invention is a quinazoline derivative of the Formula I wherein:—

$X^1$ is O;

p is 2 and the $R^1$ groups, which may be the same or different, are located at the 6- and 7-positions and are selected from methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

q is 0 or q is 1 and the $R^2$ group is fluoro, chloro, methyl or methoxy;

the —C($R^3$)($R^4$)—CON($R^5$) group is located at the 4-position (relative to the $X^1$ group);

each of $R^3$, $R^4$ and $R^5$ is hydrogen;

Ring A is pyridyl; and r is 0, 1 or 2 and each $R^6$ group that is present is selected from fluoro, chloro, trifluoromethyl, cyano, methyl, ethyl, propyl, isopropyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl- N-methylaminomethyl, N-cyclopropyl-N-methylaminomethyl, pyrrolidin-1-yl, piperidino, morpholino, piperazin-1-yl, pyrrolidin-1-ylmethyl, morpholinomethyl, piperidinomethyl and piperazin-1-ylmethyl, and wherein any heterocyclyl group within the $R^6$ group optionally bears a methyl or ethyl substituent;

or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 6-methoxy group and the second $R^1$ group is located at the 7-position and is selected from methoxy, ethoxy, 2-hydroxyethoxy and 2-methoxyethoxy;

q is 0 or q is 1 and the $R^2$ group is fluoro;

the —C($R^3$)($R^4$)—CON($R^5$) group is located at the 4-position (relative to the $X^1$ group);

each of $R^3$, $R^4$ and $R^5$ is hydrogen;

Ring A is 2-pyridyl; and r is 1 or 2 and the first $R^6$ group is located at the 3-position (relative to the CON($R^5$) group) and is selected from methylamino, ethylamino, propylamino, isopropylamino, cyclopropylamino, 2-hydroxyethylamino, 2-methoxyethylamino, dimethylamino, N-cyclopropyl-N-methylamino, pyrrolidin-1-yl, piperidino, morpholino and piperazin-1-yl, and any second $R^6$ group that is present is selected from fluoro, chloro, methyl, ethyl, methoxy and ethoxy, and wherein any heterocyclyl group within the $R^6$ group optionally bears a methyl or ethyl substituent;

or a pharmaceutically-acceptable salt, solvate or pro-drug thereof.

A further particular compound of the invention is a quinazoline derivative of the Formula I wherein:—

$X^1$ is O;

p is 2 and the $R^1$ groups, which may be the same or different, are located at the 6- and 7-positions and are selected from methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

q is 0 or q is 1 and the $R^2$ group is fluoro, chloro, methyl or methoxy;

the —C($R^3$)($R^4$)—CON($R^5$) group is located at the 4-position (relative to the $X^1$ group);

each of $R^3$, $R^4$ and $R^5$ is hydrogen;

Ring A is selected from thiazolyl, isothiazolyl, oxazolyl, isoxazolyl, imidazolyl and pyrazolyl; and r is 0, 1 or 2 and each $R^6$ group that is present is selected from fluoro, chloro, trifluoromethyl, cyano, methyl, ethyl, propyl, isopropyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, pyrrolidin-1-yl, piperidino, morpholino, piperazin-1-yl, pyrrolidin-1-ylmethyl, morpholinomethyl, piperidinomethyl and piperazin-1-ylmethyl, and wherein any heterocyclyl group within the $R^6$ group optionally bears a methyl or ethyl substituent;

or a pharmaceutically-acceptable salt, solvate or pro-drug thereof.

A further particular compound of the invention is a quinazoline derivative of the Formula I wherein:—

$X^1$ is O;

p is 2 and the first $R^1$ group is a 6-methoxy group and the second $R^1$ group is located at the 7-position and is selected from methoxy, ethoxy, 2-hydroxyethoxy and 2-methoxyethoxy;

q is 0 or q is 1 and the $R^2$ group is fluoro;

the —C($R^3$)($R^4$)—CON($R^5$) group is located at the 4-position (relative to the $X^1$ group);

each of $R^3$, $R^4$ and $R^5$ is hydrogen;

Ring A is 2-thiazolyl, 2-oxazolyl, 3-isoxazolyl, 5-isoxazolyl, 2-imidazolyl, 3-pyrazolyl or 4-pyrazolyl; and r is 0, 1 or 2 and each $R^6$ group that is present is selected from fluoro, chloro, cyano, methyl, ethyl, propyl, isopropyl, tert-butyl, cyclopropyl, methoxy, ethoxy and acetyl;

or a pharmaceutically-acceptable salt, solvate or pro-drug thereof.

Particular compounds of the invention are, for example, the quinazoline derivatives of the Formula I that are disclosed within Examples 1 and 2 that are set out hereinafter.

A further particular compound of the invention is, for example, a quinazoline derivative of the Formula I selected from:—

N-(6-dimethylaminopyridin-2-yl)-2-[4-(6,7-dimethoxyquinazolin-4-yloxy)phenyl]acetamide, N-(6-dimethylaminopyridin-2-yl)-2-{4-[6-methoxy-7-(2-methoxyethoxy)quinazolin-4-yloxy]phenyl}acetamide, N-(5-dimethylaminopyridin-2-yl)-2-[4-(6,7-dimethoxyquinazolin-4-yloxy)phenyl]acetamide, N-(5-dimethylaminopyridin-2-yl)-2-[4-(7-ethoxy-6-methoxyquinazolin-4-yloxy)phenyl]acetamide, N-(5-dimethylaminopyridin-2-yl)-2-{4-[6-methoxy-7-(2-methoxyethoxy)quinazolin-4-yloxy]phenyl}acetamide, N-(5-dimethylaminopyridin-2-yl)-2-{4-[6,7-di-(2-methoxyethoxy)quinazolin-4-yloxy]phenyl}acetamide, N-(5-dimethylaminopyridin-2-yl)-2-{4-[7-(2-hydroxyethoxy)-6-methoxyquinazolin-4-yloxy]phenyl}acetamide, N-(5-dimethylaminopyridin-2-yl)-2-{3-fluoro-4-[7-(2-hydroxyethoxy)-6-methoxyquinazolin-4-yloxy]phenyl}acetamide, N-(4-dimethylaminopyridin-2-yl)-2-[4-(6,7-dimethoxyquinazolin-4-yloxy)phenyl]acetamide, N-(4-dimethylaminopyridin-2-yl)-2-{4-[6-methoxy-7-(2-methoxyethoxy)quinazolin-4-yloxy]phenyl}acetamide, N-(4-dimethylaminopyridin-2-yl)-2-{4-[6,7-di-(2-methoxyethoxy)quinazolin-4-yloxy]phenyl}acetamide and N-(4-dimethylaminopyridin-2-yl)-2-[4-(6,7-dimethoxyquinazolin-4-yloxy)-3-fluorophenyl]acetamide;

or a pharmaceutically-acceptable salt, solvate or pro-drug thereof.

A further particular compound of the invention is, for example, a quinazoline derivative of the Formula I selected from:—

N-(4-methylthiazol-2-yl)-2-[4-(6,7-dimethoxyquinazolin-4-yloxy)phenyl]acetamide, N-(4-methylthiazol-2-yl)-2-{4-[6-methoxy-7-(2-methoxyethoxy)quinazolin-4-yloxy]phenyl}acetamide, N-(4-methylthiazol-2-yl)-2-{4-[7-(2-hydroxyethoxy)-6-methoxyquinazolin-4-yloxy]phenyl}acetamide, N-(5-methylthiazol-2-yl)-2-[4-(6,7-dimethoxyquinazolin-4-yloxy)phenyl]acetamide, N-(5-methylthiazol-2-yl)-2-[4-(6,7-dimethoxyquinazolin-4-yloxy)-3-fluorophenyl]acetamide, N-(5-methylthiazol-2-yl)-2-{4-[7-(2-hydroxyethoxy)-6-methoxyquinazolin-4-yloxy]phenyl}acetamide, N-(4,5-dimethylthiazol-2-yl)-2-{4-[7-(2-hydroxyethoxy)-6-methoxyquinazolin-4-yloxy]phenyl}acetamide, N-(5-methylisoxazol-3-yl)-2-{4-[6-methoxy-7-(2-methoxyethoxy)quinazolin-4-yloxy]phenyl}acetamide, N-(1,5-dimethylpyrazol-3-yl)-2-[4-(6,7-dimethoxyquinazolin-4-yloxy)phenyl]acetamide, N-(1-ethylpyrazol-3-yl)-2-[4-(6,7-dimethoxyquinazolin-4-yloxy)phenyl]acetamide, N-(1-methylpyrazol-4-yl)-2-[4-(6,7-dimethoxyquinazolin-4-yloxy)phenyl]acetamide, N-(1-ethylpyrazol-4-yl)-2-[4-(6,7-dimethoxyquinazolin-4-yloxy)phenyl]acetamide, N-(1-ethylpyrazol-4-yl)-2-[4-(6,7-dimethoxyquinazolin-4-yloxy)-3-fluorophenyl]acetamide, N-(1-isopropylpyrazol-4-yl)-2-[4-(6,7-dimethoxyquinazolin-4-yloxy)phenyl]acetamide, N-(1-isopropylpyrazol-4-yl)-2-[4-(7-ethoxy-6-methoxyquinazolin-4-yloxy)phenyl]acetamide, N-(1-isopropylpyrazol-4-yl)-2-{4-[6-methoxy-7-(2-methoxyethoxy)quinazolin-4-yloxy]phenyl}acetamide and N-(1-isopropylpyrazol-4-yl)-2-{4-[7-(2-hydroxyethoxy)-6-methoxyquinazolin-4-yloxy]phenyl}acetamide;

or a pharmaceutically-acceptable salt, solvate or pro-drug thereof.

A quinazoline derivative of the Formula I, or a pharmaceutically-acceptable salt, solvate or pro-drug thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, each of $X^1$, p, $R^1$, q, $R^2$, $R^3$, $R^4$, $R^5$, Ring A, r and $R^6$ has any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction of a quinazoline of the Formula II

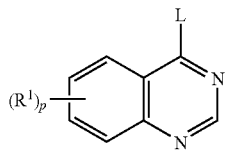

II wherein L is a displaceable group and p and $R^1$ have any of the meanings defined hereinbefore except that any functional group is protected if necessary, with a phenylacetamide of the Formula III

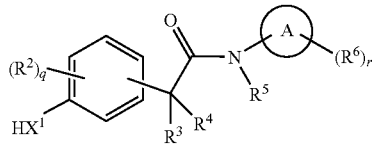

III wherein $X^1$, q, $R^2$, $R^3$, $R^4$, $R^5$, Ring A, r and $R^6$ have any of the meanings defined hereinbefore except that any functional group is protected if necessary, whereafter any protecting group that is present is removed.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 150° C.

Typically, the quinazoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinazoline starting materials of the Formula II may be obtained by conventional procedures such as those disclosed in International Patent Applications WO 01/94341, WO 02/00649, WO 02/16352 and WO 03/055491. For example, a 1,4-dihydroquinolin-4-one of the Formula IV

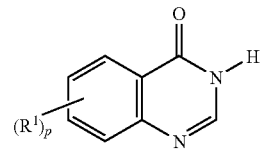

IV wherein p and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

Phenylacetamide starting materials of the Formula III may be obtained by conventional procedures. For example, an acetic acid of the Formula V

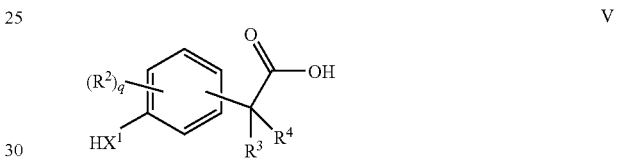

V or a reactive derivative thereof, wherein $X^1$, q, $R^2$, $R^3$ and $R^4$ have any of the meanings defined hereinbefore except that any functional group is protected if necessary, may be reacted with an amine of the Formula VI

VI wherein $R^5$, Ring A, r and $R^6$ have any of the meanings defined hereinbefore except that any functional group is protected if necessary, whereafter any protecting group that is present is removed.

A suitable reactive derivative of an acetic acid of the Formula V is, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or 1-(3-dimethylaminopropyl)-3-ethylcarbodiimide or with a uronium compound such as 2-(7-azabenzotriazol-1-yl)-1,1,3,3-tetramethyluronium hexafluorophosphate(V) or 2-(benzotriazol-1-yl)-1,1,3,3-tetramethyluronium tetrafluoroborate.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Acetic acid derivatives of the Formula V and amines of the Formula VI may be obtained by conventional procedures such as those disclosed in the Examples that are set out hereinafter.

(b) The coupling, conveniently in the presence of a suitable base, of a quinazoline of the Formula VII

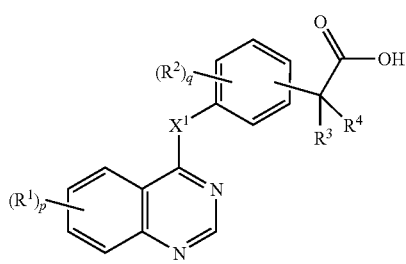

VII or a reactive derivative thereof as defined hereinbefore, wherein p, $R^1$, $X^1$, q, $R^2$, $R^3$ and $R^4$ have any of the meanings defined hereinbefore except that any functional group is protected if necessary, with an amine of the Formula VI

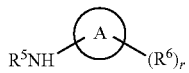

VI wherein $R^5$, Ring A, r and $R^6$ have any of the meanings defined hereinbefore except that any functional group is protected if necessary, whereafter any protecting group that is present is removed.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Quinazoline derivatives of the Formula VII and amines of the Formula VI may be obtained by conventional procedures such as those disclosed in the Examples that are set out hereinafter.

(c) For the production of those compounds of the Formula I wherein at least one $R^1$ group is a group of the formula $Q^1$-$X^2$— wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^2$ is an oxygen atom, the coupling, conveniently in the presence of a suitable dehydrating agent, of a quinazoline of the Formula VIII

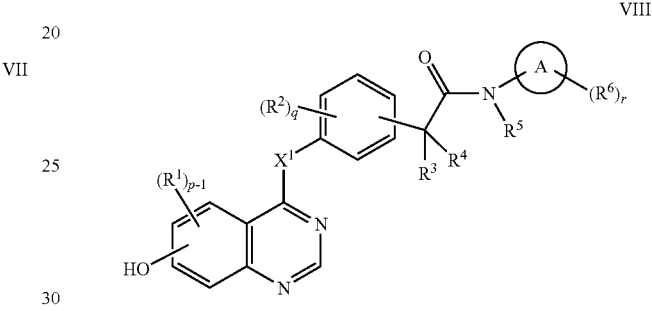

VIII wherein each of p, $R^1$, $X^1$, q, $R^2$, $R^3$, $R^4$, $R^5$, Ring A, r and $R^6$ has any of the meanings defined hereinbefore except that any functional group is protected if necessary, with an appropriate alcohol wherein any functional group is protected if necessary, whereafter any protecting group that is present is removed.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

Quinazoline derivatives of the Formula VIII may be obtained by conventional procedures.

(d) For the production of those compounds of the Formula I wherein a $R^6$ group is a group of the formula —$X^7$—$R^{17}$ wherein $X^7$ has any of the meanings defined hereinbefore and $R^{17}$ is an amino-substituted (1-6C)alkyl group (such as a dimethylaminomethyl, 2-dimethylaminoethyl or 4-methylpiperazin-1-ylmethyl group), the reaction, conveniently in the presence of a suitable base as defined hereinbefore, of a compound of the Formula I wherein a $R^6$ group is a group of the formula —$X^7$—$R^7$ wherein $R^{17}$ is a halogeno-substituted (1-6C)alkyl group with an appropriate amine or with a nitrogen-containing heterocyclyl compound.

The reaction is conveniently carried out in the presence of a suitable inert solvent or diluent as defined hereinbefore and at a temperature in the range, for example, 10 to 180° C., conveniently in the range 20 to 120° C., more conveniently at or near ambient temperature.

Compounds of the Formula I wherein a $R^6$ group is a group of the formula —$X^7$—$R^{17}$ wherein $R^{17}$ is a halogeno-substituted (1-6C)alkyl group may be obtained by any of the representative process variants (a), (b) or (c) that are described hereinbefore.

(e) For the production of those compounds of the Formula I wherein a $R^6$ group is a group of the formula $—X^7—R^{17}$ wherein $X^7$ has any of the meanings defined hereinbefore and $R^{17}$ is an amino-substituted (1-6C)alkyl group (such as a methylaminomethyl, 2-methylaminoethyl or 2-hydroxyethylaminomethyl group), the reductive amination of a compound of the Formula I wherein a $R^6$ group is a group of the formula $—X^7—R^{17}$ wherein $R^{17}$ is a formyl or (2-6C)alkanoyl group.

A suitable reducing agent for the reductive amination reaction is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

Compounds of the Formula I wherein a $R^6$ group is a group of the formula $—X^7—R^{17}$ wherein $R^{17}$ is a formyl or (2-6C) alkanoyl group may be obtained by a conventional adaptation of any of the representative process variants (a), (b) or (c) that are described hereinbefore.

When a pharmaceutically-acceptable salt of a quinazoline derivative of the Formula I is required, for example an acid-addition salt, it may be obtained by, for example, reaction of said quinazoline derivative with a suitable acid.

When a pharmaceutically-acceptable pro-drug of a quinazoline derivative of the Formula I is required, it may be obtained using a conventional procedure. For example, an in vivo cleavable ester of a quinazoline derivative of the Formula I may be obtained by, for example, reaction of a compound of the Formula I containing a carboxy group with a pharmaceutically-acceptable alcohol or by reaction of a compound of the Formula I containing a hydroxy group with a pharmaceutically-acceptable carboxylic acid. For example, an in vivo cleavable amide of a quinazoline derivative of the Formula I may be obtained by, for example, reaction of a compound of the Formula I containing a carboxy group with a pharmaceutically-acceptable amine or by reaction of a compound of the Formula I containing an amino group with a pharmaceutically-acceptable carboxylic acid.

Many of the intermediates defined herein are novel and these are provided as a further feature of the invention. For example, many compounds of the Formulae III, VI and VII are novel compounds.

Biological Assays

The following assays can be used to measure the effects of the compounds of the present invention as inhibitors of PDGFRα, PDGFRβ and KDR tyrosine kinase enzymes, as inhibitors in vitro of the phosphorylation of PDGFR expressed on MG63 osteosarcoma cells, as inhibitors in vitro of the proliferation of MG63 osteosarcoma cells, as inhibitors in vitro of the proliferation of human umbilical vein endothelial cells (HUVECs), and as inhibitors in vivo of the growth in nude mice of xenografts of human tumour tissue such as CaLu-6 and Colo205.

(a) In Vitro Enzyme Assays

The ability of test compounds to inhibit the phosphorylation of a tyrosine containing polypeptide substrate by the tyrosine kinase enzymes PDGFRα, PDGFRβ and KDR was assessed using conventional ELISA assays.

DNA encoding the PDGFRα, PDGFRβ or KDR receptor cytoplasmic domains may be obtained by total gene synthesis (*International Biotechnology Lab.,* 1987, 5(3), 19-25) or by cloning. The DNA fragments may be expressed in a suitable expression system to obtain polypeptide with tyrosine kinase activity. For example, PDGFRα, PDGFRβ and KDR receptor cytoplasmic domains, obtained by expression of recombinant protein in insect cells, can be shown to display intrinsic tyrosine kinase activity. In the case of the VEGF receptor KDR (Genbank Accession No. L04947), a DNA fragment encoding most of the cytoplasmic domain, commencing with methionine 806 and including the termination codon may be cloned into a baculovirus transplacement vector [for example pAcYM1 (see The Baculovirus Expression System: A Laboratory Guide, L. A. King and R. D. Possee, Chapman and Hall, 1992) or pAc360 or pBlueBacHis (available from Invitrogen Corporation)]. This recombinant construct may be co-transfected into insect cells [for example Spodoptera frugiperda 21 (Sf21) or Spodoptera frugiperda 9 (Sf9)] with viral DNA (for example Pharmingen BaculoGold) to prepare recombinant baculovirus. Details of the methods for the assembly of recombinant DNA molecules and the preparation and use of recombinant baculovirus can be found in standard texts, for example Sambrook et al., 1989, Molecular cloning—A Laboratory Manual, 2nd edition, Cold Spring Harbour Laboratory Press and O'Reilly et al., 1992, Baculovirus Expression Vectors—A Laboratory Manual, W.H. Freeman and Co, New York).

For expression, Sf9 cells were infected with plaque-pure KDR recombinant virus and harvested 48 hours later. Harvested cells were washed with ice cold phosphate buffered saline solution (PBS) containing 10 mM sodium phosphate pH7.4 buffer, 138 mM sodium chloride and 2.7 mM potassium chloride) and resuspended in ice cold cell diluent comprising 20 mM Hepes pH7.5 buffer, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA) and 1 mM PMSF (phenylmethylsulphonyl fluoride) [the PMSF is added just before use from a freshly-prepared 100 mM solution in methanol] using 1 ml cell diluent per 10 million cells. The suspension was centrifuged for 10 minutes at 13,000 rpm at 4° C. The supernatant (stock enzyme solution) was removed and stored in aliquots at −70° C.

A substrate solution [100 μl of a 2 μg/ml solution of the poly-amino acid Poly(Glu, Ala, Tyr) 6:3:1 (Sigma-Aldrich Company Ltd., Poole, Dorset; Catalogue No. P3899) in phosphate buffered saline (PBS)] was added to each well of a number of Nunc 96-well MaxiSorp immunoplates (Nunc, Roskilde, Denmark; Catalogue No. 439-454) and the plates were sealed and stored at 4° C. for 16 hours. The excess of substrate solution was discarded and the wells were washed in turn with PBS containing 0.05% v/v Tween 20 (PBST; 300 μl/well) and twice with Hepes pH7.4 buffer (50 mM, 300 μl/well) before being blotted dry.

Each test compound was dissolved in DMSO and diluted with a 10% solution of DMSO in distilled water to give a series of dilutions (from 40 μM to 0.0012 μM). Aliquots (25 μl) of each dilution of test compound were transferred to wells in the washed assay plates. "Maximum" control wells contained diluted DMSO instead of compound. Aliquots (25 μl) of an aqueous manganese chloride solution (40 mM) containing adenosine-5'-triphosphate (ATP) was added to all test wells except the "blank" control wells which contained magnesium chloride without ATP. For PDGFRα enzyme, an ATP concentration of 14 μM was used; for PDGFRβ enzyme, an ATP concentration of 2.8 μM was used and for KDR enzyme, an ATP concentration of 8 μM was used.

Active human PDGFRα and PDGFRβ recombinant enzyme that had been expressed in Sf9 insect cells was obtained from Upstate Biotechnology Inc., Milton Keynes, UK (product 14-467 for PDGFRα, product 14-463 for PDGFRβ). Active human KDR recombinant enzyme was expressed in Sf9 insect cells as described above.

Each kinase enzyme was diluted immediately prior to use with an enzyme diluent comprising 100 mM Hepes pH7.4 buffer, 0.1 mM sodium orthovanadate, 0.1% Triton X-100 and 0.2 mM dithiothreitol. Aliquots (50 μl) of freshly diluted enzyme were added to each well and the plates were agitated at ambient temperature for 20 minutes. The solution in each well was discarded and the wells were washed twice with PBST. Mouse IgG anti-phosphotyrosine antibody (Upstate Biotechnology Inc.; product 05-321; 100 μl) was diluted by a factor of 1:3667 with PBST containing 0.5% w/v bovine serum albumin (BSA) and aliquots were added to each well. The plates were agitated at ambient temperature for 1.5 hours. The supernatant liquid was discarded and each well was washed with PBST (×2). Horse radish peroxidase (HRP)-linked sheep anti-mouse Ig antibody (Amersham Pharmacia Biotech, Chalfont St Giles, Buckinghamshire, UK; Catalogue No. NXA 931; 100 μl) was diluted by a factor of 1:550 with PBST containing 0.5% w/v BSA and added to each well. The plates were agitated at ambient temperature for 1.5 hours. The supernatant liquid was discarded and the wells were washed with PBST (×2). A sodium perborate (PCSB) capsule (Sigma-Aldrich Company Ltd., Poole, Dorset, UK; Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Roche Diagnostics Ltd., Lewes, East Sussex, UK; Catalogue No. 1204 521). An aliquot (100 μl) of the resultant solution was added to each well. The plates were agitated at ambient temperature for about 20 minutes until the optical density value of the "maximum" control wells, as measured at 405 nm using a plate reading spectrophotometer, was approximately 1.0. "Blank" (no ATP) and "maximum" (no compound) control values were used to determine the dilution range of test compound that gave 50% inhibition of enzyme activity.

(b) In Vitro Phospho-Tyr751 PDGFRβ ELISA Assay

This assay uses a conventional EISA method to determine the ability of test compounds to inhibit phosphorylation of tyrosine in PDGFRβ.

An MG63 osteosarcoma cell line [American Type Culture Collection (ATCC) CCL 1427] was routinely maintained at 37° C. with 7.5% $CO_2$ in Dulbecco's modified Eagle's growth medium (DMEM; Sigma-Aldrich; Catalogue No. D6546) containing 10% foetal calf serum (FCS; Sigma-Aldrich; Catalogue No. F7524) and 2 mM L-glutamine (Invitrogen Ltd., Paisley, UK; Catalogue No. 25030-024).

For the assay, the cells were detached from the culture flask using a trypsin/ethylenediaminetetraacetic acid (EDTA) mixture (Invitrogen Ltd.; Catalogue No. 15400-054) and resuspended in test media comprising DMEM without phenol red (Sigma-Aldrich; Catalogue No. D5921) containing 1% charcoal-stripped foetal calf serum (FCS) (Sigma-Aldrich; Catalogue No. F7524, stripped by incubation with dextran-coated activated charcoal at 55° C. for 30 minutes with continuous stirring followed by removal of the charcoal by centrifugation and filter sterilisation) and 2 mM L-glutamine (Invitrogen Ltd., Catalogue No. 25030-024) to give $6 \times 10^4$ cells per ml. Aliquots (100 μl) were seeded into each of the wells of columns 2-12 (excluding column 1) and rows B-G (excluding rows A and H) of a clear 96 well tissue culture plate (Corning Life Sciences, Koolhovenlaan, The Netherlands; Catalogue No. 3595) to give a density of about 6000 cells per well. Aliquots (100 μl) of culture media were placed in the outer wells to minimise edge effects. The cells were incubated overnight at 37° C. with 7.5% $CO_2$ to allow the cells to adhere to the wells.

Test compounds were prepared as 10 mM stock solutions in DMSO and serially diluted as required with test media to give a range of concentrations. Aliquots (50 μl) of each compound concentration were added to the cells in each well. Control cells received a dilution of DMSO only. The cells were incubated for 90 minutes at 37° C. with 7.5% $CO_2$.

The resultant cells were stimulated with $PDGF_{BB}$ using the following procedure. A lyophilised powder of $PDGF_{BB}$, (Sigma-Aldrich; Catalogue No. P4306) was mixed with 4 mM aqueous hydrochloric acid containing 0.1% filter-sterilised BSA to provide a stock solution of 10 μg/ml of $PDGF_{BB}$. A dilution of this stock solution into test medium provided a 200 ng/ml $PDGF_{BB}$ solution. Aliquots thereof (50 μl) were added to compound treated cells and to one set of control wells to give the "maximum" control. The "minimum" controls received media only. The cells were incubated at 37° C. with 7.5% $CO_2$ for 5 minutes. The solution from the wells was removed and the cells were lysed by the addition of 120 μl/well of RIPA buffer comprising 60 mM tris(hydroxymethyl)aminomethane hydrochloride (Tris-HCl), 150 mM sodium chloride, 1 mM EDTA, 1% v/v Igepal CA-630, 0.25% sodium deoxycholate, 1% v/v phosphatase inhibitor cocktail 1 P2850, 1% phosphatase inhibitor cocktail 2 P5726 and 0.5% v/v protease inhibitor cocktail P8340 (all chemicals and inhibitor cocktails were obtainable from the Sigma-Aldrich Company Ltd.). The resultant tissue culture plates were shaken for 5 minutes at ambient temperature to ensure full lysis and then frozen at −20° C. until required.

MaxiSorp ELISA plates (Nunc; Catalogue No. 439-454) were coated with PDGFβ antibody (R&D Systems, Abingdon, Oxfordshire, UK; Catalogue No. AF385 comprising lyophilised antibody-made up with 100 μl PBS to a final concentration of 100 μl/ml). The antibody was diluted at 1:40 into carbonate-bicarbonate buffer (Sigma-Aldrich; Catalogue No. C3041; one capsule dissolved in 100 ml of distilled water) to give a 2.5 μg/ml solution. Aliquots (100 μl) were added to each well and the plates were placed at 4° C. for 16 hours. The wells were washed 5 times (1 minute soak each time) with 300 μL per well of PBST. The wells were treated with 50 μl of 3% BSA in PBST at ambient temperature for 1 hour and subsequently washed twice with 300 μl per well of PBST.

The tissue culture plates with frozen cell lysate were allowed to warm to 0° C. Aliquots (50 μl) of the MG63 cell lysate were added to the ELISA plates. Each sample was duplicated on separate plates. The ELISA plates were agitated at ambient temperature for 2 hours. The wells were washed twice with 300 μl per well of PBST. A 1:1000 dilution of both total PDGFRβ antibody (Upstate Biotechnology Inc.; Catalogue No. 06-498) and phospho PDGFRβ antibody (Cell Signaling Technology, Beverley, Mass., USA; Catalogue No. 3161) was made into 1% BSA in PBST. Aliquots (50 μl) of the antibody solutions were added to each of the wells. Plates receiving the total antibody were labelled as 'total antibody control' plates, and plates receiving the phosphospecific antibody were labelled as 'phospho antibody' plates. The plates were agitated at ambient temperature for 1 hour. The plates were washed twice with 300 µl per well of PBST. A 1:2000 dilution of anti-rabbit horseradish peroxidase conjugated secondary antibody (Cell Signaling Technology; Catalogue No. 7074) was made into 1% BSA in PBST. Aliquots (50 µl) of the resultant dilution were added to each well and the plates were agitated at ambient temperature for 1 hour. The plates were washed 5 times with 300 µl per well of PBST. Chemiluminescent substrate was made up according to manufacturers instructions (Pierce Biotechnology Inc., Rockford Ill., USA; Catalogue No. 34080). Aliquots (50 µl) of chemiluminescent substrate solution were added to each of the wells, the plates were agitated for 2 minutes and luminescence was read on a SpectraFluor Plus plate reader (Tecan UK Ltd., Reading, Berkshire, UK). Analysis for each of the compounds was completed by determining a ratio of the 'phospho antibody' plate reading to the 'total antibody' plate reading for each test sample and these ratios were plotted to determine the $IC_{50}$ value of each test compound.

(c) In Vitro MG63 Osteosarcoma Proliferation Assay

This assay determined the ability of a test compound to inhibit the proliferation of MG63 osteosarcoma cells (ATCC CCL 1427).

MG63 cells were seeded at $1.5 \times 10^3$ cells per well into 96-well clear tissue culture-treated assay plates (Corning Life Sciences; Catalogue No. 3595) to which had been added 60 µl per well of test medium comprising DMEM without phenol red, 1% charcoal-stripped FCS and 2 mM glutamine and the cells were incubated overnight at 37° C. with 7.5% $CO_2$.

Test compounds were solubilised in DMSO to provide a 10 mM stock solution. Aliquots of the stock solution were diluted with the test medium described above and 20 µl aliquots of each dilution were added to appropriate wells. Serial dilutions were made to give a range of test concentrations. Control wells to which DMSO solution only was added were included on each plate. Each plate was duplicated. A lyophilised powder of $PDGF_{BB}$ was mixed with 4 mM aqueous hydrochloric acid containing 0.1% filter-sterilised BSA to provide a stock solution of 10 µg/ml of $PDGF_{BB}$. A dilution of this stock solution into test medium provided a 250 ng/ml $PDGF_{BB}$ solution. Aliquots (20 µl) thereof were added to one set of control wells to give the "maximum" control. Aliquots (20 µl) thereof were added to one set of the duplicate compound-treated plates and these were denoted as the "$PDGF_{BB}$ stimulated" plates. The second set of duplicate compound-treated plates received media only and these were denoted as the "basal" plates. The "minimum" controls received media only. The plates were incubated at 37° C. with 7.5% $CO_2$ for 72 hours.

BrdU labelling reagent (Roche Diagnostics Ltd., Lewes, East Sussex, UK; Catalogue No. 647 229) was diluted by a factor of 1:100 in DMEM medium containing 1% charcoal stripped FCS and aliquots (10 µl) were added to each well to give a final concentration of 10 µM. The plates were incubated at 37° C. for 2 hours. The medium was decanted. A denaturating solution (FixDenat solution, Roche Diagnostics Ltd.; Catalogue No. 647 229; 200 µl) was added to each well and the plates were agitated at ambient temperature for 30 minutes. The supernatant was decanted and the wells were washed with PBS (200 µl per well). Anti-BrdU-Peroxidase solution (Roche Diagnostics Ltd.; Catalogue No. 647 229) was diluted by a factor of 1:100 in antibody diluent (Roche Diagnostics Ltd., Catalogue No. 647 229) and 100 µl of the resultant solution was added to each well. The plates were agitated at ambient temperature for 90 minutes. The wells were washed with PBS (×3; 300 µl) to ensure removal of non-bound antibody conjugate. The plates were blotted dry and tetramethylbenzidine substrate solution (Roche Diagnostics Ltd.; Catalogue No. 647 229; 100 µl) was added to each well. The plates were gently agitated on a plate shaker while the colour developed during a 10 to 20 minute period. Aqueous sulphuric acid (1M; 50 µl) was added to the appropriate wells to stop any further reaction and the absorbance of the wells was measured at 450 nm. The extent of inhibition of cellular proliferation at a range of concentrations of each test compound was determined and an anti-proliferative $IC_{50}$ value was derived.

(d) In Vitro HUVEC Proliferation Assay

This assay determines the ability of a test compound to inhibit the growth factor-stimulated proliferation of human umbilical vein endothelial cells (HUVECs).

HUVECs were isolated in MCDB 131 (Gibco BRL) and 7.5% v/v foetal calf serum (FCS) and were plated out (at passage 2 to 8) in a mixture of MCDB 131, 2% v/v FCS, 3 µg/ml heparin and 1 µg/ml hydrocortisone, at a concentration of 1000 cells/well in 96 well plates. After a minimum of 4 hours, the cells were dosed with the appropriate growth factor (for example VEGF) and with the test compound. The cultures were incubated for 4 days at 37° C. under 7.5% $CO_2$. On day 4, the cell cultures were pulsed with 1 µCi/well of tritiated-thymidine (Amersham product TRA 61) and incubated for 4 hours. The cells were harvested using a 96-well plate harvester (Tomtek) and assayed for incorporation of tritium with a Beta plate counter. Incorporation of radioactivity into cells, expressed as counts per minute (cpm), was used to measure inhibition of growth factor-stimulated cell proliferation by each test compound.

(e) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1 \times 10^6$ CaLu-6 cells/mouse in 100 µl of a 50% (v/v) solution of Matrigel in serum free culture medium. Ten days after cellular implant, mice were allocated to groups of 8-10 animals having comparable group mean tumour volumes. Tumours were measured using vernier calipers and volumes were calculated using the formula $$(l \times w) \times \sqrt{(l \times w)} \times (\pi/6)$$

where l is the longest diameter and w the diameter perpendicular to the longest. Test compounds were administered orally once daily for a minimum of 21 days, and control animals received compound diluent only. Tumours were measured twice weekly. The level of growth inhibition was calculated by comparison of the mean tumour volume of the control group versus the treatment group using a Student's T test and/or a Mann-Whitney Rank Sum Test.

Although the pharmacological properties of the compounds of the Formula I vary with structural change as expected, in general activity possessed by compounds of the Formula I, may be demonstrated at the following concentrations or doses in one or more of the above tests (a), (b), (c), (d) and (e):—

Test (a):—$IC_{50}$ versus PDGFRα tyrosine kinase in the range, for example, 0.1 nM-5 µM;

$IC_{50}$ versus PDGFRβ tyrosine kinase in the range, for example, 0.1 nM-5 µM;

$IC_{50}$ versus KDR tyrosine kinase in the range, for example, 0.1 nM-5 µM;

Test (b):—$IC_{50}$ versus phospho-Tyr751 PDGFRβ in the range, for example, 0.1 nM-1 µM;

Test (c):—$IC_{50}$ versus MG63 osteosarcoma proliferation in the range, for example, 1 nM-5 µM;

Test (d):—$IC_{50}$ versus HUVEC proliferation in the range, for example, 1 nM-5 µM;

Test (e):—xenograft activity in the range, for example, 1-200 mg/kg/day.

For example, the quinazoline compound disclosed within Example 1 possesses activity in Test (a) with an $IC_{50}$ versus PDGFRα tyrosine kinase of approximately 0.25 µM, with an $IC_{50}$ versus PDGFRβ tyrosine kinase of approximately 0.06 µM, and with an $IC_{50}$ versus KDR tyrosine kinase of approximately 1 nM; and activity in Test (b) with an $IC_{50}$ versus phospho-Tyr751 PDGFRβ of approximately 1 nM.

For example, the quinazoline compound disclosed within Example 6 possesses activity in Test (a) with an $IC_{50}$ versus PDGFRα tyrosine kinase of approximately 0.4 µM, with an $IC_{50}$ versus PDGFRβ tyrosine kinase of approximately 0.3 µM, and with an $IC_{50}$ versus KDR tyrosine kinase of approximately 10 nM; and activity in Test (b) with an $IC_{50}$ versus phospho-Tyr751 PDGFRβ of approximately 0.5 nM.

For example, the quinazoline compound disclosed as Compound 17 within Example 9 possesses activity in Test (a) with an $IC_{50}$ versus PDGFRα tyrosine kinase of approximately 0.3 µM and with an $IC_{50}$ versus PDGFRβ tyrosine kinase of approximately 0.1 µM; and activity in Test (b) with an $IC_{50}$ versus phospho-Tyr751 PDGFRβ of approximately 2 nM.

For example, the quinazoline compound disclosed as Compound 4 within Example 10 possesses activity in Test (a) with an $IC_{50}$ versus KDR tyrosine kinase of approximately 10 nM; and activity in Test (b) with an $IC_{50}$ versus phospho-Tyr751 PDGFRβ of approximately 1 nM.

For example, the quinazoline compound disclosed as Compound 27 within Example 10 possesses activity in Test (a) with an $IC_{50}$ versus KDR tyrosine kinase of approximately 1 nM; and activity in Test (b) with an $IC_{50}$ versus phospho-Tyr751 PDGFRβ of approximately 0.1 mM.

No untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable salt, solvate or pro-drug thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, antagonism of the activity of PDGF receptor kinases, particularly inhibition of the PDGFα and/or PDGFβ receptor tyrosine kinases, is expected to be beneficial in the treatment of a number of cell proliferative disorders such as cancer, especially in inhibiting tumour growth and metastasis and in inhibiting the progression of leukaemia. In addition, antagonism of the activity of VEGF is expected to be beneficial in the treatment of a number of disease states that are associated with angiogenesis and/or increased vascular permeability such as cancer, especially in inhibiting the development of tumours.

We have now found that the novel 2-phenylacetamide derivatives described herein possess potent activity against cell proliferative disorders. It is believed that the compounds provide a useful treatment of cell proliferative disorders, for example to provide an anti-tumour effect, by way of a contribution from inhibition of PDGF receptor tyrosine kinases and/or by way of a contribution from inhibition of VEGF receptor tyrosine kinases.

According to this further aspect of the invention there is provided a quinazoline derivative of the Formula I, or a pharmaceutically-acceptable salt, solvate or pro-drug thereof, as defined hereinbefore for use as a medicament in a warm-blooded animal such as man.

According to a further aspect of the invention, there is provided a quinazoline derivative of the Formula I, or a pharmaceutically-acceptable salt, solvate or pro-drug thereof, as defined hereinbefore for use in the treatment (or prophylaxis) of cell proliferative disorders or in the treatment (or prophylaxis) of disease states associated with angiogenesis and/or vascular permeability.

According to a further aspect of the invention, there is provided the use of a quinazoline derivative of the Formula I, or a pharmaceutically-acceptable salt, solvate or pro-drug thereof, as defined hereinbefore in the manufacture of a medicament for use in the treatment (or prophylaxis) of cell proliferative disorders or in the treatment (or prophylaxis) of disease states associated with angiogenesis and/or vascular permeability.

According to this aspect of the invention there is also provided a method for the treatment (or prophylaxis) of cell proliferative disorders in a warm-blooded animal in need of such treatment (or prophylaxis) or for the treatment (or prophylaxis) of disease states associated with angiogenesis and/or vascular permeability in a warm-blooded animal in need of such treatment (or prophylaxis) which comprises administering to said animal an effective amount of a quinazoline derivative of the Formula I, or a pharmaceutically-acceptable salt, solvate or pro-drug thereof, as defined hereinbefore.

Suitable cell proliferative disorders include neoplastic disorders, for example, cancers of the lung (non-small cell lung cancer, small cell lung cancer and bronchioalveolar cancer), gastrointestine (such as colon, rectal and stomach tumours), prostate, breast, kidney, liver, brain (such as glioblastoma), bile duct, bone, bladder, head and neck, oesophagus, ovary, pancreas, testes, thyroid, cervix and vulva and skin (such as dermatofibrosarcoma protruberans) and in leukaemias and lymphomas such as chronic myelogenous leukaemia (CML), chronic myelomonocytic leukaemia (CMML), acute lymphocytic leukaemia (ALL), chronic neutrophilic leukaemia (CNL), acute myelogenous leukaemia (AML) and multiple myeloma.

According to this aspect of the invention there is also provided a method for treating cell proliferative disorders (such as solid tumour disease) in a warm-blooded animal in need of such treatment which comprises administering to said animal an effective amount of a quinazoline derivative of the Formula I, or a pharmaceutically-acceptable salt, solvate or pro-drug thereof, as defined hereinbefore.

Other suitable cell proliferative disorders include non-malignant disorders such as blood vessel disease (for example atherosclerosis and restenosis, for example in the process of restenosis subsequent to balloon angioplasty and heart arterial by-pass surgery), fibrotic diseases (for example kidney fibrosis, hepatic cirrhosis, lung fibrosis and multicystic renal dysplasia), glomerulonephritis, benign prostatic hypertrophy, inflammatory diseases (for example rheumatoid arthritis and inflammatory bowel disease), multiple sclerosis, psoriasis, hypersensitivity reactions of the skin, allergic asthma, insulin-dependent diabetes, diabetic retinopathy and diabetic nephropathy.

Suitable disease states associated with angiogenesis and/or vascular permeability include, for example, the undesirable or pathological angiogenesis seen in diabetic retinopathy, psoriasis, cancer, rheumatoid arthritis, atheroma, Kaposi's sarcoma and haemangioma.

According to a further aspect of the invention there is provided a quinazoline derivative of the Formula I, or a pharmaceutically-acceptable salt, solvate or pro-rug thereof, as defined hereinbefore for use in the treatment (or prevention) of those tumours which are sensitive to inhibition of PDGF receptor enzymes (such as PDGFα and/or PDGFβ receptor tyrosine kinase) and/or which are sensitive to inhibition of VEGF receptor tyrosine kinases (such as KDR and/or Flt-1 receptor tyrosine kinase) that are involved in the signal transduction steps which lead to the proliferation, survival, invasiveness and migratory ability of tumour cells.

According to a further feature of this aspect of the invention there is provided the use of a quinazoline derivative of the Formula I, or a pharmaceutically-acceptable salt, solvate or pro-drug thereof, as defined hereinbefore in the manufacture of a medicament for use in the treatment (or prevention) of those tumours which are sensitive to inhibition of PDGF receptor enzymes (such as PDGFα and/or PDGFβ receptor tyrosine kinase) and/or which are sensitive to inhibition of VEGF receptor tyrosine kinases (such as KDR and/or Flt-1 receptor tyrosine kinase) that are involved in the signal transduction steps which lead to the proliferation, survival, invasiveness and migratory ability of tumour cells.

According to a further feature of this aspect of the invention there is provided a method for the treatment (or prevention) of a warm-blooded animal having tumours which are sensitive to inhibition of PDGF receptor enzymes (such as PDGFα and/or PDGFβ receptor tyrosine kinase) and/or which are sensitive to inhibition of VEGF receptor tyrosine kinases (such as KDR and/or Flt-1 receptor tyrosine kinase) that are involved in the signal transduction steps which lead to the proliferation, survival, invasiveness and migratory ability of tumour cells which comprises administering to said animal an effective amount of a quinazoline derivative of the Formula I, or a pharmaceutically-acceptable salt, solvate or pro-drug thereof, as defined hereinbefore.

According to a further aspect of the invention there is provided a quinazoline derivative of the Formula I, or a pharmaceutically-acceptable salt, solvate or pro-drug thereof, as defined hereinbefore for use in providing a PDGF receptor enzyme inhibitory effect (such as a PDGFα and/or PDGFβ receptor tyrosine kinase inhibitory effect) and/or a VEGF receptor tyrosine kinase inhibitory effect (such as a KDR and/or Flt-1 receptor tyrosine kinase inhibitory effect).

According to a further feature of this aspect of the invention there is provided the use of a quinazoline derivative of the Formula I, or a pharmaceutically-acceptable salt, solvate or pro-drug thereof, as defined hereinbefore in the manufacture of a medicament for use in providing a PDGF receptor enzyme inhibitory effect (such as a PDGFα and/or PDGFβ receptor tyrosine kinase inhibitory effect) and/or a VEGF receptor tyrosine kinase inhibitory effect (such as a KDR and/or Flt-1 receptor tyrosine kinase inhibitory effect).

According to a further aspect of the invention there is also provided a method for inhibiting a PDGF receptor enzyme (such as the PDGFα and/or PDGFβ receptor tyrosine kinase) and/or inhibiting a VEGF receptor tyrosine kinase (such as the KDR and/or Flt-1 receptor tyrosine kinase) which comprises administering an effective amount of a quinazoline derivative of the Formula I, or a pharmaceutically-acceptable salt, solvate or pro-drug thereof, as defined hereinbefore.

The anti-cancer treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-

(4-methylpiperazin-1-yl)ethoxy]-5-tetrahydropyran-4-ylox-yqyuinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK, AKT and/or PI3K kinases;

(v) other antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Basis for another aspect of the invention arises from the disclosure in International Patent Application WO 01/74360 that VEGF receptor tyrosine kinase inhibitors, provided that they possess suitable pharmacokinetic properties which provide reasonable bioavailability, lead to a sustained increase in blood pressure when administered to warm-blooded animals, particularly when administered chronically. In general, the compounds of the present invention possess inhibitory activity against VEGF receptor tyrosine kinases such as KDR tyrosine kinase. Accordingly, it is expected that, in general, compounds of the present invention will cause a sustained increase in blood pressure when administered to a warm-blooded animal such as man. In order to attenuate such a hypertensive effect, the anti-cancer treatment defined hereinbefore may involve the administration, in addition to the quinazoline derivative of the invention, of a conventional anti-hypertensive agent. Such an anti-hypertensive agent may include one or more of the following categories of anti-hypertensive agents:—

(i) calcium channel blockers such as amlodipine, diltiazem and felodipine;
(ii) angiotensin converting enzyme inhibitors (ACE-Inhibitors) such as captopril, enalapril, lisinopril and quinapril;
(iii) angiotensin-II receptor antagonists (A-II antagonists) such as candesartan, losartan and valsartan;
(iv) β-blockers such as atenolol, metoprolol and timolol;
(v) α-blockers such as doxazosin, prazosin and tamsulosin;
(vi) "vasodilators", which include cerebral vasodilators, coronary vasodilators and peripheral vasodilators, such as cinnarizine, fenoxedil, pentifylline and dipyridamole; and
(vii) "diuretics", which include benzothiadiazine derivatives, diuretic organomercurials, diuretic purines, diuretic steroids, diuretic sulfonamide derivatives and diuretic uracils, for example amiloride, bendroflumethiazide, hydrochlorothiazide, clopamide and furosemide.

According to this aspect of the invention there is provided a pharmaceutical product for use in the treatment of cancer which comprises a quinazoline derivative of the formula I as defined hereinbefore and an anti-hypertensive agent as defined hereinbefore.

Although the compounds of the Formula I are primarily of value as therapeutic agents for use in warm-blooded animals (including man), they are also useful whenever it is required to inhibit the effects of PDGF receptor tyrosine kinase enzymes. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as nitrogen or argon unless otherwise stated;

(ii) in general, the course of reactions was followed by thin layer chromatography (TLC) and/or analytical high pressure liquid chromatography (HPLC); the reaction times that are given are not necessarily the minimum attainable;

(iii) when necessary, organic solutions were dried over anhydrous magnesium sulphate, work-up procedures were carried out after removal of residual solids by filtration, evaporations were carried out by rotary evaporation in vacuo;

(iv) yields, where present, are not necessarily the maximum attainable, and, when necessary, reactions were repeated if a larger amount of the reaction product was required;

(v) in general, the structures of the end-products of the Formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale using a Bruker Spectrospin DPX300 spectrometer operating at a field strength of 300 MHz; the following abbreviations have been used: s, singlet; d, doublet; t, triplet; q, quartet; m, multiplet; br, broad;

(vi) unless stated otherwise compounds containing an asymmetric carbon and/or sulphur atom were not resolved;

(vii) intermediates were not necessarily fully purified but their structures and purity were assessed by TLC, analytical HPLC, infra-red (IR) and/or NMR analysis;

(viii) unless otherwise stated, column chromatography (by the flash procedure) and medium pressure liquid chromatography (MPLC) were performed on Merck Kieselgel silica (Art. 9385);

(ix) preparative HPLC was performed on C18 reversed-phase silica, for example on a Waters 'Xterra' preparative reversed-phase column (5 microns silica, 19 mm diameter, 100 mm length) using decreasingly polar mixtures as eluent, for example decreasingly polar mixtures of a 1% aqueous acetic acid or a 1% aqueous ammonium hydroxide (d=0.88) solution and acetonitrile;

(x) where certain compounds were obtained as an acid-addition salt, for example a mono-hydrochloride salt or a di-hydrochloride salt, the stoichiometry of the salt was based on the number and nature of the basic groups in the compound; generally, elemental analysis data were not obtained to determine the exact stoichiometry of the salt;

(xi) the following abbreviations have been used:—
DMSO dimethylsulphoxide
DMF N,N-dimethylformamide
DMA N,N-dimethylacetamide
THF tetrahydrofuran

EXAMPLE 1

N-(3-methoxyphenyl)-2-[4-(6,7-dimethoxyquinazolin-4-yloxy)phenyl]acetamide

Diisopropylethylamine (0.073 ml) and 2-(7-azabenzotriazol-1-yl)-1,1,3,3-tetramethyluronium hexafluorophosphate (V) (0.16 g) were added in turn to a stirred mixture of 2-[4-(6,7-dimethoxyquinazolin-4-yloxy)phenyl]acetic acid (0.12 g), 3-methoxyaniline (0.047 ml) and DMF (3 ml) and the resultant mixture was stirred at ambient temperature for 2 hours. Water was added and the precipitate was recovered by filtration and purified by column chromatography on silica using a 19:1 mixture of methylene chloride and methanol as eluent. There was thus obtained the title compound as a solid (0.122 g); $^1$H NMR: (DMSOd$_6$) 3.69 (s, 2H), 3.73 (s, 3H), 3.97 (s, 3H), 3.99 (s, 3H), 6.63 (m, 1H), 7.15 (d, 1H), 7.21 (m, 1H), 7.26 (d, 2H), 7.34 (m, 1H), 7.39 (s, 1H), 7.43 (d, 2H), 7.55 (s, 1H), 8.54 (s, 1H), 10.21 (s, 1H); Mass Spectrum: M+H$^+$ 446.

The 2-[4-(6,7-dimethoxyquinazolin-4-yloxy)phenyl]acetic acid used as a starting material was prepared as follows:—

A mixture of 4-chloro-6,7-dimethoxyquinazoline (European Patent Application No. 0566226, Example 1 thereof; 1 g), 2-(4-hydroxyphenyl)acetic acid (0.713 g), potassium carbonate (1.85 g) and DMF (10 ml) was stirred and heated to 90° C. under argon for 2 hours. The mixture was cooled to ambient temperature and diethyl ether was added. The precipitated solid was recovered by filtration and washed with diethyl ether. The solid was dissolved in water and the solution was acidified to pH3.5 by the addition of 1N aqueous hydrochloric acid. The resultant precipitate was isolated, washed with diethyl ether and dried under vacuum. There was thus obtained the required starting material (1.4 g); $^1$H NMR: (DMSOd$_6$) 3.63 (s, 2H), 3.98 (s, 3H), 3.99 (s, 3H), 7.25 (d, 2H), 7.36 (d, 2H), 7.39 (s, 1H), 7.55 (s, 1H), 8.55 (s, 1H); Mass Spectrum: M+H$^+$ 341.

EXAMPLE 2

N-(3-dimethylaminomethylphenyl)-2-[4-(6,7-dimethoxyquinazolin-4-yloxy)phenyl]acetamide Using an analogous procedure to that described in Example 1, 2-[4-(6,7-dimethoxyquinazolin-4-yloxy)phenyl] acetic acid was reacted with 3-dimethylaminomethylaniline to give the title compound in 86% yield; $^1$H NMR: (DMSOd$_6$) 2.14 (s, 3H), 3.35 (s, 2H), 3.68 (s, 2H), 3.97 (s, 3H), 3.99 (s, 3H), 6.96 (d, 1H), 7.24 (m, 1H), 7.26 (d, 2H), 7.39 (s, 1H), 7.44 (d, 2H), 7.53 (d, 1H), 7.55 (d, 1H), 7.58 (s, 1H), 8.53 (s, 1H), 10.19 (s, 1H); Mass Spectrum: M+H$^+$ 473.

The 3-dimethylaminomethylaniline used as a starting material was prepared as follows:—

Triethylamine (3.64 g) was added dropwise to a mixture of 3-nitrobenzyl bromide (2.6 g), dimethylamine hydrochloride (1.96 g) and methylene chloride (26 ml) and the resultant mixture was stirred at ambient temperature for 2 hours. The solvent was evaporated and the residue was diluted with water and extracted with ethyl acetate. The organic phase was washed with water, dried over magnesium sulphate and concentrated. There was thus obtained N,N-dimethyl-N-(3-nitrobenzyl)amine (1.6 g); $^1$H NMR: (DMSOd$_6$) 2.18 (s, 6H), 3.34 (s, 2H), 7.63 (t, 1H), 7.75 (d, 1H), 8.12 (m, 2H); Mass Spectrum: M+H$^+$ 181.

Raney nickel (0.8 g) was washed twice with ethanol and added to a solution of N,N-dimethyl-N-(3-nitrobenzyl)amine (1.6 g) in a mixture of methanol (10 ml) and ethanol (50 ml). The mixture was stirred under 1.8 atmospheres pressure of hydrogen at ambient temperature for 1 hour. The reaction mixture was filtered and the filtrate was evaporated. The residue was purified by column chromatography on silica using a solvent gradient from a 19:1 to a 9:1 mixture of methylene chloride and methanol followed by a 9:1 to a 18:3 mixture of methylene chloride and a 7M methanolic ammonia solution as eluent. There was thus obtained 3-dimethylaminomethylaniline (0.85 g); $^1$H NMR: (DMSOd$_6$) 2.11 (s, 6H), 3.2 (s, 2H), 4.96 (br s, 2H), 6.41 (m, 2H), 6.51 (s, 1H), 6.92 (t, 1H); Mass Spectrum: M+H$^+$ 151.

EXAMPLE 3

Using an analogous procedure to that described in Example 1, the appropriate 2-phenylacetic acid was reacted with the appropriate aniline to give the compounds described in Table I. Unless otherwise stated, each reaction product was purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent. Unless otherwise stated, each aniline was a commercially available material.

TABLE I

| No. & Note | $(R^1)_p$ | $(R^2)_q$ | $(R^6)_r$ |
|---|---|---|---|
| [1] | 6,7-dimethoxy | H | 4-chloro-3-hydroxymethyl |
| [2] | 6,7-dimethoxy | H | 6-fluoro-3-hydroxymethyl |
| [3] | 6,7-dimethoxy | H | 3-hydroxymethyl-4-methoxy |
| [4] | 6,7-dimethoxy | H | 3-(N-cyclopropyl-N-methylaminomethyl)-5-methyl |
| [5] | 6-methoxy-7-(2-hydroxyethoxy) | H | 3-(N-cyclopropyl-N-methylaminomethyl)-5-methyl |

Notes The products gave the characterising data shown below.

[1] $^1$H NMR: (DMSOd$_6$) 3.7 (s, 2H), 3.97 (s, 3H), 3.99 (s, 3H), 4.52 (d, 2H), 5.44 (t, 1H), 7.26 (d, 2H), 7.32 (d, 1H), 7.39 (s, 1H), 7.44 (d, 2H), 7.55 (s, 1H), 7.63 (m, 1H), 7.78 (m, 1H), 8.53 (s, 1H), 10.36 (s, 1H); Mass Spectrum: M+H$^+$ 480 and 482.

4-Chloro-3-hydroxymethylaniline is described in *Liebig's Annalen der Chemie*, 1986, 438.

[2] $^1$H NMR: (DMSOd$_6$) 3.78 (s, 2H), 3.98 (s, 3H), 3.99 (s, 3H), 4.43 (d, 2H), 5.23 (t, 1H), 7.08 (m, 1H), 7.2 (t, 1H), 7.27 (d, 2H), 7.39 (s, 1H), 7.44 (d, 2H), 7.56 (s, 1H), 7.84 (m, 1H), 8.54 (s, 1H), 9.98 (s, 1H); Mass Spectrum: M+H$^+$ 464.

The 6-fluoro-3-hydroxymethylaniline used as a starting material was prepared as follows:—

A mixture of 4-fluoro-3-nitrobenzyl alcohol (0.5 g), 10% platinum-on-carbon catalyst (0.1 g) and ethyl acetate (25 ml) was stirred under 1.8 atmospheres pressure of hydrogen for 1 hour. The reaction mixture was filtered and the filtrate was evaporated. The residue was purified by column chromatography on silica using a 2:1 mixture of methylene chloride and ethyl acetate as eluent. There was thus obtained 6-fluoro-3-hydroxymethylaniline $^1$H NMR: (DMSOd$_6$) 4.41 (d, 2H), 5.19 (m, 3H) 6.42 (m, 1H), 6.77 (s, 1H), 6.95 (m, 1H).

[3] $^1$H NMR: (DMSOd$_6$) 3.65 (s, 2H), 3.74 (s, 3H), 3.97 (s, 3H), 3.99 (s, 3H), 4.46 (d, 2H), 5.05 (t, 1H), 6.87 (d, 1H), 7.26 (d, 2H), 7.39 (s, 1H), 7.44 (d, 2H), 7.55 (m, 3H), 8.53 (s, 1H), 10.07 (s, 1H); Mass Spectrum: M+H$^+$ 476.

The 3-hydroxymethyl-4-methoxyaniline used as a starting material was prepared as follows:—

A mixture of 2-methoxy-5-nitrobenzaldehyde (3 g), platinum oxide (0.3 g) and methanol (150 ml) was stirred under 2 atmospheres pressure of hydrogen for 3 hours. The catalyst was removed by filtration and the filtrate was evaporated. There was thus obtained 3-hydroxymethyl-4-methoxyaniline as a solid (2.08 g); $^1$H NMR: (DMSOd$_6$) 3.63 (s, 3H), 4.38 (d, 2H), 4.56 (br s, 2H), 4.82 (t, 1H), 6.38 (m, 1H), 6.62 (d, 1H), 6.67 (m, 1H).

[4] $^1$H NMR: (DMSOd$_6$) 0.32-0.37 (m, 2H), 0.43-0.49 (m, 2H), 1.7-1.76 (m, 1H), 2.13 (s, 3H), 2.25 (s, 3H), 3.53 (s, 2H), 3.66 (s, 2H), 3.97 (s, 3H), 3.99 (s, 3H), 6.75 (s, 1H), 7.25 (d, 2H), 7.26 (s, 1H), 7.39 (s, 1H), 7.4 (br s, 1H), 7.43 (d, 2H), 7.55 (s, 1H), 8.53 (s, 1H), 10.1 (s, 1H); Mass Spectrum: M+H$^+$ 513.

The 3-(N-cyclopropyl-N-methylaminomethyl)-5-methylaniline used as a starting material was prepared as follows:—

A mixture of 1,3-dimethyl-5-nitrobenzene (15.15 g), N-bromosuccinimide (2 g), benzoyl peroxide (0.484 g) and carbon tetrachloride (250 ml) was stirred and heated to reflux. Further portions of N-bromosuccinimide (totaling 21 g) were added portionwise during 4 hours to the heated reaction mixture. The mixture was cooled to ambient temperature. Petroleum ether (b.p. 60-80° C.) was added. The mixture was filtered and the filtrate was evaporated to give an oil (25 g) which was shown by NMR analysis to be a mixture of 3-methyl-5-nitrobenzyl bromide (76%), unreacted starting material (~19%) and 3-bromomethyl-5-nitrobenzyl bromide (~15%). This mixture was used in the next step.

A portion (15 g) of the oil so obtained was dissolved in methylene chloride (15 ml) and added slowly to a stirred mixture of cyclopropylamine (15.3 ml) and ethanol (15 ml) at such a rate that the temperature of the reaction mixture was maintained below 40° C. The resultant reaction mixture was stirred at ambient temperature for 6 hours. The mixture was evaporated and the residue was purified by column chromatography on silica using increasingly polar mixtures of methylene chloride and diethyl ether as eluent. There was thus obtained N-cyclopropyl-N-(3-methyl-5-nitrobenzyl)amine (5.45 g); $^1$H NMR: (DMSOd$_6$) 0.25 (m, 2H), 0.35 (m, 2H), 2.03 (m, 1H), 2.88 (br s, 1H), 3.8 (s, 3H), 7.6 (s, 1H), 7.92 (s, 1H), 7.99 (s, 1H).

Sodium triacetoxyborohydride (1.78 g) was added portionwise to a stirred mixture of N-cyclopropyl-N-(3-methyl-5-nitrobenzyl)amine (1.44 g), formaldehyde (37% aqueous solution, 0.81 ml), acetic acid (0.48 ml), methylene chloride (20 ml) and methanol (10 ml) and the reaction mixture was stirred at ambient temperature for 2 hours. The mixture was evaporated and the residue was purified by column chromatography on silica using increasingly polar mixtures of methylene chloride and diethyl ether as eluent. There was thus obtained N-cyclopropyl-N-methyl-N-(3-methyl-5-nitrobenzyl)amine (1.32 g); $^1$H NMR: (DMSOd$_6$) 0.35 (m, 2H), 0.46 (m, 2H), 1.77 (m, 1H), 2.17 (s, 3H), 2.42 (s, 3H), 3.7 (s, 2H), 7.54 (s, 1H), 7.88 (s, 1H), 7.95 (s, 1H); Mass Spectrum: M+H$^+$ 221.

A mixture of the material so obtained, platinum oxide (0.1 g), methanol (5 ml) and ethyl acetate (20 ml) was stirred under 1.8 atmospheres pressure of hydrogen for 2.5 hours. The catalyst was removed by filtration and the filtrate was evaporated. The residue was purified by column chromatography on silica using a solvent gradient from 5:5:0 to 5:5:1 of methylene chloride, ethyl acetate and 3M methanolic ammonia as eluent. There was thus obtained 3-(N-cyclopropyl-N-methylaminomethyl)-5-methylaniline (1.04 g); $^1$H NMR: (DMSOd$_6$) 0.32 (m, 2H), 0.44 (m, 2H), 1.69 (m, 1H), 2.1 (s, 3H), 2.11 (s, 3H), 3.95 (s, 2H), 4.86 (s, 2H), 6.2 (s, 1H), 6.23 (s, 1H), 6.26 (s, 1H).

[5] 2-(Benzotriazol-1-yl)-1,1,3,3-tetramethyluronium tetrafluoroborate was used in place of 2-(7-azabenzotriazol-1- yl)-1,1,3,3-tetramethyluronium hexafluorophosphate(V) and the reaction mixture was stirred at ambient temperature for 18 hours. The product so obtained gave the following characterising data:—$^1$H NMR: (DMSOd$_6$) 0.35 (m, 2H), 0.45 (m, 2H), 1.75 (m, 1H), 2.15 (s, 3H), 2.25 (s, 3H), 3.55 (s, 2H), 3.65 (s, 2H), 3.8 (m, 2H), 4.0 (s, 3H), 4.2 (m, 2H), 5.0 (m, 1H), 6.75 (s, 1H), 7.25 (m, 3H), 7.4 (m, 4H), 7.55 (s, 1H), 8.5 (s, 1H), 10.1 (s, 1H); Mass Spectrum: M+H$^+$ 543.

EXAMPLE 4

N-(4-chloro-3-isopropylaminomethylphenyl)-2-[4-(6,7-dimethoxyquinazolin-4-yloxy)phenyl]acetamide Sodium triacetoxyborohydride (0.072 g) was added portionwise to a stirred mixture of N-(4-chloro-3-formylphenyl)-2-[4-(6,7-dimethoxyquinazolin-4-oxy)phenyl]acetamide (0.08 g), isopropylamine (0.021 g), trimethyl orthoformate (0.2 ml), methanol (0.2 ml) and methylene chloride (0.6 ml) and the resultant mixture was stirred at ambient temperature for 12 hours. The mixture was evaporated and the residue was purified by preparative HPLC using a Waters 'β Basic Hypersil' reversed-phase column (5 microns silica, 20 mm diameter, 100 mm length) and decreasingly polar mixtures of water (containing 0.2% ammonium carbonate) and acetonitrile as eluent. There was thus obtained the title compound as a solid (0.031 g); $^1$H NMR: (DMSOd$_6$) 1.03 (d, 6H), 1.88 (br s, 1H), 2.71-2.8 (m, 1H), 3.7 (s, 2H), 3.72 (br s, 2H), 3.97 (s, 3H), 3.99 (s, 3H), 7.26 (d, 2H), 7.32 (d, 1H), 7.39 (s, 1H), 7.44 (d, 2H), 7.55 (s, 1H), 7.64 (m, 1H), 7.73 (d, 1H), 8.53 (s, 1H), 10.34 (s, 1H); Mass Spectrum: M+H$^+$ 521 and 523.

The N-(4-chloro-3-formylphenyl)-2-[4-(6,7-dimethoxyquinazolin-4-yloxy)phenyl]acetamide used as a starting material was prepared as follows:—

N-Methylmorpholine N-oxide (0.674 g) and tetra-n-propylammonium ruthenium tetroxide (0.15 g) were added in turn to a stirred mixture of N-(4-chloro-3-hydroxymethylphenyl)-2-[4-(6,7-dimethoxyquinazolin-4-yloxy)phenyl]acetamide (2.3 g), 4 Å molecular sieves (1.5 g), methylene chloride (30 ml) and acetonitrile (30 ml). The resultant mixture was heated to 50° C. for 12 hours. The mixture was evaporated and the residue was purified by column chromatography on silica using a 19:1 mixture of methylene chloride and methanol as eluent. There was thus obtained the required starting material as a solid (1.45 g); $^1$H NMR: (DMSOd$_6$) 3.73 (s, 2H), 3.97 (s, 3), 3.99 (s, 3H), 7.26 (d, 2H), 7.39 (s, 1H), 7.44 (d, 2H), 7.55 (s, 1H), 7.59 (d, 1H), 7.93 (m, 1H), 8.18 (m, 1H), 8.53 (s, 1H), 10.31 (s, 1H), 10.6 (s, 1H).

EXAMPLE 5

Using an analogous procedure to that described in Example 4, the appropriate N-(3-formylphenyl)-2-phenylacetamide was reacted with the appropriate amine or heterocycle to give the compounds described in Table II. Unless otherwise stated, each required amine or heterocycle starting material was commercially available.

TABLE II

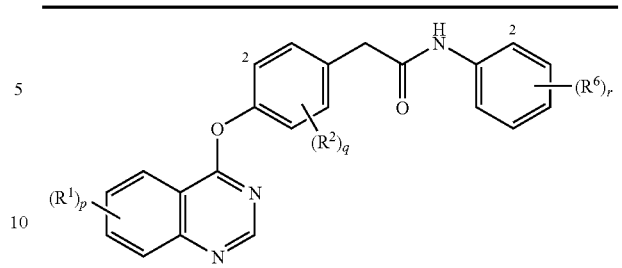

| No. & Note | (R$^1$)$_p$ | (R$^2$)$_q$ | (R$^6$)$_r$ |
|---|---|---|---|
| [1] | 6,7-dimethoxy | H | 4-chloro-3-ethylaminomethyl |
| [2] | 6,7-dimethoxy | H | 4-chloro-3-(N-ethyl-N-methylaminomethyl) |
| [3] | 6,7-dimethoxy | H | 4-chloro-3-(2-methylprop-2-en-1-ylaminomethyl) |
| [4] | 6,7-dimethoxy | H | 4-chloro-3-cycloprop-1-ylmethylaminomethyl |
| [5] | 6,7-dimethoxy | H | 4-chloro-3-(2-hydroxypropylaminomethyl) |
| [6] | 6,7-dimethoxy | H | 4-chloro-3-(2-hydroxy-1-methylethylaminomethyl) |
| [7] | 6,7-dimethoxy | H | 3-azetidin-1-ylmethyl-4-chloro |
| [8] | 6,7-dimethoxy | H | 4-chloro-3-[(2S)-2-hydroxymethylpyrrolidin-1-ylmethyl] |
| [9] | 6,7-dimethoxy | H | 4-chloro-3-[(2R)-2-hydroxymethylpyrrolidin-1-ylmethyl |
| [10] | 6,7-dimethoxy | H | 4-chloro-3-[(N-methylpyrrol-2-yl)methylaminomethyl] |
| [11] | 6,7-dimethoxy | H | 4-chloro-3-furfurylaminomethyl |
| [12] | 6,7-dimethoxy | H | 4-chloro-3-pyrid-3-ylmethylaminomethyl] |
| [13] | 6,7-dimethoxy | H | 3-ethylaminomethyl-6-fluoro |
| [14] | 6,7-dimethoxy | H | 3-(N-ethyl-N-methylaminomethyl)-6-fluoro |
| [15] | 6,7-dimethoxy | H | 6-fluoro-3-isopropylaminomethyl |
| [16] | 6,7-dimethoxy | H | 6-fluoro-3-(2-methylprop-2-en-1-ylaminomethyl) |
| [17] | 6,7-dimethoxy | H | 3-cycloprop-1-ylmethylaminomethyl-6-fluoro |
| [18] | 6,7-dimethoxy | H | 6-fluoro-3-(2-hydroxypropylaminomethyl) |
| [19] | 6,7-dimethoxy | H | 6-fluoro-3-(2-hydroxy-1-methylethylaminomethyl) |
| [20] | 6,7-dimethoxy | H | 3-azetidin-1-ylmethyl-6-fluoro |
| [21] | 6,7-dimethoxy | H | 6-fluoro-3-[(2R)-2-hydroxymethylpyrrolidin-1-ylmethyl] |
| [22] | 6,7-dimethoxy | H | 6-fluoro-3-[(N-methylpyrrol-2-yl)methylaminomethyl] |
| [23] | 6,7-dimethoxy | H | 6-fluoro-3-furfurylaminomethyl |
| [24] | 6,7-dimethoxy | H | 6-fluoro-3-pyrid-3-ylmethylaminomethyl |
| [25] | 6,7-dimethoxy | H | 3-ethylaminomethyl-4-methoxy |
| [26] | 6,7-dimethoxy | H | 3-(N-ethyl-N-methylaminomethyl)-4-methoxy |
| [27] | 6,7-dimethoxy | H | 3-isopropylaminomethyl-4-methoxy |
| [28] | 6,7-dimethoxy | H | 4-methoxy-3-(2-methylprop-2-en-1-ylaminomethyl) |
| [29] | 6,7-dimethoxy | H | 3-cycloprop-1-ylmethylaminomethyl-4-methoxy |
| [30] | 6,7-dimethoxy | H | 3-(2-hydroxypropylaminomethyl)-4-methoxy |

TABLE II-continued

[Structure: quinazoline with 4-oxy linker to phenyl(R²)q-CH₂-C(O)-NH-phenyl(R⁶)r, with (R¹)p on the quinazoline]

| No. & Note | (R¹)p | (R²)q | (R⁶)r |
|---|---|---|---|
| [31] | 6,7-dimethoxy | H | 3-(2-hydroxy-1-methylethylaminomethyl)-4-methoxy |
| [32] | 6,7-dimethoxy | H | 3-azetidin-1-ylmethyl-4-methoxy |
| [33] | 6,7-dimethoxy | H | 3-[(2R)-2-hydroxymethyl-pyrrolidin-1-ylmethyl]-4-methoxy |
| [34] | 6,7-dimethoxy | H | 4-methoxy-3-[(N-methylpyrrol-2-yl)methylaminomethyl] |
| [35] | 6,7-dimethoxy | H | 3-furfurylaminomethyl-4-methoxy |
| [36] | 6,7-dimethoxy | H | 4-methoxy-3-pyrid-3-ylmethylaminomethyl |
| [37] | 6,7-dimethoxy | 3-methoxy | 3-dimethylaminomethyl |
| [38] | 7-ethoxy-6-methoxy | 3-methoxy | 3-dimethylaminomethyl |

Notes The products gave the characterising data shown below.

[1] Mass Spectrum: M+H⁺ 507 and 509.

[2] ¹H NMR: (DMSOd₆) 1.05 (t, 3H), 2.16 (s, 3H), 2.1 (br s, 1H), (2.40-2.47 (m, 2H), 3.5 (s, 2H), 3.69 (s, 2H), 3.97 (s, 3H), 3.99 (s, 3H), 7.26 (d, 2H), 7.34 (d, 1H), 7.39 (s, 1H), 7.43 (d, 2H), 7.55 (s, 1H), 7.63 (m, 1H), 7.73 (d, 1H), 8.53 (s, 1H), 10.34 (br s, 1H); Mass Spectrum: M+H⁺ 521 and 523.

[3] ¹H NMR: (DMSOd₆) 1.72 (s, 3H), 2.25 (br s, 1H), 3.11 (s, 2H), 3.67 (s, 2H), 3.7 (s, 2H), 3.97 (s, 3H), 3.99 (s, 3H), 4.82 (br s, 1H), 4.91 (br s, 1H), 7.26 (d, 2H), 7.33 (d, 1H), 7.39 (s, 1H), 7.44 (d, 2H), 7.55 (s, 1H), 7.62 (m, 1H), 7.76 (d, 1H), 8.53 (s, 1H), 10.34 (s, 1H); Mass Spectrum: M+H⁺ 533 and 535.

[4] ¹H NMR: (DMSOd₆) 0.09-0.14 (m, 2H), 0.38-0.44 (m, 2H), 0.89-0.97 (m, 1H), 2.42 (d, 2H), 3.7 (s, 2H), 3.75 (s, 2H), 3.98 (s, 3H), 3.99 (s, 3H), 7.26 (d, 2H), 7.33 (d, 1H), 7.39 (s, 1H), 7.44 (d, 2H), 7.55 (s, 1H), 7.63 (m, 1H), 7.74 (d, 1H), 8.53 (s, 1H), 10.34 (s, 1H); Mass Spectrum: M+H⁺ 533 and 535.

[5] ¹H NMR: (DMSOd₆) 1.06 (d, 3H), 2.07 (br s, 1H), 2.43-2.47 (m, 2H), 3.68-3.75 (m, 1H), 3.7 (s, 2H), 3.74 (s, 2H), 3.97 (s, 3H), 3.99 (s, 3H), 4.5 (d, 1H), 7.26 (d, 2H), 7.33 (d, 1H), 7.39 (s, 1H), 7.44 (d, 2H), 7.55 (s, 1H), 7.62 (m, 1H), 7.72 (d, 1H), 8.53 (s, 1H), 10.34 (s, 1H); Mass Spectrum: M+H⁺ 537 and 539.

[6] ¹H NMR: (DMSOd₆) 0.97 (d, 3H), 2.02 (br s, 1H), 2.6-2.68 (m, 1H), 3.24-3.33 (m, 2H), 3.7 (s, 2H), 3.7-3.82 (m, 2H), 3.97 (s, 3H), 3.99 (s, 3H), 4.56 (t, 1H), 7.26 (d, 2H), 7.33 (d, 1H), 7.39 (s, 1H), 7.43 (d, 2H), 7.55 (s, 1H), 7.63 (m, 1H), 7.73 (d, 1H), 8.53 (s, 1H), 10.34 (s, 1H); Mass Spectrum: M+H⁺ 537 and 539.

[7] ¹H NMR: (DMSOd₆) 1.99-2.06 (m, 2H), 3.18-3.24 (m, 4H), 3.56 (s, 2H), 3.7 (s, 2H), 3.97 (s, 3H), 3.99 (s, 3H), 7.27 (d, 2H), 7.32 (d, 1H), 7.39 (s, 1H), 7.44 (d, 2H), 7.55 (s, 1H), 7.61 (m, 1H), 7.67 (d, 1H), 8.54 (s, 1H), 10.34 (s, 1H); Mass Spectrum: M+H³⁰ 519 and 521.

[8] ¹H NMR: (DMSOd₆) 1.51-1.72 (m, 3H), 1.84-1.94 (m, 1H), 2.14-2.21 (m, 1H), 2.61-2.68 (m, 1H), 2.87-2.94 (m, 1H), 3.27-3.33 (m, 1H), 3.45-3.52 (m, 2H), 3.7 (s, 2H), 3.97 (s, 3H), 3.99 (s, 3H), 4.06 (d, 1H), 4.43 (t, 1H), 7.26 (d, 2H), 7.32 (d, 1H), 7.39 (d, 2H), 7.43 (s, 1H), 7.56 (s, 1H), 7.67 (m, 1H), 7.68 (s, 1H), 8.54 (s, 1H), 10.34 (s, 1H); Mass Spectrum: M+H⁺ 563 and 565.

[9] ¹H NMR: (DMSOd₆) 1.52-1.72 (m, 3H), 1.84-1.93 (m, 1H), 2.14-2.22 (m, 1H), 2.6-2.68 (m, 1H), 2.87-2.94 (m, 1H), 3.26-3.32 (m, 1H), 3.45-3.52 (m, 2H), 3.7 (s, 2H), 3.97 (s, 3H), 3.99 (s, 3H), 4.07 (d, 1H), 4.42 (t, 1H), 7.26 (d, 2H), 7.32 (d, 1H), 7.39 (s, 1H), 7.43 (d, 2H), 7.55 (s, 1H), 7.66 (m, 1H), 7.68 (d, 1H), 8.54 (s, 1H), 10.34 (s, 1H); Mass Spectrum: M+H⁺ 563 and 565.

[10] ¹H NMR: (DMSOd₆) 2.15 (br s, 1H), 3.59 (s, 3H), 3.66 (s, 2H), 3.7 (s, 2H), 3.72 (s, 2H), 3.97 (s, 3H), 3.99 (s, 3H), 5.87 (m, 1H), 5.92 (m, 1H), 6.64 (m, 1H), 7.26 (d, 2H), 7.33 (d, 1H), 7.39 (d, 1H), 7.44 (d, 2H), 7.55 (s, 1H), 7.61 (m, 1H), 7.78 (d, 1H), 8.53 (s, 1H), 10.34 (s, 1H); Mass Spectrum: M+H⁺ 572 and 574.

[11] ¹H NMR: (DMSOd₆) 3.7 (s, 2H), 3.7-3.74 (m, 4H), 3.97 (s, 3H), 3.99 (s, 3H), 6.29 (d, 1H), 6.40 (m, 1H), 7.26 (d, 2H), 7.33 (d, 1H), 7.39 (s, 1H), 7.44 (d, 2H), 7.55 (s, 1H), 7.57 (m, 1H), 7.64 (m, 1H), 7.75 (d, 1H), 8.53 (s, 1H), 10.35 (s, 1H); Mass Spectrum: M+H⁺ 559 and 561.

[12] ¹H NMR: (DMSOd₆) 2.75 (br s, 1H), 3.7 (s, 2H), 3.72 (s, 2H), 3.77 (s, 2H), 3.97 (s, 3H), 3.99 (s, 3H), 7.27 (d, 2H), 7.34 (d, 1H), 7.36 (m, 1H), 7.39 (s, 1H), 7.44 (d, 2H), 7.55 (s, 1H), 7.64 (m, 1H), 7.79 (m, 1H), 7.7 (d, 1H), 8.45 (m, 1H), 8.53 (s, 1H), 8.58 (d, 1H), 10.36 (s, 1H); Mass Spectrum: M+H⁺ 570 and 572.

[13] ¹H NMR: (DMSOd₆) 1.01 (t, 3H), 2.05 (br s, 1H), 2.47-2.51 (m, 2H), 3.62 (s, 2H), 3.78 (s, 2H), 3.98 (s, 3H), 3.99 (s, 3H), 7.09 (m, 1H), 7.17 (m, 1H), 7.27 (d, 2H), 7.39 (s, 1H), 7.44 (d, 2H), 7.56 (s, 1H), 7.83 (m, 1H), 8.54 (s, 1H), 9.96 (s, 1H); Mass Spectrum: M+H⁺ 491.

The N-(6-fluoro-3-formylphenyl)-2-[4-(6,7-dimethoxyquinazolin-4-yloxy) phenyl]acetamide used as a starting material was prepared as follows:—

Using an analogous procedure to that described in the portion of Example 4 that is concerned with the preparation of starting materials, N-(6-fluoro-3-hydroxymethylphenyl)-2-[4-(6,7-dimethoxyquinazolin-4-yloxy) phenyl]acetamide (Example 3(2) above) was oxidised to give the required starting material in 64% yield; ¹H NMR: (DMSOd₆) 3.73 (s, 2H), 3.97 (s, 3H), 3.99 (s, 3H), 7.27 (d, 2H), 7.39 (s, 1H), 7.44 (d, 2H), 7.55 (s, 1H), 7.59 (d, 1H), 7.92 (m, 1H), 8.18 (m, 1H), 8.53 (s, 1H), 10.31 (s, 1H), 10.6 (s, 1H).

[14] ¹H NMR: (DMSOd₆) 1.0 (t, 3H), 2.08 (s, 3H), 2.34 (d, 1H), 2.37 (d, 1H), 3.38 (s, 2H), 3.78 (s, 2H), 3.97 (s, 3H), 3.99 (s, 3H), 7.05 (m, 1H), 7.18 (m, 1H), 7.27 (d, 2H), 7.39 (s, 1H), 7.44 (d, 2H), 7.56 (s, 1H), 7.85 (m, 1H), 8.54 (s, 1H), 9.97 (s, 1H); Mass Spectrum: M+H⁺ 505.

[15] ¹H NMR: (DMSOd₆) 0.98 (d, 6H), 1.86 (br s, 1H), 2.62-2.73 (m, 1H), 3.63 (s, 2H), 3.77 (s, 2H), 3.97 (s, 3H), 3.99 (s, 3H), 7.11 (m, 1H), 7.17 (m, 1H), 7.27 (d, 2H), 7.39 (s, 1H), 7.44 (d, 2H), 7.56 (s, 1H), 7.83 (m, 1H), 8.54 (s, 1H), 9.95 (s, 1H); Mass Spectrum: M+H⁺ 505.

[16] ¹H NMR: (DMSOd₆) 1.68 (s, 3H), 2.25 (br s, 1H), 3.01 (s, 2H), 3.58 (s, 2H), 3.78 (s, 2H), 3.97 (s, 3H), 3.99 (s, 3H), 4.76-4.81 (m, 1H), 4.84-4.87 (m, 1H), 7.10 (m, 1H), 7.18 (m, 1H), 7.27 (d, 2H), 7.39 (s, 1H), 7.45 (d, 2H), 7.56 (s, 1H), 7.84 (m, 1H), 8.54 (s, 1H), 9.96 (s, 1H); Mass Spectrum: M+H⁺ 517.

[17] $^1$H NMR: (DMSOd$_6$) 0.04-0.1 (m, 2H), 0.35-0.41 (m, 2H), 0.82-0.92 (m, 1H), 2.05 (br s, 1H), 2.33 (d, 2H), 3.65 (s, 2H), 3.78 (s, 2H), 3.98 (s, 3H), 3.99 (s, 3H), 7.09 (m, 1H), 7.17 (m, 1H), 7.26 (d, 2H), 7.39 (s, 1H), 7.44 (d, 2H), 7.56 (s, 1H), 7.83 (m, 1H), 8.54 (s, 1H), 9.95 (s, 1H); Mass Spectrum: M+H$^+$ 517.

[18] $^1$H NMR: (DMSOd$_6$) 1.01 (d, 3H), 2.13 (br s, 1H), 2.38 (d, 2H), 3.64 (s, 2H), 3.65-3.71 (m, 1H), 3.78 (s, 2H), 3.97 (s, 3H), 3.99 (s, 3H), 4.45 (d, 1H), 7.10 (m, 1H), 7.18 (m, 1H), 7.27 (d, 2H), 7.39 (d, 1H), 7.45 (d, 2H), 7.56 (s, 1H), 7.83 (m, 1H), 8.54 (s, 1H), 9.96 (s, 1H); Mass Spectrum: M+H$^+$ 521.

[19] $^1$H NMR: (DMSOd$_6$) 0.92 (d, 3H), 1.94 (br s, 1H), 2.55-2.63 (m, 1H), 3.22-3.3 (m, 2H), 3.62 (d, 1H), 3.71 (d, 1H), 3.78 (d, 2H), 3.97 (s, 3H), 3.99 (s, 3H), 4.51 (t, 1H), 7.11 (m, 1H), 7.18 (m, 1H), 7.27 (d, 2H), 7.39 (s, 1H), 7.45 (d, 2H), 7.56 (s, 1H), 7.85 (m, 1H), 8.54 (s, 1H), 9.96 (s, 1H); Mass Spectrum: M+H$^+$ 521.

[20] $^1$H NMR: (DMSOd$_6$) 1.91-2.0 (m, 2H), 3.05-3.11 (m, 4H), 3.44 (s, 2H), 3.78 (s, 2H), 3.98 (s, 3H), 3.99 (s, 3H), 7.01 (m, 1H), 7.17 (m, 1H), 7.27 (d, 2H), 7.39 (s, 1H), 7.44 (d, 2H), 7.56 (s, 1H), 7.81 (s, 1H), 8.54 (s, 1H), 9.96 (s, 1H); Mass Spectrum: M+H$^+$ 503.

[21] $^1$H NMR: (DMSOd$_6$) 1.5-1.65 (m, 3H), 1.77-1.88 (m, 1H), 2.09-2.15 (m, 1H), 2.51-2.57 (m, 1H), 2.73-2.8 (m, 1H), 3.22-3.3 (m, 2H), 3.36-3.48 (m, 2H), 3.78 (s, 2H), 3.97 (s, 3H), 3.99 (s, 3H), 4.42 (t, 1H), 7.08 (m, 1H), 7.17 (m, 1H), 7.27 (d, 2H), 7.39 (s, 1H), 7.44 (d, 2H), 7.56 (s, 1H), 7.81 (m, 1H), 8.54 (s, 1H), 9.96 (s, 1H); Mass Spectrum: M+H$^+$ 547.

[22] $^1$H NMR: (DMSOd$_6$) 2.26 (br s, 1H), 3.55 (s, 3H), 3.56 (s, 2H), 3.62 (s, 2H), 3.78 (s, 2H), 3.98 (s, 3H), 3.99 (s, 3H), 5.83-5.88 (m, 2H), 6.61 (m, 1H), 7.11 (m, 1H), 7.19 (m, 1H), 7.27 (d, 2H), 7.39 (s, 1H), 7.45 (d, 2H), 7.56 (s, 1H), 7.87 (m, 1H), 8.54 (s, 1H), 9.97 (s, 1H); Mass Spectrum: M+H$^+$ 556.

[23] $^1$H NMR: (DMSOd$_6$) 3.62 (s, 4H), 3.78 (s, 2H), 3.98 (s, 3H), 3.99 (s, 3H), 6.24 (d, 1H), 6.38 (m, 1H), 7.10 (m, 1H), 7.19 (m, 1H), 7.27 (d, 2H), 7.39 (s, 1H), 7.45 (d, 2H), 7.55 (m, 1H), 7.56 (s, 1H), 7.84 (m, 1H), 8.54 (s, 1H), 9.97 (s, 1H); Mass Spectrum: M+H$^+$ 543.

[24] $^1$H NMR: (DMSOd$_6$) 3.63 (s, 2H), 3.67 (s, 2H), 3.78 (s, 2H), 3.98 (s, 3H), 3.99 (s, 3H), 7.12 (m, 1H), 7.2 (m, 1H), 7.27 (d, 2H), 7.33 (m, 1H), 7.39 (s, 1H), 7.45 (d, 2H), 7.56 (s, 1H), 7.75 (m, 1H), 7.88 (m, 1H), 8.43 (m, 1H), 8.52 (d, 1H), 8.54 (s, 1H), 9.98 (s, 1H); Mass Spectrum: M+H$^+$ 554.

[25] $^1$H NMR: (DMSOd$_6$) 1.01 (t, 3H), 1.93 (br s, 1H), 2.52 (d, 1H), 2.55 (d, 1H), 3.62 (s, 2H), 3.65 (s, 2H), 3.74 (s, 3H), 3.97 (s, 3H), 3.99 (s, 3H), 6.88 (d, 1H), 7.26 (d, 2H), 7.39 (s, 1H), 7.43 (d, 2H), 7.49 (d, 1H), 7.54 (m, 1H), 7.55 (s, 1H), 8.53 (s, 1H), 10.05 (s, 1H); Mass Spectrum: M+H$^+$ 503.

The N-(3-formyl-4-methoxyphenyl)-2-[4-(6,7-dimethoxyquinazolin-4-yloxy)phenyl]acetamide used as a starting material was prepared as follows:—

Using an analogous procedure to that described in the portion of Example 4 that is concerned with the preparation of starting materials, N-(3-hydroxymethyl-4-methoxyphenyl)-2-[4-(6,7-dimethoxyquinazolin-4-yloxy)phenyl]acetamide (Example 3(3) above) was oxidised to give the required starting material in 78% yield; $^1$H NMR: (DMSOd$_6$) 3.68 (s, 2H), 3.9 (s, 3H), 3.97 (s, 3H), 3.99 (s, 3H), 7.22 (d, 1H), 7.26 (d, 2H), 7.39 (s, 1H), 7.44 (d, 2H), 7.55 (s, 1H), 7.88 (m, 1H), 7.97 (m, 1H), 8.53 (s, 1H), 10.29 (s, 1H), 10.34 (s, 1H); Mass Spectrum: M+H$^+$ 474.

[26] $^1$H NMR: (DMSOd$_6$) 1.01 (t, 3H), 2.12 (s, 3H), 2.38 (d, 1H), 2.41 (d, 1H), 3.4 (s, 2H), 3.65 (s, 2H), 3.73 (s, 3H), 3.97 (s, 3H), 3.99 (s, 3H), 6.9 (d, 1H), 7.26 (d, 2H), 7.39 (s, 1H), 7.43 (d, 2H), 7.52 (d, 1H), 7.55 (s, 1H), 7.56 (m, 1H), 8.54 (s, 1H), 10.06 (s, 1H); Mass Spectrum: M+H$^+$ 517.

[27] $^1$H NMR: (DMSOd$_6$) 1.0 (d, 6H), 1.66 (br s, 1H), 2.66-2.76 (m, 1H), 3.63 (s, 2H), 3.65 (s, 2H), 3.75 (s, 3H), 3.97 (s, 3H), 3.99 (s, 3H), 6.88 (d, 1H), 7.25 (d, 2H), 7.39 (s, 1H), 7.43 (d, 2H), 7.49 (d, 1H), 7.55 (m, 1H), 7.56 (s, 1H), 8.54 (s, 1H), 10.05 (s, 1H); Mass Spectrum: M+H$^+$ 517.

[28] $^1$H NMR: (DMSOd$_6$) 1.7 (s, 3H), 1.97 (br s, 1H), 3.07 (s, 2H), 3.57 (s, 2H), 3.65 (s, 2H), 3.74 (s, 3H), 3.97 (s, 3H), 3.99 (s, 3H), 4.8 (br s, 1H), 4.89 (br s, 1H), 6.89 (d, 1H), 7.26 (d, 2H), 7.39 (s, 1H), 7.43 (d, 2H), 7.50 (d, 1H), 7.53 (m, 1H), 7.55 (s, 1H), 8.53 (s, 1H), 10.05 (s, 1H); Mass Spectrum: M+H$^+$ 529.

[29] $^1$H NMR: (DMSOd$_6$) 0.06-0.12 (m, 2H), 0.36-0.44 (m, 2H), 0.85-0.95 (m, 1H), 1.82 (br s, 1H), 2.38 (d, 2H), 3.64 (s, 2H), 3.65 (s, 2H), 3.75 (s, 3H), 3.97 (s, 3H), 3.99 (s, 3H), 6.88 (d, 1H), 7.26 (d, 2H), 7.39 (s, 1H), 7.43 (d, 2H), 7.5 (d, 1H), 7.53 (m, 1H), 7.55 (s, 1H), 8.53 (s, 1H), 10.05 (s, 1H); Mass Spectrum: M+H$^+$ 529.

[30] $^1$H NMR: (DMSOd$_6$) 1.04 (d, 3H), 1.86 (br s, 1H), 2.39-2.45 (m, 2H), 3.58-3.67 (m, 2H), 3.65 (s, 2H), 3.66-3.72 (m, 1H), 3.74 (s, 3H), 3.97 (s, 3H), 3.99 (s, 3H), 4.46 (d, 1H), 6.9 (d, 1H), 7.26 (d, 2H), 7.39 (s, 1H), 7.43 (d, 2H), 7.48 (d, 1H), 7.53 (m, 1H), 7.55 (s, 1H), 8.53 (s, 1H), 10.05 (s, 1H); Mass Spectrum: M+H$^+$ 533.

[31] $^1$H NMR: (DMSOd$_6$) 0.94 (d, 3H), 1.9 (br s, 1H), 2.57-2.64 (s, 1H), 3.19-3.26 (m, 1H), 3.26-3.33 (m, 1H), 3.61 (d, 1H), 3.65 (s, 2H), 3.69 (d, 1H), 3.75 (s, 3H), 3.97 (s, 3H), 3.99 (s, 3H), 4.52 (t, 1H), 6.89 (d, 1H), 7.26 (d, 2H), 7.39 (s, 1H), 7.43 (d, 2H), 7.48 (d, 1H), 7.54 (m, 1H), 7.56 (s, 1H), 8.53 (s, 1H), 10.05 (s, 1H); Mass Spectrum: M+H$^+$ 533.

[32] $^1$H NMR: (DMSOd$_6$) 1.94-2.03 (m, 2H), 3.11-3.19 (m, 4H), 3.45 (s, 2H), 3.65 (s, 2H), 3.73 (s, 3H), 3.97 (s, 3H), 3.99 (s, 3H), 6.87 (d, 1H), 7.26 (d, 2H) 7.39 (s, 1H), 7.43 (d, 2H), 7.45 (d, 1H), 7.53 (m, 1H), 7.56 (s, 1H), 8.54 (s, 1H), 10.05 (s, 1H); Mass Spectrum: M+H$^+$ 515.

[33] $^1$H NMR: (DMSOd$_6$) 1.5-1.69 (m, 3H), 1.81-1.89 (m, 1H), 2.1-2.18 (m, 1H), 2.54-2.62 (m, 1H), 2.87-2.93 (m, 1H), 3.25-3.33 (m, 1H), 3.4 (d, 1H), 3.43-3.49 (m, 1H), 3.65 (s, 2H), 3.74 (s, 3H), 3.91 (d, 1H), 3.97 (s, 3H), 3.99 (s, 3H), 4.31 (t, 1H), 6.88 (d, 1H), 7.26 (d, 2H), 7.39 (s, 1H), 7.43 (d, 2H), 7.46 (d, 1H), 7.56 (s, 1H), 7.58 (m, 1H), 8.54 (s, 1H), 10.05 (s, 1H); Mass Spectrum: M+H$^+$ 559.

[34] $^1$H NMR: (DMSOd$_6$) 1.99 (br s, 1H), 3.57 (s, 3H), 3.62 (br s, 4H), 3.65 (s, 2H), 3.75 (s, 3H), 3.97 (s, 3H), 3.99 (s, 3H), 5.86 (m, 1H), 5.90 (m, 1H), 6.62 (m, 1H), 6.9 (d, 1H), 7.26 (d, 2H), 7.39 (s, 1H), 7.44 (d, 2H), 7.52 (s, 1H), 7.53 (m, 1H), 7.55 (s, 1H), 8.53 (s, 1H), 10.05 (s, 1H); Mass Spectrum: M+H$^+$ 568.

[35] $^1$H NMR: (DMSOd$_6$) 2.26 (br s, 1H), 3.62 (s, 2H), 3.65 (s, 2H), 3.68 (s, 2H), 3.74 (s, 3H), 3.97 (s, 3H), 3.99 (s, 3H), 6.26 (d, 1H), 6.39 (m, 1H), 6.9 (d, 1H), 7.26 (d, 2H), 7.39 (s, 1H), 7.44 (d, 2H), 7.51 (d, 1H), 7.53-7.57 (m, 3H), 8.53 (s, 1H), 10.06 (s, 1H); Mass Spectrum: M+H$^+$ 555.

[36] $^1$H NMR: (DMSOd$_6$) 3.62 (s, 2H), 3.66 (s, 2H), 3.73 (s, 2H), 3.74 (s, 3H), 3.97 (s, 3H), 3.99 (s, 3H), 6.9 (d, 1H), 7.26 (d, 2H), 7.35 (m, 1H), 7.39 (s, 1H), 7.44 (d, 2H), 7.54-7.57 (m, 3H), 7.77 (m, 1H), 8.44 (m, 1H), 8.53 (s, 1H), 8.55 (d, 1H), 10.07 (s, 1); Mass Spectrum: M+H$^+$ 566.

[37] $^1$H NMR: (CDCl$_3$) 2.28 (s, 6H), 3.45 (s, 2H), 3.74 (s, 2H), 3.94 (s, 3H), 4.08 (s, 6H), 6.89 (s, 1H), 6.9 (m, 1H), 7.05 (d, 1H), 7.27 (m, 1H), 7.34 (s, 2H), 7.41 (d, 1H), 7.53 (d, 1H), 7.56 (s, 1H), 7.65 (br s, 1H), 8.64 (s, 1H); Mass Spectrum: M+H$^+$ 503.

The N-(3-formylphenyl)-2-[4-(6,7-dimethoxyquinazolin-4-yloxy)-2-methoxyphenyl]acetamide used as a starting material was prepared as follows:—

A mixture of 4-hydroxy-2-methoxybenzaldehyde (5.57 g), benzyl bromide (3.98 ml), potassium iodide (8.22 g), potassium carbonate (6.83 g) and DMA (20 ml) was stirred and heated to 50° C. for 2 hours. The resultant mixture was cooled and evaporated. The residue was purified by column chromatography on silica using increasingly polar mixtures of diethyl ether and ethyl acetate as eluent. There was thus obtained 4-benzyloxy-2-methoxybenzaldehyde (8.05 g); $^1$H NMR: (CDCl$_3$) 3.88 (s, 3H), 5.13 (s, 2H), 6.53 (s, 1H), 6.63 (m, 1H), 7.34-7.44 (m, 5H), 7.81 (d, 1H).

A solution of 4-toluenesulphonyl isocyanide (3.33 g) in 1,2-dimethoxyethane (10 ml) was added portionwise to a stirred solution of potassium tert-butoxide (3.79 g) in 1,2-dimethoxyethane (50 ml) that had been cooled to −78° C. A solution of 4-benzyloxy-2-methoxybenzaldehyde (3.9 g) in 1,2-dimethoxyethane (10 ml) was added whilst the temperature of the reaction mixture was maintained at −78° C. The resultant mixture was allowed to warm to ambient temperature and was stirred for 1 hour. Methanol (85 ml) was added and the mixture was heated to reflux for 2 hours. The mixture was evaporated and the residue was purified by column chromatography on silica using increasingly polar mixtures of methylene chloride and ethyl acetate as eluent. There was thus obtained 2-(4-benzyloxy-2-methoxyphenyl) acetonitrile (3.46 g); $^1$H NMR: (CDCl$_3$) 3.6 (s, 2H), 3.82 (s, 3H), 5.05 (s, 2H), 6.54 (m, 2H), 7.21-7.44 (m, 6H); Mass Spectrum: M+H$^+$ 254.

A mixture of the material so obtained, a 6N aqueous sodium hydroxide solution (40 ml), THF (40 ml) and methanol (40 ml) was stirred and heated to 85° C. for 24 hours. The mixture was concentrated by evaporation. The residual aqueous mixture was acidified to pH2 by the addition of 6N aqueous hydrochloric acid and extracted with methylene chloride. The organic solution was dried over magnesium sulphate and evaporated. There was thus obtained 2-(4-benzyloxy-2-methoxyphenyl)acetic acid (2.36 g); $^1$H NMR: (CDCl$_3$) 3.59 (s, 2H), 3.79 (s, 3H), 5.04 (s, 2H), 6.53 (m, 2H), 7.08 (d, 1H), 7.31-7.44 (m, 5H); Mass Spectrum: M+H$^+$ 272.

Using an analogous procedure to that described in Example 1, 2-(4-benzyloxy-2-methoxyphenyl)acetic acid was reacted with 3-(1,1-dimethoxymethyl)aniline to give N-[3-(1,1-dimethoxymethyl)phenyl]-2-(4-benzyloxy-2-methoxyphenyl)acetamide in 51% yield. The compound was obtained as a mixture of the dimethoxyacetal and the corresponding aldehyde.

The mixture of compounds so obtained, 10% platinum-on-carbon catalyst, ethanol (2 ml) and ethyl acetate (30 ml) was stirred under 3 atmospheres pressure of hydrogen for 5 hours to give N-[3-(1,1-dimethoxymethyl)phenyl]-2-(4-hydroxy-2-methoxyphenyl) acetamide. This compound was also obtained as a mixture of the dimethoxyacetal and the corresponding aldehyde.

The mixture of compounds so obtained was dissolved in methylene chloride (10 ml) and a 2% aqueous sulphuric acid solution (10 ml) and trifluoroacetic acid (0.2 ml) were added in turn. The resultant mixture was stirred at ambient temperature for 2 hours. The mixture was extracted with methylene chloride and the organic phase was dried over magnesium sulphate and evaporated. There was thus obtained N-(3-formylphenyl)-2-(4-hydroxy-2-methoxyphenyl) acetamide (0.44 g, 67%); $^1$H NMR: (CDCl$_3$) 3.66 (s, 2H), 3.91 (s, 3H), 6.44 (m, 1H), 6.51 (m, 1H), 7.13 (d, 1H), 7.46 (t, 1H), 7.58 (d, 1H), 7.75 (br s, 1H), 7.83 (m, 2H), 9.96 (s, 1H); Mass Spectrum: M+H$^+$ 286.

A mixture of the compound so obtained was reacted with 4-chloro-6,7-dimethoxyquinazoline using an analogous procedure to that described in Example 15 hereinafter. The reaction product was purified by column chromatography on silica using increasingly polar mixtures of methylene chloride and methanol as eluent. There was thus obtained N-(3-formylphenyl)-2-[4-(6,7-dimethoxyquinazolin-4-yloxy)-2-methoxyphenyl]acetamide in 67% yield; $^1$H NMR: (CDCl$_3$) 3.78 (s, 2H), 3.96 (s, 3H), 4.08 (m, 6H), 6.92 (m, 2H), 7.35 (s, 1H), 7.42 (d, 1H), 7.49 (t, 1H), 7.55 (s, 1H), 7.6 (d, 1H), 7.83 (s, 1H), 7.88 (m, 2H), 8.65 (s, 1H); Mass Spectrum: M+H$^+$ 474.

[38] $^1$H NMR: (CDCl$_3$) 1.59 (t, 3H), 2.22 (s, 6H), 3.39 (s, 2H), 3.74 (s, 2H), 3.93 (s, 3H), 4.07 (s, 3H), 4.29 (d, 1H), 4.32 (d, 1H), 6.88 (s, 1H), 6.9 (m, 1H), 7.03 (d, 1H), 7.26 (m, 1H), 7.29 (m, 1H), 7.32 (s, 1H), 7.4 (s, 1H), 7.5 (d, 1H), 7.55 (s, 1H), 7.61 (br s, 1H), 8.63 (s, 1H); Mass Spectrum: M+H$^+$ 517.

The N-(3-formylphenyl)-2-[4-(7-ethoxy-6-methoxyquinazolin-4-yloxy)-2-methoxyphenyl]acetamide used as a starting material was prepared as follows:—

A mixture of N-(3-formylphenyl)-2-(4-hydroxy-2-methoxyphenyl)acetamide was reacted with 4-chloro-7-ethoxy-6-methoxyquinazoline using an analogous procedure to that described in Example 15 hereinafter. The reaction product was purified by column chromatography on silica using increasingly polar mixtures of methylene chloride and methanol as eluent. There was thus obtained N-(3-formylphenyl)-2-[4-(7-ethoxy-6-methoxyquinazolin-4-yloxy)-2-methoxyphenyl]acetamide in 79% yield; Mass Spectrum: M+H$^+$ 488.

EXAMPLE 6

N-(5-dimethylaminopyridin-2-yl)-2-[4-(6,7-dimethoxyquinazolin-4-yloxy)phenyl]acetamide 1-(3-Dimethylaminopropyl)-3-ethylcarbodiimide hydrochloride (0.101 g) and 2-hydroxypyridine N-oxide (0.059 g) were added in turn to a stirred mixture of 2-[4-(6,7-dimethoxyquinazolin-4-yloxy)phenyl]acetic acid (0.15 g), 2-amino-5-dimethylaminopyridine (0.073 g), diisopropylethylamine (0.092 ml) and DMF (2 ml) and the resultant mixture was stirred at ambient temperature for 16 hours. The resultant reaction mixture was transferred onto a Waters 'β Basic Hypersil' reversed-phase preparative HPLC column (5 microns silica, 30 mm diameter, 250 mm length) that was eluted with decreasingly polar mixtures of water (containing 0.2% ammonium carbonate) and acetonitrile as eluent. There was thus obtained the title compound (0.148 g); $^1$H NMR: (DMSOd$_6$) 2.88 (s, 6H), 3.71 (s, 2H), 3.98 (s, 3H), 3.98 (s, 3H), 7.19 (m, 1H), 7.25 (d, 2H), 7.38 (s, 1H), 7.44 (d, 2H), 7.55 (s, 1H), 7.84 (d, 1H), 7.90 (d, 1H), 8.53 (s, 1H), 10.43 (s, 1H); Mass Spectrum: M+H$^+$ 460.

The 2-amino-5-dimethylaminopyridine used as a starting material was prepared as follows:—

An aqueous solution of dimethylamine (40%, 11.3 ml) was added to a stirred suspension of 5-bromo-2-nitropyridine (6.1 g) in ethanol (60 ml) and the resultant mixture was heated to reflux for 16 hours. The mixture was cooled to ambient temperature and the solid was isolated, washed with water and dried under vacuum. There was thus obtained 5-dimethylamino-2-nitropyridine (4 g); $^1$H NMR: (CDCl$_3$) 3.16 (s, 6H), 6.98 (m, 1H), 7.96 (m, 1H), 8.17 (m, 1H); Mass Spectrum: M+H$^+$ 168.

A mixture of the material so obtained, platinum oxide catalyst (0.27 g) ethanol (60 ml) and ethyl acetate (60 ml) was stirred under 5 atmospheres pressure of hydrogen for 3 hours. The catalyst was filtered off and the filtrate was evaporated. There was thus obtained 2-amino-5-dimethylaminopyridine (3 g); ¹H NMR: (CDCl₃) 2.83 (s, 6H), 4.08 (br s, 2H), 6.49 (m, 1H), 7.08 (m, 1H), 7.67 (m, 1H); Mass Spectrum: M+H⁺ 138.

EXAMPLE 7

N-(3-methylpyrazol-5-yl)-2-[4-(6,7-dimethoxyquinazolin-4-yloxy)phenyl]acetamide 1-(3-Dimethylaminopropyl)-3-ethylcarbodiimide hydrochloride (0.113 g) and 2-hydroxypyridine N-oxide (0.065 g) were added in turn to a stirred mixture of 2-[4-(6,7-dimethoxyquinazolin-4-yloxy)phenyl]acetic acid (0.1 g), 5-amino-3-methylpyrazole (0.058 g), diisopropylethylamine (0.051 ml) and DMA (1 ml) and the resultant mixture was stirred at ambient temperature for 16 hours. The resultant reaction mixture was transferred onto a Waters 'β Basic Hypersil' reversed-phase preparative HPLC column (5 microns silica, 30 mm diameter, 250 mm length) that was eluted with decreasingly polar mixtures of water (containing 0.2% ammonium carbonate) and acetonitrile as eluent. There was thus obtained the title compound (0.064 g); ¹H NMR: (DMSOd₆) 2.18 (s, 3H), 3.64 (s, 2H), 3.97 (s, 3H), 3.99 (s, 3H), 6.25 (s, 1H), 7.24 (d, 2H), 7.38 (s, 1H), 7.41 (d, 2H), 7.55 (s, 1H), 8.53 (s, 1H), 10.53 (br s, 1H), 11.99 (br s, 1H); Mass Spectrum: M+H⁺ 420.

EXAMPLE 8

Using an analogous procedure to that described in Example 6, the appropriate 2-phenylacetic acid was reacted with the appropriate aniline to give the compounds described in Table III. Unless otherwise stated, each aniline, heterocyclylamine or heteroarylamine was a commercially available material.

TABLE III

| No. & Note | (R¹)ₚ | (R²)_q | (R⁶)ᵣ |
|---|---|---|---|
| [1] | 7-ethoxy-6-methoxy | H | 3-methoxy |
| [2] | 6-methoxy-7-(2-methoxyethoxy) | H | 3-methoxy |
| [3] | 6,7-dimethoxy | H | 2,4-dimethoxy |
| [4] | 7-ethoxy-6-methoxy | H | 3-hydroxymethyl |
| [5] | 6-methoxy-7-(2-methoxyethoxy) | H | 3-hydroxymethyl |
| [6] | 6-methoxy-7-(2-hydroxyethoxy) | H | 3-hydroxymethyl |
| [7] | 6,7-dimethoxy | H | 4-oxazol-5-yl |

Notes

[1] DMA was used as the solvent. The product gave the following characterising data:—¹H NMR: (CDCl₃) 1.59 (t, 3H), 3.79 (s, 2H), 3.8 (s, 3H), 4.07 (s, 3H), 4.31 (q, 2H), 6.67 (m, 1H), 6.92 (m, 1H), 7.19 (br s, 1H), 7.20 (m, 1H), 7.27 (br s, 1H), 7.3 (d, 2H), 7.35 (s, 1H), 7.46 (d, 2H), 7.55 (s, 1H), 8.62 (s, 1H); Mass Spectrum: M+H⁺ 460.

The 2-[4-(7-ethoxy-6-methoxyquinazolin-4-yloxy)phenyl]acetic acid used as a starting material was prepared as follows:—

Diethyl azodicarboxylate (0.673 ml) was added to a stirred mixture of 4-chloro-7-hydroxy-6-methoxyquinazoline (International Patent Application WO 03/064413, Example 4 thereof; 0.6 g), ethanol (0.182 ml), triphenylphosphine (1.12 g) and methylene chloride (12 ml) and the resultant mixture was stirred at ambient temperature for 10 minutes. The mixture was evaporated and the residue was purified by column chromatography on silica using a solvent gradient from a 17:3 to a 4:1 mixture of methylene chloride and ethyl acetate as eluent. There was thus obtained 4-chloro-7-ethoxy-6-methoxyquinazoline as a solid (0.391 g); ¹H NMR: (CDCl₃) 1.58 (t, 3H), 4.07 (s, 3H), 4.29 (q, 2H), 7.32 (s, 1H), 7.39 (s, 1H), 8.86 (s, 1H).

A mixture of 4-chloro-7-ethoxy-6-methoxyquinazoline as a solid (5 g), 2-(4-hydroxyphenyl)acetic acid (3.34 g), potassium carbonate (8.7 g) and DMF (40 ml) was stirred and heated to 90° C. for 2 hours. The resultant mixture was cooled to ambient temperature and diluted with diethyl ether. The solid was filtered off and dissolved in water. The aqueous solution was acidified to pH3 by the addition of 6N aqueous hydrochloric acid and the resultant precipitate was isolated by filtration, washed in turn with water, ethyl acetate and diethyl ether and dried. There was thus obtained 2-[4-(7-ethoxy-6-methoxyquinazolin-4-yloxy) phenyl]acetic acid (6.8 g); ¹H NMR: (DMSOd₆) 1.43 (t, 3H), 3.64 (s, 2H), 3.98 (s, 3H), 4.25 (q, 2H), 7.24 (d, 2H), 7.36 (m, 3H), 7.55 (s, 1H), 8.54 (s, 1H); Mass Spectrum: M+H⁺ 355.

[2] DMA was used as the solvent. The product gave the following characterising data:—¹H NMR: (DMSOd₆) 3.35 (s, 3H), 3.69 (s, 2H), 3.72 (s, 3H), 3.74-3.79 (m, 2H), 3.98 (s, 3H), 4.29-4.36 (m, 2H), 6.63 (m, 1H), 7.15 (d, 1H), 7.21 (m, 1H), 7.26 (d, 2H), 7.34 (m, 1H), 7.4 (s, 1H), 7.43 (d, 2H), 7.56 (s, 1H), 8.53 (s, 1H), 10.21 (s, 1H); Mass Spectrum: M+H⁺ 490.

The 2-{4-[7-(2-methoxyethoxy)-6-methoxyquinazolin-4-yloxy]phenyl}acetic acid used as a starting material was prepared as follows:—

Using analogous procedures to those described in the portion of Note [1] above that is concerned with the preparation of starting materials, 4-chloro-7-hydroxy-6-methoxyquinazoline was reacted with 2-methoxyethanol to give 4-chloro-6-methoxy-7-(2-methoxyethoxy) quinazoline in 100% yield; ¹H NMR: (CDCl₃) 3.49 (s, 3H), 3.89 (t, 2H), 4.05 (s, 3H), 4.35 (t, 2H), 7.26 (s, 1H), 7.35 (s, 1H), 8.86 (s, 1H); Mass Spectrum: M+H⁺ 269; which in turn was reacted with 2-(4-hydroxyphenyl)acetic acid to give the required starting material in 99% yield; ¹H NMR: (DMSOd₆) 3.35 (s, 3H), 3.63 (s, 2H), 3.76 (m, 2H), 3.98 (s, 3H), 4.33 (m, 2H), 7.25 (d, 2H), 7.36 (d, 2H), 7.4 (s, 1H), 7.56 (s, 1H), 8.54 (s, 1H); Mass Spectrum: M+H⁺ 385.

[3] DMA was used as the solvent. The product gave the following characterising data:—¹H NMR: (DMSOd₆) 3.71-3.76 (m, 5H), 3.82 (s, 3H), 3.98 (s, 3H), 3.99 (s, 3H), 6.47 (m, 1H), 6.62 (d, 1H), 7.26 (d, 2H), 7.39 (s, 1H), 7.44 (d, 2H), 7.56 (s, 1H), 7.7 (d, 1H), 8.54 (s, 1H), 9.23 (s, 1H); Mass Spectrum: M+H⁺ 476.

[4] DMA was used as the solvent. The product gave the following characterising data:—¹H NMR: (DMSOd₆) 1.44 (t, 3H), 3.69 (s, 2H), 3.98 (s, 3H), 4.26 (q, 2H), 4.47 (d, 2H), 5.19 (t, 1H), 6.99 (d, 1H), 7.25 (m, 1H), 7.26 (d, 2H), 7.37 (s, 1H), 7.44 (d, 2H), 7.51 (d, 1H), 7.55 (s, 1H), 7.59 (br s, 1H), 8.52 (s, 1H), 10.20 (s, 1H); Mass Spectrum: M+H⁺ 460.

[5] DMA was used as the solvent. The product gave the following characterising data:—¹H NMR: (DMSOd₆) 3.35

(s, 3H), 3.7 (s, 2H), 3.74-3.79 (m, 2H), 3.98 (s, 3H), 4.3-4.36 (m, 2H), 4.47 (d, 2H), 5.2 (t, 1H), 6.99 (d, 1H), 7.25 (m, 1H), 7.27 (d, 2H), 7.41 (s, 1H), 7.45 (d, 2H), 7.51 (d, 1H), 7.56 (s, 1H), 7.59 (s, 1H), 8.53 (s, 1H), 10.21 (s, 1H); Mass Spectrum: M+H$^+$ 490.

[6] DMA was used as the solvent. The product gave the following characterising data:—$^1$H NMR: (DMSOd$_6$) 3.69 (s, 2H), 3.82 (m, 2H), 3.98 (s, 3H), 4.22 (m, 2H), 4.46 (d, 2H), 4.98 (t, 1H), 5.19 (t, 1H), 6.98 (d, 1H), 7.26 (m, 3H), 7.39 (s, 1H), 7.44 (d, 2H), 7.51 (d, 1H), 7.57 (d, 2H), 8.52 (s, 1H), 10.21 (s, 1H); Mass Spectrum: M−H$^−$ 474.

The 2-{4-[7-(2-hydroxyethoxy)-6-methoxyquinazolin-4-yloxy]phenyl}acetic acid used as a starting material was prepared as follows:—

Di-tert-butyl azodicarboxylate (16.42 g) was added portionwise to a stirred mixture of 4-chloro-7-hydroxy-6-methoxyquinazoline (10 g), 2-(2-hydroxyethoxy)tetrahydropyran (7.72 ml), triphenylphosphine (18.71 g) and methylene chloride (500 ml) that was cooled to about 5° C. The resultant mixture was stirred at ambient temperature for 2.5 hours. The mixture was evaporated and the residue was triturated under diethyl ether. The precipitated triphenylphosphine oxide was separated by filtration and the filtrate was evaporated. The residue was purified by column chromatography on silica using increasingly polar mixtures of petroleum ether (b.p. 40-60° C.) and ethyl acetate as eluent. There was thus obtained 4-chloro-6-methoxy-7-(2-tetrahydropyran-2-yloxyethoxy) quinazoline (10 g).

Using an analogous procedure to that described in the portion of Note [1] above that is concerned with the preparation of starting materials, 4-chloro-6-methoxy-7-(2-tetrahydropyran-2-yloxyethoxy) quinazoline was reacted with 2-(4-hydroxyphenyl)acetic acid to give 2-{4-[6-methoxy-7-(2-tetrahydropyran-2-yloxyethoxy)quinazolin-4-yloxy]phenyl}acetic acid in 74% yield; $^1$H NMR: (DMSOd$_6$) 1.5 (m, 4H), 1.7 (m, 2H), 3.45 (m, 1H), 3.6 (s, 2H), 3.8 (m, 2H), 3.95 (s, 3H), 4.0 (m, 1H), 4.35 (m, 2H), 4.7 (s, 1H), 7.25 (d, 2H), 7.35 (d, 2H), 7.4 (s, 1H), 7.55 (s, 1H), 8.55 (s, 1H); Mass Spectrum: M+H$^+$ 455.

A mixture of the material so obtained (9 g), glacial acetic acid (86 ml), water (50 ml) and THF (14 ml) was stirred and heated to 45° C. for 3 hours. The reaction mixture was poured into water (850 ml) and the mixture was basified to pH3.5 by the addition of 2N aqueous sodium hydroxide solution. The resultant solid was isolated, washed with diethyl ether and dried at 40° C. under vacuum. There was thus obtained 2-{4-[7-(2-hydroxyethoxy)-6-methoxyquinazolin-4-yloxy]phenyl}acetic acid (5.8 g) which was used without further purification; Mass Spectrum: M+H$^+$ 371.

[7] DMA was used as the solvent. The product gave the following characterising data:—$^1$H NMR: (DMSOd$_6$) 3.73 (s, 2H), 3.97 (s, 3H), 3.99 (s, 3H), 7.27 (d, 2H), 7.39 (s, 1H), 7.45 (d, 2H), 7.56 (s, 1H), 7.59 (s, 1H), 7.68 (d, 2H), 7.74 (d, 2H), 8.4 (s, 1H), 8.53 (s, 1H), 10.4 (s, 1H); Mass Spectrum: M+H$^+$ 483.

EXAMPLE 9

Using an analogous procedure to that described in Example 6, the appropriate 2-phenylacetic acid was reacted with the appropriate aniline, heterocyclylamine or heteroarylamine to give the compounds described in Table IV. For the Compounds [1] to [23], [26] to [28], [31] to [33], [35] to [55] and [57] to [81] below, DMA was used in place of DMF as the reaction solvent. Unless otherwise stated, each aniline, heterocyclylamine and heteroarylamine was a commercially available material.

TABLE IV

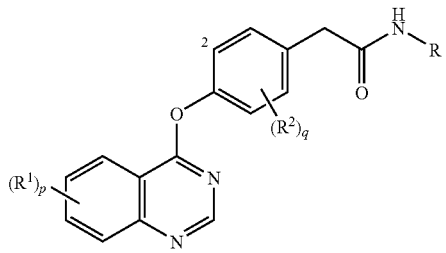

| No. & Note | $(R^1)_p$ | $(R^2)_q$ | R |
|---|---|---|---|
| [1] | 7-ethoxy-6-methoxy | H | 2,3-methylenedioxyphenyl |
| [2] | 6-methoxy-7-(2-methoxyethoxy) | H | 2,3-methylenedioxyphenyl |
| [3] | 7-ethoxy-6-methoxy | H | 3,4-methylenedioxyphenyl |
| [4] | 6-methoxy-7-(2-methoxyethoxy) | H | 3,4-methylenedioxyphenyl |
| [5] | 7-ethoxy-6-methoxy | H | 2,3-ethylenedioxyphenyl |
| [6] | 6-methoxy-7-(2-methoxyethoxy) | H | 2,3-ethylenedioxyphenyl |
| [7] | 6,7-di-(2-methoxyethoxy) | H | 2,3-ethylenedioxyphenyl |
| [8] | 7-ethoxy-6-methoxy | H | 3,4-ethylenedioxyphenyl |
| [9] | 6-methoxy-7-(2-methoxyethoxy) | H | 3,4-ethylenedioxyphenyl |
| [10] | 6-methoxy-7-(2-methoxyethoxy) | H | 3-oxo-1,3-dihydroisobenzofuran-5-yl |
| [11] | 6,7-dimethoxy | H | 2-oxoindolin-5-yl |
| [12] | 6,7-dimethoxy | H | 2-oxoindolin-6-yl |
| [13] | 6,7-dimethoxy | H | 1,3-dioxoisoindolin-5-yl |
| [14] | 6,7-dimethoxy | H | 2-methyl-1,3-dioxoisoindolin-5-yl |
| [15] | 6,7-dimethoxy | H | 2-oxo-2,3-dihydrobenzimidazol-5-yl |
| [16] | 6,7-dimethoxy | H | 2-thiazolyl |
| [17] | 6,7-dimethoxy | H | 4-methylthiazol-2-yl |
| [18] | 6,7-dimethoxy | H | 5-methylthiazol-2-yl |
| [19] | 7-ethoxy-6-methoxy | H | 4-methylthiazol-2-yl |
| [20] | 6-methoxy-7-(2-methoxyethoxy) | H | 4-methylthiazol-2-yl |
| [21] | 7-ethoxy-6-methoxy | H | 5-methylthiazol-2-yl |
| [22] | 6-methoxy-7-(2-methoxyethoxy) | H | 5-methylthiazol-2-yl |
| [23] | 6,7-di-(2-methoxyethoxy) | H | 5-methylthiazol-2-yl |
| [24] | 6,7-dimethoxy | 2-fluoro | 5-methylthiazol-2-yl |
| [25] | 6,7-di-(2-methoxyethoxy) | 2-fluoro | 5-methylthiazol-2-yl |
| [26] | 6,7-dimethoxy | H | 4,5-dimethylthiazol-2-yl |
| [27] | 6-methoxy-7-(2-methoxyethoxy) | H | 5-cyanothiazol-2-yl |
| [28] | 6,7-dimethoxy | H | 5-acetyl-4-methylthiazol-2-yl |
| [29] | 6,7-dimethoxy | 2-fluoro | 5-cyanothiazol-2-yl |
| [30] | 6-methoxy-7-(2-hydroxyethoxy) | 2-fluoro | 5-cyanothiazol-2-yl |
| [31] | 6,7-dimethoxy | H | 5-methylisoxazol-3-yl |
| [32] | 7-ethoxy-6-methoxy | H | 5-methylisoxazol-3-yl |
| [33] | 6-methoxy-7-(2-methoxyethoxy) | H | 5-methylisoxazol-3-yl |
| [34] | 6,7-dimethoxy | 2-fluoro | 4,5-dimethylimidazol-2-yl |
| [35] | 7-ethoxy-6-methoxy | H | 3-methylpyrazol-5-yl |
| [36] | 6,7-dimethoxy | H | 3-isopropylpyrazol-5-yl |
| [37] | 6,7-dimethoxy | H | 3-ethylpyrazol-5-yl |
| [38] | 6,7-dimethoxy | H | 3-tert-butylpyrazol-5-yl |
| [39] | 6,7-dimethoxy | H | 3-cyclopropylpyrazol-5-yl |
| [40] | 6,7-dimethoxy | H | 1-ethylpyrazol-5-yl |
| [41] | 6,7-dimethoxy | H | 1-ethylpyrazol-3-yl |
| [42] | 6,7-dimethoxy | H | 1,5-dimethylpyrazol-3-yl |
| [43] | 6,7-dimethoxy | H | 3-cyclopropyl-1-methylpyrazol-5-yl |
| [44] | 6,7-dimethoxy | H | 3-(2-furyl)pyrazol-5-yl |
| [45] | 6-methoxy-7-(2-hydroxyethoxy) | 2-fluoro | 3-ethylpyrazol-5-yl |
| [46] | 6,7-dimethoxy | H | 1-methylpyrazol-4-yl |
| [47] | 6,7-dimethoxy | H | 1-ethylpyrazol-4-yl |

TABLE IV-continued

Structure: quinazoline with (R¹)ₚ substituents, linked via O to a phenyl ring bearing (R²)_q and a —CH₂—C(=O)—NH—R group.

| No. & Note | (R¹)ₚ | (R²)_q | R |
|---|---|---|---|
| [48] | 6,7-dimethoxy | H | 1-isopropylpyrazol-4-yl |
| [49] | 7-ethoxy-6-methoxy | H | 1-isopropylpyrazol-4-yl |
| [50] | 6-methoxy-7-(2-methoxyethoxy) | H | 1-isopropylpyrazol-4-yl |
| [51] | 6,7-dimethoxy | H | 5-indolyl |
| [52] | 7-ethoxy-6-methoxy | H | 5-indolyl |
| [53] | 6-methoxy-7-(2-methoxyethoxy) | H | 5-indolyl |
| [54] | 6-methoxy-7-(2-methoxyethoxy) | H | 1-methylindol-5-yl |
| [55] | 6,7-di-(2-methoxyethoxy) | H | 1-methylindol-5-yl |
| [56] | 6,7-dimethoxy | 2-fluoro | 1-methylindol-5-yl |
| [57] | 6,7-dimethoxy | H | 6-indazolyl |
| [58] | 6-methoxy-7-(2-methoxyethoxy) | H | 6-indazolyl |
| [59] | 6,7-dimethoxy | H | 5-indazolyl |
| [60] | 7-ethoxy-6-methoxy | H | 5-indazolyl |
| [61] | 6-methoxy-7-(2-methoxyethoxy) | H | 5-indazolyl |
| [62] | 6,7-dimethoxy | H | 7-indazolyl |
| [63] | 6,7-dimethoxy | H | 5-benzotriazolyl |
| [64] | 6,7-dimethoxy | H | 1H-benzimidazol-6-yl |
| [65] | 6,7-dimethoxy | H | 6-benzothiazolyl |
| [66] | 6,7-dimethoxy | H | 2-methylbenzothiazol-5-yl |
| [67] | 6,7-dimethoxy | H | 1H-benzimidazol-2-yl |
| [68] | 6,7-dimethoxy | H | 1-methyl-1H-benzimidazol-2-yl |
| [69] | 6-methoxy-7-(2-methoxyethoxy) | H | 1-methyl-1H-pyrrolo[3,2-b]pyridin-5-yl |
| [70] | 6,7-di-(2-methoxyethoxy) | H | 1-methyl-1H-pyrrolo[3,2-b]pyridin-5-yl |
| [71] | 6,7-dimethoxy | H | 2-quinolyl |
| [72] | 7-ethoxy-6-methoxy | H | 1-isoquinolyl |
| [73] | 6,7-dimethoxy | H | 3-isoquinolyl |
| [74] | 6,7-dimethoxy | H | 2-methylquinolin-6-yl |
| [75] | 7-ethoxy-6-methoxy | H | 6-quinolyl |
| [76] | 6-methoxy-7-(2-methoxyethoxy) | H | 6-quinolyl |
| [77] | 6,7-dimethoxy | H | 6-quinoxalinyl |
| [78] | 7-ethoxy-6-methoxy | H | 6-quinoxalinyl |
| [79] | 6-methoxy-7-(2-methoxyethoxy) | H | 6-quinoxalinyl |
| [80] | 6,7-dimethoxy | H | 2,6-naphthyridin-3-yl |
| [81] | 6,7-dimethoxy | H | 1,7-naphthyridin-6-yl |
| [82] | 6,7-dimethoxy | H | 3-pyridyl |

Notes The products gave the characterising data shown below.

[1] $^1$H NMR: (DMSOd$_6$) 1.44 (t, 3H), 3.74 (s, 1H), 4.26 (q, 2H), 6.05 (s, 2H) 6.72 (d, 1H), 6.79 (t, 1H), 7.27 (m, 3H), 7.37 (s, 1H), 7.43 (d, 2H), 7.56 (s, 1H), 8.53 (s, 1H), 9.96 (s, 1H); Mass Spectrum: M+H$^+$ 474.

2,3-Methylenedioxyaniline is described in *J. Med. Chem.*, 1979, 22, 1354.

[2] $^1$H NMR: (DMSOd$_6$) 3.35 (s, 3H), 3.74 (s, 2H), 3.75-3.79 (m, 2H), 3.99 (s, 3H), 4.3-4.36 (m, 2H), 6.05 (s, 2H), 6.73 (d, 1H), 6.8 (m, 1H), 7.27 (d, 2H), 7.29 (d, 1H), 7.41 (s, 1H), 7.44 (d, 2H), 7.57 (s, 1H), 8.54 (s, 1H), 8.96 (s, 1H); Mass Spectrum: M+H$^+$ 504.

[3] $^1$H NMR: (DMSOd$_6$) 1.44 (t, 3H), 3.66 (s, 2H), 3.98 (s, 3H), 4.26 (q, 2H), 5.98 (s, 2H), 6.86 (d, 1H), 6.98 (m, 1H), 7.26 (d, 2H), 7.34 (d, 1H), 7.37 (s, 1H), 7.43 (d, 2H), 7.55 (s, 1H), 8.53 (s, 1H), 10.13 (s, 1H); Mass Spectrum: M+H$^+$ 474.

3,4-Methylenedioxyaniline is described in European Patent Application No. 0549263, Example 3 thereof.

[4] $^1$H NMR: (DMSOd$_6$) 3.35 (s, 3H), 3.66 (s, 2H), 3.74-3.79 (m, 2H), 3.99 (s, 3H), 4.3-4.36 (m, 2H), 5.98 (s, 2H), 6.86 (d, 1H), 6.99 (m, 1H), 7.27 (d, 2H), 7.34 (d, 1H), 7.41 (s, 1H), 7.43 (d, 2H), 7.56 (s, 1H), 8.53 (s, 1H), 10.14 (s, 1H); Mass Spectrum: M+H$^+$ 504.

[5] $^1$H NMR: (CDCl$_3$) 1.59 (t, 3H), 3.8 (s, 2H), 4.07 (s, 3H), 4.22-4.3 (m, 4H), 4.31 (q, 2H), 6.63 (m, 1H), 6.82 (m, 1H), 7.28 (d, 2H), 7.36 (br s, 1H), 7.48 (d, 2H), 7.56 (s, 1H), 7.66 (br s, 1H), 7.91 (d, 1H), 8.6 (br s, 1H); Mass Spectrum: M+H$^+$ 488.

2,3-Ethylenedioxyaniline is described in *J. Med. Chem.*, 1995, 38, 4044.

[6] $^1$H NMR: (DMSOd$_6$) 3.35 (s, 3H), 3.74-3.78 (m, 2H), 3.79 (s, 2H), 3.98 (s, 3H), 3.23-3.29 (m, 2H), 3.3-3.36 (m, 4H), 6.62 (d, 1H), 6.75 (m, 1H), 7.26 (d, 2H), 7.4 (d, 1H), 7.44 (d, 2H), 7.5 (d, 1H), 7.56 (s, 1H), 8.53 (s, 1H), 9.41 (s, 1H); Mass Spectrum: M+H$^+$ 518.

[7] $^1$H NMR: (DMSOd$_6$) 3.36 (s, 3H), 3.37 (s, 3H), 3.65 (s, 2H), 3.74-3.81 (m, 4H), 4.16-4.24 (m, 4H), 4.29-4.38 (m, 4H), 6.79 (d, 1H), 6.99 (m, 1H), 7.26 (d, 2H), 7.27 (s, 1H), 7.41 (s, 1H), 7.42 (d, 2H), 7.6 (s, 1H), 8.53 (s, 1H), 10.05 (br s, 1H); Mass Spectrum: M+H$^+$ 562.

The 2-{4-[6,7-di-(2-methoxyethoxy)quinazolin-4-yloxy]phenyl}acetic acid used as a starting material was prepared as follows:—

Using analogous procedures to those described in the portion of Note [1] below Table III in Example 8 that is concerned with the preparation of starting materials, 4-chloro-6,7-di-(2-methoxyethoxy) quinazoline (International Patent Application WO 01/021596) was reacted with 2-(4-hydroxyphenyl) acetic acid to give the required starting material in 60% yield; $^1$H NMR: (DMSOd$_6$) 3.35 (s, 6H), 3.76 (m, 4H), 4.34 (m, 4H), 7.25 (d, 2H), 7.36 (d, 2H), 7.41 (s, 1H), 7.6 (s, 1H), 8.54 (a, 1H); Mass Spectrum: M+H$^+$ 429.

[8] $^1$H NMR: (CDCl$_3$) 1.59 (t, 3H), 3.78 (s, 2H), 4.07 (s, 3H), 4.2-4.26 (m, 4H), 4.3 (q, 2H), 6.68 (d, 1H), 6.85 (m, 1H), 7.09 (br s, 1H), 7.11 (d, 1H), 7.29 (d, 2H), 7.33 (s, 1H), 7.46 (d, 2H), 7.56 (s, 1H), 8.59 (s, 1H); Mass Spectrum: M+H$^+$ 488.

[9] $^1$H NMR: (DMSOd$_6$) 3.35 (s, 3H), 3.64 (s, 2H), 3.74-3.79 (m, 2H), 3.98 (s, 3H), 4.16-4.24 (m, 4H), 4.3-4.36 (m, 2H), 6.78 (d, 1H), 6.99 (m, 1H), 7.24-7.28 (d, 3H), 7.39-7.44 (m, 3H), 7.56 (s, 1H), 8.56 (s, 1H), 10.05 (s, 1H); Mass Spectrum: M+H$^+$ 518.

[10] $^1$H NMR: (DMSOd$_6$) 3.35 (s, 3H), 3.74-3.78 (m, 4H), 3.98 (s, 3H), 4.31-4.36 (m, 2H), 5.38 (s, 2H), 7.28 (s, 2H), 7.41 (s, 1H), 7.46 (d, 2H), 7.56 (d, 1H), 7.64 (d, 1H), 7.86 (m, 1H), 8.24 (d, 1H), 8.53 (s, 1H), 10.6 (s, 1H); Mass Spectrum: M+H$^+$ 516.

[11] $^1$H NMR: (DMSOd$_6$) 3.46 (s, 2H), 3.66 (s, 2H), 3.98 (s, 3H), 3.99 (s, 3H), 6.75 (d, 1H), 7.26 (d, 2H), 7.36 (m, 1H), 7.39 (s, 1H), 7.44 (d, 2H), 7.54 (s, 1H), 7.56 (s, 1H), 8.54 (s, 1H), 10.7 (s, 1H), 10.3 (s, 1H); Mass Spectrum: M+H$^+$ 471.

[12] $^1$H NMR: (DMSOd$_6$) 3.4 (s, 2H), 3.69 (s, 2H), 3.98 (s, 3H), 3.99 (s, 3H), 7.06 (m, 1H), 7.12 (d, 1H), 7.27 (d, 2H), 7.37 (d, 1H), 7.39 (s, 1H), 7.44 (d, 2H), 7.56 (s, 1H), 8.54 (s, 1H), 10.18 (s, 1H), 10.38 (s, 1H); Mass Spectrum: M+H$^+$ 471.

[13] $^1$H NMR: (DMSOd$_6$) 3.79 (s, 2H), 3.98 (s, 3H), 3.99 (s, 3H), 6.22 (br s, 1H), 7.28 (s, 2H), 7.39 (s, 1H), 746 (d, 2H), 7.56 (s, 1H), 7.79 (d, 1H), 7.90 (m, 1H), 8.18 (d, 1H), 8.54 (s, 1H), 10.83 (br s, 1H); Mass Spectrum: M+H$^+$ 485.

[14] $^1$H NMR: (DMSOd$_6$) 3.01 (s, 3H), 3.79 (s, 2H), 3.97 (s, 3H), 3.99 (s, 3H), 7.28 (d, 2H), 7.39 (s, 1H), 7.45 (d, 2H), 7.55 (s, 1H), 7.82 (d, 1H), 7.89 (m, 1H), 8.22 (d, 1H), 8.53 (s, 1H), 10.82 (s, 1H); Mass Spectrum: M+H⁺ 499.

[15] $^1$H NMR: (DMSOd$_6$) 3.67 (s, 2H), 3.98 (s, 3H), 3.99 (s, 3H), 6.84 (d, 1H), 7.04 (m, 1H), 7.26 (d, 2H), 7.39 (s, 1H), 7.44 (d, 2H), 7.48 (d, 1H), 7.56 (s, 1H), 8.54 (s, 1H), 10.08 (s, 1H), 10.49 (s, 1H), 10.56 (s, 1H); Mass Spectrum: M+H⁺ 472.

[16] $^1$H NMR: (DMSOd$_6$) 3.8 (s, 2H), 3.97 (s, 3H), 3.99 (s, 3H), 7.22 (d, 1H), 7.27 (d, 2H), 7.39 (s, 1H), 7.44 (d, 2H), 7.49 (d, 1H), 7.55 (s, 1H), 8.54 (s, 1H); Mass Spectrum: M–H⁻ 421.

[17] $^1$H NMR: (DMSOd$_6$) 2.27 (s, 3H), 3.79 (s, 2H), 3.97 (s, 3H), 3.99 (s, 3H), 6.75 (d, 1H), 7.27 (d, 2H), 7.39 (s, 1H), 7.45 (d, 2H), 7.55 (s, 1H), 8.54 (s, 1H), 12.32 (br s, 1H); Mass Spectrum: M+H⁺ 437.

[18] $^1$H NMR: (DMSOd$_6$) 2.33 (s, 3H), 3.79 (s, 2H), 3.97 (s, 3H), 3.99 (s, 3H), 7.14 (s, 1H), 7.27 (d, 2H), 7.39 (s, 1H), 7.42 (d, 2H), 7.55 (s, 1H), 8.54 (s, 1H), 12.20 (br s, 1H); Mass Spectrum: M+H⁺ 437.

[19] $^1$H NMR: (DMSOd$_6$) 1.44 (t, 3H), 2.27 (s, 3H), 3.9 (s, 2H), 3.98 (s, 3H), 4.26 (q, 2H), 6.76 (d, 1H), 7.27 (d, 2H), 7.36 (s, 1H), 7.43 (d, 2H), 7.55 (s, 1H), 8.53 (s, 1H); Mass Spectrum: M+H⁺ 451.

[20] $^1$H NMR: (DMSOd$_6$) 2.27 (s, 3H), 3.35 (s, 3H), 3.75-3.78 (m, 2H), 3.8 (s, 2H), 3.98 (s, 3H), 4.31-4.35 (m, 2H), 6.76 (s, 1H), 7.28 (d, 2H), 7.41 (s, 1H), 7.44 (d, 2H), 7.56 (s, 1H), 8.53 (s, 1H), 12.32 (s, 1H); Mass Spectrum: M+H⁺ 481.

[21] $^1$H NMR: (DMSOd$_6$) 1.44 (t, 3H), 2.34 (s, 3H), 3.8 (s, 2H), 3.98 (s, 3H), 4.26 (q, 2H), 7.15 (s, 1H), 7.27 (d, 2H), 7.37 (s, 1H), 7.43 (d, 2H), 7.55 (s, 1H), 8.53 (s, 1H), 12.2 (s, 1H); Mass Spectrum: M+H⁺ 481.

[22] $^1$H NMR: (DMSOd$_6$) 2.34 (s, 3H), 3.35 (s, 3H), 3.74-3.79 (m, 2H), 3.8 (s, 2H), 3.99 (s, 3H), 4.3-4.36 (m, 2H), 7.15 (d, 1H), 7.27 (d, 2H), 7.41 (s, 1H), 7.43 (d, 2H), 7.56 (s, 1H), 8.53 (s, 1H), 12.2 (s, 1H); Mass Spectrum: M+H⁺ 481.

[23] $^1$H NMR: (DMSOd$_6$) 2.33 (s, 3H), 3.35 (s, 3H), 3.36 (s, 3H), 3.72-3.79 (m, 4H), 3.8 (s, 2H), 4.29-4.37 (m, 4H), 7.14 (s, 1H), 7.27 (d, 2H), 7.41 (s, 1H), 7.42 (d, 2H), 7.59 (s, 1H), 8.53 (s, 1H), 12.2 (br s, 1H); Mass Spectrum: M+H⁺ 525.

[24] $^1$H NMR: (DMSOd$_6$) 2.35 (s, 3H), 3.85 s, 2H), 3.99 (s, 3H, 4.0 (s, 3H, 7.15 (s, 1H, 7.25 (d, 1H), 7.4 (m, 3H), 7.6 (s, 1H), 8.6 (s, 1H); Mass Spectrum: M–H⁻ 453.

[25] $^1$H NMR: (DMSOd$_6$) 2.35 (s, 3H), 3.36 (s, 6H), 3.75 (m, 4H), 3.85 (s, 2H), 4.35 (m, 4H), 7.15 (s, 1H), 7.25 (d, 1H), 7.4 (d, 1H), 7.45 (m, 2H), 7.6 (s, 1H), 8.55 (s, 1H); Mass Spectrum: M+H⁺ 543.

The 2-{3-fluoro-4-[6,7-di-(2-methoxyethoxy)quinazolin-4-yloxy]phenyl}acetic acid used as a starting material was prepared as follows:—

Using an analogous procedure to that described in the portion of Note [1] below Table III in Example 8 that is concerned with the preparation of starting materials, 4-chloro-6,7-di-(2-methoxyethoxy) quinazoline was reacted with 2-(3-fluoro-4-hydroxyphenyl)acetic acid to give 2-{3-fluoro-4-[6,7-di-(2-methoxyethoxy)quinazolin-4-yloxy] phenyl}acetic acid in 41% yield; Mass Spectrum: M+H⁺ 447.

[26] $^1$H NMR: (DMSOd$_6$) 2.17 (s, 3H), 2.22 (s, 3H), 3.83 (s, 2H), 4.02 (s, 3H), 4.06 (s, 3H), 7.32 (d, 2H), 7.48 (d, 2H), 7.5 (s, 1H), 7.74 (s, 1H), 8.12 (s, 1H); Mass Spectrum: M+H³⁰ 451.

[27] $^1$H NMR: (DMSOd$_6$) 3.35 (s, 3H), 3.75-3.79 (m, 2H), 3.92 (s, 2H), 3.98 (s, 3H), 4.31-4.36 (m, 2H), 7.29 (d, 2H), 7.41 (s, 1H), 7.44 (d, 2H), 7.56 (s, 1H), 8.39 (s, 1H), 8.54 (s, 1H), 13.21 (br s, 1H); Mass Spectrum: M+H⁺ 492.

[28] $^1$H NMR: (DMSOd$_6$) 2.47 (s, 3H), 2.58 (s, 3H), 3.85 (s, 3H), 3.97 (s, 3H), 4.0 (s, 3H), 7.27 (d, 2H), 7.39 (s, 1H), 7.43 (d, 2H), 7.55 (s, 1H), 8.54 (s, 1H), 12.76 (br s, 1H); Mass Spectrum: M+H⁺ 479.

[29] $^1$H NMR: (DMSOd$_6$) 3.91 (s, 2H), 3.97 (s, 3H), 3.99 (s, 3H), 7.28 (d, 2H), 7.38 (s, 1H), 7.43 (d, 2H), 7.55 (s, 1H), 8.38 (s, 1H), 8.53 (s, 1H); Mass Spectrum: M+H⁺ 448.

[30] The reactants were 2-amino-5-cyanothiazole and 2-{3-fluoro-4-[6-methoxy-7-(2-tetrahydropyran-2-yloxy-ethoxy) quinazolin-4-yloxy]phenyl}acetic acid the reaction mixture was heated to 130° C. for 5 minutes in a microwave oven. The solvent was evaporated and the residue was purified by column chromatography on silica using increasingly polar mixtures of methylene chloride and methanol as eluent. A mixture of the material so obtained (0.182 g), a 2M solution of hydrogen chloride in 1,4-dioxane (2 ml) and methylene chloride (3 ml) was stirred at ambient temperature for 15 minutes. The resultant mixture was evaporated and the residue was purified by preparative HPLC using a Water's 'Xterra' reversed-phase column and decreasingly polar mixtures of water and acetonitrile as eluent. The solvent was evaporated and the residue was triturated under diethyl ether to give the required product as a solid (0.016 g) which gave the following characterising data:—$^1$H NMR: (DMSOd$_6$) 3.8 (m, 2H), 3.95 (s, 2H), 4.0 (s, 3H), 4.25 (m, 2H), 5.0 (m, 1H), 6.8 (s, 1H), 7.25 (d, 1H), 7.45 (m, 3H), 7.6 (s, 1H), 8.4 (s, 1H), 8.6 (s, 1H); Mass Spectrum: M+H⁺ 496.

[31] $^1$H NMR: (DMSOd$_6$) 2.37 (s, 3H), 3.73 (s, 2H), 3.97 (s, 3H), 3.99 (s, 3H), 6.63 (s, 1H), 7.26 (d, 2H), 7.39 (s, 1H), 7.41 (d, 2H), 7.55 (s, 1H), 8.54 (s, 1H), 11.18 (br s, 1H); Mass Spectrum: M+H⁺ 421.

[32] $^1$H NMR: (DMSOd$_6$) 1.44 (t, 3H), 2.37 (s, 3H), 3.71 (s, 2H), 3.98 (s, 3H), 4.26 (q, 2H), 6.63 (s, 1H), 7.26 (d, 2H), 7.37 (s, 1H), 7.42 (d, 2H), 7.55 (s, 1H), 8.53 (s, 1H), 11.18 (s, 1H); Mass Spectrum: M+H⁺ 435.

[33] $^1$H NMR: (DMSOd$_6$) 2.33 (s, 3H), 3.35 (s, 3H), 3.73 (s, 2H), 3.75-3.78 (m, 2H), 3.98 (s, 3H), 4.3-4.36 (m, 2H), 6.63 (s, 1H), 7.27 (d, 2H), 7.41 (s, 1H), 7.42 (d, 2H), 7.56 (s, 1H), 8.53 (s, 1H), 11.18 (s, 1H); Mass Spectrum: M+H⁺ 465.

[34] $^1$H NMR: (DMSOd$_6$) 2.0 (s, 6H), 3.65 (s, 2H), 3.97 (s, 3H), 3.99 (s, 3H), 7.25 (d, 2H), 7.4 (s, 1H), 7.45 (d, 2H), 7.55 (s, 1H), 8.55 (s, 1H), 11.09 (s, 1H); Mass Spectrum: M+H⁺ 434.

The 2-amino-4,5-dimethylimidazole used as a starting material was prepared as follows:—

A mixture of 3-bromobutan-2-one (5 g), 1-acetylguanidine (10 g) and DMF (100 ml) was stirred at ambient temperature for 7 days. The resultant mixture was concentrated by evaporation under vacuum and water was added to the residue. The precipitate was collected by filtration and dried under vacuum. There was thus obtained N-(4,5-dimethylimidazol-2-yl) acetamide (1.92 g); $^1$H NMR: (DMSOd$_6$) 1.98 (s, 6H), 2.0 (s, 3H).

A mixture of the material so obtained, concentrated sulphuric acid (1 ml), methanol (50 ml) and water (50 ml) was heated to reflux for 3 days. The methanol was evaporated and the residual acidic aqueous solution was basified to pH9 by the addition of 2N aqueous sodium hydroxide solution. The resultant mixture was evaporated and the residue was purified by column chromatography on silica using increasingly polar solvent mixtures of methylene chloride and a saturated methanolic ammonia solution. There was thus obtained the required starting material (0.54 g).

[35] $^1$H NMR: (DMSOd$_6$) 1.44 (t, 3H), 2.18 (s, 3H), 3.64 (s, 2H), 3.98 (s, 3H), 4.26 (q, 2H), 6.27 (s, 1H), 7.24 (d, 2H), 7.36 (s, 1H), 7.42 (d, 2H), 7.55 (s, 1H), 8.53 (s, 1H), 10.52 (s, 1H); Mass Spectrum: M+H⁺ 434.

[36] $^1$H NMR: (DMSOd$_6$+CF$_3$CO$_2$D) 1.2 (d, 6H), 2.86-2.96 (m, 1H), 3.66 (s, 2H), 3.98 (s, 3H), 4.0 (s, 3H), 6.3 (s, 1H), 7.25 (d, 2H), 7.38 (s, 1H), 7.44 (d, 2H), 7.56 (s, 1H), 8.54 (s, 1H); Mass Spectrum: M+H⁺ 448.

The 5-amino-3-isopropyl-1H-pyrazole used as a starting material was prepared as follows:—

Acetonitrile (1.17 ml) was added dropwise to a stirred solution of n-butyllithium (1.6M in hexane, 14.06 ml) that had been cooled to −78° C. and the mixture was stirred at that temperature for 1 hour. Ethyl isobutyrate (1.5 ml) was added dropwise and the reaction medium was allowed to warm to −45° C. and stirred at that temperature for 2 hours. The resultant mixture was acidified to pH2 by the addition of 2N aqueous hydrochloric acid and concentrated by evaporation. The residue was extracted with methylene chloride and the organic extract was dried over magnesium sulphate and evaporated. There was thus obtained 4-methyl-3-oxopentanenitrile (1.22 g); $^1$H NMR: (CDCl$_3$) 1.18 (d, 6H), 2.82 (m, 1H), 3.52 (s, 2H).

A mixture of a portion (0.6 g) of the material so obtained, hydrazine hydrate (0.288 ml) and ethanol (45 ml) was heated at 70° C. for 12 hours. The solvent was evaporated and the residue was purified by column chromatography on silica using a 19:1 mixture of methylene chloride and methanol as eluent. There was thus obtained the required starting material (0.574 g); $^1$H NMR: (DMSOd$_6$) 1.13 (d, 6H), 2.76 (m, 1H), 4.31 (br s, 2H), 5.17 (br s, 1H), 11.05 (br s, 1H); Mass Spectrum: M+H$^+$ 126.

[37] $^1$H NMR: (DMSOd$_6$+CF$_3$CO$_2$D) 1.17 (t, 3H), 2.57 (q, 2H), 3.67 (s, 2H), 3.98 (s, 3H), 4.0 (s, 3H), 6.31 (s, 1H), 7.25 (d, 2H), 7.38 (s, 1H), 7.44 (d, 2H), 7.56 (s, 1H), 8.55 (s, 1H); Mass Spectrum: M+H$^+$ 434.

The 5-amino-3-ethyl-1H-pyrazole used as a starting material was prepared as follows:—

Using analogous procedures to those described in the portion of Note [36] immediately above that is concerned with the preparation of starting materials, ethyl propionate was reacted with acetonitrile to give 3-oxopentanenitrile in 80% yield; $^1$H NMR: (CDCl$_3$) 1.14 (t, 3H), 2.66 (q, 2H), 3.46 (s, 2H); which in turn was reacted with hydrazine hydrate to give the required starting material in 51% yield; $^1$H NMR: (DMSOd$_6$) 1.04 (t, 3H), 2.41 (q, 2H), 4.4 (br s, 2H).

[38] The reaction product was purified by column chromatography on silica using increasingly polar mixtures of ethyl acetate and methanol as eluent and gave the following characterising data:—$^1$H NMR: (DMSOd$_6$) 1.24 (s, 9H), 3.63 (s, 2H), 3.97 (s, 3H), 3.99 (s, 3H), 6.28 (s, 1H), 7.24 (d, 2H), 7.38 (s, 1H), 7.42 (d, 2H), 7.55 (s, 1H), 8.53 (s, 1H), 10.57 (br s, 1H); Mass Spectrum: M+H$^+$ 462.

The 5-amino-3-tert-butyl-1H-pyrazole used as a starting material was prepared as follows:—

Using analogous procedures to those described in the portion of Note [36] immediately above that is concerned with the preparation of starting materials, ethyl pivaloate was reacted with acetonitrile to give 4,4-dimethyl-3-oxopentanenitrile which in turn was reacted with hydrazine hydrate to give the required starting material.

[39] $^1$H NMR: (DMSOd$_6$+CF$_3$CO$_2$D) 0.63-0.69 (m, 2H), 0.88-0.94 (m, 2H), 1.82-1.88 (m, 1H), 3.65 (s, 2H), 3.98 (s, 3H), 3.99 (s, 3H), 5.96 (s, 1H), 6.17 (s, 1H), 7.25 (d, 2H), 7.38 (s, 1H), 7.43 (d, 2H), 7.56 (s, 1H), 8.54 (s, 1H); Mass Spectrum: M+H$^+$ 446.

The 5-amino-3-cyclopropyl-1H-pyrazole used as a starting material was prepared as follows:—

Using analogous procedures to those described in the portion of Note [36] immediately above that is concerned with the preparation of starting materials, ethyl cyclopropane-1-carboxylate was reacted with acetonitrile to give cyclopropyl cyanomethyl ketone which in turn was reacted with hydrazine hydrate to give the required starting material.

[40] The reaction product was purified by column chromatography on silica using increasingly polar mixtures of ethyl acetate and methanol as eluent and gave the following characterising data:—$^1$H NMR: (DMSOd$_6$) 1.26 (t, 3H), 3.76 (s, 2H), 3.98 (s, 3H), 3.99 (s, 3H), 4.01 (q, 2H), 6.2 (s, 1H), 7.27 (d, 2H), 7.35 (s, 1H), 7.39 (s, 1H), 7.44 (d, 2H), 7.56 (s, 1H), 8.54 (s, 1H), 10.11 (s, 1H); Mass Spectrum: M+H$^+$ 434.

[41] The reaction product was purified by column chromatography on silica using increasingly polar mixtures of ethyl acetate and methanol as eluent and gave the following characterising data:—$^1$H NMR: (DMSOd$_6$) 1.34 (t, 3H), 3.64 (s, 2H), 3.97 (s, 3H), 3.99 (s, 3H), 4.03 (q, 2H), 6.42 (s, 1H), 7.24 (m, 2H), 7.42 (m, 3H), 7.55 (s, 1H), 7.58 (m, 1H), 8.53 (s, 1H), 10.7 (s, 1H); Mass Spectrum: M+H$^+$ 434.

The 3-amino-1-ethyl-1H-pyrazole used as a starting material is described in Chemical Abstracts, 1975, 82, 156172).

[42] $^1$H NMR: (DMSOd$_6$) 2.2 (s, 3H), 3.61 (s, 3H), 3.62 (s, 2H), 3.97 (s, 3H), 3.99 (s, 3H), 6.27 (s, 1H), 7.24 (d, 2H), 7.38 (s, 1H), 7.4 (d, 2H), 7.55 (s, 1H), 8.53 (s, 1H), 10.53 (s, 1H); Mass Spectrum: M+H$^+$ 434.

The 3-amino-1,5-dimethyl-1H-pyrazole used as a starting material is described in J. Heterocyclic Chem., 1982, 19, 1267.

[43] $^1$H NMR: (DMSOd$_6$) 0.55-0.6 (m, 2H), 0.76-0.83 (m, 2H), 1.73-1.8 (m, 1H), 3.56 (s, 3H), 3.73 (s, 2H), 3.98 (s, 3H), 3.99 (s, 3H), 7.27 (d, 2H), 7.39 (s, 1H), 7.42 (d, 2H), 7.56 (s, 1H), 8.54 (s, 1H), 10.1 (s, 1H); Mass Spectrum: M+H$^+$ 460.

The 5-amino-3-cyclopropyl-1-methyl-1H-pyrazole used as a starting material was prepared as follows:—

Using analogous procedures to those described in the portion of Note [36] immediately above that is concerned with the preparation of starting materials, ethyl cyclopropane-1-carboxylate was reacted with acetonitrile to give cyclopropyl cyanomethyl ketone which in turn was reacted with 1-methylhydrazine hydrate to give the required starting material.

[44] The reaction product was purified by column chromatography on silica using increasingly polar mixtures of ethyl acetate and methanol as eluent and gave the following characterising data:—$^1$H NMR: (DMSOd$_6$) 1.24 (s, 9H), 3.63 (s, 2H), 3.97 (s, 3H), 3.99 (s, 3H), 6.28 (s, 1H), 7.24 (d, 2H), 7.38 (s, 1H), 7.42 (d, 2H), 7.55 (s, 1H), 8.53 (s, 1H), 10.57 (br s, 1H); Mass Spectrum: M+H$^+$ 472.

[45] The reactants were 5-amino-3-ethyl-1H-pyrazole (0.19 g) and 2-{3-fluoro-4-[6-methoxy-7-(2-tetrahydropyran-2-yloxyethoxy)quinazolin-4-yloxy]phenyl}acetic acid (0.62 g) and the reaction mixture was heated to 50° C. for 2.5 hours. The solvent was evaporated and the residue was purified by column chromatography on silica using increasingly polar mixtures of methylene chloride and methanol as eluent. The material so obtained (0.46 g) was dissolved in methylene chloride (6 ml) and the solution was cooled to 0° C. A 2M solution of hydrogen chloride in 1,4-dioxane (2 ml) was added dropwise and the reaction mixture was stirred at 0° C. for 10 minutes and at ambient temperature for 30 minutes. The resultant mixture was evaporated and the residue was purified by column chromatography on silica using increasingly polar mixtures of methylene chloride and methanol as eluent. There was thus obtained the required product (0.21 g) which gave the following characterising data:—$^1$H NMR: (DMSOd$_6$) 1.3 (t, 3H), 2.55 (q, 2H), 3.7 (s, 2H), 3.85 (t, 2H), 4.0 (s, 3H), 4.25 (t, 2H), 6.3 (s, 1H), 7.25 (d, 1H), 7.4 (m, 3H), 7.6 (s, 1H), 8.6 (s, 1H), 10.6 (s, 1H); Mass Spectrum: M+H$^+$ 482.

[46] $^1$H NMR: (DMSOd$_6$) 3.62 (s, 2H), 3.78 (s, 3H), 3.98 (s, 3H), 3.99 (s, 3H), 7.27 (d, 2H), 7.37-7.43 (m, 4H), 7.55 (s, 1H), 7.86 (s, 1H), 8.53 (s, 1H), 10.2 (s, 1H); Mass Spectrum: M+H$^+$ 420.

The 4-amino-1-methyl-1H-pyrazole used as a starting material was prepared as follows:—

4-Nitropyrazole is available commercially from the N.D. Zelinsky Institute, Organic Chemistry, Leninsky prospect 47, 117913 Moscow B-334, Russia. The compound may also be prepared as follows:—

Fuming nitric acid (9.5 ml) was added dropwise to a stirred solution of pyrazole (13.6 g) in glacial acetic acid (51 ml) that had been cooled to −10° C. using an ice-salt bath. A voluminous precipitate was formed. Acetic anhydride (27 ml) was added dropwise and the resultant mixture was stirred at ambient temperature for 2.5 hours. The mixture was poured onto ice and the acidity of the mixture was reduced to pH5 by the addition of potassium carbonate. The precipitate was isolated by filtration. The resultant solid was dissolved in water and the aqueous solution was extracted with diethyl ether. The organic solution was dried over magnesium sulphate and filtered. Petroleum ether (b.p. 60-80° C., 50 ml) was added to the filtrate which was concentrated by evaporation to a volume of about 50 ml. A precipitate formed which was isolated by filtration. This solid was believed to be 1-nitropyrazole (20.6 g); $^1$H NMR: (DMSOd$_6$) 6.71 (s, 1H), 7.88 (s, 1H), 8.81 (s, 1H). The compound may be explosive and should be handled cautiously.

Concentrated sulphuric acid (80 ml) was added dropwise to a stirred sample of 1-nitropyrazole (20.3 g) that was cooled in an ice-bath. The resultant mixture was stirred for 16 hours and allowed to warm to ambient temperature. The mixture was poured onto ice and stirred for 20 minutes. The resultant solid was isolated and washed with water. The filtrate was neutralised by the addition of potassium carbonate and extracted with diethyl ether. The recovered solid was added to the diethyl ether solution and the resultant solution was washed with a saturated aqueous sodium chloride solution, dried over magnesium sulphate and filtered. Petroleum ether (b.p. 60-80° C.) was added to the filtrate which was concentrated by evaporation to a volume of about 50 ml. A precipitate formed which was isolated by filtration. There was thus obtained 4-nitropyrazole (16 g); $^1$H NMR: (DMSOd$_6$+CF$_3$CO$_2$H) 8.57 (s, 2H).

Dimethyl sulphate (5 ml) was slowly added to a stirred solution of 4-nitropyrazole (2 g) in 1N aqueous sodium hydroxide solution (20 ml) that had been warmed to 30° C. and the resultant mixture was stirred at that temperature for 48 hours. The mixture was cooled to ambient temperature and the precipitate was isolated, washed with cold water and dried under vacuum. There was thus obtained 1-methyl-4-nitro-1H-pyrazole (1.5 g); $^1$H NMR: (DMSOd$_6$) 3.91 (s, 1H), 8.24 (s, 1H), 8.85 (s, 1H).

A mixture of a portion (0.7 g) of the material so obtained, platinum oxide (0.05 g), ethyl acetate (5 ml) and ethanol (15 ml) was stirred under 3 atmospheres pressure of hydrogen for 2 hours. The catalyst was removed by filtration and the filtrate was evaporated. There was thus obtained the required starting material (0.6 g); $^1$H NMR: (DMSOd$_6$) 3.64 (s, 3H), 6.86 (s, 1H), 6.97 (s, 1H).

[47] $^1$H NMR: (DMSOd$_6$) 1.32 (t, 3H), 3.61 (s, 2H), 3.98 (s, 3H), 3.99 (s, 3H), 4.07 (q, 2H), 7.25 (d, 2H), 7.39 (s, 1H), 7.41 (d, 2H), 7.55 (s, 1H), 7.9 (s, 1H), 8.53 (s, 1H), 10.21 (s, 1H); Mass Spectrum: M+H$^+$ 434.

The 4-amino-1-ethyl-1H-pyrazole used as a starting material was prepared as follows:—

Diethyl sulphate (5.23 ml) was slowly added to a stirred solution of 4-nitropyrazole (2.26 g) in 1N aqueous sodium hydroxide solution (22 ml) that had been warmed to 30° C. and the resultant mixture was stirred at that temperature for 48 hours. The mixture was cooled to ambient temperature and the precipitate was isolated, washed with cold water and dried under vacuum. There was thus obtained 1-ethyl-4-nitro-1H-pyrazole (1.71 g); $^1$H NMR: (DMSOd$_6$) 1.4 (t, 3H), 4.2 (q, 2H), 8.25 (s, 1H), 8.9 (s, 1H).

The material so obtained was hydrogenated over platinum oxide using an analogous procedure to that described in the portion of Note [46] immediately above that is concerned with the preparation of starting materials. There was thus obtained the required starting material in 89% yield; $^1$H NMR: (DMSOd$_6$) 1.27 (t, 3H), 3.77 (br s, 2H), 3.92 (q, 2H), 6.87 (s, 1H), 7.01 (s, 1H).

[48] $^1$H NMR: (DMSOd$_6$) 1.39 (d, 6H), 3.64 (s, 2H), 3.98 (s, 3H), 4.0 (s, 3H), 4.39-4.49 (m, 1H), 7.25 (d, 2H), 7.39 (s, 1H), 7.43 (d, 2H), 7.45 (s, 1H), 7.56 (s, 1H), 7.91 (s, 1H), 8.54 (s, 1H); Mass Spectrum: M+H$^+$ 448.

The 4-amino-1-isopropyl-1H-pyrazole used as a starting material was prepared as follows:—

A mixture of 4-nitropyrazole (1.13 g), isopropyl iodide (1 ml), potassium carbonate (1.38 g) and DMF (30 ml) was stirred and heated to 70° C. for 2 hours. The resultant mixture was poured into water and the precipitate was isolated, washed with water and dried under vacuum. There was thus obtained 1-isopropyl-4-nitro-1H-pyrazole (0.845 g); $^1$H NMR: (DMSOd$_6$) 1.44 (d, 6H), 4.59 (m, 1H), 8.26 (s, 1H), 8.93 (s, 1H).

A mixture of a portion (0.8 g) of the material so obtained, platinum oxide (0.1 g), ethyl acetate (10 ml) and ethanol (30 ml) was stirred under 3 atmospheres pressure of hydrogen for 2 hours. The catalyst was removed by filtration and the filtrate was evaporated. There was thus obtained the required starting material as a colourless oil (0.607 g); $^1$H NMR: (DMSOd$_6$) 1.31 (d, 6H), 3.76 (br s, 2H), 4.27 (m, 1H), 6.88 (s, 1H), 7.03 (s, 1H).

[49] The reaction product was purified by column chromatography on silica using increasingly polar mixtures of ethyl acetate and methanol as eluent and gave the following characterising data:—$^1$H NMR: (DMSOd$_6$) 1.37 (d, 6H), 1.43 (t, 3H), 3.61 (s, 2H), 3.97 (s, 3H), 4.25 (q, 2H), 4.44 (m, 1H), 7.24 (m, 2H), 7.36 (s, 1H), 7.42 (m, 3H), 7.54 (s, 1H), 7.9 (s, 1H), 8.52 (s, 1H); Mass Spectrum: M+H$^+$ 462.

[50] The reaction product was purified by column chromatography on silica using increasingly polar mixtures of ethyl acetate and methanol as eluent and gave the following characterising data:—$^1$H NMR: (DMSOd$_6$) 1.37 (d, 6H), 3.31 (s, 3H), 3.61 (s, 2H), 3.76 (t, 2H), 3.98 (s, 3H), 4.33 (t, 2H), 4.43 (m, 1H), 7.25 (d, 2H), 7.4 (m, 4H), 7.56 (s, 1H), 7.89 (s, 1H), 8.52 (s, 1H), 10.21 (s, 1H); Mass Spectrum: M+H$^+$ 492.

[51] $^1$H NMR: (DMSOd$_6$) 3.71 (s, 2H), 3.98 (s, 3H), 3.99 (s, 3H), 6.35 (m, 1H), 7.06 (m, 1H), 7.26 (m, 1H), 7.27 (d, 2H), 7.39 (s, 1H), 7.44 (d, 1H), 7.47 (d, 2H), 7.56 (s, 1H), 7.99 (s, 1H), 8.54 (s, 1H), 10.11 (s, 1H), 11.02 (s, 1H); Mass Spectrum: M+H$^+$ 455.

[52] $^1$H NMR: (DMSOd$_6$) 1.44 (t, 3H), 3.69 (s, 2H), 3.98 (s, 3H), 4.26 (q, 2H), 6.37 (m, 1H), 7.23 (m, 1H), 7.27 (d, 2H), 7.3 (d, 1H), 7.32 (d, 1H), 7.36 (s, 1H), 7.47 (d, 2H), 7.56 (s, 1H), 7.89 (d, 1H), 8.53 (s, 1H), 10.01 (s, 1H), 11.0 (s, 1H); Mass Spectrum: M+H$^+$ 469.

[53] $^1$H NMR: (DMSOd$_6$) 3.35 (s, 3H), 3.69 (s, 2H), 3.74-3.79 (m, 2H), 3.98 (s, 3H), 4.3-4.36 (m, 2H), 6.37 (s, 1H), 7.23 (m, 1H), 7.27 (d, 2H), 7.31 (s, 1H), 7.32 (d, 1H), 7.41 (s, 1H), 7.47 (d, 2H), 7.57 (s, 1H), 7.89 (d, 1H), 8.53 (s, 1H), 10.01 (s, 1H), 11.0 (s, 1H); Mass Spectrum: M+H$^+$ 499.

[54] $^1$H NMR: (DMSOd$_6$) 3.35 (s, 3H), 3.69 (s, 2H), 3.75-3.78 (m, 2H), 3.77 (s, 3H), 3.99 (s, 3H), 4.31-4.35 (m, 2H), 6.36 (d, 1H), 7.25-7.32 (m, 4H), 7.37 (d, 1H), 7.41 (s, 1H), 7.47 (d, 2H), 7.57 (s, 1H), 7.9 (d, 1H), 8.53 (s, 1H), 10.04 (s, 1H); Mass Spectrum: M+H$^+$ 513.

The 5-amino-1-methylindole used as a starting material was prepared as follows:—

Sodium hydride (60% dispersion in mineral oil, 0.54 g) was added to a mixture of 5-nitroindole (2 g) and DMF (25 ml) and the mixture was stirred at ambient temperature for 15 minutes. Methyl iodide (0.85 ml) was added and the resultant mixture was stirred at ambient temperature for 3 hours. The mixture was poured into a mixture of water and ethyl acetate and extracted with ethyl acetate. The organic phase was washed with water and with brine, dried over magnesium sulphate and evaporated. There was thus obtained 1-methyl-5-nitroindole as a solid (1.83 g); $^1$H NMR: (CDCl$_3$) 3.85 (s, 3H), 6.7 (d, 1H), 7.2 (d, 1H), 7.35 (d, 1H), 8.15 (d, 1H), 8.6 (s, 1H).

A mixture of a portion of the material so obtained (0.88 g), 10% palladium-on-carbon catalyst (0.12 g) and ethanol (10 ml) was stirred under an atmospheres pressure of hydrogen for 2 hours. The resultant mixture was filtered and the filtrate was evaporated. The residue was purified by column chromatography on silica using increasingly polar mixtures of petroleum ether (b.p. 40-60° C.) and ethyl acetate as eluent. There was thus obtained the required starting material as a solid (0.635 g).

[55] $^1$H NMR: (DMSOd$_6$) 3.36 (s, 3H), 3.37 (s, 3H), 3.69 (s, 2H), 3.74-3.8 (m, 4H), 3.76 (s, 3H), 4.3-4.38 (m, 4H), 6.36 (d, 1H), 7.25-7.31 (m, 4H), 7.37 (d, 1H), 7.41 (s, 1H), 7.47 (d, 2H), 7.6 (s, 1H), 7.9 (d, 1H), 8.53 (s, 1H), 10.04 (s, 1H); Mass Spectrum: M+H$^+$ 557.

[56] The reaction mixture was heated to 45° C. for 4 hours. The solvent was evaporated and the residue was purified using a Waters 'β Basic Hypersil' reversed-phase preparative HPLC column chromatography as described in Example 6. The product gave the following characterising data:—$^1$H NMR: (DMSOd$_6$) 3.75 (s, 2H), 3.76 (s, 3H), 3.99 (s, 3H), 4.0 (s, 3H), 6.35 (d, 1H), 7.3 (m, 3H), 7.4 (m, 4H), 7.6 (s, 1H), 7.9 (s, 1H), 8.6 (s, 1H); Mass Spectrum: M+H$^+$ 487.

[57] $^1$H NMR: (DMSOd$_6$) 3.75 (s, 2H), 3.97 (s, 3H), 3.99 (s, 3H), 7.13 (m, 1H), 7.27 (d, 2H), 7.39 (s, 1H), 7.46 (d, 2H), 7.56 (s, 1H), 6.67 (d, 1H), 7.97 (s, 1H), 8.17 (s, 1H), 8.53 (s, 1H), 10.36 (s, 1H); Mass Spectrum: M+H$^+$ 456.

[58] $^1$H NMR: (DMSOd$_6$) 3.35 (s, 3H), 3.74-3.78 (m, 2H), 3.75 (s, 2H), 3.98 (s, 3H), 4.31-4.35 (m, 2H), 7.14 (m, 1H), 7.28 (d, 2H), 7.41 (s, 1H), 7.47 (d, 2H), 7.56 (s, 1H), 7.68 (d, 1H), 7.97 (s, 1H), 8.17 (s, 1H), 8.53 (s, 1H), 10.37 (s, 1H), 12.91 (br s, 1H); Mass Spectrum: M+H$^+$ 500.

[59] $^1$H NMR: (DMSOd$_6$) 3.71 (s, 2H), 3.97 (s, 3H), 3.99 (s, 3H), 7.27 (d, 2H), 7.39 (s, 1H), 7.43-7.52 (m, 4H), 7.56 (s, 1H), 8.01 (s, 1H), 8.15 (s, 1H), 8.53 (s, 1H), 10.21 (s, 1H) 12.99 (s, 1H); Mass Spectrum: M+H$^+$ 456.

[60] $^1$H NMR: (DMSOd$_6$) 1.44 (t, 3H), 3.72 (s, 2H), 3.98 (s, 3H), 4.26 (q, 2H), 7.27 (d, 2H), 7.37 (s, 1H), 7.43-7.52 (m, 4H), 7.56 (s, 1H), 8.01 (s, 1H), 8.15 (s, 1H), 8.52 (s, 1H), 10.22 (s, 1H), 12.98 (s, 1H); Mass Spectrum: M+H$^+$ 470.

[61] $^1$H NMR: (DMSOd$_6$) 3.35 (s, 3H), 3.72 (s, 2H), 3.74-3.79 (m, 2H), 3.98 (s, 3H), 4.3-4.36 (m, 2H), 7.27 (d, 2H), 7.41 (s, 1H), 7.43-7.52 (m, 4H), 7.56 (s, 1H), 8.01 (s, 1H), 8.15 (s, 1H), 8.53 (s, 1H), 10.23 (s, 1H), 12.98 (s, 1H); Mass Spectrum: M+H$^+$ 500.

[62] $^1$H NMR: (DMSOd$_6$) 3.84 (s, 2H), 3.97 (s, 3H), 3.99 (s, 3H), 7.08 (m, 1H), 7.29 (d, 2H), 7.39 (s, 1H), 7.51 (d, 2H), 7.55 (d, 1H), 7.56 (s, 1H), 7.59 (d, 1H), 8.1 (s, 1H), 8.54 (s, 1H), 10.15 (s, 1H), 12.7 (s, 1H); Mass Spectrum: M+H$^+$ 456.

[63] $^1$H NMR: (DMSOd$_6$) 3.76 (s, 2H), 3.97 (s, 3H), 3.99 (s, 3H), 7.28 (d, 2H), 7.39 (s, 1H), 7.4 (m, 1H), 7.46 (d, 2H), 7.55 (s, 1H), 7.89 (s, 1H), 8.36 (d, 1H), 8.53 (s, 1H), 10.48 (s, 1H), 11.67 (br s, 1H); Mass Spectrum: M+H$^+$ 457.

[64] Mass Spectrum: M+H$^+$ 456.

[65] $^1$H NMR: (DMSOd$_6$) 3.76 (s, 2H), 3.97 (s, 3H), 3.99 (s, 3H), 7.27 (d, 2H), 7.39 (s, 1H), 7.47 (d, 2H), 7.56 (s, 1H), 7.63 (m, 1H), 8.03 (d, 1H), 8.53 (s, 1H), 8.57 (d, 1H), 9.27 (s, 1H), 10.51 (s, 1H); Mass Spectrum: M+H$^+$ 473.

[66] $^1$H NMR: (DMSOd$_6$) 2.78 (s, 3H), 3.75 (s, 2H), 3.98 (s, 3H), 3.99 (s, 3H), 7.28 (d, 2H), 7.39 (s, 1H), 7.47 (d, 2H), 7.56 (s, 1H), 7.58 (m, 1H), 7.94 (d, 1H), 8.32 (d, 1H), 8.54 (s, 1H), 10.42 (s, 1H); Mass Spectrum: M+H$^+$ 487.

[67] $^1$H NMR: (DMSOd$_6$) 3.84 (s, 2H), 3.98 (s, 3H), 3.99 (s, 3H), 7.05-7.12 (m, 2H), 7.29 (d, 2H), 7.39 (s, 1H), 7.41-7.46 (m, 2H), 7.49 (d, 1H), 7.56 (s, 1H), 8.54 (s, 1H); Mass Spectrum: M+H$^+$ 456.

[68] $^1$H NMR: (DMSOd$_6$) 3.59 (s, 3H), 3.78 (br s, 2H), 3.98 (s, 3H), 3.99 (s, 3H), 7.16-7.33 (m, 4H), 7.39 (s, 1H), 7.41-7.56 (m, 4H), 7.57 (s, 1H), 8.55 (s, 1H), 10.95 (br s, 1H); Mass Spectrum: M+H$^+$ 470.

[69] $^1$H NMR: (DMSOd$_6$) 3.35 (s, 3H), 3.73-3.79 (m, 4H), 3.81 (s, 3H), 3.98 (s, 3H), 4.3-4.36 (m, 2H), 6.41 (d, 1H), 7.27 (d, 2H), 7.4 (s, 1H), 7.48 (d, 2H), 7.56 (s, 1H), 7.57 (d, 1H), 7.88 (d, 1H), 7.96 (d, 1H), 8.53 (s, 1H), 10.6 (br s, 1H); Mass Spectrum: M+H$^+$ 514.

The 5-amino-1-methyl-1H-pyrrolo[3,2-b]pyridine used as a starting material was prepared as follows:—

Sodium hydride (60% dispersion in oil, 0.093 g) was added to a stirred mixture of N$^1$,N$^1$-dimethyl-N$^2$-(1H-pyrrolo[3,2-b]pyridin-5-yl)formamidine (*J. Med. Chem.*, 2003, 46, 3060; 0.418 g) and DMF (8 ml) and the reaction mixture was stirred at ambient temperature for 10 minutes. Methyl iodide (0.138 ml) was added and the reaction mixture was stirred at ambient temperature for 16 hours. Water was added and the mixture was extracted with methylene chloride. The organic phase was washed with water and with brine, dried over magnesium sulphate and evaporated. There was thus obtained N$^1$,N$^1$-dimethyl-N$^2$-[1-methyl-1H-pyrrolo [3,2-b]pyridin-5-yl]formamidine (0.212 g); $^1$H NMR: (DMSOd$_6$) 2.95 (s, 3H), 3.1 (s, 3H), 3.85 (s, 3H), 6.3 (d, 1H), 6.7 (d, 1H), 7.4 (d, 1H), 7.7 (d, 1H), 8.45 (s, 1H).

A mixture of the material so obtained, potassium hydroxide (0.12 g), water (0.5 ml) and methanol (2 ml) was stirred and heated to 75° C. for 24 hours. The resultant mixture was diluted with water and extracted with a mixture of methylene chloride and methanol. The organic phase was washed with water and with brine, dried over magnesium sulphate and evaporated. There was thus obtained a 2:3 mixture (0.16 g) of unreacted starting material and 5-amino-1-methyl-1H-pyrrolo[3,2-b]pyridine; $^1$H NMR: (DMSOd$_6$) 3.7 (s, 3H), 5.35 (br s, 2H), 6.1 (d, 1H), 6.35 (d, 1H), 7.25 (d, 1H), 7.5 (d, 1H.

[70] $^1$H NMR: (DMSOd$_6$) 3.37 (s, 3H), 3.37 (s, 3H), 3.74-3.79 (m, 6H), 3.81 (s, 3H), 3.29-3.38 (m, 4H), 6.41 (d, 1H), 7.27 (d, 2H), 7.41 (d, 1H), 7.47 (d, 2H), 7.57 (d, 1H), 7.6 (s, 1H), 7.88 (d, 1H), 7.96 (d, 1H), 8.53 (s, 1H), 10.6 (br s, 1H); Mass Spectrum: M+H$^+$ 558.

[71] $^1$H NMR: (DMSOd$_6$) 3.85 (s, 2H), 3.98 (s, 3H), 3.99 (s, 3H), 7.28 (d, 2H), 7.39 (s, 1H), 7.5 (d, 2H), 7.51 (m, 1H), 7.56 (s, 1H), 7.73 (m, 1H), 7.84 (d, 1H), 7.92 (d, 1H), 8.31 (d, 1H), 8.37 (d, 1H), 8.54 (s, 1H), 11.12 (s, 1H); Mass Spectrum: M+H$^+$ 467.

[72] $^1$H NMR: (DMSOd$_6$) 1.44 (t, 3H), 3.91 (s, 2H), 3.99 (s, 3H), 4.26 (q, 2H), 7.3 (d, 2H), 7.37 (s, 1H), 7.52 (d, 2H), 7.75 (s, 1H), 7.65 (m, 1H), 7.75 (d, 1H), 7.78 (m, 1H), 7.95-8.02 (m, 2H), 8.34 (d, 1H), 8.55 (s, 1H), 10.75 (s, 1H); Mass Spectrum: M+H$^+$ 481.

[73] $^1$H NMR: (DMSOd$_6$) 3.74 (s, 2H), 3.98 (s, 3H), 3.99 (s, 3H), 7.28 (d, 2H), 7.39 (s, 1H), 7.5 (d, 2H), 7.54 (m, 1H), 7.56 (s, 1H), 7.71 (m, 1H), 7.88 (d, 1H), 8.06 (d, 1H), 8.48 (s, 1H), 8.53 (s, 1H), 9.17 (s, 1H), 10.91 (s, 1H); Mass Spectrum: M+H$^+$ 467.

[74] $^1$H NMR: (DMSOd$_6$) 2.62 (s, 3H), 3.78 (s, 2H), 3.98 (s, 3H), 3.99 (s, 3H), 7.28 (d, 2H), 7.37 (d, 1H), 7.39 (s, 1H), 7.48 (d, 2H), 7.56 (s, 1H), 7.78 (m, 1H), 7.88 (d, 1H), 8.16 (d, 1H), 8.34 (d, 1H), 8.53 (s, 1H), 10.51 (s, 1H); Mass Spectrum: M+H$^+$ 481.

[75] $^1$H NMR: (DMSOd$_6$) 1.44 (t, 3H), 3.79 (s, 2H), 3.98 (s, 3H), 4.26 (q, 2H), 7.29 (d, 2H), 7.37 (s, 1H), 7.48 (d, 1H), 7.49 (d, 2H), 7.56 (s, 1H), 7.84 (m, 1H), 7.99 (d, 1H), 8.28 (d, 1H), 8.41 (d, 1H), 8.52 (s, 1H), 8.79 (m, 1H), 10.57 (s, 1H); Mass Spectrum: M+H$^+$ 481.

[76] $^1$H NMR: (DMSOd$_6$) 3.35 (s, 3H), 3.74-3.78 (m, 2H), 3.79 (s, 2H), 3.98 (s, 3H), 4.31-4.35 (m, 2H), 7.29 (d, 2H), 7.41 (s, 1H), 7.49 (d, 2H), 7.5 (d, 1H), 7.57 (s, 1H), 7.84 (m, 1H), 7.99 (d, 1H), 8.29 (d, 1H), 8.41 (d, 1H), 8.53 (s, 1H), 8.79 (m, 1H), 10.58 (s, 1H); Mass Spectrum: M+H$^+$ 511.

[77] $^1$H NMR: (DMSOd$_6$) 3.83 (s, 2H), 3.97 (s, 3H), 3.99 (s, 3H), 7.29 (d, 2H), 7.39 (s, 1H), 7.49 (d, 2H), 7.56 (s, 1H), 7.96 (m, 1H), 8.07 (d, 1H), 8.54 (s, 1H), 8.55 (d, 1H), 8.82 (d, 1H), 8.88 (d, 1H), 10.76 (s, 1H); Mass Spectrum: M+H$^+$ 468.

[78] $^1$H NMR: (DMSOd$_6$) 1.44 (t, 3H), 3.83 (s, 2H), 3.98 (s, 3H), 4.26 (q, 2H), 7.29 (d, 2H), 7.37 (s, 1H), 7.47 (d, 2H), 7.56 (s, 1H), 7.96 (m, 1H), 8.05 (d, 1H), 8.53 (d, 1H), 8.56 (d, 1H), 8.82 (d, 1H), 8.89 (d, 1H), 10.76 (s, 1H); Mass Spectrum: M+H$^+$ 482.

[79] $^1$H NMR: (DMSOd$_6$) 3.35 (s, 3H), 3.74-3.79 (m, 2H), 3.83 (s, 2H), 3.98 (s, 3H), 4.3-4.36 (m, 2H), 7.3 (d, 2H), 7.41 (s, 1H), 7.49 (d, 2H), 7.57 (s, 1H), 7.97 (m, 1H), 8.07 (d, 1H), 8.53 (s, 1H), 8.56 (d, 1H), 8.83 (d, 1H), 8.89 (d, 1H), 10.76 (s, 1H); Mass Spectrum: M+H$^+$ 512.

[80] $^1$H NMR: (DMSOd$_6$) 3.86 (s, 2H), 3.97 (s, 3H), 3.99 (s, 3H), 7.28 (d, 2H), 7.38 (s, 1H), 7.5 (d, 2H), 7.55 (s, 1H), 7.94 (d, 1H), 8.53 (s, 1H), 8.56 (d, 1H), 8.63 (s, 1H), 9.31 (s, 1H), 9.38 (s, 1H); Mass Spectrum: M+H$^+$ 468.

3-Amino-2,6-naphthyridine is described in *Tetrahedron Letters*, 1965, 2737-2744.

[81] $^1$H NMR: (DMSOd$_6$) 3.86 (s, 2H), 3.97 (s, 3H), 3.99 (s, 3H), 7.28 (d, 2H), 7.38 (s, 1H), 7.5 (d, 2H), 7.55 (s, 1H), 7.7 (m, 1H), 8.38 (d, 1H), 8.53 (m, 2H), 8.91 (m, 1H), 9.24 (s, 1H); Mass Spectrum: M+H$^+$ 468.

6-Amino-1,7-naphthyridine is described in *Tetrahedron Letters*, 1965, 2737-2744.

[82] $^1$H NMR: (DMSOd$_6$) 3.75 (s, 2H), 3.97 (s, 3H), 3.99 (s, 3H), 7.27 (d, 2H), 7.35 (m, 1H), 7.39 (s, 1H), 7.45 (d, 2H), 7.56 (s, 1H), 8.07 (m, 1H), 8.27 (m, 1H), 8.54 (s, 1H), 8.77 (d, 1H), 10.45 (s, 1H); Mass Spectrum: M+H$^+$ 417.

EXAMPLE 10

Using an analogous procedure to that described in Example 6, the appropriate 2-phenylacetic acid was reacted with the appropriate pyridylamine to give the compounds described in Table V.

Unless otherwise stated, for the Compounds [26] to [47] below, DMA was used as the solvent and, on completion of the reaction, a saturated aqueous sodium bicarbonate solution and ethyl acetate were added in turn to the reaction mixture. The resultant mixture was stirred at ambient temperature for 1 hour. The precipitate was isolated by filtration and purified by reversed-phase preparative HPLC using a Waters 'β Basic Hypersil' reversed-phase column (5 microns silica, 30 mm diameter, 250 mm length) which was eluted with decreasingly polar mixtures of water (containing 0.2% ammonium carbonate) and acetonitrile.

Further, unless otherwise stated, each pyridylamine was a commercially available material.

TABLE V

| No. & Note | $(R^1)_p$ | $(R^2)_q$ | $(R^6)_r$ |
|---|---|---|---|
| [1] | 6,7-dimethoxy | H | 4-methyl |
| [2] | 6,7-dimethoxy | H | 5-methyl |
| [3] | 6,7-dimethoxy | H | 6-methyl |
| [4] | 6,7-dimethoxy | H | 6-dimethylamino |
| [5] | 6-methoxy-7-(2-methoxyethoxy) | H | 6-dimethylamino |
| [6] | 6,7-dimethoxy | H | 6-methylamino |
| [7] | 6-methoxy-7-(2-methoxyethoxy) | H | 6-methylamino |
| [8] | 6,7-di-(2-methoxyethoxy) | H | 6-methylamino |
| [9] | 6,7-dimethoxy | H | 6-ethylamino |
| [10] | 6-methoxy-7-(2-methoxyethoxy) | H | 6-ethylamino |
| [11] | 6,7-di-(2-methoxyethoxy) | H | 6-ethylamino |
| [12] | 6,7-dimethoxy | H | 6-(2-hydroxyethylamino) |
| [13] | 6-methoxy-7-(2-methoxyethoxy) | H | 6-(2-hydroxyethylamino) |
| [14] | 6,7-di-(2-methoxyethoxy) | H | 6-(2-hydroxyethylamino) |
| [15] | 6,7-dimethoxy | H | 6-(2-methoxyethylamino) |
| [16] | 6-methoxy-7-(2-methoxyethoxy) | H | 6-(2-methoxyethylamino) |
| [17] | 6,7-di-(2-methoxyethoxy) | H | 6-(2-methoxyethylamino) |
| [18] | 6,7-dimethoxy | H | 6-pyrrolidin-1-yl |
| [19] | 6-methoxy-7-(2-methoxyethoxy) | H | 6-pyrrolidin-1-yl |
| [20] | 6,7-di-(2-methoxyethoxy) | | 6-pyrrolidin-1-yl |
| [21] | 6,7-dimethoxy | H | 6-morpholino |
| [22] | 6-methoxy-7-(2-methoxyethoxy) | H | 6-morpholino |
| [23] | 6,7-di-(2-methoxyethoxy) | H | 6-morpholino |
| [24] | 7-ethoxy-6-methoxy | H | 5-dimethylamino |
| [25] | 6-methoxy-7-(2-methoxyethoxy) | H | 5-dimethylamino |
| [26] | 6,7-di-(2-methoxyethoxy) | H | 5-dimethylamino |
| [27] | 6,7-dimethoxy | H | 4-dimethylamino |
| [28] | 6-methoxy-7-(2-methoxyethoxy) | H | 4-dimethylamino |
| [29] | 6,7-di-(2-methoxyethoxy) | H | 4-dimethylamino |
| [30] | 6,7-dimethoxy | H | 4-methylamino |
| [31] | 6-methoxy-7-(2-methoxyethoxy) | H | 4-methylamino |
| [32] | 6,7-di-(2-methoxyethoxy) | H | 4-methylamino |
| [33] | 6,7-dimethoxy | H | 4-ethylamino |
| [34] | 6-methoxy-7-(2-methoxyethoxy) | H | 4-ethylamino |
| [35] | 6,7-di-(2-methoxyethoxy) | H | 4-ethylamino |
| [36] | 6,7-dimethoxy | H | 4-isopropylamino |
| [37] | 6-methoxy-7-(2-methoxyethoxy) | H | 4-isopropylamino |
| [38] | 6,7-di-(2-methoxyethoxy) | H | 4-isopropylamino |
| [39] | 6,7-dimethoxy | H | 4-cyclopropylamino |
| [40] | 6-methoxy-7-(2-methoxyethoxy) | H | 4-cyclopropylamino |

TABLE V-continued

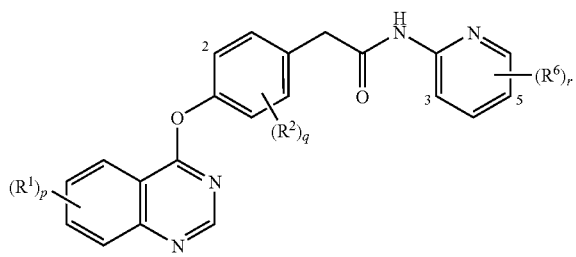

| No. & Note | $(R^1)_p$ | $(R^2)_q$ | $(R^6)_r$ |
|---|---|---|---|
| [41] | 6,7-di-(2-methoxyethoxy) | H | 4-cyclopropylamino |
| [42] | 6,7-dimethoxy | H | 4-pyrrolidin-1-yl |
| [43] | 6-methoxy-7-(2-methoxyethoxy) | H | 4-pyrrolidin-1-yl |
| [44] | 6,7-di-(2-methoxyethoxy) | H | 4-pyrrolidin-1-yl |
| [45] | 6,7-dimethoxy | H | 4-morpholino |
| [46] | 6-methoxy-7-(2-methoxyethoxy) | H | 4-morpholino |
| [47] | 6,7-di-(2-methoxyethoxy) | H | 4-morpholino |
| [48] | 6,7-dimethoxy | H | H |

Notes The products gave the characterising data shown below.

[1] $^1$H NMR: (DMSOd$_6$) 2.3 (s, 3H), 3.76 (s, 2H), 3.97 (s, 3H), 3.99 (s, 3H), 6.94 (d, 1H), 7.26 (d, 2H), 7.39 (s, 1H), 7.45 (d, 2H), 7.55 (s, 1H), 7.94 (s, 1H), 8.18 (d, 1H), 8.53 (s, 1H), 10.68 (s, 1H); Mass Spectrum: M+H$^+$ 431.

[2] $^1$H NMR: (DMSOd$_6$) 2.25 (s, 3H), 3.75 (s, 2H), 3.97 (s, 3H), 3.99 (s, 3H), 7.26 (d, 2H), 7.39 (s, 1H), 7.45 (d, 2H), 7.55 (s, 1H), 7.6 (m, 1H), 7.98 (d, 1H), 8.16 (s, 1H), 8.53 (s, 1H), 10.67 (s, 1H); Mass Spectrum: M+H$^+$ 431.

[3] $^1$H NMR: (DMSOd$_6$) 2.42 (s, 3H), 3.76 (s, 2H), 3.97 (s, 3H), 3.99 (s, 3H), 6.97 (d, 1H), 7.26 (d, 2H), 7.38 (s, 1H), 7.45 (d, 2H), 7.55 (s, 1H), 7.66 (m, 1H), 7.89 (d, 1H), 8.53 (s, 1H), 10.7 (s, 1H); Mass Spectrum: M+H$^+$ 431.

[4] DMA was used as the solvent. On completion of the reaction, a saturated aqueous sodium bicarbonate solution (2 ml) and ethyl acetate (2 ml) were added in turn to the reaction mixture. The resultant mixture was stirred at ambient temperature for 1 hour. The resultant product was isolated by filtration and dried under vacuum. The product gave the following characterising data:—$^1$H NMR: (DMSOd$_6$) 3.02 (s, 6H), 3.76 (s, 2H), 3.97 (s, 3H), 3.99 (s, 3H), 6.34 (d, 1H), 7.25 (d, 2H), 7.29 (d, 1H), 7.39 (s, 1H), 7.44 (d, 2H), 7.47 (m, 1H), 7.55 (s, 1H), 8.54 (s, 1H), 10.13 (s, 1H); Mass Spectrum: M+H$^+$ 460.

The 2-amino-6-dimethylaminopyridine used as a starting material was prepared as follows:—

A mixture of 2-amino-6-chloropyridine (0.4 g) and an aqueous solution of dimethylamine (40%, 1.41 ml) was stirred and heated to 190° C. for 1 hour in a microwave oven. The reaction mixture was purified by column chromatography on silica using a 20:1 mixture of methylene chloride and methanol as eluent. There was thus obtained the required starting material (0.38 g); $^1$H NMR: (CDCl$_3$) 3.02 (s, 6H), 4.15 (br s, 2H), 5.79 (d, 1H), 5.9 (d, 1H), 7.25 (t, 1H); Mass Spectrum: M+H$^+$ 138.

[5] DMA was used as the solvent and, on completion of the reaction, an analogous work-up to that described in Note [4] immediately above was used. The product so obtained gave the following characterising data:—$^1$H NMR: (DMSOd$_6$) 3.01 (s, 6H), 3.35 (s, 3H), 3.73-3.79 (m, 4H), 3.98 (s, 3H), 4.31-4.35 (m, 2H), 6.34 (d, 1H), 7.26 (d, 2H), 7.29 (d, 1H), 7.4 (s, 1H), 7.44 (d, 2H), 7.46 (m, 1H), 7.56 (s, 1H), 8.53 (s, 1H), 10.13 (s, 1H); Mass Spectrum: M+H$^+$ 504.

[6] $^1$H NMR: (DMSOd$_6$) 2.78 (d, 3H), 3.75 (s, 2H), 3.97 (s, 3H), 3.99 (s, 3H), 6.15 (d, 1H), 6.34 (q, 1H), 7.22 (d, 1H), 7.25 (d, 2H), 7.33 (m, 1H), 7.38 (s, 1H), 7.44 (d, 2H), 7.55 (s, 1H), 8.53 (s, 1H), 10.09 (s, 1H); Mass Spectrum: M+H$^+$ 446.

The 2-amino-6-methylaminopyridine used as a starting material was prepared as follows:—

A mixture of 2-amino-6-chloropyridine (0.5 g) and an aqueous solution of methylamine (40%, 2.19 ml) was placed in a glass cylinder which was sealed and heated to 200° C. for 2 hours. The reaction mixture was cooled to ambient temperature and purified by column chromatography on silica using increasingly polar mixtures of methylene chloride and methanol as eluent. There was thus obtained the required starting material (0.11 g); $^1$H NMR: (CDCl$_3$) 2.84 (s, 3H), 4.15 (br s, 2H), 4.28 (br s, 1H), 5.76 (d, 1H), 5.83 (d, 1H), 7.25 (t, 1H).

[7] $^1$H NMR: (DMSOd$_6$) 2.77 (s, 3H), 3.34 (s, 3H), 3.7-3.81 (m, 4H), 3.98 (s, 3H), 4.26-4.37 (m, 2H), 6.15 (d, 1H), 6.35 (br s, 1H), 7.17-7.3 (m, 3H), 7.34 (m, 1H), 7.4 (s, 1H), 7.43 (d, 2H), 7.56 (s, 1H), 8.53 (s, 1H), 10.1 (s, 1H); Mass Spectrum: M+H$^+$ 490.

[8] $^1$H NMR: (DMSOd$_6$) 2.78 (d, 3H), 3.35 (s, 3H), 3.36 (s, 3H), 3.7-3.8 (m, 6H), 4.29-4.37 (m, 4H), 6.15 (d, 1H), 6.34 (q, 1H), 7.22 (d, 1H), 7.25 (d, 2H), 7.34 (m, 1H), 7.41 (s, 1H), 7.43 (d, 2H), 7.59 (s, 1H), 8.53 (s, 1H), 10.09 (s, 1H); Mass Spectrum: M+H$^+$ 534.

[9] $^1$H NMR: (DMSOd$_6$) 1.13 (t, 3H), 3.26 (q, 2H), 3.75 (s, 2H), 3.97 (s, 3H), 3.99 (s, 3H), 6.16 (d, 1H), 6.34 (t, 1H), 7.19 (d, 1H), 7.25 (d, 2H), 7.31 (m, 1H), 7.39 (s, 1H), 7.43 (d, 2H), 7.55 (s, 1H), 8.54 (s, 1H), 10.03 (s, 1H); Mass Spectrum: M+H$^+$ 460.

The 2-amino-6-ethylaminopyridine used as a starting material was prepared as follows:—

Using an analogous procedure to that described in the portion of Note [6] above that is concerned with the preparation of starting materials but with heating to 170° C. for 16 hours, 2-amino-6-chloropyridine was reacted with ethylamine. There was thus obtained the required starting material in 31% yield; $^1$H NMR: (CDCl$_3$) 1.23 (t, 3H), 3.21 (m, 2H), 4.13 (br s, 2H), 4.2 (br s, 1H), 5.76 (d, 1H), 5.82 (d, 1H), 7.23 (t, 1H); Mass Spectrum: M+H$^+$ 138.

[10] $^1$H NMR: (DMSOd$_6$) 1.13 (t, 3H), 3.23-3.3 (m, 2H), 3.35 (s, 3H), 3.71-3.8 (m, 4H), 3.98 (s, 3H), 4.3-4.36 (m, 2H), 6.16 (d, 1H), 6.34 (t, 1H): 7.19 (d, 1H), 7.25 (d, 2H), 7.31 (m, 1H), 7.4 (s, 1H), 7.43 (d, 2H), 7.56 (s, 1H), 8.53 (s, 1H): 10.03 (s, 1H); Mass Spectrum: M+H$^+$ 504.

[11] $^1$H NMR: (DMSOd$_6$) 1.13 (t, 3H), 3.24-3.3 (m, 2H), 3.35 (s, 3H), 3.36 (s, 3H), 3.72-3.8 (m, 6H), 4.29-4.37 (m, 4H), 6.16 (d, 1H), 6.34 (t, 1H), 7.19 (d, 1H), 7.25 (d, 2H), 7.31 (m, 1H), 7.41 (s, 1H), 7.43 (d, 2H), 7.59 (s, 1H), 8.53 (s, 1H), 10.03 (s, 1H); Mass Spectrum: M+H$^+$ 548.

[12] $^1$H NMR: (DMSOd$_6$) 3.31-3.34 (m, 2H), 3.54 (t, 2H), 3.74 (s, 2H), 3.97 (s, 3H), 3.99 (s, 3H), 6.21 (d, 1H), 6.35 (d, 1H), 7.2 (d, 1H), 7.25 (d, 2H), 7.32 (m, 1H), 7.38 (s, 1H), 7.43 (d, 2H), 7.55 (s, 1H), 8.53 (s, 1H), 10.06 (s, 1H); Mass Spectrum: M+H$^+$ 476.

The 2-amino-6-(2-hydroxyethylamino)pyridine used as a starting material was prepared as follows:—

Using an analogous procedure to that described in the portion of Note [6] above that is concerned with the preparation of starting materials but with heating to 210° C. for 30 minutes in a microwave oven, 2-amino-6-chloropyridine was reacted with ethanolanune. There was thus obtained the required starting material in 19% yield; ¹H NMR: (CDCl₃) 3.45 (m, 2H), 3.77 (m, 2H), 4.19 (br s, 2H), 4.63 (br s, 1H), 5.81 (m, 2H), 7.19 (m, 1H); Mass Spectrum: M+H⁺ 154.

[13] ¹H NMR: (DMSOd₆) 3.33 (t, 2H), 3.34 (s, 3H), 3.54 (t, 2H), 3.71-3.79 (m, 4H), 3.98 (s, 3H), 4.3-4.35 (m, 2H), 6.21 (d, 1H), 6.35 (t, 1H), 7.2 (d, 1H), 7.25 (d, 2H), 7.32 (m, 1H), 7.4 (s, 1H), 7.43 (d, 2H), 7.56 (s, 1H), 8.53 (s, 1H), 10.05 (s, 1H); Mass Spectrum: M−H⁻ 518.

[14] ¹H NMR: (DMSOd₆) 3.31-3.35 (m, 2H), 3.36 (s, 3H), 3.37 (s, 3H), 3.54 (t, 2H), 3.73-3.79 (m, 6H), 4.2-4.37 (m, 4H), 6.21 (d, 1H), 6.35 (t, 1H), 7.2 (d, 1H), 7.25 (d, 2H), 7.31 (m, 1H), 7.41 (d, 2H), 7.43 (s, 1H), 7.59 (s, 1H), 8.53 (s, 1H), 10.05 (s, 1H); Mass Spectrum: M−H⁻ 562.

[15] ¹H NMR: (DMSOd₆) 3.28 (s, 3H), 3.41-3.49 (m, 4H), 3.75 (s, 2H), 3.97 (s, 3H), 3.99 (s, 3H), 6.22 (d, 1H), 6.45 (t, 1H), 7.2 (d, 1H), 7.25 (d, 2H), 7.31 (m, 1H), 7.39 (s, 1H), 7.43 (d, 2H), 7.55 (s, 1H), 8.54 (s, 1H), 10.05 (s, 1H); Mass Spectrum: M+H⁺ 490.

The 2-amino-6-(2-methoxyethylamino)pyridine used as a starting material was prepared as follows:—

A mixture of 2-amino-6-chloropyridine (1.5 g), 2-methoxyethylamine (3.04 ml) and water (0.5 ml) was heated to 210° C. in a microwave oven for 30 minutes. The reaction mixture was purified by column chromatography on silica using increasingly polar mixtures of methylene chloride and ethyl acetate as eluent. There was thus obtained the required starting material (0.38 g); ¹H NMR: (CDCl₃) 3.76 (s, 3H), 3.42 (t, 2H), 3.56 (t, 2H), 4.14 (br s, 2H), 4.58 (br s, 1H), 5.79 (d, 1H), 5.82 (d, 1H), 7.21 (t, 1H).

[16] ¹H NMR: (DMSOd₆) 3.28 (s, 3H), 3.35 (s, 3H), 3.41-3.49 (m, 4H), 3.72-3.78 (m, 4H), 3.98 (s, 3H), 4.31-4.35 (m, 2H), 6.22 (d, 1H), 6.45 (t, 1H), 7.2 (d, 1H), 7.24 (d, 2H), 7.31 (m, 1H), 7.4 (s, 1H), 7.43 (d, 2H), 7.56 (s, 1H), 8.53 (s, 1H), 10.06 (s, 1H); Mass Spectrum: M+H⁺ 534.

[17] ¹H NMR: (DMSOd₆) 3.28 (s, 3H), 3.35 (s, 3H), 3.36 (s, 3H), 3.41-3.50 (m, 4H), 3.72-3.8 (m, 6H), 4.29-4.37 (m, 4H), 6.22 (d, 1H), 6.44 (t, 1H), 7.2 (d, 1H), 7.25 (d, 2H), 7.31 (m, 1H), 7.41 (s, 1H), 7.43 (d, 2H), 7.59 (s, 1H), 8.53 (s, 1H), 10.05 (s, 1H); Mass Spectrum: M+H⁺ 578.

[18] ¹H NMR: (DMSOd₆) 1.89-1.98 (m, 4H), 3.35-3.42 (m, 4H), 3.76 (s, 2H), 3.97 (s, 3H), 3.99 (s, 3H), 6.15 (d, 1H), 7.25 (d, 2H), 7.27 (d, 1H), 7.39 (s, 1H), 7.41-7.47 (m, 3H), 7.55 (s, 1H), 8.53 (s, 1H), 10.11 (s, 1H); Mass Spectrum: M+H⁺ 486.

The 2-amino-6-pyrrolidin-1-ylpyridine used as a starting material was prepared as follows:—

A mixture of 2-amino-6-chloropyridine (0.5 g), pyrrolidine (1.3 ml) and water (0.5 ml) was heated to 205° C. in a microwave oven for 30 minutes. The reaction mixture was purified by column chromatography on silica using increasingly polar mixtures of methylene chloride and ethyl acetate as eluent. There was thus obtained the required starting material (0.36 g); ¹H NMR: (CDCl₃) 1.94 (m, 4H), 3.95 (m, 4H), 4.15 (br s, 2H), 5.75 (m, 2H), 7.23 (m, 1H); Mass Spectrum: M+H⁺ 164.

[19] ¹H NMR: (DMSOd₆) 1.89-1.98 (m, 4H), 3.34 (s, 3H), 3.35-3.41 (m, 4H), 3.73-3.79 (m, 4H), 3.98 (s, 3H), 4.3-4.35 (m, 2H), 6.15 (d, 1H), 7.25 (d, 2H), 7.28 (d, 1H), 7.4 (s, 1H), 7.41-7.47 (m, 3H), 7.56 (s, 1H), 8.53 (s, 1H), 10.11 (s, 1H); Mass Spectrum: M+H⁺ 530.

[20] ¹H NMR: (DMSOd₆) 1.88-1.97 (m, 4H), 3.34-3.4 (m, 4H), 3.35 (s, 3H), 3.36 (s, 3H): 3.73-3.79 (m, 6H), 4.29-4.37 (m, 4H), 6.15 (d, 1H), 7.25 (d, 2H), 7.27 (d, 1H), 7.4-7.46 (m, 4H), 7.59 (s, 1H), 8.53 (s, 1H), 10.11 (s, 1H); Mass Spectrum: M+H⁺ 574.

[21] ¹H NMR: (DMSOd₆) 3.42-3.48 (m, 4H), 3.66-3.73 (m, 4H), 3.72 (s, 2H), 3.97 (s, 3H), 3.99 (s, 3H), 6.52 (d, 1H), 7.25 (d, 2H), 7.39 (s, 1H), 7.4 (d, 1H), 7.43 (d, 2H), 7.53 (m, 1H), 7.55 (s, 1H), 8.53 (s, 1H), 10.23 (s, 1H); Mass Spectrum: M+H⁺ 502.

The 2-amino-6-morpholinopyridine used as a starting material was prepared as follows:—

Using an analogous procedure to that described in the portion of Note [18] above that is concerned with the preparation of starting materials, 2-amino-6-chloropyridine was reacted with morpholine to give the required starting material in 69% yield; ¹H NMR: (CDCl₃) 3.43 (m, 4H), 3.79 (m, 4H), 4.2 (br s, 2H), 5.91 (d, 1H), 5.98 (d, 1H), 7.31 (t, 1H); Mass Spectrum: M+H⁺ 180.

[22] ¹H NMR: (DMSOd₆) 3.34 (s, 3H), 3.42-3.48 (m, 4H), 3.67-3.72 (m, 4H), 3.73-3.79 (m, 4H), 3.98 (s, 3H), 4.3-4.35 (m, 2H), 6.52 (d, 2H), 7.26 (d, 2H), 7.39 (d, 1H), 7.4 (d, 2H), 7.43 (d, 2H), 7.53 (m, 1H), 7.56 (s, 1H), 8.53 (s, 1H), 10.22 (s, 1H); Mass Spectrum: M+H⁺ 546.

[23] ¹H NMR: (DMSOd₆) 3.35 (s, 3H), 3.36 (s, 3H), 3.41-3.49 (m, 4H), 3.66-3.72 (m, 4H), 3.73-3.79 (m, 6H): 4.28-4.38 (m, 4H), 6.52 (d, 1H), 7.25 (d, 2H), 7.39 (d, 1H), 7.41 (s, 1H), 7.43 (d, 2H), 7.53 (m, 1H), 7.59 (s, 1H), 8.52 (s, 1H), 10.22 (s, 1H); Mass Spectrum: M+H⁺ 590.

[24] ¹H NMR: (DMSOd₆) 1.44 (t, 3H), 2.88 (s, 6H), 3.71 (s, 2H), 3.98 (s, 3H), 4.26 (q, 2H), 7.19 (m, 1H), 7.26 (d, 2H), 7.36 (s, 1H), 7.44 (d, 2H), 7.55 (s, 1H), 7.84 (d, 1H), 7.91 (d, 1H), 8.52 (s, 1H), 10.44 (s, 1H); Mass Spectrum: M+H⁺ 474.

[25] ¹H NMR: (DMSOd₆) 2.88 (s, 6H), 3.35 (s, 3H), 3.71 (s, 2H), 3.74-3.79 (m, 2H), 3.98 (s, 3H), 4.3-4.36 (m, 2H), 7.18 (m, 1H), 7.26 (d, 2H), 7.4 (s, 1H), 7.45 (d, 2H), 7.56 (s, 1H), 7.84 (d, 1H), 7.91 (d, 1H), 8.53 (s, 1H), 10.43 (s, 1H); Mass Spectrum: M+H⁺ 504.

[26] ¹H NMR: (DMSOd₆) 2.88 (s, 6H), 3.36 (s, 3H), 3.37 (s, 3H), 3.72 (s, 2H), 3.73-3.81 (m, 4H), 4.29-4.38 (m, 4H), 7.19 (m, 1H), 7.26 (d, 2H), 7.41 (s, 1H), 7.44 (d, 2H), 7.6 (s, 1H), 7.84 (d, 1H), 7.91 (d, 1H), 8.53 (s, 1H), 10.43 (br s, 1H); Mass Spectrum: M+H⁺ 548.

[27] ¹H NMR: (DMSOd₆) 2.94 (s, 6H), 3.73 (s, 2H), 3.97 (s, 3H) 3.99 (s, 3H), 6.38 (m, 1H), 7.25 (d, 2H), 7.39 (s, 1H), 7.44 (d, 2H), 7.46 (br s, 1H), 7.55 (s, 1H), 7.88 (d, 1H), 8.53 (s, 1H), 10.37 (s, 1H); Mass Spectrum: M+H⁺ 460.

The 2-amino-4-dimethylaminopyridine used as a starting material was prepared as follows:—

Using an analogous procedure to that described in the portion of Note [18] above that is concerned with the preparation of starting materials, 2-amino-4-chloropyridine (*Organic Preparation and Procedure*, 1997, 29, 117-122; 0.4 g) and an aqueous solution of dimethylamine (40%) were stirred and heated to 175° C. for 35 minutes in a microwave oven. The reaction mixture was purified by reversed-phase preparative HPLC as described in Example 6. There was thus obtained the required starting material in 94% yield; ¹H NMR: (CDCl₃) 2.95 (s, 6H), 4.19 (br s, 2H), 5.68 (m, 1H), 6.05 (m, 1H), 7.77 (m, 1H); Mass Spectrum: M+H⁺ 138.

[28] ¹H NMR: (DMSOd₆) 2.94 (s, 6H), 3.35 (s, 3H), 3.74 (s, 2H), 3.75-3.79 (m, 2H), 3.99 (s, 3H), 4.3-4.36 (m, 2H), 6.39 (m, 1H), 7.26 (d, 2H), 7.41 (s, 1H), 7.44 (d, 2H), 7.46 (br s, 1H), 7.56 (s, 1H), 7.88 (d, 1H), 8.53 (s, 1H), 10.37 (br s, 1H); Mass Spectrum: M+H⁺ 504.

[29] ¹H NMR: (DMSOd₆) 2.94 (s, 6H), 3.35 (s, 3H), 3.36 (s, 3H), 3.73 (s, 2H), 3.74-3.78 (m, 4H), 4.3-4.37 (m, 4H), 6.38 (m, 1H), 7.25 (d, 2H), 7.41 (s, 1H), 7.43 (d, 2H), 7.46 (br s, 1H), 7.59 (s, 1H), 7.88 (d, 1H), 8.52 (s, 1H), 10.37 (s, 1H); Mass Spectrum: M+H⁺ 548.

[30] ¹H NMR: (DMSOd₆) 2.67 (d, 3H), 3.72 (s, 2H), 3.98 (s, 3H), 3.99 (s, 3H), 6.23 (m, 1H), 6.58 (q, 1H), 7.26 (d, 2H), 7.31 (s, 1H), 7.39 (s, 1H), 7.44 (d, 2H), 7.56 (s, 1H), 7.79 (d, 1H), 8.54 (s, 1H), 10.28 (s, 1H); Mass Spectrum: M+H⁺ 446.

The 2-amino-4-methylaminopyridine used as a starting material was prepared as follows:—

Using an analogous procedure to that described in the portion of Note [18] above that is concerned with the preparation of starting materials, 2-amino-4-chloropyridine and an aqueous solution of methylamine (40%) were stirred and heated to 175° C. for 35 minutes in a microwave oven. The reaction mixture was purified by reversed-phase preparative HPLC as described in Example 6. There was thus obtained the required starting material in 77% yield; $^1$H NMR: (CDCl$_3$) 2.28 (d, 3H), 4.06 (br s, 1H), 4.24 (br s, 1H), 5.64 (m, 1H), 5.95 (m, 1H), 7.71 (d, 1H).

[31] $^1$H NMR: (DMSOd$_6$) 2.67 (d, 3H), 3.36 (s, 3H), 3.72 (d, 2H), 3.74-3.79 (m, 2H), 3.98 (s, 3H), 4.31-4.35 (m, 2H), 6.23 (m, 1H), 6.58 (q, 1H), 7.26 (d, 2H), 7.31 (br s, 1H), 7.41 (s, 1H), 7.44 (d, 2H), 7.56 (s, 1H), 7.79 (d, 1H), 8.53 (s, 1H), 10.28 (s, 1H); Mass Spectrum: M+H$^+$ 490.

[32] $^1$H NMR: (DMSOd$_6$) 2.67 (d, 3H), 3.36 (s, 3H), 3.37 (s, 3H), 3.72 (s, 2H), 3.74-3.79 (m, 4H), 4.3-4.37 (m, 4H), 6.23 (m, 1H), 6.58 (q, 1H), 7.26 (d, 2H), 7.31 (br s, 1H), 7.41 (s, 1H), 7.44 (d, 2H), 7.6 (s, 1H), 7.79 (d, 1H), 8.58 (s, 1H), 10.28 (s, 1H); Mass Spectrum: M+H$^+$ 534.

[33] $^1$H NMR: (DMSOd$_6$) 1.13 (t, 3H), 3.0-3.1 (m, 2H), 3.20 (br s, 1H), 3.72 (d, 2H), 3.97 (s, 3H), 3.99 (s, 3H), 6.24 (m, 1H), 6.55 (d, 1H), 7.25 (d, 2H), 7.32 (br s, 1H), 7.38 (s, 1H), 7.44 (d, 2H), 7.55 (s, 1H), 7.78 (d, 1H), 8.54 (s, 1H), 10.26 (s, 1H); Mass Spectrum: M+H$^+$ 460.

The 2-amino-4-ethylaminopyridine used as a starting material was prepared as follows:—

A mixture of 2-amino-4-chloropyridine (0.4 g) and an aqueous solution of ethylamine (70%, 0.8 ml) was heated in a microwave oven to 160° C. for 1 hour. The resultant mixture was cooled, diluted with water (2 ml) and purified by reversed-phase preparative HPLC as described in Example 6. There was thus obtained the required starting material (0.273 g); $^1$H NMR: (CDCl$_3$) 1.24 (t, 3H), 3.15 (m, 2H), 3.91 (br s, 1H), 4.22 (br s, 2H), 5.63 (m, 1H), 5.93 (m, 1H), 7.7 (m, 1H); Mass Spectrum: M+H$^+$ 138.

[34] $^1$H NMR: (DMSOd$_6$) 1.14 (t, 3H), 3.01-3.09 (m, 2H), 3.35 (s, 3H), 3.72 (s, 2H), 3.74 (m, 2H), 3.98 (s, 3H), 4.3-4.36 (m, 2H), 6.24 (m, 1H), 6.54 (t, 1H), 7.26 (d, 2H), 7.32 (br s, 1H), 7.41 (s, 1H), 7.44 (d, 2H), 7.56 (s, 1H), 7.78 (d, 1H), 8.53 (s, 1H), 10.26 (s, 1H); Mass Spectrum: M+H$^+$ 504.

[35] $^1$H NMR: (DMSOd$_6$) 1.14 (t, 3H), 3.01-3.09 (m, 2H), 3.36 (s, 3H), 3.37 (s, 3H), 3.72 (s, 2H), 3.74-3.8 (m, 4H), 4.29-4.38 (m, 4H), 6.24 (m, 1H), 6.55 (t, 1H), 7.26 (d, 2H), 7.32 (br s, 1H), 7.41 (s, 1H), 7.44 (d, 2H), 7.6 (s, 1H), 7.78 (d, 1H), 8.53 (s, 1H), 10.26 (s, 1H); Mass Spectrum: M+H$^+$ 548.

[36] $^1$H NMR: (DMSOd$_6$) 1.13 (d, 6H), 3.48-3.59 (m, 1H), 3.72 (s, 2H), 3.98 (s, 3H), 3.99 (s, 3H), 6.24 (m, 1H), 6.44 (d, 1H), 7.26 (d, 2H), 6.33 (s, 1H), 7.39 (s, 1H), 7.44 (d, 2H), 7.56 (s, 1H), 7.76 (d, 1H), 8.54 (s, 1H), 10.25 (s, 1H); Mass Spectrum: M+H$^+$ 474.

The 2-amino-4-isopropylaminopyridine used as a starting material was prepared as follows:—

Using an analogous procedure to that described in the portion of Note [18] above that is concerned with the preparation of starting materials, 2-amino-4-chloropyridine was reacted with isopropylamine by heating the mixture in a microwave oven to 175° C. for 6 hours. The resultant mixture was cooled and purified by column chromatography on silica using increasingly polar mixtures of methylene chloride and 2M methanolic ammonia as eluent. There was thus obtained the required starting material in 24% yield; $^1$H NMR: (CDCl$_3$) 1.2 (d, 6H), 3.61 (m, 1H), 4.23 (br s, 1H), 5.61 (m, 1H), 5.9 (m, 1H), 7.68 (m, 1H); Mass Spectrum: M+H$^+$ 152.

[37] $^1$H NMR: (DMSOd$_6$) 1.13 (d, 6H), 3.35 (s, 3H), 3.48-3.59 (m, 1H), 3.72 (s, 2H), 3.74-3.79 (m, 2H), 3.98 (s, 3H), 4.31-4.35 (m, 2H), 6.24 (m, 1H), 6.44 (d, 1H), 7.26 (d, 2H), 7.33 (br s, 1H), 7.41 (s, 1H), 7.44 (d, 2H), 7.56 (s, 1H), 7.77 (d, 1H), 8.54 (s, 1H), 10.25 (br s, 1H); Mass Spectrum: M+H$^+$ 518.

[38] $^1$H NMR: (DMSOd$_6$) 1.13 (d, 6H), 3.36 (s, 3H), 3.37 (s, 3H), 3.49-3.58 (m, 1H), 3.72 (s, 2H), 3.74-3.8 (m, 4H), 4.3-4.38 (m, 4H), 6.24 (m, 1H), 6.44 (d, 1H), 7.26 (d, 2H), 7.32 (br s, 1H), 7.41 (s, 1H), 7.44 (d, 2H), 7.6 (s, 1H), 7.76 (d, 1H), 8.53 (s, 1H), 10.25 (br s, 1H); Mass Spectrum: M+H$^+$ 562.

[39] $^1$H NMR: (DMSOd$_6$) 0.36-0.43 (m, 2H), 0.67-0.74 (m, 2H), 2.32-2.39 (m, 1H), 3.72 (s, 2H), 3.98 (s, 3H), 3.99 (s, 3H), 6.36 (m, 1H), 6.93 (s, 1H), 7.26 (d, 2H), 7.39 (s, 1H), 7.44 (d, 2H), 7.51 (br s, 1H), 7.56 (s, 1H), 7.81 (d, 1H), 8.54 (s, 1H), 10.59 (s, 1H); Mass Spectrum: M+H$^+$ 472.

The 2-amino-4-cyclopropylaminopyridine used as a starting material was prepared as follows:—

A mixture of 4-chloropyridine-2-carboxylic acid (1 g), cyclopropylamine (0.66 ml), diisopropylethylamine (2.2 ml) and water (1 ml) was heated to 170° C. in a microwave oven for 5 minutes. The mixture was cooled to ambient temperature and delivered to a preparative HPLC C18 reversed-phase column (a Waters 'Oasis MCX 6' column; 5 microns silica, 19 mm diameter, 100 mm length). The column was eluted with a gradient of 100:0 to 17:3 of water and methanol. There was thus obtained 4-cyclopropylaminopyridine-2-carboxylic acid (0.51 g); $^1$H NMR: (DMSOd$_6$) 0.51 (m, 2H), 0.83 (m, 2H), 2.6 (m, 1H), 6.81 (m, 1H), 7.31 (m, 1H), 8.09 (m, 1H), 8.3 (m, 1H).

Diphenylphosphoryl azide (1.45 ml) and triethylamine (0.39 ml) were added in turn to a stirred mixture of 4-cyclopropylaminopyridine-2-carboxylic acid (0.5 g), tert-butanol (5 ml) and 1,4-dioxane (20 ml) and the resultant mixture was heated to reflux for 5 hours. The solvent was evaporated and the residue was purified by column chromatography on silica using a gradient of 50:50:0 to 9:9:2 of methylene chloride, ethyl acetate and methanol as eluent. There was thus obtained 2-(tert-butoxycarbonylamino)-4-cyclopropylaminopyridine (0.56 g); $^1$H NMR: (CDCl$_3$) 0.54 (m, 2H), 0.82 (m, 2H), 1.51 (s, 9H), 2.51 (m, 1H), 4.65 (br s, 1H), 6.37 (m, 1H), 7.3 (m, 1H), 7.84 (m, 1H); Mass Spectrum: M+H$^+$ 250.

The material so obtained was dissolved in methylene chloride and treated with a solution of 4N aqueous hydrochloric acid in 1,4-dioxane at ambient temperature for 1 hour. The mixture was evaporated and the residue was triturated under a 1:19 mixture of a 7M methanolic ammonia solution and methylene chloride. The resultant mixture was filtered and the filtrate was evaporated. The residue was purified by column chromatography on silica using a gradient of 19:1 of methylene chloride and methanol to 19:1 of methylene chloride and a 3M methanolic ammonia solution as eluent. There was thus obtained 2-amino-4-cyclopropylaminopyridine in 32% yield; $^1$H NMR: (CDCl$_3$) 0.54 (m, 2H), 0.76 (m, 2H), 2.43 (m, 1H), 4.52 (br s, 1H), 4.57 (br s, 1H), 5.89 (m, 1H), 6.04 (m, 1H), 7.65 (m, 1H); Mass Spectrum: M+H$^+$ 150.

[40] $^1$H NMR: (DMSOd$_6$) 0.37-0.42 (m, 2H), 0.67-0.73 (m, 2H), 2.33-2.39 (m, 1H), 3.35 (s, 3H), 3.72 (s, 2H), 3.74-3.79 (m, 2H), 3.98 (s, 3H), 4.31-4.36 (s, 2H), 6.36 (m, 1H), 6.93 (s, 1H), 7.26 (d, 2H), 7.41 (s, 1H), 7.44 (d, 2H), 7.5 (br s, 1H), 7.56 (s, 1H), 7.81 (d, 1H), 7.54 (s, 1H), 10.29 (s, 1H); Mass Spectrum: M+H$^+$ 516.

[41] $^1$H NMR: (DMSOd$_6$) 0.37-0.43 (m, 2H), 0.67-0.73 (m, 2H), 2.32-2.39 (m, 1H), 2.36 (s, 3H), 2.37 (s, 3H), 3.72 (s, 2H), 3.74-3.8 (m, 4H), 4.29-4.38 (m, 4H), 6.36 (m, 1H), 6.93

(s, 1H), 7.26 (d, 2H), 7.41 (s, 1H), 7.44 (d, 2H), 7.51 (br s, 1H), 7.59 (s, 1H), 7.82 (d, 1H), 8.53 (s, 1H), 10.29 (s, 1H); Mass Spectrum: M+H+ 560.

[42] $^1$H NMR: (DMSOd$_6$) 1.9-2.0 (m, 4H), 3.20-3.28 (m, 4H), 3.74 (s, 2H), 3.98 (s, 3H), 3.99 (s, 3H), 6.24 (m, 1H), 7.26 (d, 2H), 7.32 (s, 1H), 7.39 (s, 1H), 7.44 (d, 2H), 7.56 (s, 1H), 7.86 (d, 1H), 8.54 (s, 1H), 10.33 (s, 1H); Mass Spectrum: M+H+ 486.

The 2-amino-4-pyrrolidin-1-ylpyridine used as a starting material was prepared as follows:—

A mixture of 2-amino-4-chloropyridine (1 g) and pyrrolidine (2.59 ml) was heated to 205° C. in a microwave oven for 30 minutes. The reaction mixture was purified by column chromatography on silica using a 10:1 mixture of methylene chloride and a 3M methanolic ammonia solution as eluent. There was thus obtained the required starting material (1.05 g); $^1$H NMR: (CDCl$_3$) 2.0 (m, 4H), 3.28 (m, 4H), 4.49 (br s, 2H), 5.56 (m, 1H), 5.95 (m, 1H), 7.69 (d, 1H); Mass Spectrum: M+H+ 164.

[43] $^1$H NMR: (DMSOd$_6$) 1.9-2.0 (m, 4H), 3.19-3.28 (m, 4H), 3.35 (s, 3H), 3.74 (s, 2H), 3.75-3.79 (m, 2H), 3.99 (s, 3H), 4.3-4.36 (m, 2H), 6.24 (m, 1H), 7.26 (d, 2H), 7.32 (br s, 1H), 7.41 (s, 1H), 7.44 (d, 2H), 7.56 (s, 1H), 7.86 (d, 1H), 8.53 (s, 1H), 10.33 (s, 1H); Mass Spectrum: M+H+ 530.

[44] $^1$H NMR: (DMSOd$_6$) 1.9-2.0 (m, 4H), 3.19-3.27 (m, 4H), 3.36 (s, 3H), 3.37 (s, 3H), 3.73 (s, 2H), 3.74-3.74 (m, 4H), 4.29-4.38 (m, 4H), 6.24 (m, 1H), 7.26 (d, 2H), 7.32 (br s, 1H), 7.41 (s, 1H), 7.42 (d, 2H), 7.6 (s, 1H), 7.86 (d, 1H), 8.53 (s, 1H), 10.33 (s, 1H); Mass Spectrum: M+H+ 574.

[45] $^1$H NMR: (DMSOd$_6$) 3.2-3.26 (m, 4H), 3.68-3.73 (m, 4H), 3.75 (s, 2H), 3.98 (s, 3H), 3.99 (s, 3H), 6.63 (m, 1H), 7.26 (d, 2H), 7.39 (s, 1H), 7.44 (d, 2H), 7.56 (s, 1H), 7.66 (br s, 1H), 7.97 (d, 1H), 8.53 (s, 1H), 10.49 (s, 1H); Mass Spectrum: M+H+ 502.

The 2-amino-4-morpholinopyridine used as a starting material was prepared by the reaction of 2-amino-4-chloropyridine and morpholine using an analogous procedure to that described in Note [42] immediately above. The required starting material gave the following characterising data; $^1$H NMR: (CDCl$_3$) 3.26 (m, 4H), 3.81 (m, 4H), 4.71 (br s, 2H), 5.87 (m, 1H), 6.19 (m, 1H), 7.76 (d, 1H); Mass Spectrum: M+H+ 180.

[46] $^1$H NMR: (DMSOd$_6$) 3.2-3.26 (m, 4H), 3.35 (s, 3H), 3.68-3.73 (m, 4H), 3.73-3.79 (m, 2H), 3.75 (s, 2H), 3.98 (s, 3H), 4.31-4.36 (s, 2H), 6.63 (m, 1H), 7.26 (d, 2H), 7.41 (s, 1H), 7.44 (d, 2H), 7.56 (s, 1H), 7.66 (br s, 1H), 7.97 (d, 1H), 8.53 (s, 1H), 10.49 (s, 1H); Mass Spectrum: M+H+ 546.

[47] $^1$H NMR: (DMSOd$_6$) 3.2-3.26 (m, 4H), 3.36 (s, 3H), 3.37 (s, 3H), 3.69-3.73 (m, 4H), 3.73-3.8 (m, 4H), 3.75 (s, 2H), 4.3-4.37 (m, 4H), 6.63 (s, 1H), 7.26 (d, 2H), 7.42 (s, 1H), 7.44 (d, 2H), 7.6 (s, 1H), 7.66 (br s, 1H), 7.97 (d, 1H), 8.53 (s, 1H), 10.49 (s, 1H), Mass Spectrum. M+H+ 590.

[48] $^1$H NMR: (DMSOd$_6$) 3.78 (s, 2H), 3.97 (s, 3H), 3.99 (s, 3H), 7.11 (m, 1H), 7.26 (d, 2H), 7.39 (s, 1H), 7.45 (d, 2H), 7.55 (s, 1H), 7.78 (m, 1H), 8.08 (d, 1H), 8.33 (m, 1H), 8.53 (s, 1H), 10.76 (s, 1H); Mass Spectrum: M+H+ 417.

EXAMPLE 11

Using an analogous procedure to that described in Example 1, the appropriate 2-phenylacetic acid was reacted with the appropriate pyridylamine to give the compounds described in Table VI; Unless otherwise stated, each reaction product was purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent. Unless otherwise stated, each pyridylamine was a commercially available material.

TABLE VI

| No. & Note | $(R^1)_p$ | $(R^2)_q$ | $(R^6)_r$ |
| --- | --- | --- | --- |
| [1] | 6-methoxy-7-(2-hydroxyethoxy) | H | 5-dimethylamino |
| [2] | 6,7-dimethoxy | 2-fluoro | 5-dimethylanilno |
| [3] | 6-methoxy-7-(2-hydroxyethoxy) | 2-fluoro | 5-dimethylamino |
| [4] | 6,7-dimethoxy | 2-fluoro | 4-dimethylamino |
| [5] | 6,7-dimethoxy | 2-fluoro | 4-ethylamino |

Notes The products gave the characterising data shown below.

[1] 2-(Benzotriazol-1-yl)-1,1,3,3-tetramethyluronium tetrafluoroborate was used in place of 2-(7-azabenzotriazol-1-yl)-1,1,3,3-tetramethyluronium hexafluorophosphate(V) and the reaction mixture was stirred at ambient temperature for 18 hours. The product so obtained gave the following characterising data:—$^1$H NMR: (DMSOd$_6$) 2.9 (s, 6H), 3.7 (s, 2H), 3.8 (m, 2H), 4.0 (s, 3H), 4.2 (t, 2H), 5.0 (m, 1H), 7.2 (d, 2H), 7.25 (d, 2H), 7.4 (s, 1H), 7.45 (d, 2H), 7.55 (s, 1H), 7.85 (d, 1H), 7.9 (d, 1H), 8.55 (s, 1H); Mass Spectrum: M+H+ 490.

[2] $^1$H NMR: (DMSOd$_6$) 2.9 (s, 6H), 3.75 (s, 2H), 3.98 (s, 3H), 4.0 (s, 3H), 7.2 (d, 1H), 7.25 (d, 1H), 7.4 (m, 3H), 7.6 (s, 1H), 7.85 (s, 1H), 7.9 (d, 1H), 8.55 (s, 1H); Mass Spectrum: M+H+ 478.

The 2-[3-fluoro-4-(6,7-dimethoxyquinazolin-4-yloxy) phenyl]acetic acid used as a starting material was prepared as follows:—

A mixture of 4-chloro 6,7-dimethoxyquinazoline (0.85 g), 2-(3-fluoro-4-hydroxyphenyl) acetic acid (0.966 g), potassium carbonate (2.08 g) and DMA (60 ml) was stirred and heated to 70° C. for 16 hours. Diethyl ether was added and the precipitate was collected by filtration. The solid so obtained was slurried in water (200 ml) and the mixture was acidified to pH5 by the addition of 2N aqueous hydrochloric acid. The aqueous phase was concentrated to about 50 ml and the pH was adjusted again to pH5 by the addition of 2N aqueous hydrochloric acid. The precipitate was collected by filtration, washed with diethyl ether and dried overnight under vacuum. There was thus obtained the required starting material (1.05 g); $^1$H NMR: (DMSOd$_6$) 3.6 (s, 2H), 3.94 (s, 3H), 3.95 (s, 3H), 7.15 (d, 1H), 7.3 (d, 1H), 7.4 (m, 2H), 7.55 (s, 1H), 8.55 (s, 1H); Mass Spectrum: M+H+ 359.

[3] $^1$H NMR: (DMSOd$_6$) 2.9 (s, 6H), 3.75 (s, 2H), 3.85 (m, 2H), 4.0 (s, 3H), 4.25 (m, 2H), 5.0 (m, 1H), 7.2 (d, 1H), 7.25 (d, 1H), 7.4 (m, 3H), 7.6 (s, 1H), 7.85 (s, 1H), 7.9 (d, 1H), 8.55 (s, 1H), 10.5 (s, 1H); Mass Spectrum: M+H+ 508.

The 2-{3-fluoro-4-[7-(2-hydroxyethoxy)-6-methoxyquinazolin-4-yloxy]phenyl}acetic acid used as a starting material was prepared as follows:—

Using an analogous procedure to that described in the portion of Note [1] below Example 8 that is concerned with the preparation of starting materials, 4-chloro-6-methoxy-7-(2-tetrahydropyran-2-yloxyethoxy) quinazoline was reacted with 2-(3-fluoro-4-hydroxyphenyl) acetic acid to give 2-{3-fluoro-4-[6-methoxy-7-(2-tetrahydropyran-2-yloxyethoxy) quinazolin-4-yloxy]phenyl}acetic acid in 52% yield; Mass Spectrum: M+H$^+$ 473.

A mixture of the material so obtained (2 g), glacial acetic acid (8 ml), water (5 ml) and THF (2 ml) was stirred and heated to 45° C. for 2 hours. The reaction mixture was poured into water (150 ml) and the mixture was basified to pH3.5 by the addition of 2N aqueous sodium hydroxide solution. The resultant gum was isolated and dried at 40° C. under vacuum. There was thus obtained 2-{3-fluoro-4-[7-(2-hydroxyethoxy)-6-methoxyquinazolin-4-yloxy]phenyl}acetic acid which was used without further purification; Mass Spectrum: M+H$^+$ 387.

[4] On completion of the reaction, a saturated aqueous sodium bicarbonate solution and ethyl acetate were added in turn to the reaction mixture. The resultant mixture was stirred at ambient temperature for 1.5 hours. The precipitate was isolated by filtration, washed with diethyl ether and dried under vacuum. The product so obtained gave the following characterising data:—$^1$H NMR: (DMSOd$_6$) 2.9 (s, 6H), 3.75 (s, 2H), 3.99 (s, 3H), 4.0 (s, 3H), 6.4 (d, 1H), 7.3 (d, 1H), 7.45 (m, 4H), 7.6 (s, 1H), 7.9 (d, 1H), 8.6 (s, 1H); Mass Spectrum: M+H$^+$ 478.

[5] $^1$H NMR: (DMSOd$_6$) 1.15 (t, 3H), 3.05 (m, 2H), 3.75 (s, 2H), 3.98 (s, 3H), 4.0 (s, 3H), 6.25 (d, 1H), 6.55 (m, 1H), 7.25 (d, 1H), 7.3 (s, 1H), 7.4 (m, 3H), 7.6 (s, 1H), 7.8 (d, 1H), 8.55 (s, 1H); Mass Spectrum: M+H$^+$ 478.

EXAMPLE 12

N-(3-cyclopropylaminomethyl-5-methoxyphenyl)-2-[4-(6,7-dimethoxyquinazolin-4-yloxy)phenyl]acetamide A mixture of N-[3-(N-tert-butoxycarbonyl-N-cyclopropylaminomethyl)-5-methoxyphenyl]-2-[4-(6,7-dimethoxyquinazolin-4-yloxy)phenyl]acetamide (0.2 g), trifluoroacetic acid (6 ml) and methylene chloride (3 ml) was stirred at ambient temperature for 16 hours. The resultant mixture was evaporated. The residue was dissolved in ethyl acetate (5 ml) and diethyl ether was added. The resultant precipitate was isolated and dried under vacuum. The material so obtained was dissolved in a 4:1 mixture of methylene chloride and methanol. A basic polystrene resin (methylpolystyrene carbonate resin; 0.72 g) was added and the mixture was stirred at ambient for 4 hours. The mixture was filtered and the filtrate was evaporated. There was thus obtained the title compound (0.131 g); $^1$H NMR: (DMSOd$_6$) 0.22-0.27 (m, 2H), 0.31-0.37 (m, 2H), 2.01-2.07 (m, 1H), 2.6 (br s, 1H), 3.65 (s, 2H), 3.67 (s, 2H), 3.71 (s, 3H), 3.97 (s, 3H), 3.99 (s, 3H), 6.61 (s, 1H), 7.08 (s, 1H), 7.23 (m, 1H), 7.26 (d, 2H), 7.39 (s, 1H), 7.43 (d, 2H), 7.55 (s, 1H), 8.53 (s, 1H), 10.16 (s, 1H); Mass Spectrum: M+H$^+$ 515.

The N-[3-(N-tert-butoxycarbonyl-N-cyclopropylaminomethyl)-5-methoxyphenyl]-2-[4-(6,7-dimethoxyquinazolin-4-yloxy)phenyl]acetamide used as a starting material was prepared as follows:—

Diborane (1M solution in THF, 20 ml) was added portionwise to a stirred solution of 3-methoxy-5-nitrobenzoic acid (J. Med. Chem., 2004, 2897-2905; 0.79 g) in THF (20 ml) and the resultant mixture was stirred at ambient temperature for 6 hours. Water was added carefully to destroy any excess reducing agent. A 2N aqueous hydrochloric acid solution was added and the mixture was extracted with diethyl ether. The organic solvent was evaporated and the residue was purified by column chromatography on silica using a 19:1 mixture of methylene chloride and methanol as eluent. There was thus obtained 3-methoxy-5-nitrobenzyl alcohol in 91% yield; $^1$H NMR: (DMSOd$_6$) 3.87 (s, 3H), 4.58 (d, 2H), 5.53 (t, 1H), 7.34 (s, 1H), 7.58 (s, 1H), 7.79 (s, 1H).

A solution of phosphorus tribromide (0.94 ml) in diethyl ether (5 ml) was slowly added to a solution of 3-methoxy-5-nitrobenzyl alcohol (1.83 g) in methylene chloride (30 ml) that had been cooled to 5° C. and the resultant mixture was stirred at ambient temperature for 5 hours. The mixture was poured into cooled water, neutralised by the addition of solid sodium bicarbonate and extracted with diethyl ether. The organic solution was dried over magnesium sulphate and evaporated. There was thus obtained 3-methoxy-5-nitrobenzyl bromide as a solid (1.48 g); $^1$H NMR: (DMSOd$_6$) 3.89 (s, 3H), 4.8 (s, 2H), 7.51 (s, 1H), 7.67 (m, 1H), 7.94 (s, 1H).

Cyclopropylamine (1.67 ml) was slowly added to a solution of 3-methoxy-5-nitrobenzyl bromide (1.48 g) in methylene chloride (4 ml) and the mixture was stirred at ambient temperature for 6 hours. The mixture was washed with a 2N aqueous potassium carbonate solution. The organic phase was dried over magnesium sulphate and evaporated. There was thus obtained N-cyclopropyl-N-(3-methoxy-5-nitrobenzyl)amine (1.35 g; containing about 10% of dialkylated amine); $^1$H NMR: (DMSOd$_6$) 0.26 (m, 2H), 0.37 (m, 2H), 2.04 (s, 1H), 2.96 (br s, 1H), 3.82 (s, 2H), 3.88 (s, 3H), 7.39 (s, 1H), 7.59 (s, 1H), 7.82 (s, 1H); Mass Spectrum: M+H$^+$: 223.

A mixture of N-cyclopropyl-N-(3-methoxy-5-nitrobenzyl)amine (1 g), di-tert-butyl dicarbonate (1.25 g) and methylene chloride (20 ml) was stirred at ambient temperature for 4 hours. The solvent was evaporated and the residue was purified by column chromatography on silica using methylene chloride as eluent. There was thus obtained N-tert-butoxycarbonyl-N-cyclopropyl-N-(3-methoxy-5-nitrobenzyl) amine in 82% yield; $^1$H NMR: (DMSOd$_6$) 0.59 (m, 2H), 0.67 (m, 2H), 1.41 (s, 9H), 2.48 (m, 1H), 3.87 (s, 3H), 4.45 (s, 2H), 7.21 (s, 1H), 7.63 (m, 2H).

A mixture of the material so obtained, platinum oxide (0.2 g) and ethyl acetate (25 ml) was stirred under 1.8 atmospheres pressure of hydrogen for 30 minutes. The catalyst was removed by filtration and the filtrate was evaporated. There was thus obtained 3-(N-tert-butoxycarbonyl-N-cyclopropylaminomethyl)-5-methoxyaniline in 94% yield; $^1$H NMR: (DMSOd$_6$) 0.57 (m, 2H), 0.63 (m, 2H), 1.41 (s, 9H), 2.39 (m, 1H), 3.62 (s, 3H), 4.16 (s, 2H), 5.07 (s, 2H), 5.91 (m, 1H), 6.01 (m, 2H); Mass Spectrum: M+H$^+$ 293.

Using an analogous procedure to that described in Example 1, 2-[4-(6,7-dimethoxyquinazolin-4-yloxy)phenyl] acetic acid was reacted with 3-(N-tert-butoxycarbonyl-N-cyclopropylaminomethyl)-5-methoxyaniline. On completion of the reaction, the reaction mixture was concentrated and the residue was purified by column chromatography on silica using a gradient of 49:1 to 19:1 of methylene chloride and methanol as eluent. There was thus obtained N-[3-(N-tert-butoxycarbonyl-N-cyclopropylaminomethyl)-5-methoxyphenyl]-2-[4-(6,7-dimethoxyquinazolin-4-yloxy)phenyl] acetamide (0.235 g); $^1$H NMR: (DMSOd$_6$) 0.59 (m, 2H), 0.65 (m, 2H), 1.41 (br s, 9H), 1.43 (m, 1H), 3.68 (s, 2H), 3.71 (s, 3H), 3.99 (s, 3H), 4.0 (s, 3H), 4.29 (m, 2H), 6.45 (s, 1H), 7.05 (s, 1H), 7.25 (m, 3H), 7.39 (s, 1H), 7.43 (d, 2H), 7.55 (s, 1H), 8.53 (s, 1H); Mass Spectrum: M+H$^+$ 615.

EXAMPLE 13

N-(6-indolinyl)-2-{4-[6-methoxy-7-(2-methoxyethoxy)quinazolin-4-yloxy]phenyl}acetamide A mixture of N-[1-(N-tert-butoxycarbonyl)indolin-6-yl]-2-{4-[6-methoxy-7-(2-methoxyethoxy)quinazolin-4-yloxy] phenyl}acetamide (0.4 g), a 4M solution of hydrogen chloride in 1,4-dioxane (6 ml) and methylene chloride (6 ml) was stirred at ambient temperature for 7 hours. The resultant mixture was evaporated. A 7M methanolic ammonia solution was added and the resultant mixture was stirred for 10 minutes. The mixture was evaporated and the residue was purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent. There was thus obtained the title compound (0.125 g); $^1$H NMR: 2.85 (t, 2H), 3.35 (s, 3H), 3.4 (t, 2H), 3.65 (s, 2H), 3.75 (m, 2H), 4.0 (s, 3H), 4.3 (m, 2H), 5.55 (s, 1H), 6.7 (d, 1H), 6.9 (d, 1H), 6.95 (s, 1H), 7.25 (d, 1H), 7.4 (m, 3H), 7.55 (s, 1H), 8.55 (s, 1H), 9.9 (s, 1H); Mass Spectrum: M+H$^+$ 501.

The N-[1-(N-tert-butoxycarbonyl)indolin-6-yl]-2-{4-[6-methoxy-7-(2-methoxyethoxy)quinazolin-4-yloxy] phenyl}acetamide used as a starting material was prepared as follows:—

Di-tert-butyl dicarbonate (7.2 g) was added to a mixture of 6-nitroindoline (4.92 g) and methylene chloride (50 ml) and the mixture was stirred at ambient temperature for 1 hour. 4-Dimethylaminopyridine (0.37 g) was added and the reaction mixture was stirred at ambient temperature for 16 hours. The resultant mixture was evaporated and the residue was purified column chromatography on silica using increasingly polar mixtures of petroleum ether (b.p. 40-60° C.) and ethyl acetate as eluent. There was thus obtained tert-butyl 6-nitroindoline-1-carboxylate as a solid (5.45 g); $^1$H NMR: (CDCl$_3$) 1.6 (s, 9H), 3.2 (t, 21), 4.1 (t, 2H), 7.2 (d, 1H), 7.85 (d, 1H), 8.3 (br s, 0.5H), 8.7 (br s, 0.5H).

A mixture of a portion (2.64 g) of the material so obtained, 10% palladium-on-carbon catalyst (0.5 g) and ethyl acetate (200 ml) was stirred under 2.7 atmospheres pressure of hydrogen for 5 hours. The resultant mixture was filtered and the filtrate was evaporated. The residue was purified by column chromatography on silica using increasingly polar mixtures of petroleum ether (b.p. 40-60° C.) and ethyl acetate as eluent. There was thus obtained tert-butyl 6-aminoindoline-1-carboxylate (1.5 g). $^1$H NMR: (CDCl$_3$) 2.95 (m, 2H), 3.9 (m, 2H), 6.3 (d, 1H), 6.9 (d, 1H), 7.25 (s, 1H).

Using a similar procedure to that described in Example 6, 2-{4-[6-methoxy-7-(2-methoxyethoxy)quinazolin-4-yloxy] phenyl}acetic acid (0.3 g) was reacted with tert-butyl 6-aminoindoline-1-carboxylate (0.183 g). On completion of the reaction, water was added and the mixture was stirred at ambient temperature for 30 minutes. The resultant solid was collected by filtration, washed with diethyl ether and dried overnight under vacuum. There was thus obtained N-[1-(N-tert-butoxycarbonyl)indolin-6-yl]-2-{4-[6-methoxy-7-(2-methoxyethoxy)quinazolin-4-yloxy]phenyl}acetamide (0.4 g); Mass Spectrum: M+H$^+$ 601.

EXAMPLE 14

Using an analogous procedure to that described in Example 12, the appropriate N-tert-butoxycarbonyl-protected amine was reacted with trifluoroacetic acid to give the compounds described in Table VII.

TABLE VII

| No. & Note | $(R^1)_p$ | $(R^2)^q$ | R |
|---|---|---|---|
| [1] | 6,7-dimethoxy | H | 3-cyclopropylaminomethyl-5-methylphenyl |
| [2] | 6-methoxy-7-(2-methoxyethoxy) | H | 3-cyclopropylaminomethyl-5-methylphenyl |
| [3] | 6,7-di-(2-methoxyethoxy) | H | 3-cyclopropylaminomethyl-5-methylphenyl |
| [4] | 6,7-dimethoxy | 2-fluoro | 3-cyclopropylaminomethyl-5-methylphenyl |
| [5] | 6-methoxy-7-(2-hydroxyethoxy) | 2-fluoro | 3-cyclopropylaminomethyl-5-methylphenyl |
| [6] | 6,7-dimethoxy | H | 3-cyclopropylaminomethyl-5-fluorophenyl |
| [7] | 6,7-dimethoxy | H | 6-indolinyl |
| [8] | 6,7-di-(2-methoxyethoxy) | H | 6-indolinyl |
| [9] | 6,7-dimethoxy | H | 5-propylaminopyridin-2-yl |
| [10] | 6,7-dimethoxy | H | 5-methylaminopyridin-2-yl |
| [11] | 6-methoxy-7-(2-methoxyethoxy) | H | 5-methylaminopyridin-2-yl |
| [12] | 6,7-di-(2-methoxyethoxy) | H | 5-methylaminopyridin-2-yl |
| [13] | 6,7-dimethoxy | H | 5-ethylaminopyridin-2-yl |
| [14] | 6-methoxy-7-(2-methoxyethoxy) | H | 5-ethylaminopyridin-2-yl |
| [15] | 6,7-di-(2-methoxyethoxy) | H | 5-ethylaminopyridin-2-yl |
| [16] | 6,7-dimethoxy | H | 5-isopropylaminopyridin-2-yl |
| [17] | 6-methoxy-7-(2-methoxyethoxy) | H | 5-isopropylaminopyridin-2-yl |
| [18] | 6,7-di-(2-methoxyethoxy) | H | 5-isopropylaminopyridin-2-yl 2-yl |
| [19] | 6,7-dimethoxy | H | 5-cyclopropylaminopyridin-2-yl |
| [20] | 6-methoxy-7-(2-methoxyethoxy) | H | 5-cyclopropylaminopyridin-2-yl |
| [21] | 6,7-di-(2-methoxyethoxy) | H | 5-cyclopropylaminopyridin-2-yl |

Notes The products gave the characterising data shown below.

[1] $^1$H NMR: (DMSOd$_6$) 0.22-0.27 (m, 2H), 0.31-0.37 (m, 2H), 2.01-2.07 (m, 1H), 2.25 (s, 3H), 3.64 (s, 2H), 3.66 (s, 2H), 3.97 (s, 3H), 3.99 (s, 3H), 6.83 (s, 1H), 7.26 (d, 2H), 7.32 (s, 1H), 7.35 (s, 1H), 7.39 (s, 1H), 7.43 (d, 2H), 7.55 (s, 1H), 8.53 (s, 1H), 10.09 (s, 1H); Mass Spectrum: M+H$^+$ 499.

The N-[3-(N-tert-butoxycarbonyl-N-cyclopropylaminomethyl)-5-methylphenyl]-2-[4-(6,7-dimethoxyquinazolin-4-yloxy) phenyl]acetamide used as a starting material was prepared as follows:—

Using analogous procedures to those described in the portion of Example 12 that is concerned with the preparation of starting materials, N-cyclopropyl-N-(3-methyl-5-nitrobenzyl) amine was converted into N-tert-butoxycarbonyl-N-cyclopropyl-N-(3-methyl-5-nitrobenzyl) amine in 100% yield; $^1$H NMR: (DMSOd$_6$) 0.6 (m, 2H), 0.67 (m, 2H), 1.34 (s, 9H), 2.44 (s, 3H), 2.48 (m, 1H), 4.45 (s, 2H), 7.48 (s, 1H), 7.84 (s, 1H), 7.97 (s, 1H); and which in turn was converted into 3-(N-tert-butoxycarbonyl-N-cyclopropylaminomethyl)-5-methylaniline; $^1$H NMR: (DMSOd$_6$) 0.56 (m, 2H), 0.63 (m, 2H), 1.4 (s, 9H), 2.12 (s, 3H), 2.37 (m, 1H), 4.16 (s, 2H), 4.95 (s, 2H), 6.16 (s, 1H), 6.21 (s, 1H), 6.24 (s, 1H); Mass Spectrum: M+H$^+$ 277.

Using an analogous procedure to that described in Example 1, 2-[4-(6,7-dimethoxyquinazolin-4-yloxy)phenyl] acetic acid was reacted with 3-(N-tert-butoxycarbonyl-N-cyclopropylaminomethyl)-5-methylaniline. On completion of the reaction, the reaction mixture was concentrated and the residue was purified by column chromatography on silica using a gradient of 49:1 to 19:1 of methylene chloride and methanol as eluent. There was thus obtained N-[3-(N-tert-butoxycarbonyl-N-cyclopropylaminomethyl)-5-methylphenyl]-2-[4-(6,7-dimethoxyquinazolin-4-yloxy) phenyl]acetamide in 100% yield; $^1$H NMR: (DMSOd$_6$) 0.6 (m, 2H), 0.65 (m, 2H), 1.4 (br s, 9H), 2.26 (s, 3H), 2.42 (m, 1H), 3.67 (s, 2H), 3.97 (s, 3H), 3.99 (s, 3H), 4.28 (s, 2H), 6.71 (s, 1H), 7.25 (d, 2H), 7.3 (s, 1H), 7.36 (s, 1H), 7.39 (s, 1H), 7.43 (d, 2H), 7.55 (s, 1H), 7.95 (s, 1H), 8.53 (s, 1H); Mass Spectrum: M+H$^+$ 599.

[2] $^1$H NMR: (DMSOd$_6$) 0.21-0.27 (m, 2H), 0.31-0.37 (m, 2H), 2.01-2.07 (m, 1H), 2.25 (s, 3H), 3.34 (s, 3H), 3.64 (s, 2H), 3.66 (s, 2H), 3.74-3.79 (m, 2H), 3.98 (s, 3H), 4.34-4.35 (m, 2H), 6.83 (s, 1H), 7.26 (d, 2H), 7.33 (s, 1H), 7.36 (s, 1H), 7.4 (s, 1H), 7.43 (d, 2H), 7.56 (s, 1H), 8.52 (s, 1H), 10.09 (s, 1H); Mass Spectrum: M+H$^+$ 543.

The N-[3-(N-tert-butoxycarbonyl-N-cyclopropylaminomethyl)-5-methylphenyl]-2-{4-[6-methoxy-7-(2-methoxyethoxy) quinazolin-4-yloxy]phenyl}acetamide used as a starting material was prepared as follows:—

Using an analogous procedure to that described in Example 1, 2-{4-[6-methoxy-7-(2-methoxyethoxy)quinazolin-4-yloxy]phenyl}acetic acid was reacted with 3-(N-tert-butoxycarbonyl-N-cyclopropylaminomethyl)-5-methylaniline. On completion of the reaction, the reaction mixture was concentrated and the residue was purified by column chromatography on silica using a gradient of 49:1 to 19:1 of methylene chloride and methanol as eluent. There was thus obtained N-[3-(N-tert-butoxycarbonyl-N-cyclopropylaminomethyl)-5-methylphenyl]-2-{4-[6-methoxy-7-(2-methoxyethoxy) quinazolin-4-yloxy]phenyl}acetamide in 100% yield; $^1$H NMR: (DMSOd$_6$) 0.6 (m, 2H), 0.65 (m, 2H), 1.4 (br s, 9H), 2.26 (s, 3H), 2.42 (m, 1H), 3.33 (s, 3H), 3.68 (s, 2H), 3.76 (t, 2H), 3.98 (s, 3H), 4.28 (s, 2H), 4.33 (t, 2H), 6.71 (s, 1H), 7.26 (d, 2H), 7.3 (s, 1H), 7.36 (s, 1H), 7.42 (m, 3H), 7.56 (s, 1H), 7.95 (s, 1H), 8.52 (s, 1H); Mass Spectrum: M+H$^+$ 643.

[3] $^1$H NMR: (DMSOd$_6$) 0.21-0.26 (m, 2H), 0.31-0.37 (m, 2H), 2.01-2.08 (m, 1H), 2.25 (s, 3H), 3.35 (s, 3H), 3.36 (s, 3H), 3.64 (s, 4H), 3.66 (s, 4H), 4.29-4.37 (m, 4H), 6.82 (s, 1H), 7.25 (d, 2H), 7.33 (s, 1H), 7.35 (s, 1H), 7.41 (s, 1H), 7.43 (d, 2H), 7.59 (s, 1H), 8.52 (s, 1H), 10.09 (s, 1H); Mass Spectrum: M+H$^+$ 587.

The N-[3-(N-tert-butoxycarbonyl-N-cyclopropylaminomethyl)-5-methylphenyl]-2-{4-[6,7-di-(2-methoxyethoxy) quinazolin-4-yloxy]phenyl}acetamide used as a starting material was prepared as follows:—

Using an analogous procedure to that described in Example 1, 2-{4-[6,7-di-(2-methoxyethoxy)quinazolin-4-yloxy]phenyl}acetic acid was reacted with 3-(N-tert-butoxycarbonyl-N-cyclopropylaminomethyl)-5-methylaniline. On completion of the reaction, the reaction mixture was concentrated and the residue was purified by column chromatography on silica using a gradient of 49:1 to 19:1 of methylene chloride and methanol as eluent. There was thus obtained N-[3-(N-tert-butoxycarbonyl-N-cyclopropylaminomethyl)-5-methylphenyl]-2-{4-[6,7-di-(2-methoxyethoxy) quinazolin-4-yloxy]phenyl}acetamide in 100% yield; $^1$H NMR: (DMSOd$_6$) 0.6 (m, 2H), 0.65 (m, 2H), 1.4 (br s, 9H), 2.26 (s, 3H), 2.42 (m, 1H), 3.33 (m, 6H), 3.67 (s, 2H), 3.76 (m, 4H), 4.28 (s, 2H), 4.33 (m, 4H), 6.71 (s, 1H), 7.25 (d, 2H), 7.3 (s, 1H), 7.35 (s, 1H), 7.42 (m, 3H), 7.59 (s, 1H), 8.52 (s, 1H); Mass Spectrum: M–H$^-$ 685.

[4] The N-tert-butoxycarbonyl-protecting group was cleaved using hydrogen chloride in 1,4-dioxane according to the procedure described in Example 13. The product so obtained gave the following characterising data:—$^1$H NMR: (DMSOd$_6$) 0.45 (m, 4H), 2.25 (m, 1H), 2.27 (s, 3H), 3.7 (s, 2H), 3.8 (m, 2H), 3.99 (s, 3H), 4.0 (s, 3H), 6.9 (s, 1H), 7.25 (d, 1H), 7.4 (m, 5H), 7.55 (s, 1H), 8.55 (s, 1H), 10.2 (s, 1H); Mass Spectrum: M+H$^+$ 517.

The N-[3-(N-tert-butoxycarbonyl-N-cyclopropylaminomethyl)-5-methylphenyl]-2-[3-fluoro-4-(6,7-dimethoxyquinazolin-4-yloxy) phenyl]acetamide used as a starting material was prepared as follows:—

Using an analogous procedure to that described in Example 1, 2-[3-fluoro-4-(6,7-dimethoxyquinazolin-4-yloxy)phenyl]acetic acid was reacted with 3-(N-tert-butoxycarbonyl-N-cyclopropylaminomethyl)-5-methylaniline. On completion of the reaction, the reaction mixture was concentrated to give the required starting material which was used without further purification.

[5] N-[3-(N-tert-butoxycarbonyl-N-cyclopropylaminomethyl)-5-methylphenyl]-2-{3-fluoro-4-[6-methoxy-7-(2-tetrahydropyran-2-yloxyethoxy)quinazolin-4-yloxy] phenyl}acetamide was used as the starting material and both the O-tetrahydropyranyl and N-tert-butoxycarbonyl protecting groups were cleaved using hydrogen chloride in 1,4-dioxane according to the procedure described in Example 13. The product so obtained gave the following characterising data:—$^1$H NMR: (DMSOd$_6$) 0.25 (m, 2H), 0.35 (m, 2H), 2.05 (m, 1H), 2.25 (s, 3H), 3.65 (s, 2H), 3.7 (s, 2H), 3.8 (m, 2H), 4.0 (s, 3H), 4.25 (t, 2H), 4.95 (m, 1H), 6.85 (s, 1H), 7.27 (d, 1H), 7.4 (m, 4H), 7.6 (s, 1H), 8.55 (s, 1H), 10.1 (s, 1H); Mass Spectrum: M+H$^+$ 547.

The N-[3-(N-tert-butoxycarbonyl-N-cyclopropylaminomethyl)-5-methylphenyl]-2-{3-fluoro-4-[6-methoxy-7-(2-tetrahydropyran-2-yloxyethoxy)quinazolin-4-yloxy] phenyl}acetamide used as a starting material was prepared as follows:—

Using an analogous procedure to that described in Example 1, 2-{3-fluoro-4-[6-methoxy-7-(2-tetrahydropyran-2-yloxyethoxy) quinazolin-4-yloxy]phenyl}acetic acid was reacted with 3-(N-tert-butoxycarbonyl-N-cyclopropylaminomethyl)-5-methylaniline. On completion of the reaction, the reaction mixture was concentrated to give the required starting material which was used without further purification.

[6] $^1$H NMR: (DMSOd$_6$) 0.23-0.29 (m, 2H), 0.33-0.39 (m, 2H), 2.02-2.09 (m, 1H), 3.7 (s, 2H), 3.71 (s, 2H), 3.97 (s, 3H), 3.99 (s, 3H), 6.85 (d, 1H), 7.26 (d, 2H), 7.27 (s, 1H), 7.39 (s, 1H), 7.43 (d, 2H), 7.51 (d, 1H), 7.55 (s, 1H), 8.53 (s, 1H), 10.39 (s, 1H); Mass Spectrum: M+H$^+$ 503.

The N-[3-(N-tert-butoxycarbonyl-N-cyclopropylaminomethyl)-5-fluorophenyl]-2-[4-(6,7-dimethoxyquinazolin-4-yloxy) phenyl]acetamide used as a starting material was prepared as follows:—

A solution of lithium borohydride (2M in THF, 7.3 ml) was added slowly to a mixture of methyl-3-fluoro-5-nitrobenzoate (*JCS Chem. Comm.*, 1993, 921-922; 2.9 g) and diethyl ether (60 ml) and the resultant mixture was stirred at ambient temperature for 2 hours. Water and a 2N aqueous hydrochloric acid solution were added in turn and the mixture was extracted with diethyl ether. The organic solution was evaporated and the residue was purified by column chromatography on silica using methylene chloride as eluent. There was thus obtained an oil which crystallised on standing to give 3-fluoro-5-nitrobenzyl alcohol (2.05 g); $^1$H NMR: (DMSOd$_6$) 4.64 (s, 2H), 5.65 (s, 1H), 7.64 (m, 1H), 7.96 (m, 1H), 8.06 (s, 1H).

Carbon tetrabromide (5 g) was added dropwise to a mixture of 3-fluoro-5-nitrobenzyl alcohol (1.72 g), triphenylphosphine (3.43 g) and methylene chloride (25 ml) and the mixture was stirred at ambient temperature for 3 hours. The mixture was evaporated and the residue was purified by column chromatography on silica using a 1:1 mixture of petroleum ether (b.p. 40-60° C.) and methylene chloride as eluent. There was thus obtained 3-fluoro-5-nitrobenzyl bromide as an oil (2.2 g); $^1$H NMR: (DMSOd$_6$) 4.84 (s, 2H), 7.87 (m, 1H), 8.07 (m, 1H), 8.24 (s, 1H).

Using an analogous procedure to that described in the third paragraph of the portion of Example 12 above that is concerned with the preparation of starting materials, 3-fluoro-5-nitrobenzyl bromide was reacted with cyclopropylamine to give N-cyclopropyl N-(3-fluoro-5-nitrobenzyl)amine in 89% yield; $^1$H NMR: (DMSOd$_6$) 0.25 (m, 2H), 0.35 (m, 2H), 2.03 (m, 1H), 3.02 (br s, 1H), 3.85 (s, 2H), 7.69 (m, 1H), 7.95 (m, 1H), 8.08 (s, 1H); Mass Spectrum: M+H$^+$: 211.

Using analogous procedures to those described in the relevant portions of Note [1] above (in this Example) that are concerned with the preparation of starting materials, N-cyclopropyl-N-(3-fluoro-5-nitrobenzyl)amine was converted into N-tert-butoxycarbonyl-N-cyclopropyl-N-(3-fluoro-5-nitrobenzyl) amine in 95% yield; $^1$H NMR: (DMSOd$_6$) 0.61 (m, 2H), 0.68 (m, 2H), 1.4 (s, 9H), 2.54 (m, 1H), 4.5 (s, 2H), 7.54 (m, 1H), 7.91 (s, 1H), 8.02 (m, 1H); which in turn was converted into 3-(N-tert-butoxycarbonyl-N-cyclopropylaminomethyl)-5-fluoroaniline in 99% yield; $^1$H NMR: (DMSOd$_6$) 0.57 (m, 2H), 0.64 (m, 2H), 1.4 (s, 9H), 2.42 (m, 1H), 4.19 (s, 2H), 5.41 (s, 2H), 6.05 (m, 1H), 6.19 (m, 1H), 6.22 (s, 1H).

Using an analogous procedure to that described in Example 1, 2-[4-(6,7-dimethoxyquinazolin-4-yloxy)phenyl]acetic acid was reacted with 3-(N-tert-butoxycarbonyl-N-cyclopropylaminomethyl)-5-fluoroaniline. On completion of the reaction, the reaction mixture was concentrated and the residue was purified by column chromatography on silica using a gradient of 49:1 to 19:1 of methylene chloride and methanol as eluent. There was thus obtained the required starting material in 66% yield; $^1$H NMR: (DMSOd$_6$) 0.61 (m, 2H), 0.67 (m, 2H), 1.4 (br s, 9H), 2.5 (m, 1H), 3.71 (s, 2H), 3.97 (s, 3H), 3.99 (s, 3H), 4.33 (s, 2H), 6.9 (m, 1H), 7.22 (s, 1H), 7.26 (d, 2H), 7.39 (s, 1H), 7.43 (d, 2H), 7.51 (m, 1H), 7.55 (s, 1H), 8.53 (s, 1H); Mass Spectrum: M+H$^+$ 603.

[7] The N-tert-butoxycarbonyl-protecting group was cleaved using hydrogen chloride in 1,4-dioxane according to the procedure described in Example 13. The product so obtained gave the following characterising data:—$^1$H NMR: (DMSOd$_6$) 2.8 (t, 2H), 3.3 (t, 2H), 3.6 (s, 2H), 3.97 (s, 3H), 3.98 (s, 3H), 5.5 (s, 1H), 6.7 (d, 1H), 6.9 (d, 1H), 6.95 (s, 1H), 7.25 (d, 2H), 7.4 (s, 1H), 7.45 (d, 2H), 7.55 (s, 1H), 8.5 (s, 1H), 9.9 (s, 1H); Mass Spectrum: M+H$^+$ 459.

The N-[1-(N-tert-butoxycarbonyl)indolin-6-yl]-2-[4-(6,7-dimethoxyquinazolin-4-yloxy) phenyl]acetamide used as a starting material was prepared as follows:—

Using a similar procedure to that described in Example 6, 2-[4-(6,7-dimethoxyquinazolin-4-yloxy)phenyl]acetic acid (0.3 g) was reacted with tert-butyl 6-aminoindoline-1-carboxylate (0.206 g). On completion of the reaction, water was added and the mixture was stirred at ambient temperature for 30 minutes. The resultant solid was collected by filtration, washed with diethyl ether and dried overnight under vacuum. There was thus obtained the required starting material (0.38 g) that was used without further purification; Mass Spectrum: M+H$^+$ 557.

[8] The N-tert-butoxycarbonyl-protecting group was cleaved using hydrogen chloride in 1,4-dioxane according to the procedure described in Example 13. The product so obtained gave the following characterising data:—$^1$H NMR: (DMSOd$_6$) 2.8 (t, 1H), 3.85 (s, 3H), 3.87 (s, 3H), 3.4 (m, 2H), 3.6 (s, 2H), 3.75 (m, 4H), 4.3 (m, 4H), 5.55 (s, 1H), 6.7 (d, 1H), 6.9 (m, 2H), 7.24 (s, 1H), 7.26 (s, 1H), 7.4 (m, 3H), 7.6 (s, 1H), 8.55 (s, 1H), 9.85 (s, 1H); Mass Spectrum: M+H$^+$ 545.

The N-[1-(N-tert-butoxycarbonyl)indolin-6-yl]-2-{4-[6,7-di-(2-methoxyethoxy) quinazolin-4-yloxy] phenyl}acetamide used as a starting material was prepared as follows:—

Using a similar procedure to that described in Example 6, 2-{4-[6,7-di-(2-methoxyethoxy)quinazolin-4-yloxy] phenyl}acetic acid (0.3 g) was reacted with tert-butyl 6-aminoindoline-1-carboxylate (0.164 g). On completion of the reaction, water was added and the mixture was stirred at ambient temperature for 30 minutes. The resultant solid was collected by filtration, washed with diethyl ether and dried overnight under vacuum. There was thus obtained the required starting material (0.4 g) that was used without further purification; Mass Spectrum: M+H$^+$ 645.

[9] $^1$H NMR: (DMSOd$_6$) 0.94 (t, 3H), 1.51-1.62 (m, 2H), 2.97-3.04 (m, 2H), 3.76 (s, 2H), 3.97 (s, 3H), 3.99 (s, 3H), 7.27 (d, 2H), 7.3 (d, 1H), 7.39 (s, 1H), 7.45 (d, 2H), 7.56 (s, 1H), 7.67 (d, 1H), 7.68 (d, 1H), 8.55 (s, 1H), 10.91 (br s, 1H); Mass Spectrum: M+H$^+$ 474.

The N-[5-(N-tert-butoxycarbonyl-N-propylamino)pyridin-2-yl]-2-[4-(6,7-dimethoxyquinazolin-4-yloxy) phenyl] acetamide used as a starting material was prepared as follows:— n-Propylamine (0.25 ml) was added to a stirred mixture of 5-bromo-2-nitropyridine (0.41 g), caesium carbonate (1.45 g), 1,1'-bis(diphenylphosphino)ferrocene (0.338 g), palladium(II) acetate (0.045 g) and toluene (10 ml) and the resultant mixture was heated to 90° C. for 3.5 hours. The mixture was cooled to ambient temperature, diluted with ethyl acetate (100 ml) and filtered. The filtrate was evaporated and the residue was purified by column chromatography on silica using increasingly polar mixtures of methylene chloride and ethyl acetate as eluent. There was thus obtained 5-propylamino-2-nitropyridine (0.306 g); $^1$H NMR: (CDCl$_3$) 1.05 (t, 3H), 1.71 (m, 2H), 3.21 (m, 2H), 4.6 (br s, 1H), 6.91 (m, 1H), 7.87 (m, 1H), 8.15 (m, 1H); Mass Spectrum: M+H$^+$ 182.

A mixture of the material so obtained (0.3 g), di-tert-butyl dicarbonate (0.405 g), 4-(N,N-dimethylamino)pyridine (0.021 g) and THF (10 ml) was stirred and heated to 75° C. for 2.5 hours. The solvent was evaporated and the residue was purified by column chromatography on silica using a gradient of 9:1 to 3:2 of petroleum ether (b.p. 40-60° C.) and ethyl acetate as eluent. There was thus obtained 5-(N-tert-butoxycarbonyl-N-propylamino)-2-nitropyridine (0.49 g); $^1$H NMR: (CDCl$_3$) 0.93 (t, 3H), 1.49 (s, 9H), 1.64 (m, 2H), 3.73 (t, 2H), 7.93 (m, 1H), 8.24 (m, 1H), 8.54 (m, 1H); Mass Spectrum: M+H$^+$ 282.

A mixture of the material so obtained, platinum oxide (0.027 g), ethanol (10 ml) and ethyl acetate (10 ml) was stirred under 4 atmospheres pressure of hydrogen for 30 minutes. The mixture was filtered and the filtrate was evaporated. There was thus obtained 2-amino-5-(N-tert-butoxycarbonyl-N-propylamino)pyridine (0.379 g); $^1$H NMR: (CDCl$_3$)

0.88 (t, 3H), 1.4 (br s, 9H), 1.55 (m, 2H), 3.48 (m, 2H), 4.43 (s, 2H), 6.47 (d, 1H), 7.26 (m, 1H), 7.89 (br s, 1H); Mass Spectrum: M+H$^+$ 252.

Using a similar procedure to that described in Example 6, 2-[4-(6,7-dimethoxyquinazolin-4-yloxy)phenyl]acetic acid was reacted with 2-amino-5-(N-tert-butoxycarbonyl-N-propylamino)pyridine to give N-[5-(N-tert-butoxycarbonyl-N-propylamino) pyridin-2-yl]-2-[4-(6,7-dimethoxyquinazolin-4-yloxy)phenyl]acetamide; Mass Spectrum: M+H$^+$ 574.

[10] $^1$H NMR: (DMSOd$_6$) 2.71 (s, 3H), 3.74 (s, 2H), 3.98 (s, 3H), 3.99 (s, 3H), 7.18 (m, 1H), 7.27 (d, 2H), 7.39 (s, 1H), 7.45 (d, 2H), 7.56 (s, 1H), 7.66 (d, 1H), 7.74 (d, 1H), 8.55 (s, 1H), 10.73 (s, 1H); Mass Spectrum: M+H$^+$ 446.

The N-[5-(N-tert-butoxycarbonyl-N-methylamino)pyridin-2-yl]-2-[4-(6,7-dimethoxyquinazolin-4-yloxy) phenyl] acetamide used as a starting material was prepared as follows:—

Using analogous procedures to those described in the portion of Note [9] immediately above that is concerned with the preparation of starting materials, 5-bromo-2-nitropyridine was reacted with methylamine to give 5-methylamino-2-nitropyridine in 80% yield; $^1$H NMR: (DMSOd$_6$) 2.51 (s, 3H), 7.02 (m, 1H), 7.43 (br s, 1H), 7.86 (m, 1H), 8.13 (d, 1H); Mass Spectrum: M–H$^-$ 152; which in turn was converted into 5-(N-tert-butoxycarbonyl-N-methylamino)-2-nitropyridine in 51% yield; $^1$H NMR: (CDCl$_3$) 1.52 (s, 9H), 3.4 (s, 3H), 7.98 (m, 1H), 8.24 (m, 1H), 8.6 (m, 1H); which in turn was converted into 2-amino-5-(N-tert-butoxycarbonyl-N-methylamino)pyridine in 100% yield; $^1$H NMR: (CDCl$_3$) 1.42 (br s, 9H), 3.19 (s, 3H), 4.39 (br s, 2H), 6.46 (d, 1H), 7.3 (m, 1H), 7.94 (m, 1H); Mass Spectrum: M+H$^+$ 224; and which in turn was converted into N-[5-(N-tert-butoxycarbonyl-N-methylamino) pyridin-2-yl]-2-[4-(6,7-dimethoxyquinazolin-4-yloxy)phenyl]acetamide; Mass Spectrum: M+H$^+$ 546.

[11] $^1$H NMR: (DMSOd$_6$) 2.72 (s, 3H), 3.35 (s, 3H), 3.74-3.79 (m, 4H), 3.99 (s, 3H), 4.31-4.36 (m, 2H), 7.24-7.3 (m, 3H), 7.41 (s, 1H), 7.45 (d, 2H), 7.57 (s, 1H), 7.66 (d, 1H), 7.7 (d, 1H), 8.55 (s, 1H), 10.89 (br s, 1H); Mass Spectrum: M+H$^+$ 490.

The N-[5-(N-tert-butoxycarbonyl-N-methylamino)pyridin-2-yl]-2-{4-[6-methoxy-7-(2-methoxyethoxy) quinazolin-4-yloxy]phenyl}acetamide used as a starting material was prepared as follows:—

Using a similar procedure to that described in Example 6, 2-{4-[6-methoxy-7-(2-methoxyethoxy) quinazolin-4-yloxy] phenyl}acetic acid was reacted with 2-amino-5-(N-tert-butoxycarbonyl-N-methylamino)pyridine to give the required starting material; Mass Spectrum: M+H$^+$ 590.

[12] $^1$H NMR: (DMSOd$_6$) 2.72 (s, 3H), 3.36 (s, 3H), 3.37 (s, 3H), 3.74-3.79 (m, 6H), 4.3-4.37 (m, 4H), 7.25-7.3 (m, 3H), 7.42 (s, 1H), 7.45 (d, 2H), 7.6 (s, 1H), 7.66 (d, 1H), 7.7 (d, 1H), 8.55 (s, 1H), 10.9 (br s, 1H); Mass Spectrum: M+H$^+$ 534.

The N-[5-(N-tert-butoxycarbonyl-N-methylamino)pyridin-2-yl]-2-{4-[6,7-di-(2-methoxyethoxy) quinazolin-4-yloxy]phenyl}acetamide used as a starting material was prepared as follows:—

Using a similar procedure to that described in Example 6, 2-{4-[6,7-di-(2-methoxyethoxy)quinazolin-yloxy] phenyl}acetic acid was reacted with 2-amino-5-(N-tert-butoxycarbonyl-N-methylamino)pyridine to give the required starting material; Mass Spectrum: M+H$^+$ 634.

[13] $^1$H NMR: (DMSOd$_6$) 1.17 (t, 3H), 3.07 (q, 2H), 3.74 (s, 2H), 3.98 (s, 3H), 3.99 (s, 3H), 7.23 (m, 1H), 7.27 (d, 2H), 7.39 (s, 1H), 7.45 (d, 2H), 7.56 (s, 1H), 7.71 (d, 1H), 7.74 (d, 1H), 8.55 (s, 1H), 10.75 (br s, 1H); Mass Spectrum: M+H$^+$ 460.

The N-[5-(N-tert-butoxycarbonyl-N-ethylamino)pyridin-2-yl]-2-[4-(6,7-dimethoxyquinazolin-4-yloxy) phenyl]acetamide used as a starting material was prepared as follows:—

Using analogous procedures to those described in the portion of Note [9] immediately above that is concerned with the preparation of starting materials, 5-bromo-2-nitropyridine was reacted with ethylamine to give 5-ethylamino-2-nitropyridine in 97% yield; $^1$H NMR: (DMSOd$_6$) 1.96 (t, 3H), 3.21 (m, 2H), 7.05 (m, 1H), 7.4 (br s, 1H), 7.87 (m, 1H), 8.12 (m, 1H); Mass Spectrum: M+H$^+$ 168; which in turn was converted into 5-(N-tert-butoxycarbonyl-N-ethylamino)-2-nitropyridine in 81% yield; $^1$H NMR: (CDCl$_3$) 1.27 (t, 3H), 1.5 (s, 9H), 3.82 (m, 2H), 7.94 (m, 1H), 8.24 (m, 1H), 8.54 (m, 1H); Mass Spectrum: M+H$^+$ 268; which in turn was converted into 2-amino-5-(N-tert-butoxycarbonyl-N-ethylamino)pyridine in 59% yield; $^1$H NMR: (CDCl$_3$) 1.12 (t, 3H), 1.4 (br s, 9H), 3.58 (q, 2H), 6.48 (d, 1H), 7.24 (m, 1H), 7.89 (m, 1H); Mass Spectrum: M+H$^+$ 238; and which in turn was converted into N-[5-(N-tert-butoxycarbonyl-N-ethylamino)pyridin-2-yl]-2-[4-(6,7-dimethoxyquinazolin-4-yloxy) phenyl]acetamide; Mass Spectrum: M+H$^+$ 560.

[14] $^1$H NMR: (DMSOd$_6$) 1.17 (t, 3H), 3.08 (q, 2H), 3.35 (s, 3H), 3.74-3.78 (m, 4H), 3.99 (s, 3H), 4.31-4.36 (m, 2H), 7.28 (d, 2H), 7.3 (d, 1H), 7.41 (s, 1H), 7.45 (d, 2H), 7.57 (s, 1H), 7.69-7.74 (m, 2H), 8.55 (s, 1H), 10.87 (br s, 1H); Mass Spectrum: M+H$^+$ 504.

The N-[5-(N-tert-butoxycarbonyl-N-ethylamino)pyridin-2-yl]-2-{4-[6-methoxy-7-(2-methoxyethoxy) quinazolin-4-yloxy]phenyl}acetamide used as a starting material was prepared as follows:—

Using a similar procedure to that described in Example 6, 2-{4-[6-methoxy-7-(2-methoxyethoxy) quinazolin-4-yloxy] phenyl}acetic acid was reacted with 2-amino-5-(N-tert-butoxycarbonyl-N-ethylamino)pyridine to give the required starting material; Mass Spectrum: M+H$^+$ 604.

[15] $^1$H NMR: (DMSOd$_6$) 1.17 (t, 3H), 3.07 (q, 2H), 3.36 (s, 3H), 3.37 (s, 3H), 3.74-3.79 (s, 4H), 3.75 (s, 2H), 4.3-4.37 (m, 4H), 7.24 (d, 1H), 7.27 (d, 2H), 7.42 (s, 1H), 7.45 (d, 2H), 7.6 (s, 1H), 7.7 (d, 1H), 7.74 (d, 1H), 8.54 (s, 1H), 10.76 (br s, 1H); Mass Spectrum: M+H$^+$ 548.

The N-[5-(N-tert-butoxycarbonyl-N-ethylamino)pyridin-2-yl]-2-{4-[6,7-di-(2-methoxyethoxy) quinazolin-yloxy] phenyl}acetamide used as a starting material was prepared as follows:—

Using a similar procedure to that described in Example 6, 2-{4-[6,7-di-(2-methoxyethoxy)quinazolin-4-yloxy] phenyl}acetic acid was reacted with 2-amino-5-(N-tert-butoxycarbonyl-N-ethylamino)pyridine to give the required starting material; Mass Spectrum: M+H$^+$ 648.

[16] $^1$H NMR: (DMSOd$_6$) 1.15 (d, 6H), 3.52-3.62 (m, 1H), 3.77 (s, 2H), 3.97 (s, 3H), 3.99 (s, 3H), 7.27 (d, 2H), 7.33-7.4 (m, 1H), 7.39 (s, 1H), 7.45 (d, 2H), 7.56 (s, 1H), 7.71-7.85 (m, 2H), 8.55 (s, 1H), 10.91 (br s, 1H); Mass Spectrum: M+H$^+$ 474.

The N-[5-(N-tert-butoxycarbonyl-N-isopropylamino)pyridin-2-yl]-2-[4-(6,7-dimethoxyquinazolin-4-yloxy) phenyl] acetamide used as a starting material was prepared as follows:—

Using analogous procedures to those described in the portion of Note [9] immediately above that is concerned with the preparation of starting materials, 5-bromo-2-nitropyridine was reacted with isopropylamine to give 5-isopropylamino-2-nitropyridine in 93% yield; $^1$H NMR: (CDCl$_3$) 1.3 (d, 6H), 3.74 (m, 1H), 4.46 (br s, 1H), 6.9 (m, 1H), 7.84 (m, 1H), 8.15 (d, 1H); Mass Spectrum: M+H$^+$ 182; which in turn was converted into 5-(N-tert-butoxycarbonyl-N-isopropylamino)-2- nitropyridine in 84% yield; ¹H NMR: (CDCl₃) 1.19 (d, 6H), 1.4 (s, 9H), 4.55 (m, 1H), 7.76 (m, 1H), 8.26 (m, 1H), 8.38 (m, 1H); Mass Spectrum: M+H⁺ 282; which in turn was converted into 2-amino-5-(N-tert-butoxycarbonyl-N-isopropylamino)pyridine in 84% yield; ¹H NMR: (CDCl₃) 1.05 (d, 6H), 1.36 (br s, 9H), 4.46 (br s, 2H), 6.48 (d, 1H), 7.14 (m, 1H), 7.78 (m, 1H); Mass Spectrum: M+H⁺ 252; and which in turn was converted into N-[5-(N-tert-butoxycarbonyl-N-isopropylamino)pyridin-2-yl]-2-[4-(6,7-dimethoxyquinazolin-4-yloxy) phenyl]acetamide; Mass Spectrum: M+H⁺ 560.

[17] ¹H NMR: (DMSOd₆) 1.15 (d, 6H), 3.35 (s, 3H), 3.54-3.59 (m, 1H), 3.74-3.79 (m, 2H), 3.99 (s, 3H), 3.75 (s, 2H), 4.31-4.36 (m, 2H), 7.27 (m, 3H), 7.41 (s, 1H), 7.45 (d, 2H), 7.56 (s, 1H), 7.76 (br s, 2H), 8.54 (s, 1H), 10.77 (br s, 1H); Mass Spectrum: M+H⁺ 518.

The N-[5-(N-tert-butoxycarbonyl-N-isopropylamino)pyridin-2-yl]-2-{4-[6-methoxy-7-(2-methoxyethoxy) quinazolin-4-yloxy]phenyl}acetamide used as a starting material was prepared as follows:—

Using a similar procedure to that described in Example 6, 2-{4-[6-methoxy-7-(2-methoxyethoxy) quinazolin-4-yloxy]phenyl}acetic acid was reacted with 2-amino-5-(N-tert-butoxycarbonyl-N-isopropylamino)pyridine to give the required starting material; Mass Spectrum: M+H⁺ 618.

[18] ¹H NMR: (DMSOd₆) 1.15 (d, 6H), 3.36 (s, 3H), 3.37 (s, 3H), 3.74-3.79 (m, 4H), 3.75 (s, 2H), 3.54-3.59 (m, 1H), 4.3-4.38 (m, 4H), 7.27 (d, 2H), 7.29 (d, 1H), 7.42 (s, 1H), 7.45 (d, 2H), 7.6 (s, 1H), 7.76 (m, 2H), 8.54 (s, 1H), 10.79 (br s, 1H); Mass Spectrum: M+H⁺ 562.

The N-[5-(N-tert-butoxycarbonyl-N-isopropylamino)pyridin-2-yl]-2-{4-[6,7-di-(2-methoxyethoxy) quinazolin-4-yloxy]phenyl}acetamide used as a starting material was prepared as follows:—

Using a similar procedure to that described in Example 6, 2-{4-[6,7-di-(2-methoxyethoxy)quinazolin-4-yloxy]phenyl}acetic acid was reacted with 2-amino-5-(N-tert-butoxycarbonyl-N-isopropylamino)pyridine to give the required starting material; Mass Spectrum: M+H⁺ 662.

[19] ¹H NMR: (DMSOd₆) 0.35-0.41 (m, 2H), 0.68-0.74 (m, 2H), 2.33-2.39 (m, 1H), 3.75 (s, 2H), 3.97 (s, 3H), 3.99 (s, 3H), 7.27 (d, 2H), 7.29 (br s, 1H), 7.39 (s, 1H), 7.45 (d, 2H), 7.56 (s, 1H), 7.72 (d, 1H), 7.77 (d, 1H), 8.55 (s, 1H), 10.79 (br s, 1H); Mass Spectrum: M+H⁺ 472.

The N-[5-(N-tert-butoxycarbonyl-N-cyclopropylamino)pyridin-2-yl]-2-[4-(6,7-dimethoxyquinazolin-4-yloxy) phenyl]acetamide used as a starting material was prepared as follows:—

Using analogous procedures to those described in the portion of Note [9] immediately above that is concerned with the preparation of starting materials, 5-bromo-2-nitropyridine (0.41 g) was reacted with cyclopropylamine (0.21 ml) to give 5-cyclopropylamino-2-nitropyridine (0.322 g); ¹H NMR: (CDCl₃) 0.62 (m, 2H), 0.91 (m, 2H), 2.57 (m, 1H), 4.96 (br s, 1H), 7.19 (m, 1H), 7.99 (d, 1H), 8.16 (m, 1H); which in turn was converted into 5-(N-tert-butoxycarbonyl-N-cyclopropylamino)-2-nitropyridine (0.48 g); ¹H NMR: (CDCl₃) 0.59 (m, 2H), 1.05 (m, 2H), 1.53 (s, 9H), 3.02 (m, 1H), 8.05 (m, 1H), 8.22 (d, 1H), 8.64 (m, 1H); which in turn was converted into 2-amino-5-(N-tert-butoxycarbonyl-N-cyclopropylamino) pyridine (0.349 g); ¹H NMR: (CDCl₃) 0.5 (m, 2H), 0.79 (m, 2H), 1.44 (s, 9H), 2.95 (m, 1H), 4.39 (br s, 2H), 6.46 (d, 1H), 7.24 (m, 1H), 7.87 (m, 1H); Mass Spectrum: M+H⁺ 250; and which in turn was converted into N-[5-(N-tert-butoxycarbonyl-N-cyclopropylamino) pyridin-2-yl]-2-[4-(6,7-dimethoxyquinazolin-4-yloxy)phenyl]acetamide; Mass Spectrum: M+H⁺ 572.

[20] ¹H NMR: (DMSOd₆+CF₃CO₂D) 0.4-0.46 (m, 2H), 0.72-0.78 (m, 2H), 2.37-2.43 (m, 1H), 3.34 (s, 3H), 3.75-3.83 (m, 2H), 3.9 (s, 2H), 4.04 (s, 3H), 4.36-4.43 (m, 2H), 7.35 (d, 2H), 7.44 (d, 1H), 7.51 (d, 2H), 7.53 (s, 1H), 7.71-7.75 (m, 2H), 7.8 (m, 1H), 9.05 (s, 1H); Mass Spectrum: M+H⁺ 516.

The N-[5-(N-tert-butoxycarbonyl-N-cyclopropylamino) pyridin-2-yl]-2-{4-[6-methoxy-7-(2-methoxyethoxy) quinazolin-4-yloxy]phenyl}acetamide used as a starting material was prepared as follows:—

Using a similar procedure to that described in Example 6, 2-{4-[6-methoxy-7-(2-methoxyethoxy) quinazolin-4-yloxy] phenyl}acetic acid was reacted with 2-amino-5-(N-tert-butoxycarbonyl-N-cyclopropylamino)pyridine to give the required starting material; Mass Spectrum: M+H⁺ 616.

[21] ¹H NMR: (DMSOd₆) 0.34-0.44 (m, 2H), 0.67-0.76 (m, 2H), 2.33-2.4 (m, 1H), 3.36 (s, 3H), 3.37 (s, 3H), 3.73-3.8 (m, 4H), 3.75 (s, 2H), 4.29-4.39 (m, 4H), 7.27 (d, 2H), 7.29 (d, 1H), 7.42 (s, 1H), 7.45 (d, 2H), 7.61 (s, 1H), 7.72 (d, 1H), 7.78 (d, 1H), 8.55 (s, 1H), 10.8 (br s, 1H); Mass Spectrum: M+H⁺ 560.

The N-[5-(N-tert-butoxycarbonyl-N-cyclopropylamino) pyridin-2-yl]-2-{4-[6,7-di-(2-methoxyethoxy) quinazolin-4-yloxy]phenyl}acetamide used as a starting material was prepared as follows:—

Using a similar procedure to that described in Example 6, 2-{4-[6,7-di-(2-methoxyethoxy)quinazolin-4-yloxy] phenyl}acetic acid was reacted with 2-amino-5-(N-tert-butoxycarbonyl-N-cyclopropylamino)pyridine to give the required starting material; Mass Spectrum: M+H⁺ 660.

EXAMPLE 15

N-(5-dimethylaminopyridin-2-yl)-2-[4-(6,7-dimethoxyquinazolin-4-yloxy)-2-methoxyphenyl]acetamide A mixture of N-(5-dimethylaminopyridin-2-yl)-2-(4-hydroxy-2-methoxyphenyl) acetamide (0.111 g), 4-chloro-6,7-dimethoxyquinazoline (0.075 g), potassium carbonate (0.2 g) and DMA (2 ml) was stirred and heated to 140° C. in a microwave oven for 20 minutes. The reaction mixture was purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent. There was thus obtained the title compound (0.137 g); ¹H NMR: (CDCl₃) 2.92 (s, 6H), 3.75 (s, 2H), 3.91 (s, 3H), 4.07 (s, 3H), 4.08 (s, 3H), 6.86 (s, 1H), 6.88 (m, 1H), 7.10 (m, 1H), 7.33 (s, 1H), 7.41 (d, 1H), 7.55 (s, 1H), 7.73 (d, 1H), 8.09 (d, 1H), 8.16 (br s, 1H), 8.64 (s, 1H); Mass Spectrum: M+H⁺ 490.

The N-(5-dimethylaminopyridin-2-yl)-2-(4-hydroxy-2-methoxyphenyl)acetamide used as a starting material was prepared as follows:—

Using an analogous procedure to that described in Example 1,2-(4-benzyloxy-2-methoxyphenyl)acetic acid was reacted with 2-amino-5-dimethylaminopyridine to give N-(5-dimethylaminopyridin-2-yl)-2-(4-benzyloxy-2-methoxyphenyl)acetamide in 54% yield; ¹H NMR: (CDCl₃) 2.91 (s, 6H), 3.64 (s, 2H), 3.85 (s, 3H), 5.05 (s, 2H), 6.57 (m, 2H), 7.07 (m, 1H), 7.18 (m, 1H), 7.26-7.45 (m, 4H), 7.71 (m, 1H), 8.06 (m, 2H); Mass Spectrum: M+H⁺ 292.

A mixture of the material so obtained (0.467 g), 10% platinum-on-carbon catalyst (0.1 g), ethanol (2 ml) and ethyl acetate (30 ml) was stirred under 3 atmospheres pressure of hydrogen for 8 hours. The reaction mixture was filtered and the filtrate was evaporated to give N-(5-dimethylaminopyridin-2-yl)-2-(4-hydroxy-2-methoxyphenyl)acetamide (0.34 g); $^1$H NMR: (CDCl$_3$) 2.92 (s, 6H), 3.62 (s, 2H), 3.74 (s, 3H), 6.21 (m, 1H), 6.26 (s, 1H), 6.94 (m, 1H), 7.14 (m, 1H), 7.64 (m, 1H), 8.17 (m, 2H), 9.05 (br s, 1H); Mass Spectrum: M+H$^+$ 302.

EXAMPLE 16

N-(5-dimethylaminopyridin-2-yl)-2-[4-(7-ethoxy-6-methoxyquinazolin-4-yloxy)-2-methoxyphenyl]acetamide Using an analogous procedure to that described in Example 15, N-(5-dimethylaminopyridin-2-yl)-2-(4-hydroxy-2-methoxyphenyl)acetamide was reacted with 4-chloro-7-ethoxy-6-methoxyquinazoline. There was thus obtained the title compound in 67% yield; $^1$H NMR: (CDCl$_3$) 1.59 (t, 3H), 2.92 (s, 6H), 3.75 (s, 2H), 3.91 (s, 3H), 4.07 (s, 3H), 4.29 (d, 1H), 4.32 (d, 1H), 6.85 (s, 1H), 6.87 (m, 1H), 7.11 (m, 1H), 7.32 (s, 1H), 7.4 (d, 1H), 7.54 (s, 1H), 7.72 (d, 1H), 8.09 (d, 1H), 8.20 (br s, 1H), 8.63 (s, 1H); Mass Spectrum: M+H$^+$ 504.

EXAMPLE 17

N-(5-dimethylaminopyridin-2-yl)-2-{4-[7-(2-methoxyethoxy)-6-methoxyquinazolin-4-yloxy]-2-methoxyphenyl}acetamide Using an analogous procedure to that described in Example 15, N-(5-dimethylaminopyridin-2-yl)-2-(4-hydroxy-2-methoxyphenyl)acetamide was reacted with 4-chloro-7-(2-methoxyethoxy)-6-methoxyquinazoline. There was thus obtained the title compound in 74% yield; $^1$H NMR: (CDCl$_3$) 2.93 (s, 6H), 3.5 (s, 3H), 3.75 (s, 2H), 3.88-3.93 (m, 2H), 3.91 (s, 3H), 4.05 (s, 3H), 4.32-4.38 (m, 2H), 6.86 (s, 1H), 6.87 (m, 1H), 7.10 (m, 1H), 7.33 (s, 1H), 7.4 (d, 1H), 7.53 (d, 1H), 7.73 (d, 1H), 8.09 (d, 1H), 8.18 (br s, 1H), 8.63 (s, 1H); Mass Spectrum: M+H$^+$ 534.

EXAMPLE 18

Using an analogous procedure to that described in Example 1, the appropriate 2-phenylacetic acid was reacted with the appropriate heteroarylamine to give the compounds described in Table VIII. Unless otherwise stated, each reaction product was purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent.

For Compounds [2] to [4], [19] to [20] below, 2-(benzotriazol-1-yl)-1,1,3,3-tetramethyluronium tetrafluoroborate was used in place of 2-(7-azabenzotriazol-1-yl)-1,1,3,3-tetramethyluronium hexafluorophosphate(V) and the reaction mixture was stirred at ambient temperature for 18 hours.

Unless otherwise stated, each heteroarylamine was a commercially available material.

TABLE VIII

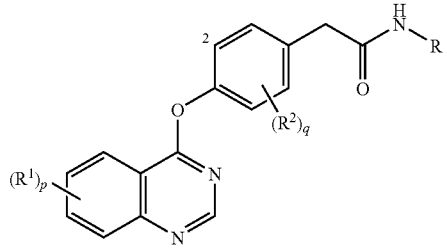

| No. & Note | $(R^1)_p$ | $(R^2)_q$ | R |
|---|---|---|---|
| [1] | 6,7-dimethoxy | 2-fluoro | 2,3-dihydrofuro[3,2-b]pyridin-5-yl |
| [2] | 6-methoxy-7-(2-hydroxyethoxy) | H | 4-methylthiazol-2-yl |
| [3] | 6-methoxy-7-(2-hydroxyethoxy) | H | 4,5-dimethylthiazol-2-yl |
| [4] | 6-methoxy-7-(2-hydroxyethoxy) | H | 5-methylthiazol-2-yl |
| [5] | 6,7-dimethoxy | 2-fluoro | 4,5-dimethylthiazol-2-yl |
| [6] | 6,7-dimethoxy | H | 4,5-tetramethylenethiazol-2-yl |
| [7] | 6,7-dimethoxy | H | 4-tert-butylthiazol-2-yl |
| [8] | 6,7-dimethoxy | H | 5-chlorothiazol-2-yl |
| [9] | 6,7-dimethoxy | H | 5-methoxythiazol-2-yl |
| [10] | 6,7-dimethoxy | H | 4-cyclopropylthiazol-2-yl |
| [11] | 6-methoxy-7-(2-hydroxyethoxy) | 2-fluoro | 5-methylthiazol-2-yl |
| [12] | 6-methyoxy-7-(2-hydroxyethoxy) | 2-fluoro | 4-methylthiazol-2-yl |
| [13] | 6,7-dimethoxy | 3-methoxy | 5-methylthiazol-2-yl |
| [14] | 6,7-dimethoxy | H | 5-methyloxazol-2-yl |
| [15] | 6,7-dimethoxy | H | 4,5-dimethyloxazol-2-yl |
| [16] | 6-methoxy-7-(2-methoxyethoxy) | H | 4,5-dimethyloxazol-2-yl |
| [17] | 6-methoxy-7-(2-hydroxyethoxy) | 2-fluoro | 4,5-dimethyloxazol-2-yl |
| [18] | 6,7-dimethoxy | 2-fluoro | 1-ethylpyrazol-4-yl |
| [19] | 6-methoxy-7-(2-hydroxyethoxy) | H | 1-isopropylpyrazol-4-yl |
| [20] | 6-methoxy-7-(2-hydroxyethoxy) | H | 1-methyl-1H-pyrrolo[3,2-b]pyridin-5-yl |
| [21] | 6-methoxy-7-(2-hydroxyethoxy) | 2-fluoro | 1-methyl-1H-pyrrolo[3,2-b]pyridin-5-yl |
| [22] | 6,7-dimethoxy | H | 1,2,3,4-tetrahydroquinolin-7-yl |
| [23] | 6,7-di-(2-methoxyethoxy) | H | 1,2,3,4-tetrahydroquinolin-7-yl |

Notes The products gave the characterising data shown below.

[1] $^1$H NMR: (DMSOd$_6$) 3.2 (t, 2H), 3.75 (s, 2H), 3.98 (s, 3H), 4.0 (s, 3H), 4.6 (t, 2H), 7.15 (d, 1H), 7.25 (d, 1H), 7.4 (m, 3H), 7.55 (s, 1H), 7.8 (d, 1H), 8.55 (s, 1H); Mass Spectrum: M+H$^+$ 477.

5-Amino-2,3-dihydrofuro[3,2-b]pyridine that was used as a starting material is described in *Chem. Pharm. Bull.*, 1984, 32, 4914.

[2] $^1$H NMR: (DMSOd$_6$) 2.25 (s, 3H), 3.8 (s, 2H), 3.85 (m, 2H), 4.0 (s, 3H), 4.2 (t, 2H), 5.0 (m, 1H), 6.75 (s, 1H), 7.25 (d, 2H), 7.4 (s, 1H), 7.42 (d, 2H), 7.55 (s, 1H), 8.55 (s, 1H); Mass Spectrum: M−H$^−$ 465.

[3] $^1$H NMR: (DMSOd$_6$) 2.15 (s, 3H), 2.25 (s, 3H), 3.75 (s, 2H), 2.85 (m, 2H), 4.0 (s, 3H), 4.2 (t, 2H), 5.0 (m, 1H), 7.25 (d, 2H), 7.4 (m, 3H), 7.55 (s, 1H), 8.55 (s, 1H); Mass Spectrum: M−H$^−$ 479.

[4] $^1$H NMR: (DMSOd$_6$) 2.35 (s, 3H), 3.8 (s, 2H), 3.85 (m, 2H), 4.0 (s, 3H), 4.2 (t, 2H), 5.0 (m, 1H), 7.15 (s, 1H), 7.25 (d, 2H), 7.4 (s, 1H), 7.42 (d, 2H), 7.55 (s, 1H), 8.55 (s, 1H); Mass Spectrum: M−H$^−$ 465.

[5] ¹H NMR: (DMSOd₆) 2.15 (s, 3H), 2.2 (s, 3H), 3.8 (s, 2H), 3.98 (s, 3H), 4.0 (s, 3H), 7.2 (d, 1H), 7.4 (m, 3H), 7.6 (s, 1H), 8.55 (s, 1H); Mass Spectrum: M+H⁺ 469.

[6] ¹H NMR: (CDCl₃) 1.8-1.88 (m, 4H), 2.58-2.63 (m, 2H), 2.67-2.72 (m, 2H), 3.85 (s, 2H), 4.08 (s, 3H), 4.09 (s, 3H), 7.28 (d, 2H), 7.34 (s, 1H), 7.42 (d, 2H), 7.56 (s, 1H), 8.62 (s, 1H), 8.78 (br s, 1H); Mass Spectrum: M+H⁺ 477.

[7] ¹H NMR: (DMSOd₆) 1.27 (s, 9H), 3.79 (s, 2H), 3.97 (s, 3H), 3.99 (s, 3H), 6.75 (s, 1H), 7.27 (d, 2H), 7.39 (s, 1H), 7.43 (d, 2H), 7.55 (s, 1H), 8.54 (s, 1H); Mass Spectrum: M+H⁺ 479.

[8] ¹H NMR: (DMSOd₆) 3.84 (s, 2H), 3.98 (s, 3H), 3.99 (s, 3H), 7.27 (d, 2H), 7.39 (s, 1H), 7.42 (d, 2H), 7.53 (s, 1H), 7.55 (s, 1H), 8.54 (s, 1H); Mass Spectrum: M–H⁻ 455 and 457.

[9] ¹H NMR: (CDCl₃) 3.85 (s, 2H), 3.89 (s, 3H), 4.07 (s, 3H), 4.08 (s, 3H), 6.7 (s, 1H), 7.28 (d, 2H), 7.33 (s, 1H), 7.43 (d, 2H), 7.56 (s, 1H), 8.61 (s, 1H), 8.49 (br s, 1H); Mass Spectrum: M+H⁺ 453.

The 2-amino-5-methoxythiazole used as a starting material was prepared as follows:—

Sodium methoxide (0.724 g) was added to a solution of 2-amino-5-bromothiazole (0.6 g) in methanol (6 ml) and the resultant mixture was stirred at ambient temperature for 12 hours. The mixture was evaporated and the residue was purified by column chromatography on silica using increasingly polar mixtures of methylene chloride and ethyl acetate as eluent. There was thus obtained the required starting material (0.132 g); ¹H NMR: (CDCl₃) 3.82 (s, 3H), 4.53 (br s, 2H), 6.41 (s, 1H).

[10] ¹H NMR: (DMSOd₆) 0.75 (m, 2H), 0.85 (m, 2H), 1.98 (m, 1H), 3.78 (s, 2H), 3.97 (s, 3H), 3.99 (s, 3H), 6.78 (s, 1H), 7.26 (d, 2H), 7.39 (s, 1H), 7.42 (d, 1H), 7.55 (s, 1H), 8.53 (s, 1H); Mass Spectrum: M+H⁺ 463.

The 2-amino-4-cyclopropylthiazole used as a starting material was prepared as follows:—

Bromine (1.3 ml) was added to a stirred solution of cyclopropy methyl ketone in methanol (15 ml) that had been cooled to 0° C. The resultant mixture was stirred at ambient temperature for 45 minutes. Water (30 ml) was added and the mixture was extracted with diethyl ether. The organic phase was dried over magnesium sulphate and evaporated. The residue was dissolved in ethanol (15 ml) and this solution was added dropwise to a stirred suspension of thiourea (3.84 g) in ethanol (25 ml). The resultant mixture was heated to reflux for 1 hour. The mixture was cooled to ambient temperature and the precipitate was isolated and triturated under diethyl ether. The solid so obtained was dissolved in water (30 ml) and the solution was basified by the addition of a concentrated aqueous sodium bicarbonate solution. The solution was extracted with methylene chloride and the organic phase was dried over magnesium sulphate and evaporated. There was thus obtained the required starting material (2 g); ¹H NMR: (CDCl₃) 0.78 (m, 2H), 0.84 (m, 2H), 1.83 (m, 1H), 5.05 (br s, 2H), 6.06 (s, 1H); Mass Spectrum: M+H⁺ 141.

[11] The reactants were 2-amino-5-methylthiazole and 2-{3-fluoro-4-[6-methoxy-7-(2-tetrahydropyran-2-yloxy-ethoxy)quinazolin-4-yloxy]phenyl}acetic acid. A mixture of the material so obtained (2 g), glacial acetic acid (8 ml), water (5 ml) and THF (2 ml) was stirred and heated to 45° C. for 2 hours. The reaction mixture was poured into water (150 ml) and the mixture was basified to pH3.5 by the addition of 2N aqueous sodium hydroxide solution. The resultant gum was isolated and purified by preparative HPLC using a Waters 'β Basic Hypersil' reversed-phase column (5 microns silica, 30 mm diameter, 250 mm length) and decreasingly polar mixtures of water (containing 0.2% ammonium carbonate) and acetonitrile as eluent. There was thus obtained the required product which gave the following characterising data:—¹H NMR: (DMSOd₆) 2.35 (s, 3H), 3.8 (m, 4H), 4.0 (s, 3H), 4.25 (t, 2H), 5.0 (m, 1H), 7.15 (s, 1H), 7.25 (d, 1H), 7.4 (m, 3H), 7.55 (s, 1H), 8.55 (s, 1H); Mass Spectrum: M–H⁻ 483.

[12] The reactants were 2-amino-4-methylthiazole and 2-{3-fluoro-4-[6-methoxy-7-(2-tetrahydropyran-2-yloxy-ethoxy)quinazolin-4-yloxy]phenyl}acetic acid. A mixture of the material so obtained was treated with glacial acetic acid using an analogous procedure to that described in Note [11] immediately above. There was thus obtained the required product which gave the following characterising data:—¹H NMR: (DMSOd₆) 2.25 (s, 3H), 3.8 (m, 4H), 4.0 (s, 3H), 4.25 (m, 2H), 5.0 (m, 1H), 5.8 (s, 1H), 6.8 (s, 1H), 7.25 (d, 1H), 7.45 (m, 3H), 7.6 (s, 1H), 8.55 (s, 1H); Mass Spectrum: M+H⁺ 485.

[13] ¹H NMR: (DMSOd₆) 2.33 (s, 3H), 3.73 (s, 3H), 3.76 (s, 2H), 3.98 (s, 3H), 3.99 (s, 3H), 6.85 (m, 1H) 6.98 (d, 1H), 7.13 (s, 1H), 7.29 (d, 1H), 7.4 (s, 1H), 7.56 (s, 1H), 8.57 (s, 1H); Mass Spectrum: M+H⁺ 467.

The 2-[4-(6,7-dimethoxyquinazolin-4-yloxy)-2-methoxyphenyl]acetic acid used as a starting material was prepared as follows:—

A mixture of 2-(4-benzyloxy-2-methoxyphenyl)acetic acid (2.18 g), 10% platinum-on-carbon catalyst (0.3 g), ethanol (10 ml) and ethyl acetate (80 ml) was stirred under 3 atmospheres pressure of hydrogen for 2 hours. The reaction mixture was filtered and the filtrate was evaporated. There was thus obtained 2-(4-hydroxy-2-methoxyphenyl)acetic acid (1.52 g); ¹H NMR: (DMSOd₆) 3.55 (s, 2H), 3.68 (s, 3H), 6.27 (m, 1H), 6.37 (m, 1H), 6.91 (d, 1H), 9.3 (br s, 1H).

Using an analogous procedure to that described in the portion of Note [1] below Example 8 that is concerned with the preparation of starting materials, 4-chloro-6,7-dimethoxyquinazoline was reacted with 2-(4-hydroxy-2-methoxyphenyl)acetic acid to give 2-[4-(6,7-dimethoxyquinazolin-4-yloxy)-2-methoxyphenyl]acetic acid in 87% yield; ¹H NMR: (DMSOd₆) 3.55 (s, 2H), 3.75 (s, 3H), 3.98 (s, 3H), 3.99 (s, 3H), 6.83 (d, 1H), 6.97 (s, 1H), 7.27 (d, 1H), 7.39 (s, 1H), 7.55 (s, 1H), 8.57 (s, 1H); Mass Spectrum: M+H⁺ 371.

[14] ¹H NMR: (DMSOd₆) 2.25 (s, 3H), 3.75 (s, 2H), 3.98 (s, 3H), 3.99 (s, 3H), 6.7 (s, 1H), 7.26 (s, 1H), 7.27 (s, 1H), 7.4 (m, 3H), 7.55 (s, 1H), 8.55 (s, 1H); Mass Spectrum: M+H⁺ 421.

[15] ¹H NMR: (DMSOd₆) 1.95 (s, 3H), 2.15 (s, 3H), 3.6 (br s, 2H), 3.97 (s, 3H), 3.99 (s, 3H), 7.2 (m, 2H), 7.4 (m, 3H), 7.55 (s, 1H), 8.55 (s, 1H); Mass Spectrum: M+H⁺ 435.

The 2-amino-4,5-dimethyloxazole used as a starting material was prepared as follows:—

A mixture of cyanamide (0.96 ml), 3-hydroxybutan-2-one (1 g) and water (100 ml) was warmed gently to 50° C. until complete dissolution occurred. The temperature of the reaction mixture was kept at 45° C. for 30 minutes. The reaction mixture was cooled to ambient temperature, basified to pH10 by the addition of 2N aqueous sodium hydroxide solution and extracted with diethyl ether. The organic solution was dried over magnesium sulphate and evaporated to give 2-amino-4,5-dimethyloxazole as an oil (0.66 g).

[16] ¹H NMR: (DMSOd₆) 2.0 (s, 3H), 2.15 (s, 3H), 3.3 (s, 3H), 3.5 (m, 2H), 3.55 (m, 2H), 4.0 (s, 3H), 4.35 (m, 2H), 7.25 (m, 2H), 7.4 (m, 3H), 7.55 (s, 1H), 5.5 (s, 1H); Mass Spectrum: M+H⁺ 479.

[17] The reactants were 2-amino-4,5-dimethyloxazole and 2-{3-fluoro-4-[6-methoxy-7-(2-tetrahydropyran-2-yloxy-ethoxy) quinazolin-4-yloxy]phenyl}acetic acid. A mixture of the material so obtained was treated with glacial acetic acid using an analogous procedure to that described in Note [11] immediately above. There was thus obtained the required product which gave the following characterising data:—$^1$H NMR: (DMSOd$_6$) 1.95 (s, 3H), 2.2 (s, 3H), 3.75 (br s, 2H), 3.85 (m, 2H), 4.0 (s, 3H), 4.25 (t, 2H), 5.0 (t, 1H), 7.25 (d, 1H), 7.35 (d, 1H), 7.4 (s, 1H), 7.45 (d, 1H), 7.6 (s, 1H), 8.55 (s, 1H); Mass Spectrum: M+H$^+$ 483.

[18] $^1$H NMR: (DMSOd$_6$) 1.35 (t, 3H), 3.65 (s, 2H), 3.99 (s, 3H), 4.0 (s, 3H), 4.1 (q, 2H), 7.25 (d, 1H), 7.4 (m, 4H), 7.6 (s, 1H), 7.9 (s, 1H), 8.55 (s, 1H), 10.25 (s, 1H); Mass Spectrum: M+H$^+$ 452.

[19] $^1$H NMR: (DMSOd$_6$) 1.36 (s, 3H), 1.38 (s, 3H), 3.6 (s, 2H), 3.8 (m, 2H), 4.0 (s, 3H), 4.2 (m, 2H), 4.45 (m, 1H), 5.0 (m, 1H), 7.25 (d, 2H), 7.4 (m, 3H), 7.55 (s, 1H), 7.9 (s, 1H), 7.95 (d, 1H), 8.5 (s, 1H), 10.2 (s, 1H); Mass Spectrum: M+H$^+$ 478.

[20] $^1$H NMR: (DMSOd$_6$) 3.75 (s, 2H), 3.8 (s, 3H), 3.83 (m, 2H), 4.0 (s, 3H), 4.2 (t, 2H), 5.0 (m, 1H), 6.4 (d, 1H), 7.25 (d, 2H), 7.4 (s, 1H), 7.45 (d, 2H), 7.55 (d, 2H), 7.9 (d, 1H), 7.95 (d, 1H), 8.55 (s, 1H); Mass Spectrum: M+H$^+$ 500.

[21] $^1$H NMR: (DMSOd$_6$) 3.8 (m, 7H), 4.0 (s, 3H), 4.2 (t, 2H), 5.0 (m, 1H), 6.4 (d, 1H), 7.3 (d, 1H), 7.45 (m, 3H), 7.6 (s, 2H), 7.9 (d, 1H), 7.95 (d, 1H), 8.55 (s, 1H), 10.65 (s, 1H); Mass Spectrum: M+H$^+$ 518.

[22] $^1$H NMR: (DMSOd$_6$) 1.75 (m, 2H), 2.55 (m, 2H), 3.15 (m, 2H), 3.6 (s, 2H), 3.97 (s, 3H), 3.99 (s, 3H), 5.65 (s, 1H), 6.6 (d, 1H), 6.75 (d, 1H), 6.8 (d, 1H), 7.25 (d, 2H), 7.4 (s, 1H), 7.45 (d, 2H), 7.55 (s, 1H), 8.55 (s, 1H), 9.8 (s, 1H); Mass Spectrum: M+H$^+$ 471.

The 7-amino-1,2,3,4-tetrahydroquinoline used as a starting material was prepared as follows:—

A mixture of concentrated sulphuric acid (12.03 ml) and concentrated nitric acid (4.9 ml) was added dropwise during 15 minutes to a stirred mixture of 1,2,3,4 tetrahydroquinoline (6.66 g) and concentrated sulphuric acid (118 ml) that had been cooled to 0° C. The rate of addition was such that the temperature of the reaction mixture was maintained at below 5° C. The resultant mixture was stirred at 5° C. for 15 minutes. The mixture was poured onto ice (300 ml) and neutralised by the addition of solid sodium carbonate. The aqueous mixture was extracted with ethyl acetate and the organic phase was washed with water and brine, dried over magnesium sulphate and evaporated. The residue was purified by column chromatography on silica using increasingly polar mixtures of petroleum ether (b.p. 40-60° C.) and ethyl acetate as eluent. There was thus obtained 7-nitro-1,2,3,4 tetrahydroquinoline (6.14 g) as an oil; $^1$H NMR: (CDCl$_3$) 1.95 (m, 2H), 2.8 (t, 2H), 3.35 (t, 2H), 7.05 (d, 1H), 7.3 (s, 1H), 7.4 (d, 1H).

Using an analogous procedure to that described in the second paragraph of the portion of Example 13 that is concerned with the preparation of starting materials, 7-nitro-1,2,3,4-tetrahydroquinoline was converted into 7-amino-N-methyl-1,2,3,4-tetrahydroquinoline.

[23] $^1$H NMR: (DMSOd$_6$) 1.75 (m, 2H), 2.6 (m, 2H), 3.15 (m, 2H), 3.35 (s, 3H), 3.36 (s, 3H), 3.6 (s, 2H), 3.75 (m, 4H), 4.35 (m, 4H), 4.95 (s, 2H), 5.7 (s, 1H), 6.6 (m, 1H), 6.75 (m, 2H), 7.4 (s, 1H), 7.6 (s, 1H), 7.65 (s, 1H), 8.1 (s, 1H), 8.65 (s, 1H), 9.95 (s, 1H); Mass Spectrum: M+H$^+$ 559.

EXAMPLE 19

N-(3-isopropylisoxazol-5-yl)-2-[4-(6,7-dimethoxyquinazolin-4-yloxy)phenyl]acetamide A mixture of 2-[4-(6,7-dimethoxyquinazolin-4-yloxy)phenyl]acetic acid (0.3 g) and oxalyl chloride (3.73 ml) was heated at 60° C. for 30 minutes. The excess of oxalyl chloride was evaporated. Pyridine (0.43 ml) was added to a stirred mixture of the 2-[4-(6,7-dimethoxyquinazolin-4-yloxy)phenyl]acetyl chloride so obtained, 5-amino-3-isopropylisoxazole (0.148 g) and methylene chloride (30 ml). The resultant mixture was stirred at ambient temperature for 30 minutes. The mixture was evaporated and the residue was purified by column chromatography on silica using increasingly polar mixtures of methylene chloride and ethyl acetate as eluent. There was thus obtained the title compound (0.183 g); $^1$H NMR: (DMSOd$_6$) 1.89 (d, 6H), 2.92 (m, 1H), 3.75 (s, 2H), 3.97 (s, 3H), 4.0 (s, 3H), 6.18 (s, 1H), 7.26 (d, 2H), 7.39 (s, 1H), 7.41 (d, 2H), 7.55 (s, 1H), 8.53 (s, 1H), 11.83 (br s, 1H); Mass Spectrum: M+H$^+$ 449.

The 5-amino-3-isopropylisoxazole used as a starting material was prepared as follows:—

A mixture of 4-methyl-3-oxopentanenitrile (2 g), hydroxylamine (50% solution in water, 7.21 ml) and ethanol (6 ml) was heated to 60° C. for 12 hours. The solvent was evaporated and the residue was purified by column chromatography on silica using increasingly polar mixtures of methylene chloride and methanol as eluent. There was thus obtained the required starting material (0.355 g); $^1$H NMR: (DMSOd$_6$) 1.12 (d, 6H), 2.75 (m, 1H), 4.81 (s, 1H), 6.45 (br s, 2H).

EXAMPLE 20

N-(3-ethylisoxazol-5-yl)-2-[4-(6,7-dimethoxyquinazolin-4-yloxy)phenyl]acetamide

Using an analogous procedure to that described in Example 19, 2-[4-(6,7-dimethoxyquinazolin-4-yloxy)phenyl]acetyl chloride was reacted with 5-amino-3-ethylisoxazole. There was thus obtained the title compound in 55% yield; $^1$H NMR: (DMSOd$_6$) 1.16 (t, 3H), 2.56 (q, 2H), 3.76 (s, 2H), 3.97 (s, 3H), 3.99 (s, 3H) 6.16 (s, 1H), 7.27 (d, 1H), 7.39 (s, 1H), 7.41 (d, 2H), 7.55 (s, 1H), 8.54 (s, 1H); Mass Spectrum: M+H$^+$ 435.

The 5-amino-3-ethylisoxazole used as a starting material was prepared as follows:—

Using an analogous procedure to that described in the portion of Example 19 that is concerned with the preparation of starting materials, 3-oxopentanenitrile was reacted with hydroxylamine to give the required starting material in 47% yield; $^1$H NMR: (DMSOd$_6$) 1.1 (t, 3H), 2.38 (q, 2H), 4.81 (s, 1H), 6.47 (br s, 2H).

EXAMPLE 21

(2R)-2-amino-2-[4-(6,7-dimethoxyquinazolin-4-yloxy)phenyl]-N-(4,5-dimethylthiazol-2-yl)acetamide Using an analogous procedure to that described in Example 1, (2R)-2-(N-tert-butoxycarbonylamino)-2-[4-(6,7-dimethoxyquinazolin-4-yloxy)phenyl]acetic acid was reacted with 2-amino-3,4-dimethylthiazole to give (2R)-2-(N-tert-butoxycarbonylamino)-2-[4-(6,7-dimethoxyquinazolin-4-yloxy)phenyl]-N-(4,5-dimethylthiazol-2-yl)acetamide in 72% yield; $^1$H NMR: (DMSOd$_6$) 1.4 (s, 9H), 2.14 (s, 3H), 2.22 (s, 3H), 3.96 (s, 3H), 3.98 (s, 3H), 5.46 (br s, 1H), 7.29 (d, 2H), 7.38 (s, 1H), 7.54 (s, 1H), 7.56 (d, 2H), 8.53 (s, 1H), 12.22 (br s, 1H); Mass Spectrum: M+H$^+$ 566.

A mixture of the material so obtained (0.16 g), trifluoroacetic acid (4 ml) and methylene chloride (2 ml) was stirred at ambient temperature for 3 hours. The resultant mixture was evaporated. The residue was dissolved in a 4:1 mixture of methylene chloride and ethanol. A basic polystrene resin (methylpolystyrene carbonate resin; 0.5 g) was added and the mixture was stirred at ambient for 3 hours. The mixture was filtered and the filtrate was evaporated. There was thus obtained the title compound (0.062 g); $^1$H NMR: (DMSOd$_6$) 2.14 (s, 3H), 2.22 (s, 3H), 3.97 (s, 3H), 3.98 (s, 3H), 4.67 (s, 1H), 7.26 (d, 2H), 7.38 (s, 1H), 7.54 (s, 1H), 7.55 (d, 2H), 8.53 (s, 1H); Mass Spectrum: M+H$^+$ 466.

The (2R)-2-(N-tert-butoxycarbonylamino)-2-[4-(6,7-dimethoxyquinazolin-4-yloxy)phenyl]acetic acid used as a starting material was prepared as follows:—

A solution of di-tert-butyl dicarbonate (4.8 g) in 1,4-dioxane was added to a mixture of D-(−)-4-hydroxyphenylglycine (3.34 g), sodium bicarbonate (1.68 g) and water (33 ml) and the resultant mixture was stirred at ambient temperature for 4 hours. The mixture was washed with diethyl ether. The aqueous solution was acidified to pH2.5 by the addition of 2N aqueous hydrochloric acid and extracted with diethyl ether. The organic extract so obtained was dried over magnesium sulphate and evaporated. There was thus obtained (2R)-2-(N-tert-butoxycarbonylamino)-2-(4-hydroxyphenyl)acetic acid as a solid (5.88 g); $^1$H NMR: (DMSO$_6$) 1.38 (s, 9H), 4.94 (d, 1H), 6.69 (d, 2H), 7.16 (d, 2H), 7.37 (d, 1H), 9.43 (br s, 1H); Mass Spectrum: M−H$^-$ 266.

Using an analogous procedure to that described in the portion of Note [1] below Example 8 that is concerned with the preparation of starting materials, 4-chloro-6,7-dimethoxyquinazoline was reacted with (2R)-2-(N-tert-butoxycarbonylamino)-2-(4-hydroxyphenyl)acetic acid. The material so obtained was purified by column chromatography on silica using a solvent gradient from a 1:1 mixture of methylene chloride and ethyl acetate to a 10:10:1 mixture of methylene chloride, ethyl acetate and methanol as eluent. There was thus obtained the required starting material in 64% yield; $^1$H NMR: (DMSOd$_6$) 1.39 (s, 9H), 3.97 (s, 3H), 3.98 (s, 3H), 4.88 (br s, 1H), 7.2 (d, 2H), 7.37 (s, 1H), 7.45 (d, 2H), 7.52 (s, 1H), 8.53 (s, 1H); Mass Spectrum: M+H$^+$ 456.

EXAMPLE 22

(2S)-2-amino-2-[4-(6,7-dimethoxyquinazolin-4-yloxy)phenyl]-N-(4,5-dimethylthiazol-2-yl)acetamide Using an analogous procedure to that described in Example 1, (2S)-2-(N-tert-butoxycarbonylamino)-2-[4-(6,7-dimethoxyquinazolin-4-yloxy)phenyl]acetic acid was reacted with 2-amino-3,4-dimethylthiazole to give (2S)-2-(N-tert-butoxycarbonylamino)-2-[4-(6,7-dimethoxyquinazolin-4-yloxy)phenyl]-N-(4,5-dimethylthiazol-2-yl)acetamide in 84% yield; $^1$H NMR: (DMSOd$_6$) 1.41 (s, 9H), 2.14 (s, 3H), 2.23 (s, 3H), 3.96 (s, 3H), 3.99 (s, 3H), 5.46 (br s, 1H), 7.3 (d, 2H), 7.39 (s, 1H), 7.54 (s, 1H), 7.56 (d, 2H), 8.53 (s, 1H), 12.24 (br s, 1H); Mass Spectrum: M+H$^+$ 566.

Using an analogous procedure to that described in the second paragraph of Example 21, (2S)-2-(N-tert-butoxycarbonylamino)-2-[4-(6,7-dimethoxyquinazolin-4-yloxy)phenyl]-N-(4,5-dimethylthiazol-2-yl)acetamide was reacted with trifluoroacetic acid to give the title compound in 34% yield; $^1$H NMR: (DMSOd$_6$) 2.13 (s, 3H), 2.21 (s, 3H), 3.97 (s, 3H), 3.98 (s, 3H), 4.64 (s, 1H), 7.25 (d, 2H), 7.38 (s, 1H), 7.54 (m, 3H), 8.53 (s, 1H); Mass Spectrum: M+H$^+$466.

The (2S)-2-(N-tert-butoxycarbonylamino)-2-[4-(6,7-dimethoxyquinazolin-4-yloxy)phenyl]acetic acid used as a starting material was prepared as follows:—

Using an analogous procedure to that described in the portion of Example 21 that is concerned with the preparation of starting materials, L-(+)-4-hydroxyphenylglycine was reacted with di-tert-butyl dicarbonate to give (2S)-2-(N-tert-butoxycarbonylamino)-2-(4-hydroxyphenyl)acetic acid in 100% yield; $^1$H NMR: (DMSO$_6$) 1.38 (s, 9H), 4.94 (d, 1H), 6.71 (d, 2H), 7.16 (d, 2H), 7.37 (d, 1H), 9.43 (br s, 1H); Mass Spectrum: M−H$^-$ 266.

Using an analogous procedure to that described in the portion of Note [1] below Example 8 that is concerned with the preparation of starting materials, 4-chloro-6,7-dimethoxyquinazoline was reacted with (2S)-2-(N-ten-butoxycarbonylamino)-2-(4-hydroxyphenyl)acetic acid. The material so obtained was purified by column chromatography on silica using a solvent gradient from a 1:1 mixture of methylene chloride and ethyl acetate to a 10:10:1 mixture of methylene chloride, ethyl acetate and methanol as eluent. There was thus obtained the required starting material in 34% yield; $^1$H NMR: (DMSOd$_6$) 1.39 (s, 9H), 3.97 (s, 3H), 3.99 (s, 3H), 4.84 (m, 1H), 7.2 (d, 2H), 7.38 (s, 1H), 7.44 (d, 2H), 7.53 (s, 1H), 8.54 (s, 1H); Mass Spectrum: M+H$^+$ 456.

The invention claimed is:

1. A quinazoline derivative of the Formula I

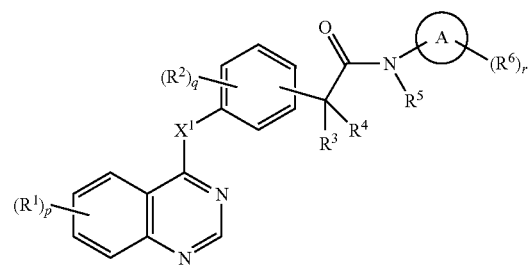

wherein
$X^1$ is O or $N(R^7)$ where $R^7$ is hydrogen or (1-8C)alkyl;
p is 0, 1, 2 or 3;
each $R^1$ group, which may be the same or different, is selected from halogeno, trifluoromethyl, cyano, hydroxy, mercapto, amino, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino and di-[(1-6C)alkyl]amino,
or from a group of the formula:

$Q^1$-$X^2$— wherein $X^2$ is a direct bond or is selected from O, S, SO, SO$_2$, $N(R^8)$, CO, CON($R^8$), $N(R^8)$CO, OC($R^8$)$_2$ and $N(R^8)C(R^8)_2$, wherein each $R^8$ is hydrogen or (1-8C)alkyl, and $Q^1$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl,
and wherein any aryl, (3-8C)cycloalkyl, (3-8C)cycloalkenyl, heteroaryl or heterocyclyl group within a $R^1$ substituent optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)

alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino,
or from a group of the formula:

$$-X^3-R^9$$

wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl,
or from a group of the formula:

$$-X^4-Q^2$$

wherein $X^4$ is a direct bond or is selected from O, CO and $N(R^{11})$, wherein $R^{11}$ is hydrogen or (1-8C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy,
and wherein any aryl, heteroaryl or heterocyclyl group within a substituent on $R^1$ optionally bears a (1-3C)alkylenedioxy group,
and wherein any heterocyclyl group within a $R^1$ substituent optionally bears 1 or 2 oxo or thioxo substituents,
and wherein any CH, $CH_2$ or $CH_3$ group within a $R^1$ substituent optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, S, SO, $SO_2$, $N(R^{12})$, CO, $CH(OR^{12})$, $CON(R^{12})$, $N(R^{12})CO$, $N(R^{12})CON(R^{12})$, $SO_2N(R^{12})$, $N(R^{12})SO_2$, CH=CH and C≡C wherein $R^{12}$ is hydrogen or (1-8C)alkyl, or, when the inserted group is $N(R^{12})$, $R^{12}$ may also be (2-6C)alkanoyl;
q is 0, 1 or 2;
each $R^2$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino;
$R^3$ is hydrogen, (1-8C)alkyl, (2-8C)alkenyl or (2-8C)alkynyl;
$R^4$ is hydrogen, hydroxy, (1-8C)alkyl, (2-8C)alkenyl or (2-8C)alkynyl or a group of the formula:

$$-X^5-R^{13}$$

wherein $X^5$ is a direct bond or is selected from O and $N(R^{14})$, wherein $R^{14}$ is hydrogen or (1-8C)alkyl, and $R^{13}$ is hydrogen, (1-8C)alkyl, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxycarbonyl-(1-6C)alkyl, (2-6C)alkanoylamino-(1-6C)alkyl or N-(1-6C)alkyl-(2-6C)alkanoylamino-(1-6C)alkyl;
or $R^3$ and $R^4$ together with the carbon atom to which they are attached form a (3-8C)cycloalkyl group;
$R^5$ is hydrogen, (1-8C)alkyl, (2-8C)alkenyl or (2-8C)alkynyl or a group of the formula:

$$-X^6-R^{15}$$

wherein $X^6$ is a direct bond or is selected from O and $N(R^{16})$, wherein $R^{16}$ is hydrogen or (1-8C)alkyl, and $R^{15}$ is halogeno-(1-6C)alkyl, hydroxy-(1-6C)alkyl, (1-6C)alkoxy-(1-6C)alkyl or cyano-(1-6C)alkyl;
Ring A is pyrazolyl;
r is 0, 1, 2 or 3; and
each $R^6$ group, which may be the same or different, is selected from halogeno, trifluoromethyl, cyano, hydroxy, mercapto, amino, carboxy, carbamoyl, sulphamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^7-R^{17}$$

wherein $X^7$ is a direct bond or is selected from O and $N(R^{18})$, wherein $R^{18}$ is hydrogen or (1-8C)alkyl, and $R^{17}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, sulphamoyl-(1-6C)alkyl, N-(1-6C)alkylsulphamoyl-(1-6C)alkyl, N,N-di-[(1-6C)alkyl]sulphamoyl-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)

alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or from a group of the formula:

—$X^8$-$Q^3$ wherein $X^8$ is a direct bond or is selected from O, S, SO, $SO_2$, $N(R^{19})$, CO, $CH(OR^{19})$, $CON(R^{19})$, $N(R^{19})CO$, $N(R^{19})CON(R^{19})$, $SO_2N(R^{19})$, $N(R^{19})SO_2$, $C(R^{19})_2O$, $C(R^{19})_2S$ and $C(R^{19})_2N(R^{19})$, wherein each $R^{19}$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or two $R^6$ groups together form a bivalent group that spans adjacent ring positions on Ring A selected from $OC(R^{20})_2O$, $OC(R^{20})_2C(R^{20})_2O$, $OC(R^{20})_2C(R^{20})_2$, $C(R^{20})_2OC(R^{20})_2$, $C(R^{20})_2C(R^{20})_2C(R^{20})_2$, $C(R^{20})_2C(R^{20})_2C(R^{20})_2$, $OC(R^{20})_2N(R^{21})$, $N(R^{21})C(R^{20})_2$, $N(R^{21})C(R^{20})_2C(R^{20})_2$, $N(R^{21})C(R^{20})_2C(R^{20})_2C(R^{20})_2$, $OC(R^{20})_2C(R^{20})_2N(R^{21})$, $C(R^{20})_2N(R^{21})C(R^{20})_2$, $CO.N(R^{20})C(R^{20})_2$, $N(R^{20})CO.C(R^{20})_2$, $N(R^{21})C(R^{20})_2CO$, $CO.N(R^{20})CO$, $N(R^{21})N(R^{20})CO$, $N(R^{20})CO.N(R^{20})$, $O.CO.N(R^{20})$, $O.CO.C(R^{20})_2$ and $CO.OC(R^{20})_2$ wherein each $R^{20}$ is hydrogen, (1-8C)alkyl, (2-8C)alkenyl or (2-8C)alkynyl, and wherein $R^{21}$ is hydrogen, (1-8C)alkyl, (2-8C)alkenyl, (2-8C)alkynyl or (2-6C)alkanoyl, and wherein any aryl, (3-8C)cycloalkyl, (3-8C)cycloalkenyl, heteroaryl or heterocyclyl group within an $R^6$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^9$—$R^{22}$ wherein $X^9$ is a direct bond or is selected from O and $N(R^{23})$, wherein $R^{23}$ is hydrogen or (1-8C)alkyl, and $R^{22}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

$X^{10}$-$Q^4$ wherein $X^{10}$ is a direct bond or is selected from O, CO and $N(R^{24})$, wherein $R^{24}$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within an $R^6$ group optionally bears a (1-3C)alkylenedioxy group, and wherein any heterocyclyl group within an $R^6$ group optionally bears 1 or 2 oxo or thioxo substituents, and wherein any CH, $CH_2$ or $CH_3$ group within an $R^6$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within an $R^6$ group are optionally separated by the insertion into the chain of a group selected from O, S, SO, $SO_2$, $N(R^{25})$, $N(R^{25})CO$, $CON(R^{25})$, $N(R^{25})CON(R^{25})$, CO, $CH(OR^{25})$, $N(R^{25})SO_2$, $SO_2N(R^{25})$, CH=CH and C≡C wherein $R^{25}$ is hydrogen or (1-8C)alkyl, or, when the inserted group is $N(R^{25})$, $R^{25}$ may also be (2-6C)alkanoyl;

or a pharmaceutically-acceptable salt, or a pharmaceutically-acceptable in vivo cleavable ester, in vivo cleavable ether or in vivo cleavable amide thereof.

2. A quinazoline derivative of the Formula I according to claim 1 wherein the —$C(R^3)(R^4)$—$CON(R^5)$ group is located at the 4-position (relative to the $X^1$ group).

3. A quinazoline derivative of the Formula I according to claim 1 wherein r is 1, 2 or 3 and each $R^6$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino.

4. A quinazoline derivative of the Formula I according to claim 1 wherein:
$X^1$ is O;
p is 2 and the $R^1$ groups, which may be the same or different, are located at the 6- and 7-positions and are selected from methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;
q is 0 or q is 1 and the $R^2$ group is fluoro, chloro, methyl or methoxy;
the —$C(R^3)(R^4)$—$CON(R^5)$ group is located at the 4-position (relative to the $X^1$ group);
each of $R^3$, $R^4$ and $R^5$ is hydrogen;
Ring A is pyrazolyl; and
r is 0, 1 or 2 and each $R^6$ group that is present is selected from fluoro, chloro, trifluoromethyl, cyano, methyl, ethyl, propyl, isopropyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, pyrrolidin-1-yl, piperidino, morpholino, piperazin-1-yl, pyrrolidin-1-ylmethyl, morpholinomethyl, piperidinomethyl and piperazin-1-ylmethyl, and wherein any heterocyclyl group within the $R^6$ group optionally bears a methyl or ethyl substituent;

or a pharmaceutically-acceptable salt, or a pharmaceutically-acceptable in vivo cleavable ester, in vivo cleavable ether or in vivo cleavable amide thereof.

5. A quinazoline derivative of the Formula I according to claim 1 wherein:

$X^1$ is O;

p is 2 and the first $R^1$ group is a 6-methoxy group and the second $R^1$ group is located at the 7-position and is selected from methoxy, ethoxy, 2-hydroxyethoxy and 2-methoxyethoxy;

q is 0 or q is 1 and the $R^2$ group is fluoro;

the —C($R^3$)($R^4$)—CON($R^5$) group is located at the 4-position (relative to the $X^1$ group);

each of $R^3$, $R^4$ and $R^5$ is hydrogen;

Ring A is 3-pyrazolyl or 4-pyrazolyl; and r is 0, 1 or 2 and each $R^6$ group that is present is selected from fluoro, chloro, cyano, methyl, ethyl, propyl, isopropyl, tert-butyl, cyclopropyl, methoxy, ethoxy and acetyl;

or a pharmaceutically-acceptable salt, or a pharmaceutically-acceptable in vivo cleavable ester, in vivo cleavable ether or in vivo cleavable amide thereof.

6. A quinazoline derivative of the Formula I according to claim 1 selected from:

N-(1,5-dimethylpyrazol-3-yl)-2-[4-(6,7-dimethoxyquinazolin-4-yloxy)phenyl]acetamide, N-(1-ethylpyrazol-3-yl)-2-[4-(6,7-dimethoxyquinazolin-4-yloxy)phenyl]acetamide, N-(1-methylpyrazol-4-yl)-2-[4-(6,7-dimethoxyquinazolin-4-yloxy)phenyl]acetamide, N-(1-ethylpyrazol-4-yl)-2-[4-(6,7-dimethoxyquinazolin-4-yloxy)phenyl]acetamide, N-(1-ethylpyrazol-4-yl)-2-[4-(6,7-dimethoxyquinazolin-4-yloxy)-3-fluorophenyl]acetamide, N-(1-isopropylpyrazol-4-yl)-2-[4-(6,7-dimethoxyquinazolin-4-yloxy)phenyl]acetamide, N-(1-isopropylpyrazol-4-yl)-2-[4-(7-ethoxy-6-methoxyquinazolin-4-yloxy)phenyl]acetamide, N-(1-isopropylpyrazol-4-yl)-2-{-4-[6-methoxy-7-(2-methoxyethoxy)quinazolin-4-yloxy]phenyl}acetamide and N-(1-isopropylpyrazol-4-yl)-2-{4-[7-(2-hydroxyethoxy)-6-methoxyquinazolin-4-yloxy]phenyl}acetamide;

and pharmaceutically-acceptable salts, and pharmaceutically-acceptable in vivo cleavable esters, in vivo cleavable ethers or in vivo cleavable amides thereof.

7. A process for the preparation of a quinazoline derivative of the Formula I, or a pharmaceutically-acceptable salt, or a pharmaceutically-acceptable in vivo cleavable ester, in vivo cleavable ether or in vivo cleavable amide thereof, according to claim 1 which comprises:

(a) the reaction of a quinazoline of the Formula II

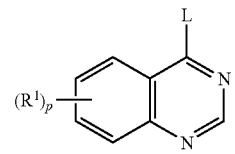

II wherein L is a displaceable group and p and $R^1$ have any of the meanings defined in claim 1 except that any functional group is optionally protected, with a phenylacetamide of the Formula III

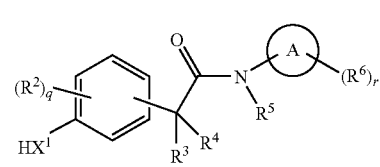

III wherein $X^1$, q, $R^2$, $R^3$, $R^4$, $R^5$, Ring A, r and $R^6$ have any of the meanings defined in claim 1 except that any functional group is optionally protected, whereafter any protecting group that is present is removed;

(b) the coupling of a quinazoline of the Formula VII

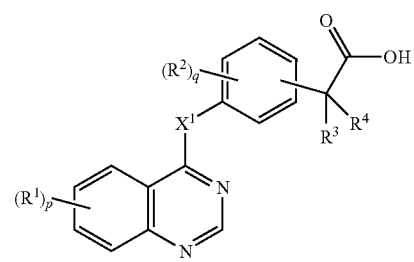

VII or a reactive derivative thereof, wherein p, $R^1$, $X^1$, q, $R^2$, $R^3$ and $R^4$ have any of the meanings defined in claim 1 except that any functional group is optionally protected, with an amine of the Formula VI

VI wherein $R^5$, Ring A, r and $R^6$ have any of the meanings defined in claim 1 except that any functional group is optionally protected, whereafter any protecting group that is present is removed;

(c) for the production of those compounds of the Formula I wherein at least one $R^1$ group is a group of the formula $Q^1$-$X^2$— wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^2$ is an oxygen atom, the coupling of a quinazoline of the Formula VIII

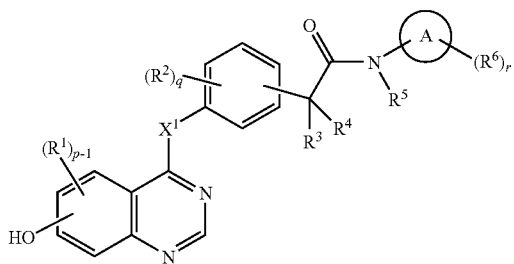

wherein each of p, $R^1$, $X^1$, q, $R^2$, $R^3$, $R^4$, $R^5$, Ring A, r and $R^6$ has any of the meanings defined in claim 1 except that any functional group is optionally protected, with an appropriate alcohol wherein any functional group is optionally protected, whereafter any protecting group that is present is removed;

(d) for the production of those compounds of the Formula I wherein a $R^6$ group is a group of the formula —$X^7$—$R^{17}$ wherein $X^7$ has any of the meanings defined in claim 1 and $R^{17}$ is an amino-substituted (1-6C)alkyl group, the reaction of a compound of the Formula I wherein a $R^6$ group is a group of the formula —$X^7$—$R^{17}$ wherein $R^{17}$ is a halogeno-substituted (1-6C)alkyl group with an appropriate amine or with a nitrogen-containing heterocyclyl compound; or (e) for the production of those compounds of the Formula I wherein a $R^6$ group is a group of the formula —$X^7$—$R^{17}$ wherein $X^7$ has any of the meanings defined in claim 1 and $R^{17}$ is an amino-substituted (1-6C)alkyl group, the reductive amination of a compound of the Formula I wherein a $R^6$ group is a group of the formula —$X^7$—$R^{17}$ wherein $R^{17}$ is a formyl or (2-6C)alkanoyl group;

and when a pharmaceutically-acceptable salt of a quinazoline derivative of the

Formula I is required it may be obtained by reaction of said quinazoline derivative with a suitable acid;

and when a pharmaceutically-acceptable in vivo cleavable ester, in vivo cleavable ether or in vivo cleavable amide of a quinazoline derivative of the Formula I is required, it may be obtained using a conventional procedure.

8. A pharmaceutical composition which comprises a quinazoline derivative of the Formula I, or a pharmaceutically-acceptable salt, or a pharmaceutically-acceptable in vivo cleavable ester, in vivo cleavable ether or in vivo cleavable amide thereof, according to claim 1 in association with a pharmaceutically-acceptable diluent or carrier.

9. A method for the treatment of prostate cancer, gastrointestinal stromal tumour, glioblastoma and chronic myeloid monomyelotic leukemia in a warm-blooded animal in need of such treatment, which comprises administering to said animal an effective amount of a quinazoline derivative of the Formula I, or a pharmaceutically-acceptable salt, or a pharmaceutically-acceptable in vivo cleavable ester, in vivo cleavable ether or in vivo cleavable amide thereof, according to claim 1.

10. A method for the treatment of diabetic retinopathy in a warm-blooded animal in need of such treatment, which comprises administering to said animal an effective amount of a quinazoline derivative of the Formula I, or a pharmaceutically-acceptable salt, or a pharmaceutically-acceptable in vivo cleavable ester, in vivo cleavable ether or in vivo cleavable amide thereof, according to claim 1.

\* \* \* \* \*